(12) United States Patent
Azzedine et al.

(10) Patent No.: US 8,728,727 B2
(45) Date of Patent: May 20, 2014

(54) DIAGNOSIS OF HEREDITARY SPASTIC PARAPLEGIAS (HSP) BY DETECTION OF A MUTATION IN THE KIAA1840 GENE OR PROTEIN

(75) Inventors: Hamid Azzedine, Bagneux (FR); Alexis Brice, Paris (FR); Giovanni Stevanin, Sevran (FR); Filippo Santorelli, Naple (IT); Paola Denora, Rome (IT)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 13/567,790

(22) Filed: Aug. 6, 2012

(65) Prior Publication Data

US 2013/0034849 A1 Feb. 7, 2013

Related U.S. Application Data

(63) Continuation of application No. 12/440,644, filed as application No. PCT/IB2007/003535 on Sep. 11, 2007, now abandoned.

(30) Foreign Application Priority Data

Sep. 11, 2006 (EP) .................................. 06291433

(51) Int. Cl.
*C07H 21/04* (2006.01)
*C12Q 1/68* (2006.01)

(52) U.S. Cl.
USPC ......... 435/6.1; 435/6.11; 435/6.12; 435/91.1; 435/91.2; 536/23.1; 536/24.3

(58) Field of Classification Search
None
See application file for complete search history.

(56) References Cited

U.S. PATENT DOCUMENTS

| 4,642,334 A | 2/1987 | Moore et al. |
|---|---|---|
| 5,270,184 A | 12/1993 | Walker et al. |
| 5,455,166 A | 10/1995 | Walker |
| 6,924,126 B1 | 8/2005 | Weissenbach et al. |
| 2007/0184444 A1* | 8/2007 | Abbas et al. ...................... 435/6 |

OTHER PUBLICATIONS

Barbas et al. (1992) *PNAS USA* 89:4457-4461.
Casali et al. (2004) *Neurology* 62:262-268.
Casari et al. (1998) *Cell* 93:973-983.
Den Dunnen and Antonarakis (2001) *Hum Genet* 109:121-124.
Engert et al. (2000) *Nat Genet* 24:120-125.
Fink (2003) *Exp.Neurol* 184:S106-S110.
Fink (2006) *Curr.Neurol.Neurosci.Rep* 6:65-76.
Harding (1983) *Lancet* 1:1151-1155.
Hazan et al. (1999) *Nature Genet.* 23:296-303.
Lossos et al. (2006) *Arch Neurol* 63:756-60.
Martinez et al. (1999) *Neurology* 53:50-56.
Moutsimilli et al. (2005) *Neuropharmacology* 49:890-900.
Olmez et al. (2006) *Neuropediatrics* 37:59-66.
Patel et al. (2002) *Nature Genet.* 31:347-348.
Shibasaki et al. (2000) *Ann Neurol* 48:108-112.
Simpson et al. (2003) *Am.J.Hum.Genet.* 73:1147-1156.
Stevanin et al. (2006) *Neurogenetics* 7:149-156.
Stevanin et al. (2007) *Nat Genet* 39(3):366-72.
Tallaksen et al. (2001) *Curr.Opin.Neurol.* 14:457-463.
Winner et al. (2004) *Arch.Neurol.* 61:117-121.
Winner et al. (2006) *Clin.Neurol.Neurosurg.* 108:692-698.
Zhao et al. (2001) *Nature Genet.* 29:326-331.
Reid (1997) *J. Med. Genet.* 34:499-503.

* cited by examiner

*Primary Examiner* — Jeanine A Goldberg
(74) *Attorney, Agent, or Firm* — B. Aaron Schulman, Esq.; Stites & Harbison, PLLC

(57) ABSTRACT

The invention relates to an ex vivo method of diagnosing or predicting an hereditary spastic paraplegias (HSP), in a subject, which method comprises detecting a mutation in the KIAA1840 gene or protein (spatacsin), wherein said mutation is indicative of an hereditary spastic paraplegias (HSP).

16 Claims, 17 Drawing Sheets

FIG.1

Figure 2:
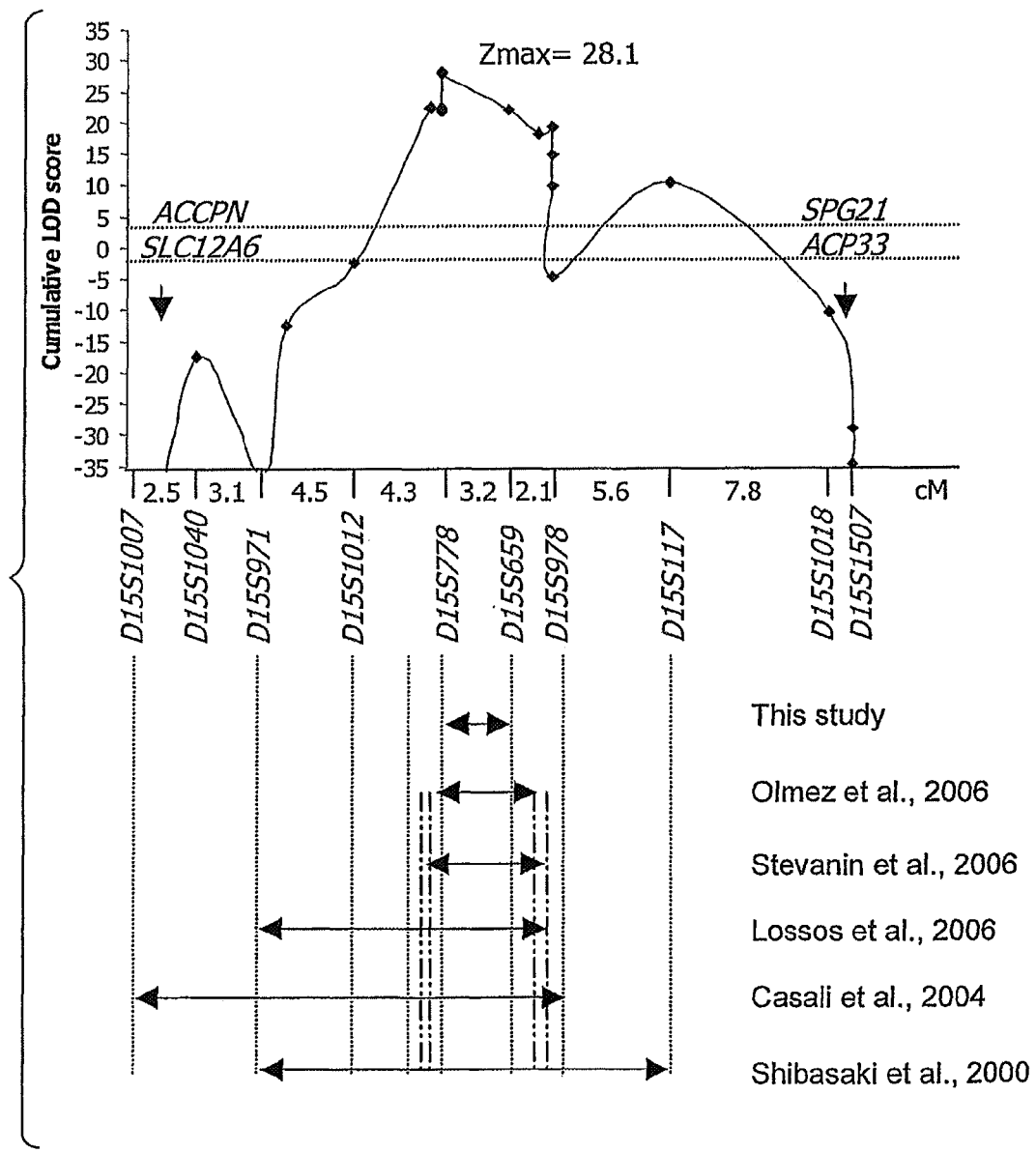

| MAP Location (cM)* | MARKERS | OS | MP | PE | FSP 75 | FSP 221 | FSP 343 | FSP 386 | FSP 393 | FSP 400 | FSP 446 | FSP 515 | FSP 670 | FSP 672 | FSP 732 | FSP 754 | SAL 1608 | SUM |
|---|---|---|---|---|---|---|---|---|---|---|---|---|---|---|---|---|---|---|
| 25.86 | D15SI007 | -4.79 | 0.60 | 0.60 | 1.30 | -8.97 | 1.33 | -7.33 | -19.48 | 2.60 | -3.84 | 0.78 | -7.23 | -4.45 | -2.67 | -4.58 | -0.17 | -56.30 |
| 28.35 | D15SI040 | 0.97 | 0.60 | 0.60 | 1.33 | -1.10 | 1.33 | -3.91 | -7.02 | 2.60 | 1.53 | 0.84 | -0.04 | -1.67 | -3.14 | -5.36 | -5.10 | -17.56 |
| 31.46 | D15S971 | 1.33 | 0.60 | 0.60 | 1.32 | -5.63 | 1.33 | -7.57 | -19.57 | 2.60 | 1.92 | 0.82 | -7.23 | -4.69 | 1.69 | -5.36 | 1.45 | -36.39 |
| 32.58 | D15SI042 | 1.33 | 0.60 | 0.60 | 1.32 | -8.09 | 1.33 | -8.90 | -12.21 | 2.60 | 1.93 | 0.82 | 2.21 | 0.81 | 1.70 | -0.01 | 1.45 | -12.52 |
| 35.95 | D15SI012 | 1.33 | 0.60 | 0.60 | 1.32 | -3.84 | 1.33 | 1.93 | -19.59 | 2.60 | 1.68 | 0.83 | 2.80 | 2.00 | 1.73 | 0.60 | 1.47 | -2.60 |
| 39.72 | D15SI044 | 1.33 | 0.60 | 0.60 | 1.32 | -1.82 | 1.33 | 1.93 | 1.80 | 2.60 | 1.87 | 0.84 | 3.08 | 2.56 | 1.79 | 0.89 | 1.50 | 22.23 |
| 40.25 | D15S214 | 1.33 | 0.60 | 0.60 | 1.33 | -2.26 | 1.33 | 1.93 | 1.81 | 2.60 | 1.93 | 0.85 | 3.08 | 2.60 | 1.80 | 0.92 | 1.50 | 21.94 |
| 40.25 | D15S129 | 1.33 | 0.60 | 0.60 | 1.33 | -2.27 | 1.25 | 1.93 | 1.81 | 2.60 | 1.93 | 0.85 | 3.08 | 2.60 | 1.80 | 0.92 | 1.50 | 21.85 |
| 40.25 | D15S994 | 1.33 | 0.60 | 0.60 | 1.33 | -1.89 | 1.33 | 1.93 | 1.81 | 2.60 | 1.92 | 0.82 | 3.08 | 2.60 | 1.80 | 0.92 | 1.50 | 22.31 |
| 40.25 | D15S968 | 1.33 | 0.60 | 0.60 | 1.33 | -2.31 | 1.33 | 1.93 | 1.81 | 2.60 | 1.93 | 0.85 | 3.08 | 2.60 | 1.80 | 0.92 | 1.50 | 21.89 |
| 40.25 | D15S14 | 1.33 | 0.60 | 0.60 | 1.33 | -2.37 | 1.33 | 1.93 | 1.81 | 2.60 | 1.93 | 0.85 | 3.08 | 2.60 | 1.80 | 0.92 | 1.50 | 21.84 |
| 40.25 | D15S779 | 1.33 | 0.60 | 0.60 | 1.33 | -2.39 | 1.33 | 1.93 | 1.81 | 2.60 | 1.93 | 0.85 | 3.08 | 2.60 | 1.80 | 0.92 | 1.50 | 21.82 |
| 40.25 | D15S780 | 1.33 | 0.60 | 0.60 | 1.33 | -2.41 | 1.33 | 1.87 | 1.81 | 2.60 | 1.93 | 0.85 | 3.08 | 2.60 | 1.80 | 0.92 | 1.50 | 21.74 |
| 40.25 | D15S15 | 1.33 | 0.60 | 0.60 | 1.33 | -1.80 | 1.33 | 1.78 | 1.81 | 2.60 | 1.93 | 0.85 | 3.08 | 2.60 | 1.80 | 0.92 | 1.50 | 22.27 |
| 40.25 | D15S778 | 1.33 | 0.60 | 0.60 | 1.33 | -2.49 | 1.33 | 1.93 | 1.81 | 2.60 | 1.93 | 0.85 | 3.08 | 2.60 | 1.80 | 0.92 | 1.50 | 21.72 |
| 40.25 | D15S784 | 1.33 | 0.60 | 0.60 | 1.33 | 3.81 | 1.33 | 1.93 | 1.81 | 2.60 | 1.93 | 0.85 | 3.08 | 2.60 | 1.80 | 0.92 | 1.50 | 28.02 |
| 40.25 | D15S783 | 1.33 | 0.60 | 0.60 | 1.33 | 3.85 | 1.33 | 1.93 | 1.81 | 2.60 | 1.93 | 0.85 | 3.08 | 2.60 | 1.80 | 0.92 | 1.50 | 28.06 |
| 40.25 | D15S781 | 1.33 | 0.60 | 0.60 | 1.33 | 3.85 | 1.33 | 1.93 | 1.81 | 2.60 | 1.93 | 0.85 | 3.08 | 2.60 | 1.80 | 0.92 | 1.50 | 28.06 |
| 40.25 | D15S182 | 1.33 | 0.60 | 0.60 | 1.33 | 3.85 | 1.33 | 1.93 | 1.81 | 2.60 | 1.93 | 0.85 | 3.08 | 2.60 | 1.80 | 0.92 | 1.50 | 28.06 |
| 40.25 | D15S537 | 1.33 | 0.60 | 0.60 | 1.33 | 3.85 | 1.33 | 1.93 | 1.81 | 2.60 | 1.93 | 0.85 | 3.08 | 2.60 | 1.80 | 0.92 | 1.50 | 28.06 |
| 40.25 | D15S516 | 1.33 | 0.60 | 0.60 | 1.33 | 3.85 | 1.33 | 1.93 | 1.80 | 2.60 | 1.93 | 0.85 | 3.08 | 2.60 | 1.80 | 0.92 | 1.50 | 28.06 |
| 40.25 | D15S517 | 1.33 | 0.60 | 0.60 | 1.33 | 3.85 | 1.33 | 1.93 | 1.80 | 2.60 | 1.86 | 0.84 | 3.08 | 2.60 | 1.80 | 0.92 | 1.50 | 27.97 |
| 40.25 | D15SI508 | 1.33 | 0.60 | 0.60 | 1.33 | 3.85 | 1.33 | 1.93 | 1.80 | 2.60 | 1.84 | 0.83 | 3.08 | 2.45 | 1.80 | 0.90 | 1.49 | 27.69 |
| 43.47 | D15S659 | 1.33 | 0.60 | 0.60 | 1.33 | -2.45 | 1.33 | 1.93 | 1.80 | 2.55 | 1.93 | 0.82 | 3.08 | -3.30 | 1.80 | 0.89 | 1.49 | 22.01 |
| 44.9 | D15S132 | 1.33 | 0.16 | 0.60 | 1.33 | -2.45 | 1.33 | 1.93 | 1.81 | 2.53 | 1.92 | 0.81 | 3.07 | -0.52 | 1.79 | 0.88 | 1.48 | 18.18 |
| 45.62 | D15S161 | 1.33 | -0.75 | 0.60 | 1.32 | 1.49 | 1.33 | 1.93 | 1.81 | -3.59 | 1.91 | 0.81 | 3.08 | -2.81 | 1.79 | 0.87 | 1.48 | 19.13 |
| 45.62 | D15SI039 | 1.33 | -0.85 | 0.60 | 1.32 | 0.96 | 1.33 | 1.93 | 1.81 | 0.58 | 1.91 | 0.81 | 3.08 | -2.78 | 1.79 | 0.87 | 1.48 | 19.04 |
| 45.62 | D15S143 | 1.33 | -0.97 | 0.60 | 1.32 | -2.51 | 1.33 | 1.93 | 1.81 | 0.56 | 1.91 | 0.81 | 3.08 | -2.81 | 1.79 | 0.87 | 1.48 | 14.83 |
| 45.62 | D15S123 | 1.33 | -1.05 | 0.60 | 1.32 | -2.45 | 1.33 | 1.93 | 1.81 | -3.50 | 1.91 | 0.81 | 3.07 | -1.48 | 1.79 | 0.87 | 1.48 | 9.77 |
| 45.62 | D15S978 | 1.33 | -5.70 | 0.60 | 1.32 | -2.45 | 1.33 | -6.66 | 1.81 | -3.50 | 1.91 | 0.81 | 3.07 | -0.72 | 1.79 | 0.87 | 1.48 | -4.72 |
| 51.21 | D15S117 | 1.30 | -0.47 | 0.52 | 1.08 | 1.49 | 1.19 | -0.77 | 1.63 | -5.49 | -3.82 | 0.80 | 2.37 | 0.97 | 1.77 | 0.87 | 1.47 | 10.26 |
| 59.05 | D15SI018 | 1.10 | -0.19 | 0.40 | 0.14 | 0.96 | 0.34 | -8.67 | -4.74 | -5.62 | 0.49 | 0.84 | -0.34 | 0.44 | 1.80 | 0.93 | 1.50 | -10.61 |
| 60.17 | D15SI08 | 1.08 | -0.17 | 0.39 | -1.91 | -2.51 | -0.64 | -4.97 | -3.41 | -6.34 | -1.50 | 0.82 | -12.05 | -2.25 | 1.80 | 0.92 | 1.50 | -29.25 |
| 60.17 | D15SI507 | 1.08 | -0.17 | 0.39 | -4.10 | -2.51 | -0.67 | -6.51 | -4.70 | -6.34 | -3.02 | 0.82 | -11.06 | -2.25 | 1.80 | 0.92 | 1.50 | -34.83 |

FSP831 (Portugal)
*Exon 3: c.529_533 delATATT, p.I177_F178>S177delfsX178*

FSP792 (Morocco)
*Exon 32: c.6100 C>T, p.R2034X*

FSP845 (Morocco)
*Exon 32: c.6100 C>T, p.R2034X*

TUN9 (Tunisia)
*Exon 32: c.6100 c>t p.R2034X*

FSP920 (Japan)
*Exon36: c.6737_6740delTTGA; p.I2246_E2247>S2246fsX2260*

ITA1 (Trukey)
*Exon32: c.6091C>T; p.R2031X*

FSP838 (Saudi-Arabia)
*Exon 30: c.5769 delT, p.S1923RfsX1950*

SPD199 (Turkey)
*Exon 4: c.704_705delAT, p.H235RfsX246*

ITA17 (Brazil)

*Exon 3: c.529_533 delATATT, p.I177_F178>S177fsX178*
*Exon 22: c.3741_3742insA, p.P1248fsX1264*

Propositus
Exon 3: M / +
Exon 22: + / M

FSP830 (Portugal)

*Exon 6: c.1282 A>T, p.K428X*
*Intron 34: c.6477+4 A>G, r.?*

FSP522 (France)

*Exon 7: c.1471_1472delCT, p.L491DfsX556*
*Exon 30: c.5532_5533delCA, p.S1844SfsX1857*

SAL646 (France)

*Exon 8: c.1668delT, p.F556LfsX577*
*Exon 36: c.6739_6742delGAGT, p.E2247_S2248>L2247fsX2260*

ITA16SB (Italy)

*Exon 8: c.1679C>G, p.S560X*
*Exon 31: c.5870C>G, p.S1957X*

DKD (Italy)

*Exon 8: c.1692delA, p.V564VfsX577*
*Exon 31: c.5982_5983insCTCT, p.L1995LfsX2000*

FSP683 (France)
*Exon 10: c.1951C>T, R651X*
*Exon 31: c.5989_5992delCTGT,p.L1997_Y1998>M1997fsX2056*

Exon 7    + M    + M
Exon 36   M +    + +

ITA28VAC (Italy)
*Exon 10: c.1951C>T; p.R651X*
*Exon 13: c.2444G>T, p.R815M and/or r.?*

ITA16 (Brazil)
*Intron 13: c.2444+1G>C, r.?*
*Exon 25: c.4307_4308 delAA, p.Q1436RfsX1442*

ITA 14 (Italy)
*Exon 15: c.2833 A>G, p.R945X*
*Exon 38: c.6857 C>T, p.R2286X*

ITA8 (Germany)
*Exon 17: c.3075_3076insA, p.E1026RfsX2029*
*Exon 30: c.5471 C>T, p.R1824X*

FSP398 (Israel)
*Exon 25: c.4307_4308delAA, p.Q1436RfsX1442*
*Exon 31: c.5986_5987insT, p.C1996LfsX1999*

DIAGNOSIS OF HEREDITARY SPASTIC PARAPLEGIAS (HSP) BY DETECTION OF A MUTATION IN THE KIAA1840 GENE OR PROTEIN

CROSS-REFERENCE TO RELATED APPLICATIONS

This application is a continuation of U.S. application Ser. No. 12/440,644, filed Jan. 4, 2010 now abandoned, which is a 371 application of PCT/IB2007/003535, filed Sep. 11, 2007, these applications are incorporated herein by reference.

The invention relates to the identification of mutations in the KIAA1840 gene or protein, associated with a hereditary spastic paraplegias (HSP), and to diagnostic applications that benefit from this identification.

Hereditary spastic paraplegias (HSP) are genetically heterogeneous Mendelian disorders characterized by weakness, spasticity and loss of vibratory sense in the lower limbs (Harding et al. 1983 and Tallaksen et al. 2001). They reveal themselves clinically through difficulties in walking possibly evolving into total paralysis of both legs. The physiopathology of this set of diseases is, to date, relatively undocumented; however, anatomopathological data make it possible to conclude that the attack is limited to the pyramidal tracts responsible for voluntary motricity in the spinal cord (Reid, 1997). The incidence of HSPs, which remains difficult to estimate because of rare epidemiological studies and the considerable clinical variability, varies from 0.9:100000 in Denmark, 3 to 9.6:100000 in certain regions of Spain (Polo et al., 1991) or 14:100000 in Norway (Skre, 1974) (approximately 3:100000 in France). Various clinical and genetic forms of HSP exist. The so-called "pure" HSPs, which correspond to isolated spasticity of the lower limbs, are clinically distinguished from the "complex" HSPs, for which the spasticity of the legs is associated with other clinical signs of neurological or non-neurological type (Bruyn et al., 1991).

Although forms of HSP have been recognized for over a century, new phenotypes are regularly described, demonstrating wide clinical heterogeneity. Genetically, autosomal dominant (AD), autosomal recessive (AR) and X-linked inheritance are observed and almost 32 genetic loci have been identified, but only 12 genes have been cloned (Flink et al. 2006). According to the putative roles of these genes, mitochondrial function, protein folding and axonal transport have been implicated in the dying back of pyramidal tract axons in these disorders.

The most common forms of AD-HSP, accounting for about 40-50% of cases, are caused by mutations in the SPG4 and SPG3A genes that encode for spastin and atlastin, respectively (Hazan et al. 1990, Zhao et al. 2001 and international patent application WO 01/18198). In contrast to AD forms, no major gene accounts for AR-HSP, which is less common and more varied in clinical presentation, implying greater genetic heterogeneity. The four AR-HSP genes cloned so far, encoding for paraplegin (SPG7, MIM#607259 (OMIM database, www.ncbi.nlm.nih.gov/entrez/query.fcgi?db=OMIM)), (Casari et al. 1998) spartin (SPG20; MIM#275900), (Patel et al. 2002) and maspardin (SPG21, MIM 248900) (Simpson et al. 2003) as well as the gene responsible for the related spastic ataxia of Charlevoix Saguenay (ARSACS, MIM#270550) (Engert et al. 2000) probably represent less than 5% of all cases (Fink et al. 2003).

A very common form of AR-HSP associates spastic paraplegia, mental or cognitive deficit and thin corpus callosum (Winner et al. 2005). The majority of the families appear to be linked to SPG11 on chromosome 15, which was the third AR-HSP locus to be identified (Martinez et al. 1999). This entity is particularly prevalent in Japan (Shibasaki et al. 2000), but is also found in North-America, the Middle-East and Europe (Martinez et al 1999 and Lossos et al. 2006 and Casali et al. 2004 and Winner et al. 2004 and Stevanin et al. 2006). The typical clinical features of SPG11 consist of early-onset spastic paraplegia (usually <20 years), urinary bladder dysfunction, deep sensory deficits in the legs and cognitive impairment that progress insidiously to severe functional disability over a period of 10-20 years. Some patients also develop arm involvement, dysarthria, contractures and muscle atrophy. Auxiliary studies frequently identify a thin corpus callosum (TCC) with white matter lesions and variable cerebral cortical atrophy on magnetic resonance imaging (MRI), variable cortical and thalamic glucose hypometabolism on positron emission tomography and predominantly axonal motor or sensorimotor peripheral neuropathy on nerve conduction studies (Winner et al. 2004).

Linkage to chromosome 15q has been reported so far in 31 families in which the patients presented with the typical SPG11 phenotype. In the initial study, a maximum multipoint combined LOD score of 3.14 was detected in seven AR-HSP families in a region between D15S1007 and D15S1012, although patients from only 2 kindreds of North-American and Italian ancestries presented with a TCC (Martinez et al. 1999). A second study reported a group of 10 out of 13 Japanese families with a homogeneous phenotype of AR-HSP-TCC with a cumulative LOD score of 9.68 in the D15S971 to D15S117 interval (Shibasaki et al. 2000). Casali et al. also reported 5 Italian kindreds that showed significant linkage (Z=3.35) to the interval flanked by markers D15S1007 and D15S978 (Casali et al. 2004). More recently, the analysis of 8 additional kindreds (Z=11.5) including 3 large consanguineous families, allowed the locus to be restricted by the inventors to the 6 cM interval between markers D15S1044 and D15S143 (Lossos et al. 2006 and Stevanin et al. 2006) a region that did not overlap with the interval defined in the originally mapped families (Martinez et al. 1999), therefore showing genetic heterogeneity among families linked to 15q and more closely resembling the locus for amyotrophic lateral sclerosis ALS5 (Hentati et al, 1998). It is of note that in the work published by Martinez et al (1999), only 2 of 8 pedigrees presented with the typical SPG11 phenotype with TCC and patients from these 2 families were linked to a larger region on chromosome 15 overlapping the region described in recent reports (Lossos et al. 2006 and Stevanin et al. 2006). More recently, the SPG11 locus was further refined to the 4.6 cM region (according to the Marschfield genetic map, http://research.marshfieldclinic.org/genetics/GeneticResearch/compMaps.asp) between markers D15S968-D15S132 (Olmez et al, 2006) confirming the results of the inventors (FIG. 2).

Figure 6:
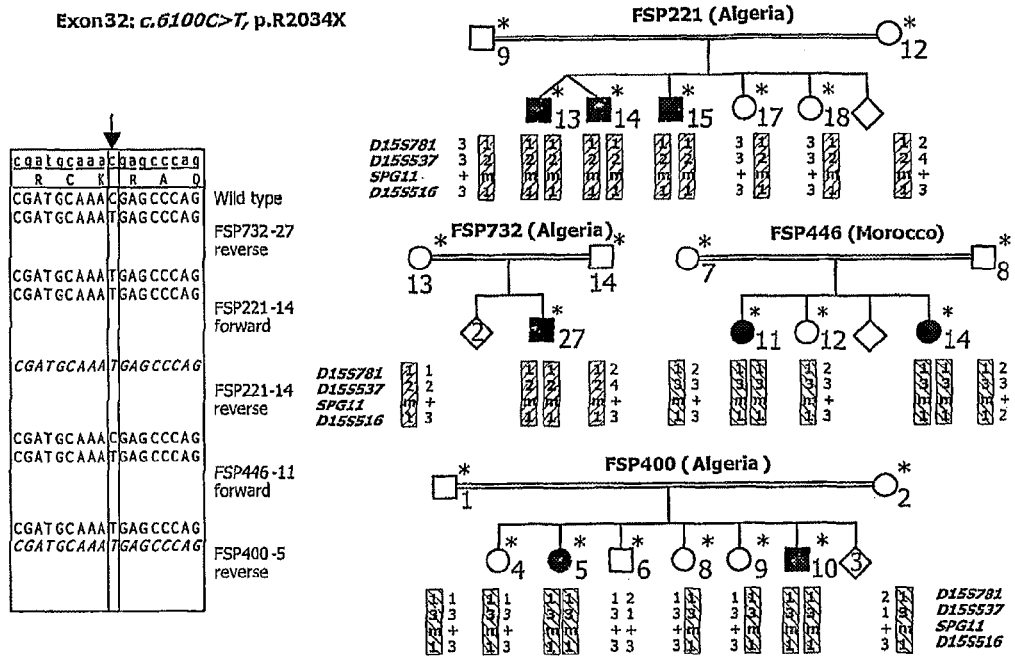
Figure 7:
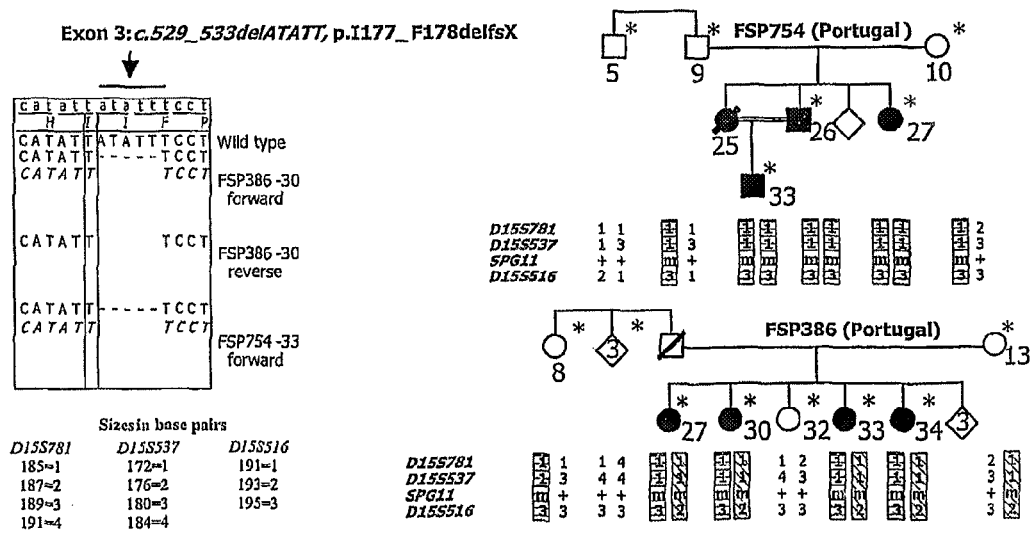
Figure 8:
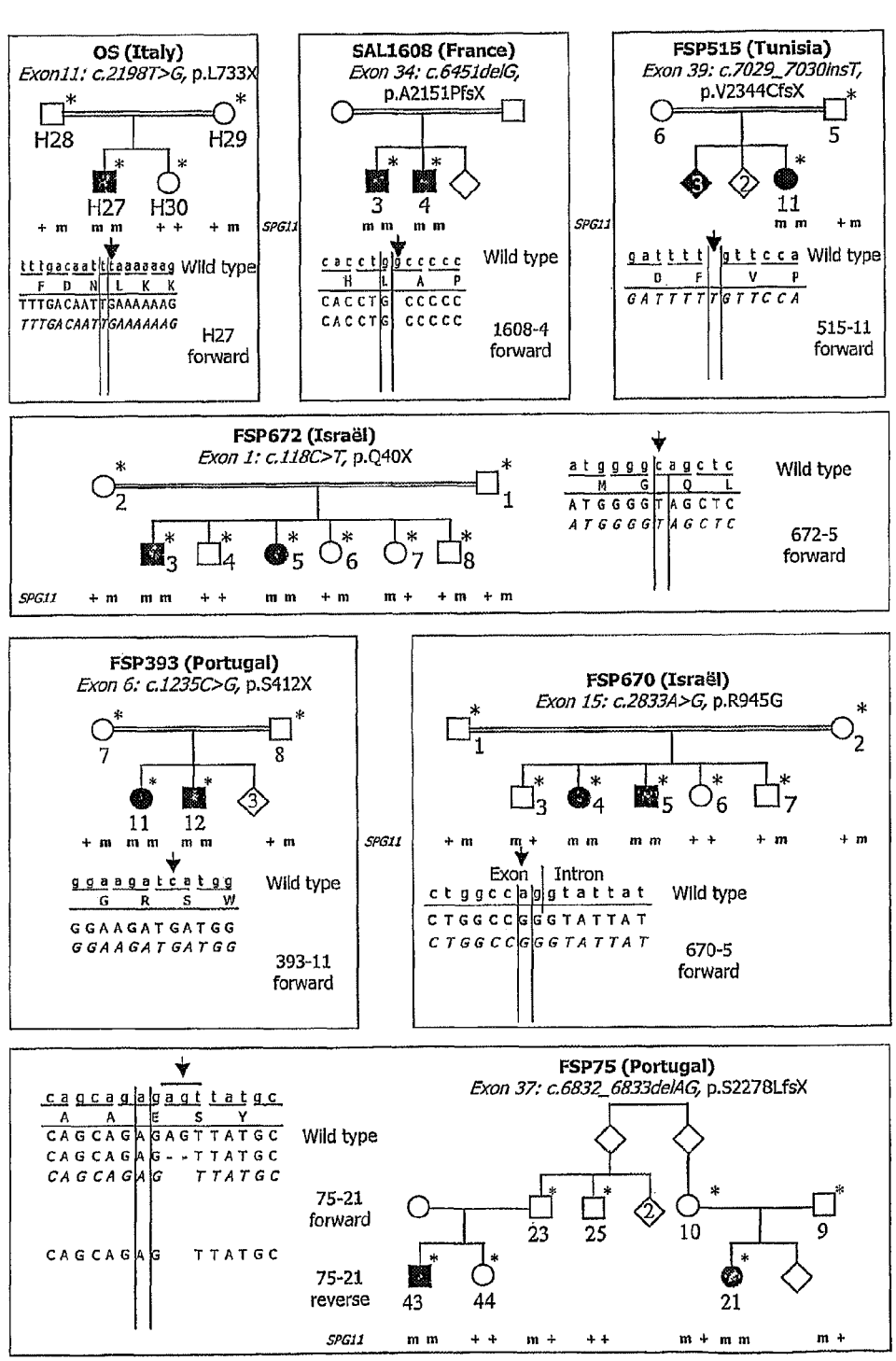
Figure 9:
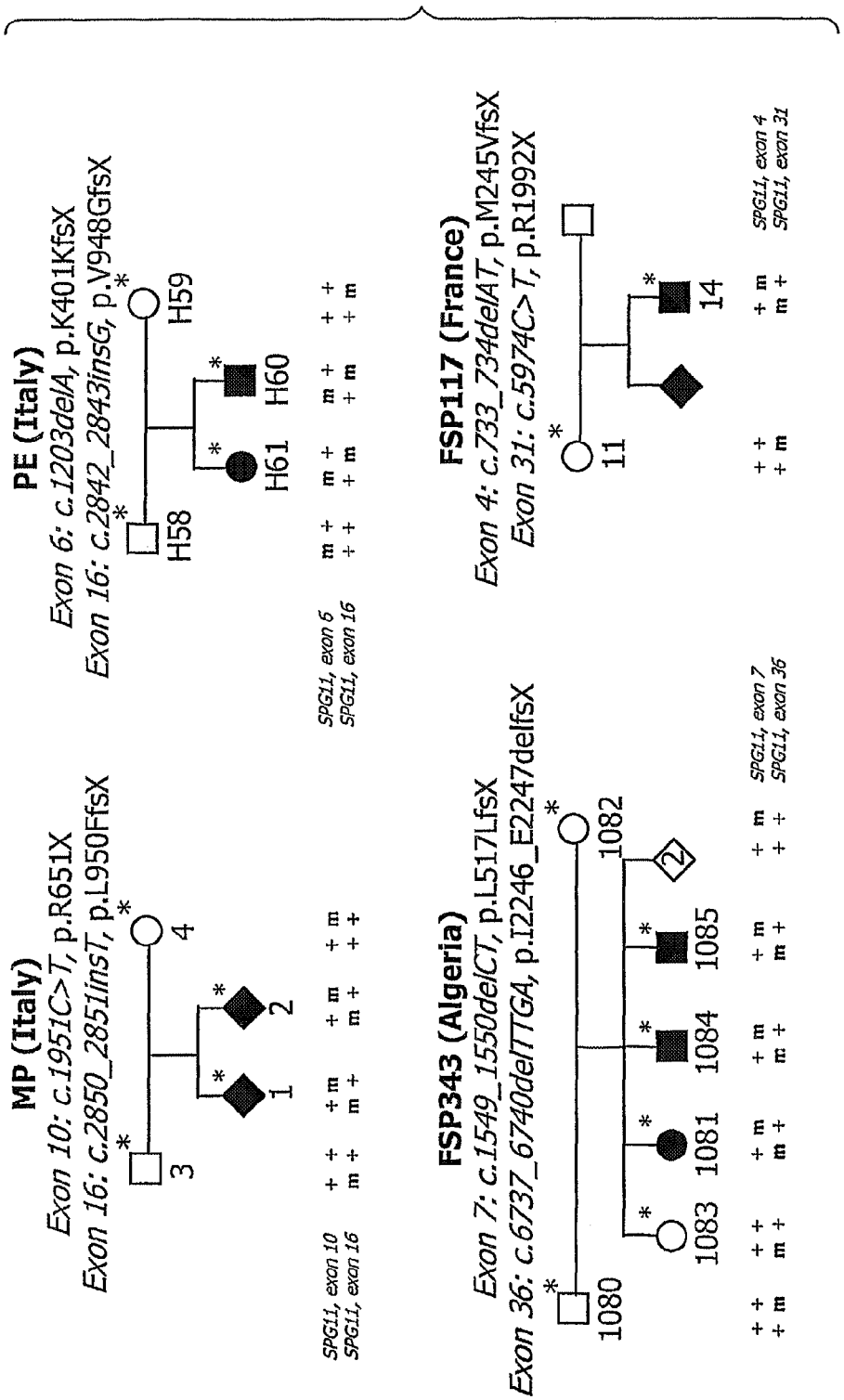

The inventors have now identified the gene responsible for the most frequent form of Autosomal Recessive Hereditary Spastic Paraplegia (AR-HSP). They have indeed demonstrated that the disease is caused by mutations in the KIAA1840 gene (also known as FLJ21439), affecting the spatacsin protein expression (Stevanin et al., 2007). This is supported by four pieces of evidence. First, the inventors have excluded 17 out of about 40 genes assigned to the SPG11 candidate interval after significant reduction of its size to the 3.2 cM interval (according to the Marschfield genetic map) between markers D15S778 and D15S659 (FIGS. 1 to 4). The analysis of 2 of these genes has been reported previously (Stevanin et al, 2006). Secondly, the inventors have identified 43 different mutations segregating in 47 families (FIGS. 5 to 9), 16 of which linked previously to the SPG11 locus with a highly significant 28.1 maximal combined lod score (FIGS. 1 and 2), 8 of them already published as linked (Casali et al, 2004; Lossos et al, 2006 and Stevanin et al, 2006). Thirdly, the inventors have identified mutations, absent in at least 140 control chromosomes, that were all, leading to abnormal splicing of the messenger RNA and/or leading to a truncated protein. Finally, the inventors have demonstrated that all mutated families, except 2 in which magnetic resonance imaging could not be performed (TUN2 and TUN14), presented with the typical AR-HSP-TCC phenotype. In addition, several of these families shared the same mutation with similar surrounding haplotypes when they came from the same geographical origins, suggesting regional founder effects (FIGS. 6 and 7). Mutations in KIAA1840 affected 47 of 91 AR-HSP-TCC families in the study carried out by the inventors making this genetic entity very frequent among AR-HSP-TCC (75% was estimated in a previous study, Stevanin et al, 2006). The invention therefore provides the identification of the major gene responsible of AR-HSP-TCC and probably of AR-HSPs in general and opens thereby new opportunities to improve diagnosis and genetic counseling of said disease. Moreover, the invention also provides a mean to improve the medical care management of patient affected with said disease. In addition, since most patients with spastic paraplegia have isolated forms, it is conceivable that this new gene could account for a small proportion of these patients as well. Indeed, in Europe, due to the small size of the families, recessively inherited diseases are often found in apparently isolated cases.

A first aspect of the invention thus relates to the identification of mutations in the KIAA1840 gene or protein, associated with a hereditary spastic paraplegias (HSP), and to diagnostic application that benefits from this identification.

A second aspect of the invention relates to an isolated nucleic acid, specifically hybridizable to a region of KIAA1840 gene sequence that contains a mutation selected from the group consisting of the substitutions: c.6100C>T, c.2198T>G, c.118C>T, c.1235C>G, c.2833A>G, c.1951C>T, c.869+1G>A, c.1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T and c.5974C>T, the deletions: c.529-533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA and c.733_734delAT, and the insertions: c.7029_7030insT, c.2850_2851insT, c.3741_3742insA, c.5982_5983insCTCT, c.5986_5987insT, c.3075_3076insA and c.2842_2843insG.

Such an isolated nucleic acid can be used as a primer or probe.

More preferentially the invention relates to an isolated nucleic acid, which comprises a KIAA1840 gene sequence that contains one or several mutation(s) selected from the group consisting of the substitutions: c.6100C>T, c.2198T>G, c.118C>T, c.1235C>G, c.2833A>G, c.1951C>T, c.869+1G>A, c.1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T c.5974C>T, the deletions: c.529-533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA c.733_734delAT, and the insertions: c.7029_7030insT, c.2850_2851insT, c.3741_3742insA, c.5982_5983insCTCT, c.5986_5987insT, c.3075_3076insA c.2842_2843insG or a sequence complementary thereto.

Another aspect of the invention relates to an isolated polypeptide which comprises the amino acid sequence of KIAA1840 containing one or several mutation(s) selected from the group consisting of p.Q40X, p.I177_F178delfsX178, p.H235RfsX246, p.M245VfsX246, p.K401KfsX415, p.S412X, p.K428X, p.L491DfsX556, p.L517LfsX556, p.F556LfsX577, p.S560X, p.V564VfsX577, p.R651X, p.L733X, p.R815M, p.W899X, p.Q906SfsX920, p.R945G, p.R945GfsX950, p.L950FfsX953, p.V948 GfsX953, p.E1026RfsX1029, p.P1248TfsX1264, p.Q1436RfsX1442, p.R1824X, p.S1844SfsX1857, p.S1923RfsX1950, p.S1957X, p.R1992X, p.L1995LfsX2000, p.C1996LfsX1999, p.L1997_1998delfsX2056, p.R2031X, p.R2034X, p.A2151PfsX2172, p.I2246_E2247delfsX2260, p.E2247_S2248delfsX2260, p.S2278LfsX2338, p.R2286X and p.V2344CfsX2349.

Another aspect of the invention relates to an isolated monoclonal or polyclonal antibody that specifically recognizes a KIAA1840 protein containing a mutation selected from the group consisting of p.Q40X, p.I177_F178delfsX178, p.H235RfsX246, p.M245VfsX246, p.K401KfsX415, p.S412X, p.K428X, p.L491DfsX556, p.L517LfsX556, p.F556LfsX577, p.S560X, p.V564VfsX577, p.R651X, p.L733X, p.R815M, p.W899X, p.Q906SfsX920, p.R945G, p.R945GfsX950, p.L950FfsX953, p.V948 GfsX953, p.E1026RfsX1029, p.P1248TfsX1264, p.Q1436RfsX1442, p.R1824X, p.S1844SfsX1857, p.S1923RfsX1950, p.S1957X, p.R1992X, p.L1995LfsX2000, p.C1996LfsX1999, p.L1997_1998delfsX2056, p.R2031X, p.R2034X, p.A2151PfsX2172, p.I2246_E2247delfsX2260, p.E2247_S2248delfsX2260, p.S2278LfsX2338, p.R2286X and p.V2344CfsX2349.

Another aspect of the present invention relates to the use of a monoclonal or polyclonal antibody recognizing the wild type protein to identify truncated forms of the protein.

Definitions

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

As used herein, the term "oligonucleotide" refers to a nucleic acid, generally of at least 10, preferably at least 15, and more preferably at least 20 nucleotides, preferably no more than 100 nucleotides, still preferably no more than 70 nucleotides, and which is hybridizable to a KIAA1840 genomic DNA, cDNA, or mRNA. Oligonucleotides can be labelled according to any technique known in the art, such as with radiolabels, fluorescent labels, enzymatic labels, sequence tags, etc. A labelled oligonucleotide may be used as a probe to detect the presence of a mutated KIAA1840 nucleic acid. Alternatively, oligonucleotides (one or both of which may be labelled) can be used for amplifying a KIAA1840 nucleic acid, for instance by PCR (Saiki et al., 1988), to detect the presence of a mutation. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A nucleic acid molecule is "hybridizable" or "hybridizes" to another nucleic acid molecule, such as a cDNA, genomic DNA, or RNA, when a single stranded form of the nucleic acid molecule can anneal to the other nucleic acid molecule under the appropriate conditions of temperature and solution ionic strength (Sambrook et al., 1989).

The conditions of temperature and ionic strength determine the "stringency" of the hybridization. For preliminary screening for homologous nucleic acids, low stringency hybridization conditions, corresponding to a Tm (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher Tm, e.g., 40% formamide, with 5× or 6×SCC. High stringency hybridization conditions correspond to the highest Tm, e.g., 50% formamide, 5× or 6×SCC. SCC is a 0.15 M NaCl, 0.015 M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., 1989, 9.50-9.51). For hybridization with shorter nucleic acids, i.e., oligonucleotides, the position of mismatches becomes more important, and the length of the oligonucleotide determines its specificity (see Sambrook et al., 1989 II.7-II.8). A minimum length for a hybridizable nucleic acid is at least about 10 nucleotides, preferably at least about 15 nucleotides, and more preferably the length is at least about 20 nucleotides.

In a specific embodiment, the term "standard hybridization conditions" refers to a Tm of 55° C., and utilizes conditions as set forth above. In a preferred embodiment, the Tm is 60° C. In a more preferred embodiment, the Tm is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

As used herein, an "amplification primer" is an oligonucleotide for amplification of a target sequence by extension of the oligonucleotide after hybridization to the target sequence or by ligation of multiple oligonucleotides which are adjacent when hybridized to the target sequence. At least a portion of the amplification primer hybridizes to the target. This portion is referred to as the target binding sequence and it determines the target-specificity of the primer. In addition to the target binding sequence, certain amplification methods require specialized non-target binding sequences in the amplification primer. These specialized sequences are necessary for the amplification reaction to proceed and typically serve to append the specialized sequence to the target. For example, the amplification primers used in Strand Displacement Amplification (SDA) include a restriction endonuclease recognition site 5' to the target binding sequence (U.S. Pat. Nos. 5,455,166 and 5,270,184). Nucleic Acid Based Amplification (NASBA), self-sustaining sequence replication (3SR) and transcription based amplification primers require an RNA polymerase promoter linked to the target binding sequence of the primer. Linking such specialized sequences to a target binding sequence for use in a selected amplification reaction is routine in the art. In contrast, amplification methods such as PCR which do not require specialized sequences at the ends of the target, generally employ amplification primers consisting of only target binding sequence.

As used herein, the terms "primer" and "probe" refer to the function of the oligonucleotide. A primer is typically extended by polymerase or ligation following hybridization to the target but a probe typically is not. A hybridized oligonucleotide may function as a probe if it is used to capture or detect a target sequence, and the same oligonucleotide may function as a primer when it is employed as a target binding sequence in an amplification primer. It will therefore be appreciated that any of the target binding sequences disclosed herein for amplification, detection or quantisation of KIAA1840 may be used either as hybridization probes or as target binding sequences in primers for detection or amplification, optionally linked to a specialized sequence required by the selected amplification reaction or to facilitate detection.

As used herein, the terms "KIAA1840 gene" (or its synonyms: FLJ21439, ENSG00000104133 or SPG11) denotes a KIAA1840 gene of any species, especially human, but also other mammals or vertebrates to which the methods of the invention can apply. The human KIAA1840 gene encodes a large protein of 2443 amino-acids (aa) of unknown function that the inventors have named Spatacsin (SEQ ID NO: 2). *Homo sapiens* KIAA1840 gene is localized on chromosome 15 and its Coding Sequence (CDS) is deposited in Genebank under accession number NM_025137, or AB058743 (5'-3' forward strand shown SEQ ID NO: 1). Human KIAA1840 gene shares 85% identity with the homologous protein in dog, and 76% and 73% identity with the mouse and rat homologues and 59% with the chicken homologue. Homology is less than 25% with orthologous proteins, of smaller sizes, in tetraodon and *drosophila*. KIAA1840 homologous proteins at NCBI database are: dog XP_544657, *gallus* XP_413940.1, mouse BAE27954, rat XP_242139.3, and at Ensembl database; *drosophila* CG13531, tetraodon GSTENG00003909001. The human KIAA1840 gene contains 40 exons spanning 101 Kbases of genomic DNA on chromosome 15q21.1. The intron-exon structure of the complementary strand of the KIAA1840 gene is further indicated in Table 1 below and in FIG. 5.

TABLE 1

Exon-intron boundaries of the human KIAA1840 gene (according to the Ensembl database)

| No | Exon/Intron | Position in SEQ ID NO: 1 | Length (bp) | Sequence |
|----|-------------|--------------------------|-------------|----------|
|    | 5' upstream sequence |                |             | . . . cgacgcagtcaggttccggcgaaagtgaccggaagtaaccgccgggccaa |
| 1  | ENSE00001183257 | 0 | 258 | GATGGCTGCAGAGGAAGGGGTCGCGAGTGCTGCTTCCGCCGGCGGTAGCTGGGGCACCGCGGCCA TGGGGCGGGTTCTACCGATGCTGTTGGTGCCAGTCCCCGCCGAGGCGATGGGGCAGCTCGGCTCC CGGGCGCAGCTGCGCACACAGCCGGAGGCTCTGGGGAGCCTGACGGCTGCGGGCAGCCTCCAAGT GCTTTCTTTGACGCCTGGCAGCCGGGGCGGGGGTCGCTGCTGCCTGGAGGGCCCCTTCTGGCA |
|    | Intron 1-2 |   | 2,774 | gtaagtgctgagggagagttgggcc . . . aataaatctaaactttttttcttag |
| 2  | ENSE00001183253 | 258 | 185 | CTTTCTATGGGAGGATTCTCGTAACAGCAGCACACCAACTGAAAAGCCCAAACTGCTCGCTCTTG GTGAAAATTATGAACTGCTTATCTATGAATTTAATTTGAAAGATGGAAGATGTGATGCAACCATT TTGTATAGCTGTAGTAGGGAGGCATTGCAAAAGCTCATTGACGATCAAGATATCA |
|    | Intron 2-3 |   | 1,128 | gtaagtatctacaggtggtctttca . . . gaaataatatcctttgttttgtag |
| 3  | ENSE00001183250 | 443 | 225 | GTATTTCCTTATTGTCTTTGAGAATCCTGTCATTTCACAATAACACATCATTACTGTTCATCAAC AAATGTGTCATCCTACATATTATATTTCCTGAAAGAGATGCTGCAATTAGAGTACTCAACTGTTT CACACTTCCCTTGCCTGCACAGGCAGTGGACATGATTATTGACACGCAGCTCTGCAGAGGAATTC TTTTTGTTTTGAGTAGTTTAGGCTGGATCT |
|    | Intron 3-4 |   | 1,782 | gtatccttggtggtagaagtgttga . . . attttcttttaactctaactaaaag |
| 4  | ENSE00001183246 | 668 | 202 | ACATTTTTGATGTTGTGGATGGTACATATGTAGCTCATGTGGATTTAGCACTTCACAAAGAAGAC ATGTGTAATGAGCAGCAACAGGAGCCAGCCAAGATTTCTTCATTTACTTCACTGAAAGTTTCTCA AGACCTCGATGTTGCAGTGATTGTCAGCTCCTCCAACTCCGCAGTTGCTCTTAACTTAAATTTGT ATTTCAG |
|    | Intron 4-5 |   | 4,828 | gtatgtagatgactgcagtttctaa . . . tgtctatcattattttaaatgtag |
| 5  | ENSE00001183241 | 870 | 138 | GCAACACCCAGGACACCTACTGTGTGAAAGAATACTAGAAGATCTTCCTATTCAAGGACCTAAGG GCGTAGATGAAGATGATCCTGTTAACTCTGCCTACAACATGAAACTGGCCAAGTTTTCCTTCCAA ATTGATAG |
|    | Intron 5-6 |   | 189 | gtacagaaacttccttttcatgtag . . . aagttatattttaccttgtttccag |
| 6  | ENSE00001183238 | 1008 | 449 | GTCTTGGAAAGCCCAGCTATCATCATTGAATGAAACAATAAAGAACTCCAAACTGGAGGTTTCCT GTTGTGCTCCATGGTTCCAGGATATTTTGCATTTGGAGTCACCTGAATCTGGTAACCACAGTACA AGTGTGCAGAGCTGGGCCTTCATTCCACAGGACATAATGCATGGGCAATATAATGTTCTACAGAA AGATCATGCCAAGACCAGTGATCCAGGAAGATCATGGAAAATAATGCACATCAGTGAACAAGAGG AACCCATAGAGCTTAAATGTGTGTCTGTGACAGGATTCAC TGCACTGTTTACTTGGGAAGTGGAAAGGATGGGCTATACCATTACCCTCTGGGATTTGGAGACCC AGGGCATGCAGTGTTTTTCCCTTGGCACAAAGTGTATTCCTGTAGACAGTAGTGGAGACCAGCAG CTGTGCTTTGTTTTGACAG |
|    | Intron 6-7 |   | 2,479 | gtgagactgtcttgtattagattga . . . aagctaacttttattttcctatag |
| 7  | ENSE00001183236 | 1457 | 146 | AGAATGGACTCTCTCTGATTTGTTTGGTTTGACTCAAGAAGAGTTTTTAAACAGACTCATGATC CATGGAAGTGCCAGCACTGTGGACACTCTTTGTCATCTCAATGGCTGGGGAAGGTGCTCAATTCC CATACATGCACTAGAG |
|    | Intron 7-8 |   | 15,228 | gtaacagaattaaatgcccaagaac . . . atttttattttcctcctcatttcag |
| 8  | ENSE00001105929 | 1603 | 133 | GCCGGGATAGAAAATCGTCAGCTGGACACAGTAAATTTCTTTTTGAAGAGCAAGGAAAATCTTTT TAATCCATCCTCAAAATCTTCTGTATCTGATCAGTTTGATCACTTGTCATCCCATTTATATTTAA GAA |
|    | Intron 8-9 |   | 4,116 | gtaagtggaataaagatttctacat . . . gttaatttctttggttctttctcag |
| 9  | ENSE00001105933 | 1736 | 156 | ATGTGGAAGAGCTGATACCAGCATTGGATTTACTTTGCTCGGCAATTAGAGAAAGTTATTCTGAA CCCCAAAGCAAACACTTTTCAGAACAATTGCTTAATCTTACACTGTCTTTCCTTAACAACCAAAT AAAGGAGCTTTTCATTCACACTGAAG |
|    | Intron 9-10 |   | 388 | gtaagaatagcagctaggaaggggg . . . attggcacattggtattttccatag |
| 10 | ENSE00001105923 | 1892 | 176 | AACTAGATGAACATCTGCAAAAAGGAGTGAACATTTTGACTAGCTACATTAATGAACTTCGAACCT TCATGATAAAGTTTCCTTGGAAGCTAACAGATGCTATAGATGAATATGATGTACATGAAAATGTCC CCAAAGTAAAGGAGAGCAATATATGGAAGAAACTCAGCTTTGAG |
|    | Intron 10-11 |   | 2,161 | gtaagtacgaataatcatcacttct . . . aaggcaaacgttttctttttccctag |

TABLE 1-continued

Exon-intron boundaries of the human KIAA1840 gene (according to the Ensembl database)

| No | Exon/Intron | Position in SEQ ID NO: 1 | Length (bp) | Sequence |
|---|---|---|---|---|
| 11 | ENSE00001105941 | 2068 | 177 | GAAGTTATTGCCAGCGCCATTTTAAACAACAAAATACCAGAGGCACAGACTTTCTTCAGGATTGAT<br>AGTCATTCTGCTCAAAAACTTGAGGAGCTTATTGGCATAGGCCTAAATTTGGTCTTTGACAATTTA<br>AAAAAGAACAATATAAAGGAAGCCTCTGAACTTTTGAAGAATATG |
|  | Intron 11-12 |  | 3,531 | gtgagtggtgtaatccataaagtct . . . ttttggttttctatgtttattttag |
| 12 | ENSE00001183220 | 2245 | 72 | GGGTTTGATGTAAAAGGCCAATTGCTCAAGATCTGCTTCTATACAACTAATAAAAATATACGTGAC<br>TTTTTG |
|  | Intron 12-13 |  | 380 | gtaggtaaaggtgagactacatagt . . . ctgctttaattacttttttattcaag |
| 13 | ENSE00001183213 | 2317 | 128 | GTTGAAATTTTAAAAGAAAAAAATTATTTTTCTGAAAAAGAGAAAAGAACTATAGACTTCGTGCAT<br>CAAGTTGAGAAGCTTTATTTGGGACATTTCCAAGAAAATATGCAAATCCAGTCATTTCCCAG |
|  | Intron 13-14 |  | 285 | gtagtctcattagtcctcttttgat . . . aaaaaatttatatcactgtttttag |
| 14 | ENSE00001183208 | 2445 | 176 | GTACTGGATAAAGGAACAAGATTTTTTCAAGCACAAGTCTGTTTTGGACTCATTCCTGAAATATGA<br>TTGTAAAGATGAATTTAACAAACAGGACCATAGAATTGTGTTAAATTGGGCTCTGTGGTGGGATCA<br>ACTAACACAAGAATCCATCCTTCTCCCCAGGATAAGTCCAGAAG |
|  | Intron 14-15 |  | 1,355 | gcaagtgtgagagagcctgaaatat . . . ttaaaatgtgttttttttcatgtag |
| 15 | ENSE00001183204 | 2621 | 214 | AATACAAATCATATTCCCCTGAAGCCCTCTGGAGATACCTCACAGCTCGCCATGATTGGTTAAACA<br>TTATCTTATGGATTGGAGAATTTCAAACCCAGCATAGTTATGCTTCACTTCAGCAGAACAAATGGC<br>CCCTTCTGACTGTTGATGTTATTAACCAGAATACTTCCTGTAACAACTACATGAGGAATGAAATTT<br>TAGATAAGCTGGCCAG |
|  | Intron 15-16 |  | 4,623 | gtattataactgttgaactaatacc . . . tgacatcctataaatctgtccatag |
| 16 | ENSE00001047610 | 2835 | 204 | GAATGGGGTTTTTTGGCATCTGAACTGGAAGACTTTGAATGCTTCCTCCTAAGACTGAGCCGTAT<br>TGGAGGTGTAATACAGGATACCCTCCCTGTTCAAAACTACAAGACCAAAGAAGGTTGGGATTTCCA<br>TTCTCAATTCATTCTCTATTGTTTGGAGCACAGTCTGCAGCATCTTCTTTATGTCTACCTTGACTG<br>TTACAA |
|  | Intron 16-17 |  | 1,826 | gtgagtactgagaatgcatttgtcc . . . aggttttgtttgttttatatacag |
| 17 | ENSE00001287244 | 3039 | 107 | ACTTAGTCCTGAAAATTGTCCCTTTTTGGAAAAAAAAGAGTTACATGAAGCACACCCTTGGTTTGA<br>ATTTTTAGTTCAGTGTCGACAAGTTGCCAGTAACTTAACAG |
|  | Intron 17-18 |  | 2,444 | gtatgggtatactgtattaaacaca . . . aaaaacactgtctttattttccag |
| 18 | ENSE00001047605 | 3146 | 146 | ATCCCAAACTGATCTTCCAGGCTAGCCTTGCAAATGCTCAGATTTTGATTCCCACCAATCAGGCCA<br>GTGTAAGCAGTATGCTATTGGAAGGACATACCCTCCTGGCCCTTGCTACTACAATGTATTCTCCTG<br>GGGGTGTCAGTCAG |
|  | Intron 18-19 |  | 2,234 | gtatggatagcactttatgacaaaa . . . acctgttatctgttttttttacttag |
| 19 | ENSE00001047617 | 3292 | 162 | GTTGTTCAGAATGAAGAAAATGAAAACTGTTTGAAGAAAGTGGATCCCCAGCTATTGAAGATGGCA<br>TTAACTCCTTACCCCAAGCTAAAAACTGCTCTCTTCCCACAGTGCACTCCTCCTAGTGTCCTGCCA<br>TCTGATATTACAATCTACCACCTTATTCAG |
|  | Intron 19-20 |  | 2,352 | gtacagtatttaggtggccaatatt . . . ctgtttaacttttcccttttcag |
| 20 | ENSE00001047612 | 3454 | 67 | TCATTATCACCCTTTGATCCTAGCAGATTGTTTGGCTGGCAGTCTGCTAACACACTAGCTATAGG<br>AG |
|  | Intron 20-21 |  | 5,392 | gtaagtcatcatgggtacttcttga . . . taatattgttttactttccccctag |
| 21 | ENSE00001047594 | 3521 | 166 | ATGCATGGAGTCATCTCCCACATTTCTCTAGCCCTGACCTGGTTAATAAATATGCTATAGTGGAAC<br>GTCTGAATTTTGCTTATTATTTACATAATGGGCGGCCATCATTTGCATTTGGTACTTTTCTGGTCC<br>AGGAATTAATCAAGAGCAAGACTCCCAAGCAGCT |
|  | Intron 21-22 |  | 1,630 | gtgagtatttaaaatataattttgt . . . tgatttgattcctttcttttcag |
| 22 | ENSE00001047598 | 3687 | 206 | GATCCAGCAAGTAGGCAATGAAGCCTATGTTATAGGGCTCTCCTCCTTCCACATACCTTCAATAGG<br>AGCTGCATGTGTTTGTTTCTTAGAATTGCTTGGCCTTGACAGCCTCAAGCTCAGAGTTGATATGAA<br>AGTGGCCAATATAATTTTGAGCTACAAGTGCAGAAATGAAGATGCTCAGTACAGCTTTATCAGAGA<br>GTCTGTAG |
|  | Intron 22-23 |  | 257 | gtacagcacctttatctggcctgc . . . attttgttgtttatatttcttacag |
| 23 | ENSE00001047622 | 3893 | 109 | CCGAAAAACTATCTAAACTAGCTGATGGTGAAAAGACAACCACAGAAGAATTGCTTGTTCTCTTAG<br>AAGAAGGTACATGGAACAGCATTCAGCAACAGGAAATAAAGAG |

TABLE 1-continued

Exon-intron boundaries of the human KIAA1840 gene (according to the Ensembl database)

| No | Exon/Intron | Position in SEQ ID NO: 1 | Length (bp) | Sequence |
|---|---|---|---|---|
| | Intron 23-24 | | 1,321 | gtttgtgagttgcagtctcagcctc . . . cccccacctctaattctgattatag |
| 24 | ENSE00001047619 | 4002 | 160 | GTTATCCAGTGAATCTAGCAGCCAATGGGCATTAGTGGTGCAGTTCTGCAGGCTACACAATATGAAACTAAGCATATCTTACCTTAGAGAATGTGCCAAAGCAAATGATTGGCTGCAGTTCATTATTCACAGCCAACTCCACAACTACCACCCAGCAGAG |
| | Intron 24-25 | | 428 | gtaagccactaattgttagcagtca . . . tttaatcatctgatatgccttctag |
| 25 | ENSE00001047603 | 4162 | 273 | GTGAAATCCCTTATCCAGTACTTCAGCCCAGTCATTCAAGACCACTTAAGGCTGGCTTTTGAGAACTTGCCCTCAGTGCCCACCTCCAAAATGGACAGCGATCAAGTCTGCAATAAGTGCCCCCAGGAACTTCAAGGAAGCAAACAAGAGATGACCGATTTATTTGAAATTCTGCTCCAATGCTCAGAGGAGCCAGACTCCTGGCACTGGCTTCTGGTTGAAGCAGTGAAACAACAGGCCCCTATCCTCAGTGTTCTGGCCTCATGTCTCCAG |
| | Intron 25-26 | | 623 | gtgaggatcatgagaagcctgaagt . . . tgttatttatttatcccgtggcag |
| 26 | ENSE00001047590 | 4435 | 201 | GGTGCCAGTGCCATTTCTTGTCTCTGTGTTTGGATCATCACTTCTGTGGAGGACAATGTTGCAACTGAAGCAATGGGACACATTCAGGACTCAACAGAGGACCATACCTGGAACCTTGAGGATCTTTCAGTCATCTGGAGAACATTATTAACAAGACAAAAGAGCAAAACTCTCATCAGAGGTTTCCAGCTTTTCTTTAAG |
| | Intron 26-27 | | 2,820 | gtagtgatagttgcttcacttctttt . . . atttttttcaaactctttgtcaaag |
| 27 | ENSE00001047613 | 4636 | 108 | GATTCCCCGTTACTACTGGTGATGGAGATGTATGAACTGTGTATGTTCTTCAGGAATTATAAAGAAGCTGAAGCTAAACTTCTGGAGTTTCAGAAGAGCCTTGAAACG |
| | Intron 27-28 | | 2,916 | gtaagttggaattatggtgctcttt . . . ctaagcttctcttttctttcatag |
| 28 | ENSE00001047595 | 4744 | 163 | CTTAACACAGCAGCCACAAAGGTCCACCCTGTCATCCCTGCCATGTGGCTGGAGGATCAGGTGTGTTTCCTTTTGAAGCTTATGCTACAGCAGTGTAAGACCCAGTATGAGCTGGGGAAGCTTTTACAGCTCTTTGTTGAAAGAGAGCATCTCTTCTCTGATG |
| | Intron 28-29 | | 3,401 | gtaagacaatccttacagttaagtt . . . ttatatccttttctctttggcacag |
| 29 | ENSE00001047608 | 4907 | 215 | GTCCAGATGTGAAAAAGCTTTGCATCCTTTGCCAGATTTTGAAGGATACATCCATAGCCATTAATCATACAATTATTACCAGCTACAGCATTGAGAATCTTCAGCATGAATGTAGATCTATTTTGGAAAGACTGCAGACAGATGGACAATTCGCTTTGGCCAGGAGGGTAGCAGAATTAGCTGAGTTACCTGTGGACAACTTGGTTATTAAAGAG |
| | Intron 29-30 | | 1,077 | gtatcatcggtctttttttttttt . . . aaatctgctttgttaaatttcacag |
| 30 | ENSE00001047607 | 5122 | 745 | ATAACACAGGAAATGCAGACCCTAAAACACATTGAACAGTGGTCACTAAAACAAGCAAGAATTGACTTCTGGAAAAAATGCCATGAGAATTTTAAGAAAAATTCAATTTCAAGCAAAGCAGCTTCTTCCTTTTTCTCAACCCAGGCCATGTGCATGTGAGCACCCAACTGGATGGAGCAGCATGGAGGAGCGCCATCTGCTGCTCACCTTGGCAGGGCACTGGCTTGCCCAGGAGGACGTGGTGCCCTTGGATAAGCTGGAGGAGCTGGAGAAGCAGATCTGGCTGTGCCGCATCACCCAGCACACTCTTGGAAGAAATCAGGAGGAAACAGAGCCCAGATTTTCTCGACAGATCTCAACTAGTGGTGAACTTTCCTTTGATAGTTTAGCCAGTGAGTTTTCCTTCTCCAAGTTGGCTGCTCTGAACACATCAAAATACTTAGAACTTAACAGCCTTCCATCCAAAGACATGCGAGAATAGATTGGATTGGAAAGAGCAGGAGTCACTAAACTTTTTGATTGGGCGCCTACTGGATGATGGCTGTGTGCATGAAGCAAGTAGAGTATGCCGGTATTTTCATTTTTATAATCCAGATGTCGCCTTGGTATTGCACTGCAGAGCACTGGCCTCAGGGGAAGCTAGTATGGAGGATCTGCACCCGAGATCCATGCTCTCCTACAAAGTGCTGAGCTGCTTGAGGAAGAAGCACCCGACATTCCCCTAAGGAGAGTCCACAGCA |
| | Intron 30-31 | | 8,772 | gtaagtgaaggagatcagatggccc . . . ccctcagacttgtatttgcttccag |
| 31 | ENSE00001047614 | 5867 | 140 | CTTCAAGTCTGGATAGTCAGAAGTTTGTGACAGTGCCCTCCAGTAATGAAGTGGTAACTAACCTGGAAGTGCTGACAAGCAAATGCCTCCATGGGAAGAACTACTGTCGACAGGTCCTCTGTCTGTATGATCTTGCCAAG |
| | Intron 31-32 | | 1,156 | gtatgtgccaaggggtggggctcct . . . ttgactggctttgtcttcctctcag |
| 32 | ENSE00001123435 | 6007 | 199 | GAGTTGGGCTGTTCCTACACAGATGTTGCTGCTCAGGATGGTGAAGCCATGCTCCGGAAAATCTTGGCCTCTCAGCAGCCTGACCGATGCAAACGAGCCCAGGCCTTCATCAGCACACAGGGCCTTAAGCCAGATACTGTGGCTGAACTCGTGGCAGAAGAGGTGACACGGGAGCTGCTTACTTCATCACAGGGAACAG |
| | Intron 32-33 | | 726 | gtgccctaccccccggggattccca . . . cctgtcttcacacctctctgtacag |
| 33 | ENSE00001123426 | 6206 | 138 | GACATAAGCAGATGTTCAACCCAACAGAGGAAAGCCAGACATTTCTTCAGCTGACCACTCTGTGTCAAGACCGCACATTGGTAGGCATGAAGTTGTTGGATAAGATTTCCTCCGTTCCCCATGGGGAACTGTCTTGCA |
| | Intron 33-34 | | 2,024 | gtaagttattgaccttttttcttaca . . . atcttaccagtgccaccctcccag |

TABLE 1-continued

Exon-intron boundaries of the human KIAA1840 gene (according to the Ensembl database)

| No | Exon/Intron | Position in SEQ ID NO: 1 | Length (bp) | Sequence |
|---|---|---|---|---|
| 34 | ENSE00001123415 | 344 | 134 | CCACAGAGCTCCTGATCCTGGCCCATCATTGCTTCACCCTGACGTGCCACATGGAGGGCATCATCCGAGTCCTACAGGCCGCCCACATGCTCACAGATAACCACCTGGCCCCCAGTGAGGAGTATGGGCTGGTG |
|  | Intron 34-35 |  | 1,019 | gtaagtagcccctcaacccagtc . . . tgcgagctgtcctcccacttcacag |
| 35 | ENSE00001123405 | 6478 | 108 | GTACGGCTCCTCACTGGCATTGGAAGGTACAACGAGATGACATACATATTTGATTTGCTGCATAAAAAGCACTACTTTGAAGTGCTAATGAGGAAGAAGTTGGATCCG |
|  | Intron 35-36 |  | 1,805 | gtaggtgcaaagtaatgagctccag . . . gcttttttcccttttattctgggcag |
| 36 | ENSE00001123397 | 6586 | 169 | AGTGGTACCCTGAAAACAGCCCTGCTGGACTACATCAAACGCTGCCGTCCTGGAGACAGTGAAAAGCACAATATGATTGCCCTGTGCTTCAGCATGTGCCGGGAGATTGGCGAGAACCACGAGGCAGCTGCCCGCATCCAACTGAAATTGATTGAGTCTCAGCCCTGGG |
|  | Intron 36-37 |  | 1,118 | gtgagtgaggtcacagccacactac . . . caaatcttctttatttcccctacag |
| 37 | ENSE00000684756 | 6755 | 89 | AGGACAGCCTCAAGGATGGGCACCAGCTGAAACAACTGCTGCTGAAGGCCCTGACTCTGATGTTGGATGCAGCAGAGAGTTATGCCAAG |
|  | Intron 37-38 |  | 207 | gtaacccaaaggcttttttcagact . . . gtgcctctccaccccttgttcctcag |
| 38 | ENSE00000684735 | 6844 | 156 | GACTCCTGTGTGCGACAGGCCCAGCACTGTCAGCGGCTCACCAAGTTGATAACTCTGCAGATTCACTTTCTGAACACTGGCCAGAACACAATGCTCATCAACTTGGGCCGCCACAAGCTGATGGACTGTATTCTGGCCCTACCTCGGTTCTACCAG |
|  | Intron 38-39 |  | 1,155 | gtgagcaagaaagcaaactgtagcc . . . gtccttcttcacctctccttttaag |
| 39 | ENSE00000684706 | 7000 | 152 | GCTTCTATTGTGGCTGAGGCCTACGATTTTGTTCCAGATTGGGCTGAAATTTTATACCAGCAAGTGATTCTTAAAGGAGACTTTAATTACTTGGAAGAATTTAAGCAGCAAAGGTTATTAAAGTCCAGTATATTTGAAGAGATTTCCAAAAA |
|  | Intron 39-40 |  | 1,245 | gtaagtattaaaagttgactgtaaa . . . ctgtacattatgtttctttatctag |
| 40 | ENSE00000884381 | 7152 | 600 | ATATAAACAACATCAGCCTACTGACATGGTCATGGAAAACCTGAAGAAATTACTCACATATTGTGAAGATGTTTACCTGTATTACAAGTTGGCATACGAACACAAGTTTTATGAAATTGTAAATGTGCTTCTGAAGGACCCTCAGACAGGTTGCTGTCTAAAGGACATGCTAGCAGGTTAGATGATTTCATAGGTGTCTGTTTTCTTGTACTGTTAGCAGATTCTGACAGATGTGATGAGAAGAAGAATGCATTGGAGATCTTTGCTAAAGTTGAACAATCCCGGTACTGTACCATATCAGTCCTTTGTGGGTAGTAGGTAGCAAGTAAGAAACTTTTCAGGAGGAAATTCCTATTTAAAATAGATTGATTTTAGATGATTGTTCATCCACACCATTTTATATAGATACTAGTATTAAGATCAAAAGCTTCCTCTTCCTCAGGACAGCTTCTACTTTAGATGATCCAATAATGATTAAAGAATACCTGTACCTGCAGATTCCAGTTTCAAAGAAATTTAATTATTATTTACACAGTTAAGGAACAGGTGATACATTTTCATTTGTTAGAAACTGATCTTTCTGTAATAAAATAGATTTTC |
|  | 3' downstream sequence |  |  | aattcagtgtatgtcattattactgctaaggaaatcttagcccttgtctg . . . |

As used herein, the term "Spatacsin" denotes the SPAsticity with Thin or Corpus callosum Syndrom protein, which is encoded by the KIAA1840 gene. The sequence of the human form is shown in SEQ ID NO:2.

The terms "mutant" and "mutation" mean any detectable change in genetic material, e.g. DNA, RNA, cDNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. Generally a mutation is identified in a subject by comparing the sequence of a nucleic acid or polypeptide expressed by said subject with the corresponding nucleic acid or polypeptide expressed in a control population. A mutation in the genetic material may also be "silent", i.e. the mutation does not result in an alteration of the amino acid sequence of the expression product.

In the context of the instant application, mutations identified in KIAA1840 gene are designated pursuant to the nomenclature of Den Dunnen et al. 2001 (http://www.genomic.unimelb.edu.au/mdi/mutnomen/). As defined by Dunnen and Antonarakis at the nucleic acid level, substitutions are designated by "c.position(nt)>(nt)", e.g. "c.118C>G denotes that at nucleotide 118 of the reference sequence C is changed to a G. The mutation at the protein level is denoted p.Q40X: which means that a glutamine (Q) at position 40 encoded by CAG is replaced by a STOP (TAG) codon (Q40X). Deletions are designated by "del" after the deleted interval (followed by the deleted nucleotides). For instance 529_533delATATT denotes a ATATT deletion from nucleotides 529 to 533. The consequence of this deletion, p.I177_F178delfsX, is a deletion of aminoacids at positions 177 and 178 and a frameshift (fs) in the coding sequence leading to the appearance of a premature STOP codon (X). An alternative nomenclature is to indicate the position of the stop codon in the resulting protein after the X; p.I177_178delfsX178 indicates that the stop codon resulting from the mutation is at codon 178. Insertions are designated by "ins," followed by the inserted nucleotides.

For example, c.7029_7030insT denotes that a T was inserted after nucleotide 7029. This leads to the replacement of valine (V) by cysteine (C) at position 2344 and to a frameshift of the coding sequence and a premature STOP codon at amino-acid 2349 (fsX): p.V2344CfsX or p.V2344CfsX2349. When a mutation is predicted to alter the splicing of the mRNA because the variant modifies a nucleotide of the consensus sequence for splicing (acceptor or donor site), the "r.?" denotes that the consequences of the mutation could not be checked at the RNA level, but is likely (as verified at http://rulai.cshl.edu/new_alt_exon_db2/HTML/score.html).

The term "hereditary spastic paraplegias (HSP)" denotes genetically heterogeneous Mendelian disorders characterized by weakness, spasticity and loss of vibratory sense in the lower limbs. The term "Autosomal Recessive Hereditary Spastic Paraplegia" or "AR-HSP" denotes spastic paraplegia that is transmitted as an autosomal recessive trait. Patients with HSP or AR-HSP can have a pure phenotype, or, more often, a complex phenotype that associates various neurological signs (cerebellar ataxia, mental retardation, peripheral neuropathy, etc). The term "AR-HSP-TCC" denotes an AR-HSP with Thin Corpus Callosum usually associated with, mental or cognitive deficit and peripheral neuropathy. Families without proved TCC can also be mutated in this gene either because of slow progression of the disease in the patient or because magnetic resonance imaging (MRI) couldn't be performed due to patient refusal or impossibility (patients leaving far from cities in North-Africa—this is the case for families FSP400, FSP393 and FSP343).

As used herein, the term "subject" denotes a mammal, such as a rodent, a feline, a canine, and a primate. Preferably a subject according to the invention is a human.

Mutations in the KIAA1840 Gene and Spatacsin Protein

The inventors identified various mutations in the KIAA1840 gene.

Forty three different mutations on human KIAA1840 gene were indeed identified in 47 families, including the 16 linked ones, all at the homozygous state, except in 16 kindreds. They were either nonsense mutations (n=13), deletions (n=17), insertions (n=7), or splice site mutations (n=6) in the coding sequence, and resulted theoretically in an abnormally spliced mRNA or a truncated protein in all cases.

In one family, linked with a maximal 3.1 multipoint lod score to SPG11, a missense R945G mutation segregated at the homozygous state in both patients and was not detected in 150 control chromosomes. The mutation is probably not only affecting the nature of the amino-acid. Position of this variant was in the 5'-splice site consensus sequence (2 bases before the end of exon 15). The score of the 5'-splicing sequence changed from 4.9 for the wild type to 2.7 for the variant (Alternative Splicing Database::http://rulai.cshl.edu/new_alt_exon_db2/HTML/score.html) suggesting that this variant could act at both the RNA level (splicing effect) and at the protein level (missense change). Indeed, this was confirmed by direct sequencing (using primers GCTCTGTGGTGG-GATCAACT and TGCTTACACTGGCCTGATTG) on mRNA isolated from lymphoblasts of an affected family member (FSP670-5) in which an alternative splice site is generated downstream in intron 15 leading to a 65 bp insertion and a premature stop codon (c.2833A>G, r.2834+1_2834+65ins, p.R945GfsX950). It cannot be excluded, however, that splicing occurs at its normal place in a small amount of messenger RNA and that a full length protein is generated with the G variant at position 945. Similarly, the mutation c.2444G>T, p.R815M likely affects not only the amino-acid but also splicing of exon 13 since the splice score down from 3.7 to 0.2 for the mutation. In addition, the c.869+1G>A, c.2316+1G>A, c.2444+1G>C and c.6477+4A>G, are all clearly affecting the acceptor splicing concensus sequence (see splice scores in table 2) and likely alter the splicing of exons 4, 12, 13 and 34, respectively. The mutations identified by the inventors are presented on the following Table 2.

TABLE 2

Mutations identified in the KIAA1840 CDS (SEQ ID NO: 1) and protein (SEQ ID NO: 2)

| Exons | Nucleotide variants | mRNA or Protein variants | SEQ ID NO: | Family code (Origins) at the homozygous state | Family code (Origins) at the heterozygous state |
|---|---|---|---|---|---|
| 1 | c.118C > T, | p.Q40X | 149 | FSP672 (Israel) | |
| 3 | c.529_533delATATT | p.I177_F178 > S177fsX178 | 150 | FSP386 (Portugal) FSP754 (Portugal) FSP831 (Portugal) | ITA17 (Brazil) |
| 4 | c.704_705delAT | p.H235RfsX246 | 166 | SPD199 (Turkey) | |
| 4 | c.733_734delAT, | p.M245VfsX246 | 151 | TUN2 (Tunisia) TUN3 (Tunisia) TUN4 (Tunisia) TUN22 (Tunisia) FSP847 (Argentina) | FSP117 (France) |
| Intron 4 | c.869 + 1G > A | r.? Splice score down from 9.8 to −0.9 | | | |
| 6 | c.1203delA, | p.K401KfsX415 | 152 | | PE (Italy) |
| 6 | c.1235C > G, | p.S412X | 153 | FSP393 (Portugal) | |
| 6 | c.1282A > T | p.K428X | 167 | | FSP830 (Portugal) |
| 7 | c.1471_1472delCT | p.L491DfsX556 | 168 | | FSP522 (France) |
| 7 | c.1549_1550delCT, | p.L517LfsX556 | 154 | | FSP343 (Algeria) (non typical) |
| 8 | c.1668delT | p.F556LfsX577 | 169 | | SAL646 |

TABLE 2-continued

Mutations identified in the KIAA1840 CDS (SEQ ID NO: 1) and protein (SEQ ID NO: 2)

| Exons | Nucleotide variants | mRNA or Protein variants | SEQ ID NO: | Family code (Origins) at the homozygous state | Family code (Origins) at the heterozygous state |
|---|---|---|---|---|---|
| 8 | c.1679C > G | p.S560X | 170 | | (France) ITA16SB (Italy) |
| 8 | c.1692delA | p.V564VfsX577 | 171 | | DKD (Italy) |
| 10 | c.1951C > T, | p.R651X | 155 | | MP (Italy) FSP683 (Romania) ITA28VAC (Italy) |
| 11 | c.2198T > G, | p.L733X | 156 | OS (Italy) | |
| Intron 12 | c.2316 + 1G > A | r.? Splice score down from 6.2 to −4.5 | | FSP892 (Norway) | |
| 13 | c.2444G > T | p.R815M and/or r.? Splice score down from 3.7 to 0.2 | 172 | | ITA28VAC (Italy) |
| Intron 13 | c.2444 + 1G > C | r.? Splice score down from 3.7 to −7 | | | ITA16 (Brazil) |
| 15 | c.2697G > A | p.W899X | 173 | ITA10 (Italy) | |
| 15 | c.2716delC | p.Q906SfsX920 | 174 | ITA9 (Italy) | |
| 15 | c.2833A > G, | r.2834 + 1__2834 + 65ins, p.R945G or p.R945GfsX950 Splice score down from 4.9 to 2.7 | 165 188 | FSP670 (Israel) | ITA14 (Italy) |
| 16 | c.2842__2843insG, | p.V948GfsX953 | 157 | | PE (Italy) |
| 16 | c.2850__2851insT, | p.L950FfsX953 | 158 | | MP (Italy) |
| 17 | c.3075__3076insA | p.E1026RfsX1029 | 175 | | ITA8 (Germany) |
| 22 | c.3741__3742insA | p.P1248TfsX1264 | 176 | | ITA17 (Brazil) |
| 25 | c.4307__4308delAA | p.Q1436RfsX1442 | 177 | | FSP398 (Israel) ITA16 (Brazil) |
| 30 | c.5470C > T | p.R1824X | 178 | | ITA8 (Germany) |
| 30 | c.5532__5533delCA | p.S1844SfsX1857 | 179 | | FSP522 (France) |
| 30 | c.5769delT | p.S1923RfsX1950 | 180 | FSP838 (Saudi-Arabia) | |
| 31 | c.5870C > G | p.S1957X | 181 | | ITA16SB (Italy) |
| 31 | c.5974C > T, | p.R1992X | 159 | | FSP117 (France) |
| 31 | c.5982__5983insCTCT | p.L1995LfsX2000 | 182 | | DKD (Italy) |
| 31 | c.5986__5987insT | p.C1996LfsX1999 | 183 | | FSP398 (Israel) |
| 31 | c.5989__5992delCTGT | p.L1997__Y1998 > M1997fsX2056 | 184 | | FSP683 (Romania) |
| 32 | c.6091C > T | p.R2031X | 185 | ITA1 (Turkey) | |
| 32 | c.6100C > T, | p.R2034X | 160 | FSP446 (Morocco), FSP221 (Algeria), FSP732 (Algeria), FSP400 (Algeria), FSP792 (Algeria), FSP845 (Morocco) TUN9 (Tunisia) TUN12 (Tunisia) TUN14 (Tunisia) | |
| 34 | c.6451delG, | p. A2151 P fsX2172 | 161 | SAL1608 (France) | |
| Intron 34 | c.6477 + 4 A > G | r.? Splice score down from 9.6 to 6.6 | | | FSP830 (Portugal) |
| 36 | c.6737__6740delTTGA, | p.I2246__E2247 > S2246fsX2260 | 162 | FSP920 (Japan) | FSP343 (Algeria) |
| 36 | c.6739__6742delGAGT | p.E2247__S2248 > L2247fsX2260 | 186 | | SAL646 (France) |
| 37 | c.6832__6833delAG, | p.S2278LfsX2338 | 163 | FSP75 (Portugal) | |
| 38 | c.6856C > T | p.R2286X | 187 | | ITA14 (Italy) |
| 39 | c.7029__7030insT, | p.V2344CfsX2349 | 164 | FSP515 (Tunisia) | |

Each mutation are herein numbered according to human KIAA1840 CDS and amino acid sequence as shown in SEQ ID NO: 1 and SEQ ID NO:2.

Accordingly, the invention relates to an isolated nucleic acid specifically hybridizable to a region of KIAA1840 gene coding sequence (SEQ ID NO:1) that contains a mutation selected from the group consisting of the substitutions c.6100C>T, c.2198T>G, c.118C>T, c.1235C>G, c.2833A>G, c.1951C>T, c.869+1G>A, c.1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T and c.5974C>T, the deletions: c.529-533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA and c.733_734delAT, and the insertions: c.7029_7030insT, c.2850_2851insT, c.3741_3742insA, c.5982_5983insCTCT, c.5986_5987insT, c.3075_3076insA and c.2842_2843insG.

In one embodiment of this aspect of the invention, the isolated nucleic acid according to the invention consists of at least 10 nucleotides, preferably 20 nucleotides, more preferably 40 nucleotides.

In a preferred embodiment, such an isolated nucleic acid is specifically hybridizable to a region consisting of 10 nucleotides upstream and 10 nucleotides downstream of a mutation selected from the group consisting of the substitutions: c.6100C>T, c.2198T>G, c.118C>T, c.1235C>G, c.2833A>G, c.1951C>T, c.869+1G>A, c.1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T c.5974C>T, the deletions: c.529-533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA c.733_734delAT, and the insertions: c.7029_7030insT, c.2850_2851insT, c.3741_3742insA, c.5982_5983insCTCT, c.5986_5987insT, c.3075_3076insA c.2842_2843insG, of the KIAA1840 gene sequence.

Preferably, "specifically hybridizable" means "hybridizable under conditions at 68° C. in 0.2×SSC, at 42° C. in 50% formamide, 4×SSC, or under conditions that afford levels of hybridization equivalent to those observed under either of these two conditions".

In an alternative manner, a sequence "specifically hybridizable" to a target sequence means a sequence showing a percentage of sequence identity with the sequence complementary of said target sequence of at least about 70%, preferably at least about 80%, more preferably at least about 90%, most preferably at least about 95%.

Said nucleic acid according to the invention may be an oligonucleotide.

Preferably, said nucleic acid or oligonucleotide is complementary to a region of the KIAA1840 gene that contains at least one of the identified mutations.

In one embodiment of this aspect of the invention, the isolated nucleic acid according to the invention consists of at least 10 nucleotides, preferably 20 nucleotides, more preferably 40 nucleotides.

Such a nucleic acid according to the invention may advantageously be used as a primer or probe.

A further object of the present invention relates to an isolated nucleic acid, which comprises or consists in a KIAA1840 gene coding sequence (SEQ ID NO:1) that contains one or several mutation(s) selected from the group consisting of the substitutions: c.6100C>T, c.2198T>G, c.118C>T, c.1235C>G, c.2833A>G, c.1951C>T, c.869+1G>A, c.1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T c.5974C>T, the deletions: c.529-533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA c.733_734delAT, and the insertions: c.7029_7030insT, c.2850_2851insT, c.3741_3742insA, c.5982_5983insCTCT, c.5986_5987insT, c.3075_3076insA c.2842_2843insG or a sequence complementary thereto.

In one embodiment of this aspect of the invention, the isolated nucleic acid according to the invention consists of at least 10 nucleotides, preferably 20 nucleotides, more preferably 40 nucleotides.

In another embodiment, the invention relates to an isolated polypeptide which comprises the polypeptide sequence of KIAA1840 containing one or several mutation(s) selected from the group consisting of p.Q40X, p.I177_F178delfsX178, p.H235RfsX246, p.M245VfsX246, p.K401KfsX415, p.S412X, p.K428X, p.L491DfsX556, p.L517LfsX556, p.F556LfsX577, p.S560X, p.V564VfsX577, p.R651X, p.L733X, p.R815M, p.W899X, p.Q906SfsX920, p.R945G, p.R945GfsX950, p.L950FfsX953, p.V948 GfsX953, p.E1026RfsX1029, p.P1248TfsX1264, p.Q1436RfsX1442, p.R1824X, p.S1844SfsX1857, p.S1923RfsX1950, p.S1957X, p.R1992X, p.L1995LfsX2000, p.C1996LfsX1999, p.L1997_1998delfsX2056, p.R2031X, p.R2034X, p.A2151PfsX2172, p.I2246_E2247delfsX2260, p.E2247_S2248delfsX2260, p.S2278LfsX2338, p.R2286X and p.V2344CfsX2349.

Diagnostic Method

The inventors have further shown that KIAA1840 mutants are associated with a hereditary spastic paraplegias (HSP) which is characterized by weakness, spasticity and often loss of vibration sense in the lower limbs. More particular, the inventors have shown that KIAA1840 mutations as above described correlate in all patients with mild mental impairment, a thin corpus callosum (TCC) (AR-HSP-TCC) and frequent polyneuropathy (72% of the patients) in a series of 45 families with the full clinical criteria of SPG11. In the 2 other kindreds, cerebral imaging was not available to verify the presence of a thin corpus callosum (TUN2 and TUN14).

Therefore the invention provides an ex vivo method of diagnosing or predicting a hereditary spastic paraplegia (HSP) in a subject, which method comprises detecting a mutation in the KIAA1840 gene or protein (spatacsin), as compared to a control population, wherein the presence of a mutation is indicative of an hereditary spastic paraplegia (HSP).

Nucleic Acids Assays:

According to a first embodiment the mutations may be detected by analysing a KIAA1840 nucleic acid molecule. In the context of the invention, KIAA1840 nucleic acid molecules include mRNA, genomic DNA and cDNA derived from mRNA. DNA or RNA can be single stranded or double stranded. These may be utilized for detection by amplification and/or hybridization with a probe, for instance.

Thus the invention provides an ex vivo method of diagnosing or predicting a hereditary spastic paraplegia (HSP), in a subject, which method may comprise the step consisting of detecting a KIAA1840 mutation in a nucleic acid sample obtained from the subject, wherein the presence of a mutation is indicative of a hereditary spastic paraplegia (HSP).

The nucleic acid sample may be obtained from any cell source or tissue biopsy. Non-limiting examples of cell sources available include without limitation blood cells, buccal cells, epithelial cells, fibroblasts, or any cells present in a tissue obtained by biopsy or post-mortem. Cells may also be obtained from body fluids, such as blood, plasma, serum, lymph, etc. DNA may be extracted using any methods known in the art, such as described in Sambrook et al., 1989. RNA may also be isolated, for instance from tissue biopsy, using standard methods well known to the one skilled in the art such as guanidium thiocyanate-phenol-chloroform extraction (Chomocyznski et al., 1987).

A KIAA1840 mutation according to the invention may be found and located in many exons, including exon 1 and exon 39 (Table 2).

KIAA1840 mutations may be detected in a RNA or DNA sample, preferably after amplification. For instance, the isolated RNA may be subjected to coupled reverse transcription and amplification, such as reverse transcription and amplification by polymerase chain reaction (RT-PCR), using specific oligonucleotide primers that are specific for a mutated site or that enable amplification of a region containing the mutated site. According to a first alternative, conditions for primer annealing may be chosen to ensure specific reverse transcription (where appropriate) and amplification; so that the appearance of an amplification product be a diagnostic of the presence of a particular KIAA1840 mutation. Otherwise, RNA may be reverse-transcribed and amplified, or DNA may be amplified, after which a mutated site may be detected in the amplified sequence by hybridization with a suitable probe or by direct sequencing, or any other appropriate method known in the art. For instance, a cDNA obtained from RNA may be cloned and sequenced to identify a mutation in KIAA1840 sequence.

Actually numerous strategies for genotype analysis are available (Antonarakis et al., 1989; Cooper et al., 1991; Grompe, 1993). Briefly, the nucleic acid molecule may be tested for the presence or absence of a restriction site. When a base substitution mutation creates or abolishes the recognition site of a restriction enzyme, this allows a simple direct enzymatic test for the mutation. Further strategies include, but are not limited to, direct sequencing, restriction fragment length polymorphism (RFLP) analysis; hybridization with allele-specific oligonucleotides (ASO) that are short synthetic probes which hybridize only to a perfectly matched sequence under suitably stringent hybridization conditions; allele-specific PCR; PCR using mutagenic primers; ligase-PCR, HOT cleavage; denaturing gradient gel electrophoresis (DGGE), temperature denaturing gradient gel electrophoresis (TGGE), single-stranded conformational polymorphism (SSCP) and denaturing high performance liquid chromatography (DHPLC) (Kuklin et al., 1997). Direct sequencing may be accomplished by any method, including without limitation chemical sequencing, using the Maxam-Gilbert method; by enzymatic sequencing, using the Sanger method; mass spectrometry sequencing; sequencing using a chip-based technology (see e.g. Little et al., 1996); and real-time quantitative PCR. Preferably, DNA from a subject is first subjected to amplification by polymerase chain reaction (PCR) using specific amplification primers. However several other methods are available, allowing DNA to be studied independently of PCR, such as the rolling circle amplification (RCA), the InvaderTMassay, or oligonucleotide ligation assay (OLA). OLA may be used for revealing base substitution mutations. According to this method, two oligonucleotides are constructed that hybridize to adjacent sequences in the target nucleic acid, with the join sited at the position of the mutation. DNA ligase will covalently join the two oligonucleotides only if they are perfectly hybridized (Nickerson et al., 1990).

The inventors designed a series of primers, manually or using Oligo6 (MBI, Cascade, Colo.), in order to amplify all coding exons of 18 genes from the candidate interval (primers and conditions available on request), including, the mutated KIAA1840 gene (see Table 4). PCR-amplified fragments of genomic DNA were then purified using exonuclease 1 (New England Biolabs, 2 U/5 µl PCR product) and shrimp alkaline phosphatase (Roche, 1 U/5 µl of PCR product) and sequenced using the fluorescent dideoxy-terminator method (BigDye v3, Applied Biosystem) on an automated ABI-3730 sequencer according to the manufacturer's recommendations. With the use of the software package SeqScape (Applied Biosystems), sequences were aligned and compared to consensus sequences.

Protein Assays

According to a second embodiment said mutation may be detected in KIAA1840 protein or a truncated form of the KIAA1840 protein may be detected, as compared to a control population.

Figure 5:
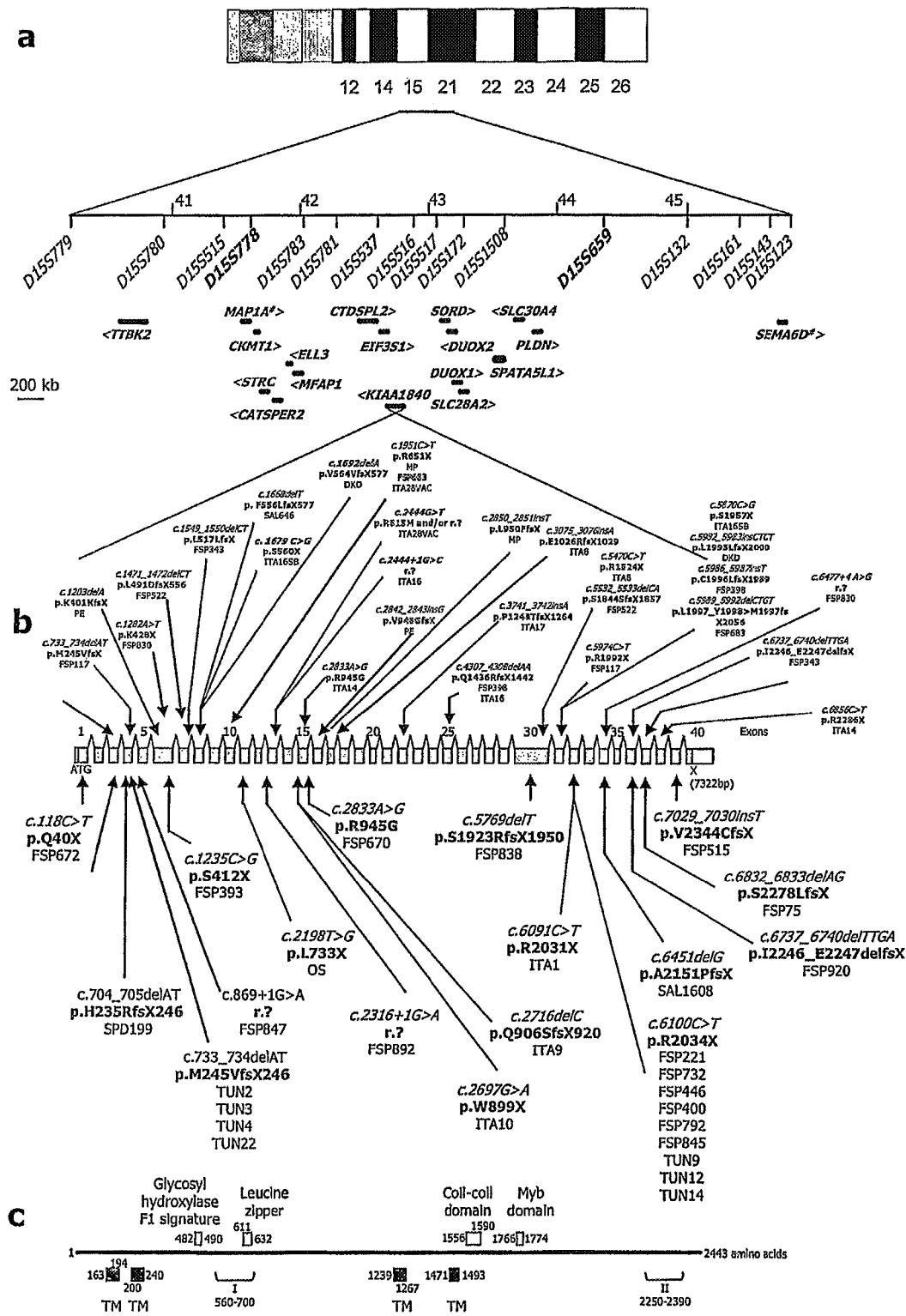

All of the identified mutations of the KIAA840 gene create some deletions of the C-terminal part of the spatacsin protein, in some cases because of aberrant splicing (FIG. 5). These deletions result in truncated proteins of sequences SEQ ID NO: 149 to SEQ ID NO:164 and SEQ ID NO:166 to SEQ ID NO:188, respectively. Those due to aberrant splicing, either very likely, could not be precised because the modification of the splicing could not be evidenced in mRNA directly, except in family FSP670 (r.2834+1_2834+65ins, p.R945GfsX950). It can not be excluded, however, that a shorten protein fragment may be synthesized due to the activation of new ATGs after the stop codon.

Said mutation may be detected according to any appropriate method known in the art. In particular a sample, such as a tissue biopsy, obtained from a subject may be contacted with antibodies specific of the mutated form of KIAA1840 protein, i.e. antibodies that are capable of distinguishing between a mutated form of KIAA1840 and the wild-type protein (or any other protein), to determine the presence or absence of a KIAA1840 specified by the antibody. An antibody recognizing the wild type protein could also be used to check the presence of the protein or its abnormal location or size and could then be used as a diagnostic tool as well.

Antibodies that specifically recognize a mutated KIAA1840 protein also make part of the invention. The antibodies are specific of mutated KIAA1840 protein, that is to say they do not cross-react with the wild-type KIAA1840 protein.

A monoclonal or polyclonal antibody recognizing the wild-type KIAA1840 protein may be used to detect the presence of the wild-type protein or one of its truncated forms. For instance, an antibody recognizing the N-terminal part of the wild-type KIAA1840 protein may also recognize one or several truncated forms and can be used to reveal by immunoblotting, the different forms, wild-type and truncated, according to their molecular weights. An antibody recognizing the wild-type KIAA1840 protein, but not recognizing the truncated forms, can be used for immunoblotting or in immunoassay as ELISA; in that case, an absence of signal reveals the presence of a truncated form in the sample or the absence of synthesis of a stable protein as compared with a positive control comprising the wild-type KIAA1840 protein.

The antibodies of the present invention may be monoclonal or polyclonal antibodies, single chain or double chain, chimeric antibodies, humanized antibodies, or portions of an immunoglobulin molecule, including those portions known in the art as antigen binding fragments Fab, Fab', F(ab')$_2$ and F(v). They can also be immunoconjugated, e.g. with a toxin, or labelled antibodies.

Whereas polyclonal antibodies may be used, monoclonal antibodies are preferred for since they are more reproducible in the long run.

Procedures for raising "polyclonal antibodies" are also well known. Polyclonal antibodies can be obtained from serum of an animal immunized against the spatacsin complex, which may be produced by genetic engineering for example according to standard methods well-known by one skilled in the art. Typically, such antibodies can be raised by administering mutated KIAA1840 protein or peptides of this protein subcutaneously to New Zealand white rabbits which have first been bled to obtain pre-immune serum. The antigens can be injected at a total volume of 100 µl per site at six different sites. Each injected material may contain adjuvants with or without pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed by Harlow et al. (1988) which is hereby incorporated in the references.

A "monoclonal antibody" in its various grammatical forms refers to a population of antibody molecules that contains only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Laboratory methods for preparing monoclonal antibodies are well known in the art (see, for example, Harlow et al., 1988). Monoclonal antibodies (mAbs) may be prepared by immunizing purified mutated KIAA1840 protein into a mammal, e.g. a mouse, rat, human and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975).

While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No.; European Patent Publications No. 0239400 to Winter et al. and No. 0125023 to Cabilly et al.

Antibody generation techniques not involving immunisation are also contemplated such as for example using phage display technology to examine naive libraries (from non-immunised animals); see Barbas et al. (1992), and Waterhouse et al. (1993).

Antibodies raised against mutated KIAA1840 protein may be cross reactive with wild-type KIAA1840 protein. Accordingly a selection of antibodies specific for mutated KIAA1840 protein is required. This may be achieved by depleting the pool of antibodies from those that are reactive with the wild-type KIAA1840 protein, for instance by submitting the raised antibodies to an affinity chromatography against wild-type KIAA1840 protein.

Alternatively, binding agents other than antibodies may be used for the purpose of the invention. These may be for instance aptamers, which are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

Kits

According to another aspect of the invention, the KIAA1840 mutation is detected by contacting the DNA of the subject with a nucleic acid probe, which is optionally labeled.

Primers may also be useful to amplify, analyse (dHPLC, Southern . . . ) or sequence the portion of the KIAA1840 gene containing the mutated positions of interest.

Such probes or primers are nucleic acids that are capable of specifically hybridizing with a portion of the KIAA1840 gene sequence containing the mutated positions of interest. That means that they are sequences that hybridize with the portion mutated KIAA1840 nucleic acid sequence to which they refer under conditions of high stringency.

The present invention further provides kits suitable for determining at least one of the mutations of the KIAA1840 gene.

The kits may include the following components:

(i) a probe, usually made of DNA, and that may be pre-labelled. Alternatively, the probe may be unlabelled and the ingredients for labelling may be included in the kit in separate containers; and (ii) hybridization reagents: the kit may also contain other suitably packaged reagents and materials needed for the particular hybridization protocol, including solid-phase matrices, if applicable, and standards.

In another embodiment, the kits may include:

(i) sequence determination or amplification primers: sequencing primers may be pre-labelled or may contain an affinity purification or attachment moiety; and (2) sequence determination or amplification reagents: the kit may also contain other suitably packaged reagents and materials needed for the particular sequencing amplification protocol. In one preferred embodiment, the kit comprises a panel of sequencing or amplification primers, whose sequences correspond to sequences adjacent to at least one of the polymorphic positions, as well as a means for detecting the presence of each polymorphic sequence.

In a particular embodiment, it is provided a kit which comprises a pair of oligonucleotide primers specific for amplifying all or part of the KIAA1840 gene comprising at least one of the mutated positions that are identified above (see Table 2).

More preferably, the kits of the invention comprise a pair of primers selected from the pairs shown in Table 3 either for detection by direct sequencing or by screening by dHPLC when they could be set-up (second set of primer pairs).

TABLE 3

Primers used for PCR or for dHPLC (in parentheses)

| Exons | Mutations | For/Rev primers | SEQ ID NO: |
|---|---|---|---|
| 1 | c.118C > T, p.Q40X | ccacaggaaacgaatggaat/ggttctgtgaggaaaccacg | 3/4 |
| 3 | c.529_533delATATT, p.I171_F178delfsX | cagggacattgtaggccatc/tcccagctcccaaaactaaa (ccagttgtaaaattgtgacc)/(tcaatcaacacttctaccac) | 5/7 (6)/(8) |
| 4 | c.733_734delAT, p.M245VfsX c.704_705delAT, p.H235RfsX246 c.869 + G > A, r.? | caggttctttcttgtggcatca/cgaggatattttaacctcttatca (gttaggcatacttacaaaactggc)/(cgaggatattttaacctcttatca) | 9/10 (11)/(12) |
| 6 | c.1203delA, p.K401KfsX; c.1235C > G, p.S412X c.1282A > T, p.K428X | gaacatctttgccctggttt/caggcactgaggcagaagta (ctgtgacaggtgttaagtta)/(atctaatacaagacagtctc) | 13/15 (16) |
| 7 | c.1549_1550delCT, p.L517LfsX | aaaaatcaattcctaaatcataatcc/tcttttaaagccaaaagggtaaa (tagtactgaagtattgagta)/(ttaagtaatgttcttgggca) | 17/19 (20) |
| 8 | c.1668delT, p.F556LfsX577 c.1679C > G, p.S560X c.1692delA, p.V564VfsX577 | cttgccccagattgcataat/tccaaaaagtacgtaaaatccca | 57/58 |
| 10 | c.1951C > T, p.R651X | cccaggactaatcatgaagga/atccccaaaccgataaaacc | 21/22 |
| 11 | c.2198T > G, p.L733X | cggtgtgtcttccactagctc/acccagccattctcagtgtt (gttacataaatgtataatccctg)/(cattttaagacttttatggattac) | 23/25 (24)/(26) |
| 12 | c.2316 + 1G > A, r.? | tttgaaagagcagaaagctatgg/tgaaggggttgtcacacttt | 61/62 |
| 13 | c.2444G > T, p.R815M and/or r.? c.2444 + 1G > C, r.? | ttgtggcaaaagaaaatttgtg/gagaatgcaggctcagttcc | 63/64 |
| 15 | c.2833A > G, r.2834 + 1_2834 + 65ins, p.R945asX950 or p.R945G c.2697G > A, p.W899X c.2716delC, pQ906SfsX920 | cacagcgagatcctgtctca/cctcactgtaagatgatgccc | 27/28 |
| 16 | c.2842_2843insG, p.V948GfsX; c.2850_2851insT, p.L950FfsX | cctttaaatactacagtggtgcaga/ccaactgttgagatggagaaaa (tgtgggcatgatttggtcta)/(acctgctcaaggacaaatgc) | 29/31 (30)/(32) |
| 17 | c.3075_3076insA, p.E1026RfsX1029 | ttgtttccagatcatgaagaatatg/tcagatagctgaccacagcc | 67/68 |
| 22 | c.3741_3742insA, p.P1248TfsX1264 | agtcagcttaagggaagcgg/gaagataaccatttctcccca | 77/78 |
| 25 | c.4307_4308delAA, p.Q1436RfsX1442 | aaaaggcaccatacagctttg/ggaaacacatgctggaacct | 83/84 |

TABLE 3-continued

Primers used for PCR or for dHPLC (in parentheses)

| Exons | Mutations | For/Rev primers | SEQ ID NO: |
|---|---|---|---|
| 30 | c.5470C > T, p.R1824X<br>c.5532_5533delCA,<br>p.S1844SfsX1857<br>c.5769delT,<br>p.S1923RfsX1950 | tgaggtgggaggatctcttg/gatgtgttcagagcagccaa<br>and<br>taagctggaggagctggaga/ttgttgtccccttaacttgg | 93/94<br><br>95/96 |
| 31 | c.5974C > T, p.R1992X<br>c.5870C > G, p.S1957X<br>c.5982_5983insCTCT,<br>p.L1995LfsX2000<br>c.5986_5987insT,<br>p.C1996LfsX1999<br>c.5989_5992delCTGT,<br>p.L1997_Y1998 > M1997fs X2056 | tttgaagtatcccagggtgg/ccaccattccccaaagataa | 33/34 |
| 32 | c.6100C > T, R2034X<br>c.6091C > T, p.R2031X | ttacctggatttggctttgg/tgcaatccagaaacttgagaga<br>(cctggcttctaaaagtggcc)/(aagcacaacatccaaatcctt) | 35/37<br>(36)(38) |
| 34 | c.6451delG, p.A2151PfsX<br>c.6477 + 4 A > G, r.? | atgttggcaggaactccatc/ctcctttggagcaacctctg | 39/40 |
| 36 | c.6737_6740delTTGA,<br>p.I2246_E2247delfsX<br>c.6739_6742delGAGT,<br>p.E2247_S2248 > L2247fs X2260 | ttccaacaggaaagcacaca/cagctacttgggaggctgag<br>(caacaggaaagcacacatgc)/(gtgtggctgtgacctcactc) | 41/43<br>(42)/(44) |
| 37 | c.6832_6833delAG,<br>p.S2278LfxX | gcattagaaggggcactgaa/ctcacaacggtattcacccc<br>(aacatggctgggatgtttct)/(ttcctggttggcctatgatg) | 45/47<br>(46)/(48) |
| 38 | c.6856C > T, p.R2286X | ttttgtccttgggctctttc/cctggttctgtcactagccc | 101/102 |
| 39 | c.7029_7030insT,<br>p.V2344CfsX | aagggtttaagataatttgggga/ggattcttgatactgctttgcc<br>(aatgccaaacacacacctga)/(ctcaaagcagaggcaaggag) | 49/51<br>(50)/(52) |

Therapeutic Methods

The inventors have demonstrated that the all, except one, mutations identified in the KIAA1840 gene cause truncation of the protein, suggesting that pathogenicity results from loss of function.

These results identify mutated KIAA1840 gene as target for the preventive or curative treatment of a hereditary spastic paraplegia.

Thus the invention further relates to a method of treatment of an HSP which comprises the step of administering a subject in need thereof with a KIAA1840 nucleic acid, i.e. a nucleic acid sequence that encodes a wild-type KIAA1840 protein, so that spatacsin is expressed in vivo by the cells of the subject that have been transfected with said nucleic acid. Accordingly, said method leads to an overexpression of wild-type spatacsin which compensates expression of defective mutated KIAA1840 protein.

The invention also relates to the use of a KIAA1840 nucleic acid for the manufacture of a medicament intended for the treatment of an HSP.

In the context of the invention, the term "treating" or "treatment", as used herein, means reversing, alleviating, inhibiting the progress of, or preventing the disorder or condition to which such term applies, or one or more symptoms of such disorder or condition.

Preferably said KIAA1840 nucleic acid is administered in a therapeutically effective amount. A "therapeutically effective amount" is intended for a minimal amount of active agent (e.g., KIAA1840 nucleic acid) which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

The administered polynucleotide comprises the nucleotide sequence SEQ ID NO:1, or any homologous or similar sequence as defined below:

a) a sequence showing at least 70%, preferably at least 75% or 80% or 85% or 90% or 95% or 99%, sequence similarity with SEQ ID NO:1;

b) a sequence hybridizing with SEQ ID NO:1, or its complementary sequence, under stringent conditions;

c) a sequence encoding a protein of sequence SEQ ID NO:2, or any sequence substantially similar with SEQ ID NO:2.

The term "sequence similarity" in all its grammatical forms refers to the degree of identity or correspondence between nucleic acid or amino acid sequences of proteins that may or may not share a common evolutionary origin. Preferably the degree of sequence identity is calculated compared with the totality of a reference sequence.

In a specific embodiment, two DNA sequences are "substantially homologous" or "substantially similar" when at least 70%, preferably at least 75% or 80% or 85% or 90% or 95% or 99%, of the nucleotides match over the defined length of the DNA sequences, as determined by sequence comparison algorithms, such as BLAST, FASTA, DNA Strider, etc. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially similar" when greater than 80%, preferably than 85% or 90% or 95% or 99%, of the amino acids are similar (functionally identical). "Functionally identical" polypeptides are those in which a given amino acid residue has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Preferably, the similar sequences are identified by alignment using, for example, the GCG (Genetics Computer Group, Program Manual for the GCG Package, Version 7, Madison, Wis.) pileup program, or any of the programs described above (BLAST, FASTA, etc.).

Preferably the KIAA1840 nucleic acid sequence according to the invention is associated with elements that enable for regulation of its expression, such as a promoter sequence.

Such a nucleic acid may be in the form of a DNA vector. The terms "vector" means the vehicle by which a DNA or RNA sequence (e.g. a foreign gene) can be introduced into a host cell, so as to transform the host and promote expression (e.g. transcription and translation) of the introduced sequence. A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA.

The KIAA1840 nucleic acid may be introduced into a target cell by means of any procedure known for the delivery of nucleic acids to the nucleus of cells, ex vivo, on cells in culture or removed from an animal or a patient, or in vivo.

Ex vivo introduction may be performed by any standard method well known by one skilled in the art, e.g. transfection, electroporation, lipofection, microinjection, transduction, cell fusion, DEAE dextran, calcium phosphate precipitation, or use of a gene gun.

The above methods do not limit the scope of the invention and it is to be understood that the one skilled in the art may readily make use of any other known appropriate methods for delivering a nucleic acid to a cell in vivo or in vitro.

The invention also relates to the use of wild-type KIAA1840 protein (spatacsin) for the manufacture of a medicament intended for the treatment of an HSP.

Thus the invention further relates to a method of treatment of an HSP which comprises the step of administering a subject in need thereof with a therapeutically effective amount of wild-type KIAA1840 protein.

The KIAA1840 protein may be introduced to a target cell by means of any procedure known for the delivery of proteins to cells, ex vivo, on cells in culture or removed from an animal or a patient, or in vivo.

Protein delivery is the process by which a protein crosses the cell plasma membrane. Traditionally, methods to introduce antibodies, peptides or other membrane-impermeable molecules into cells include micro-injection and electroporation.

A number of protein-transduction domains (PTDs) have also been developed that mediate protein delivery into cells. These PTDs or signal peptide sequences are naturally occurring polypeptides of 15 to 30 amino acids, which normally mediate protein secretion in the cells. They are composed of a positively charged amino terminus, a central hydrophobic core and a carboxyl-terminal cleavage site recognized by a signal peptidase. Examples of such membrane-transducing peptides include Trojan peptides, human immunodeficiency virus (HIV)-1 transcriptional activator (TAT) protein or its functional domain peptides, and other peptides containing protein-transduction domains (PTDs) derived from translocation proteins such as *Drosophila homeotic* transcription factor Antennapedia (Antp) and herpes simplex virus DNA-binding protein, VP22, and the like. Some commercially available peptides, for example, penetratin 1, Pep-1 (Chariot reagent, Active Motif Inc., CA) and HIV GP41 fragment (519-541), can be used for protein delivery.

Recently, the use of lipid liposomes or the like that can complex with a protein of interest and promote the delivery of the protein into the cell has also been demonstrated. Products available commercially can be used, such as BioPORTER (Gene Therapy Systems), or ProVectin (Imgenex, San Diego, Calif.).

The above methods do not limit the scope of the invention and it is to be understood that the one skilled in the art may readily make use of any other known appropriate methods for delivering a protein to a cell in vivo or in vitro.

The invention will be further illustrated by the following figures and examples.

FIGURES

FIGS. 1 and 2: Multipoint linkage analysis performed in 16 families for 34 microsatellite markers from chromosome 15q. cM=centimorgan.

(FIG. 1) Multipoint LOD score values for each family. * Relative position on the genetic map of chromosome 15 (according to http://research.marshfieldclinic.org/genetics).

(FIG. 2) Cumulative multipoint LOD scores in the 16 linked-families plotted according to the genetic map of chromosome 15.

Figure 3:
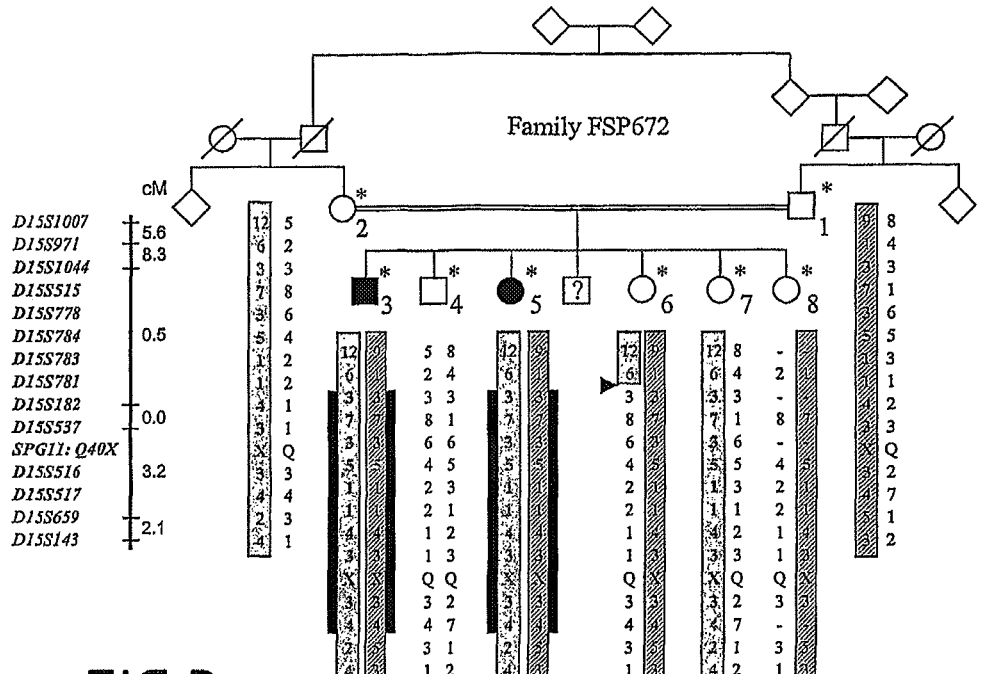
Figure 4:
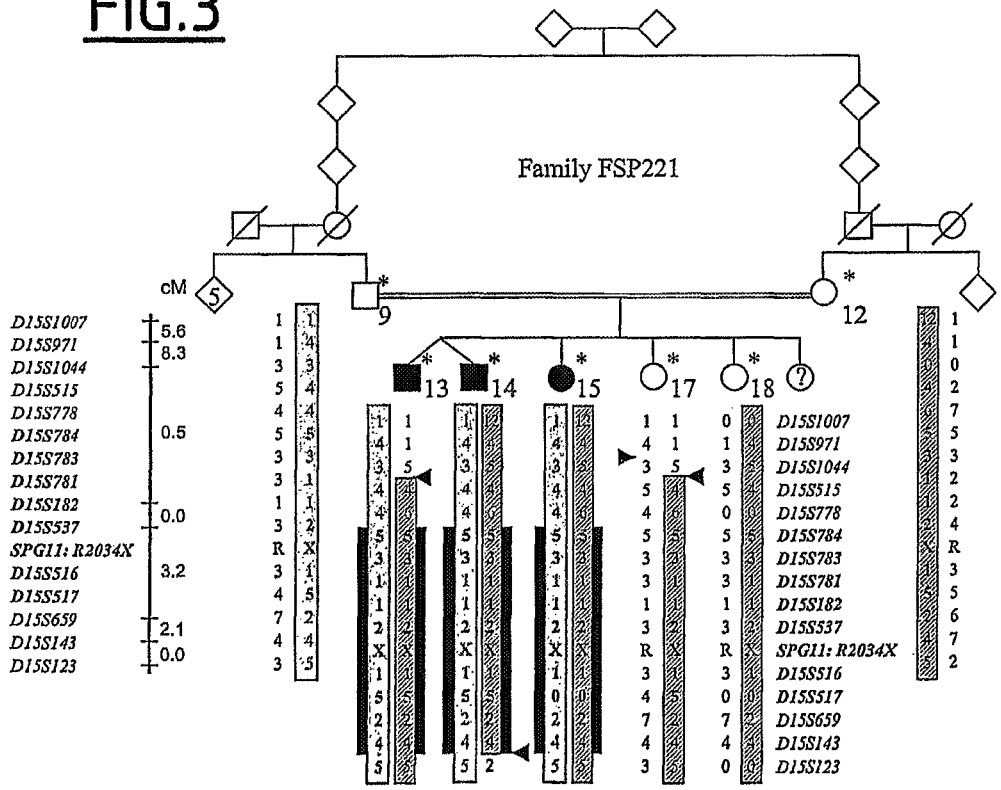

FIGS. 3 and 4: Pedigrees of 2 SPG11 families that reduced the candidate interval. Black circles (women) and squares (men) indicate affected members compared to previous publickions. The numbers are an internal reference for each sampled individual. Asterisks indicate sampled subjects. Haplotype reconstruction for selected microsatellite markers positioned according to the human genome draft sequence (www.ncbi.nlm.nih.gov, www.ensembl.org) is shown. The homozygous haplotype, in which the mutated gene has been located, is flanked by black boxes. Arrowheads indicate the position of probable recombination events. cM=centimorgan (according to http://research.marshfieldclinic.org/genetics).

FIG. 5: Critical region of SPG11. (a) Physical map of human chromosome 15q15-21 with selected genetic markers and candidate genes that were sequenced. Distances in megabases are indicated relative to chromosome 15 according to the Ensembl database. Markers defining the reduced candidate interval are in bold. # indicates that these genes (SEMA6D and MAP1A) were analyzed in a previous study (Stevanin et al, 2006). > and < indicate the orientation of the open reading frame (ORF) of each gene. (b) Exon-intron structure of the 101 Kb of the KIAA1840 gene, also known as FLJ21439, with positions of mutations identified in 17 SPG11 families. (c) Putative functional domains (boxes) and their positions on the protein sequence. TM=transmembrane domains. Regions I and II correspond to structurally similar domains based on their hydrophobicity status analysed with DomHCA software.

FIGS. 6 to 17: Pedigrees and segregation of the 17 mutations detected in KIAA1840. Square symbols are men, the circles are women. The filled symbols are affected individuals, grey or ? symbols indicate patients with an unknown status. The numbers are an internal reference for each sampled individual. Stars indicate sampled subjects. M or m=mutation; +=wild type. Electrophoregrams are shown for the homozygous mutations only. (6,7) Families with common origins sharing the same mutations. Haplotypes for three close microsatellites segregating with the mutations are highlighted. The correspondence between the numbering of alleles and their size in base pairs is indicated. (8, 10 to 14) Other homozygous mutations. (15) New homozygous mutations. (9, 16, 17) Compound heterozygous mutations.

Figure 18:
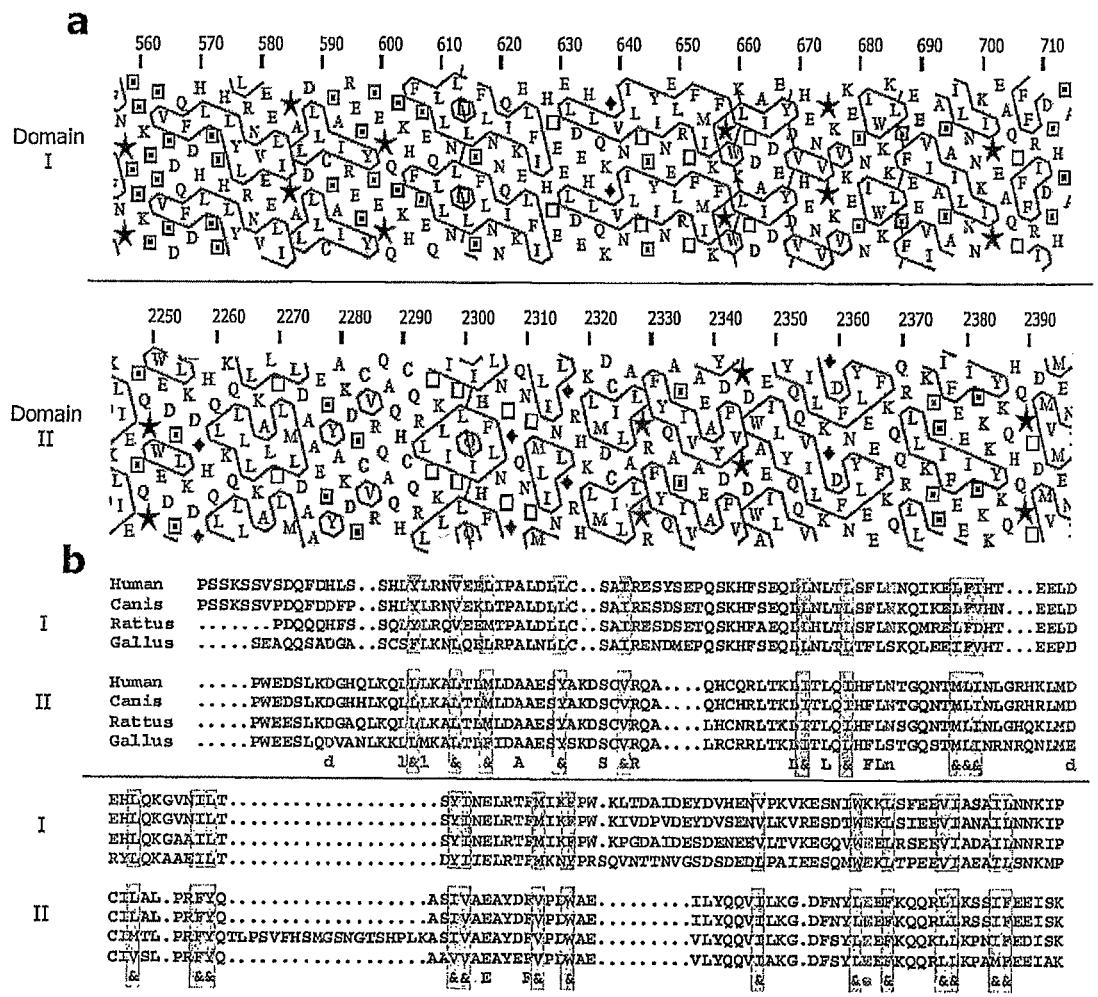

FIG. 18: Internal structural duplication in spatacsin (a) Hydrophobic cluster analysis (HCA) plots of the internal duplication of two regions in the human sequence. The HCA method is based on the use of a bidimensional plot (HCA plot) from the drawing of the 1D sequence on an alpha helix (3.6 residue/turn, connectivity distance of 4 residues separating two different clusters) which has been shown to offer the best correspondence between clusters and regular secondary structures. Examination of the HCA plot of a protein sequence enables globular regions to be easily distinguished from non globular ones and, in globular regions, secondary structures to be identified. This 2D signature, which is much more highly conserved than the 1D sequence and can be enriched from the comparison of families of highly divergent sequences, enables relevant similarities to be successfully detected at low levels of sequence identity. The form of the clusters is generally indicative of the type of secondary structures (vertical clusters are often associated with beta strands whereas horizontal ones often correspond to alpha helices). DomHCA software: http://www.lmcp.jussieu.fr/%7Emornon/hca.html. Special symbols are used for some amino acids: star for proline, square and dotted square for threonine and serine, diamond for glycine.

(b) Multiple alignment of the structural repeat domains (I and II, FIG. 3) corresponding to the HCA plots (DomHCA software). Under the multiple alignment, highly conserved residues are indicated by a capital letter when strictly conserved or in lower case if there is some homology. The character "&" means that this position is always occupied by a hydrophobic residue (amino acids FILMVW and Y).

Figure 19:
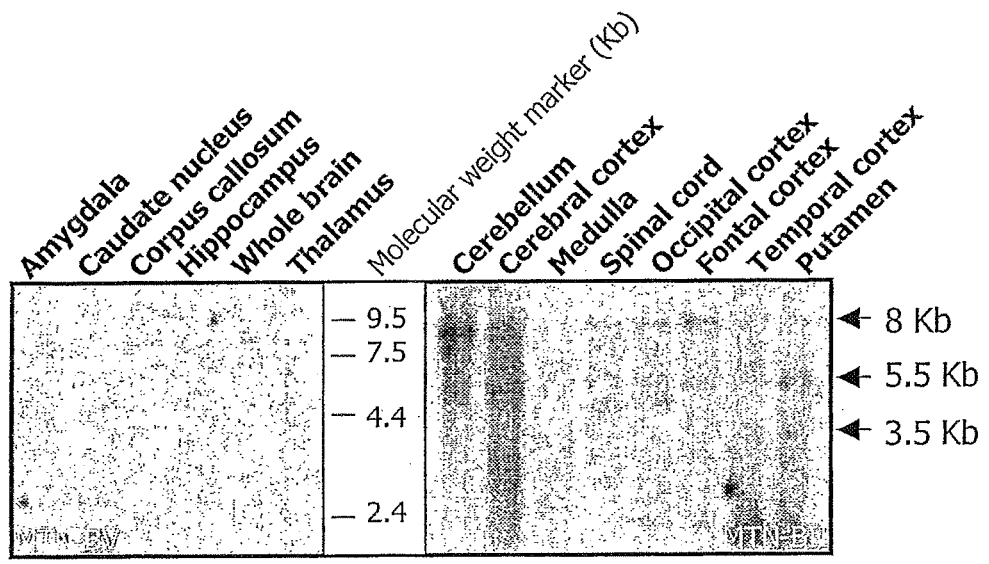

FIG. 19: Expression profile of KIAA1840 examined by northern blot in human adult brain. The transcripts were present in all brain tissues. Note the 8-Kb transcript more intensely expressed in the cerebellum while the 5.5-Kb transcript is mainly found in the cerebral cortex.

Table 1: Exon-intron boundaries in the KIAA1840 gene

Table 2: Mutations found in the KIAA1840 gene in families with AR-HSP-TCC.

Table 3: Primers used for detecting the mutations either by direct sequencing or by dHPLC Table 4: Primers used for the amplification of all exons of the KIAA1840 gene and PCR amplification conditions Table 5: PCR conditions and dHPLC conditions to analyze exons of KIAA1840.

Table 6: dHPLC primers to analyze exons of KIAA1840

EXAMPLE

Method:

Subjects: 211 individuals, including 83 affected members and 44 non mutated members, from 91 families.

All patients were examined by a neurologist. They were selected among 216 families with hereditary spastic paraparesis compatible with recessive transmission collected in our neurogenetic reference center in collaboration with the SPATAX network. They presented a typical "SPG11" phenotype defined as the presence of progressive spastic paraparesis associated with thin corpus callosum on cerebral MRI and mental retardation and neuropathy.

Blood samples was obtained after written consent from all affected patients and their relatives with approval of the local Ethic committee of Paris-Necker (approval no 03.12.07 of the comité Consultatif pour la Protection des Personnes et la Recherche Biomédicale, to A.D). Genomic DNA was extracted from leukocytes using standard procedures.

Linkage analysis: The genome scan in family FSP221 was performed using 400 microsatellites, regularly spaced on all chromosomes (ABI-Prism mapping set v2, Applied Biosystems, Foster City, Calif.) and 50 additional polymorphic markers were used to analyze the results. Genotypes were determined by PCR with a fluorescently-labeled primer, electrophoretic migration in an ABI-3730 sequencer (Applied Biosystems) and analysis with Genescan 3.5 (Applied Biosystems). Allegro 1.2c was used to calculate two-point and multipoint lod scores between the disease phenotype and each of the markers or the map of the markers assuming a complete penetrance, equal allele frequencies for the markers and a mutated allele frequency of 0.0005 (Gudbjartsson et al. 2000). Marker order and genetic distances were obtained from the Ensembl (http://www.ensembl.org) and Marshfield databases (http://research.marshfieldclinic.org/genetics), respectively.

Mutation detection: A series of primers was designed manually or using Oligo6 (MBI, Cascade, Colo.) in order to amplify all coding exons of 18 genes from the candidate interval (primers and conditions available on request). PCR-amplified fragments of genomic DNA were then purified using exonuclease 1 (New England Biolabs, 2 U/5 µl PCR product) and shrimp alkaline phosphatase (Roche, 1 U/5 µl of PCR product) and sequenced using the fluorescent dideoxy-terminator method (Big Dye v3, Applied Biosystem) on an automated ABI-3730 sequencer according to the manufacturer's recommendations. With the use of the software package SeqScape (Applied Biosystems), sequences were aligned and compared to consensus sequences.

Primers used for the amplification of the KIAA1840 gene are listed in the following Table 4.

The conditions of the PCR programme are as follows:
95° C., 12 min
then 40 cycles of:
95° C., 30 s
Annealing Temperature (see Table 4), 30 s,
72° C., 30 s
then
72° C., 10 min, and
15° C., 15 min.

PCR were performed in 25 µl final volume using 10 pmol of each primer, at final concentrations of 1.5 mM $MgCl_2$ and 0.24 mM dNTP.

Taq pol, which is commercially available from Quiagen was used except for exons 6, 12 and 40B where Taq GOLD (Applied Biosystems) was used.

TABLE 4

| Exon | Annealing temperature | SEQ ID NO: | Forward primer | Reverse primer |
|---|---|---|---|---|
| ext | 60° C. | 3/4 | ccacaggaaacgaatggaat | ggttctgtgaggaaaccacg |
| ex2 | 60° C. | 53/54 | ctgagccccacattttttgtt | caagtgctcaatagccccat |
| ex3 | 60° C. | 5/7 | cagggacattgtaggccatc | tcccagctcccaaaactaaa |
| ex4 | 60° C. | 9/10 | caggttctttattgtggcatca | cgaggatattttaacctcttatca |
| ex5 | 62° C. | 55/56 | gctaactgcccttaatagagtaaaa | aaagggtacagcgtcagcat |
| ex6 | TD62-58 | 13/15 | gaacatctttgccctggttt | caggcactgaggcagaagta |
| ex7 | 60° C. | 17/19 | aaaaatcaattcctaaatcataatcc | tcttttaaagccaaaaagggtaaa |
| ex8 | 60° C. | 57/58 | cttgccccagattgcataat | tccaaaaagtacgtaaaatccca |
| ex9 | 60° C. | 59/60 | cagcaaaagggtaatagcagtg | cccaaatgtagtaaatggcg |
| ex10 | 60° C. | 21/22 | cccaggactaatcatgaagga | atccccaaaccgataaaacc |
| ex11 | 60° C. | 23/25 | cggtgtgtcttccactagctc | acccagccattctcagtgtt |
| ex12 | TD62-58 | 61/62 | tttgaaagagcagaaagctatgg | tgaaggggttgtcacactttt |
| ex13 | 60° C. | 63/64 | ttgtggcaaaagaaaatttgtg | gagaatgcaggctcagttcc |
| ex14 | 60° C. | 65/66 | atgtggaactgagcctgcat | cgacttgcattttaaagaacctg |
| ex15 | 60° C. | 27/28 | cacagcgagatcctgtctca | cctcactgtaagatgatgccc |
| ex16 | 62° C. | 29/31 | cctttaaatactacagtggtgcaga | ccaactgttgagatggagaaaa |
| ex17 | 56° C. | 67/68 | ttgtttccagatcatgaagaatatg | tcagatagctgaccacagcc |
| ex18 | 60° C. | 69/70 | tccctcttaaggagaaaaacactg | accgggccgagatataaaat |
| ex19 | 60° C. | 71/72 | gctagtttgtcttagaaccagaaca | ttttggttgtctcactatcaca |
| ex20 | 60° C. | 73/74 | aaggaacatagccagttctgttttt | tgcgaactatttttcctttgg |
| ex21 | 60° C. | 75/76 | tgcaacttctcaggtacacatct | aggctagagtgcagtggcat |
| ex22 | 60° C. | 77/78 | agtcagcttaagggaagcgg | gaagataaccattttctcccca |
| ex23 | 60° C. | 79/80 | ttgtgagtgtttggggagaa | ggggatttagtgaaaacacca |
| ex24 | 64° C. | 81/82 | tttgttggagaatacactgtgctt | catgtctacacaacagaaagaatgc |
| ex25 | 60° C. | 83/84 | aaaaggcaccatacagctttg | ggaaacacatgctggaacct |
| ex26C | 55° C. | 85/86 | cttctgtctgcttcttggtctt | tatcatcattatctgttgttgg |
| ex27 | 60° C. | 87/88 | ttaggtgatcccactggctc | cccaggagttcaaggctgta |
| ex28 | 60° C. | 89/90 | ctgaggagggcttgttttttg | tctgtaacttgtttactcccagttg |
| ex29 | 60° C. | 91/92 | gatcacaccactgcattcca | ggcacctgtagtcccagcta |
| ex30A | 60° C. | 93/94 | tgaggtgggaggatctcttg | gatgtgttcagagcagccaa |
| ex30B | 60° C. | 95/96 | taagctggaggagctggaga | ttgttgtccccttaacttgg |
| ex31 | 60° C. | 33/34 | tttgaagtatcccagggtgg | ccaccattccccaaagataa |
| ex32 | 60° C. | 35/37 | ttacctggatttggcttttgg | tgcaatccagaaacttgagaga |
| ex33 | 60° C. | 97/98 | caataggccaagggtttcaa | tataactcctgctggagggc |
| ex34 | 62° C. | 39/40 | atgttggcaggaactccatc | ctcctttggagcaacctctg |
| ex35 | 60° C. | 99/100 | ggtagcctggaaattagccc | tgaaccagaatctgaagcca |

TABLE 4-continued

| Exon | Annealing temperature | SEQ ID NO: | Forward primer | Reverse primer |
|---|---|---|---|---|
| ex36 | 62° C. | 41/43 | ttccaacaggaaagcacaca | cagctacttgggaggctgag |
| ex37 | 60° C. | 45/47 | gcattagaagggggcactgaa | ctcacaacggtattcacccc |
| ex38 | 60° C. | 101/102 | ttttgtccttgggctctttc | cctggttctgtcactagccc |
| ex39 | 60° C. | 49/51 | aagggtttaagataatttgggga | ggattcttgatactgctttgcc |
| ex40A | 60° C. | 103/104 | aattagccagggtggtgaca | cccacaaaggactgatatgg |
| ex40B | TD62-58 | 105/106 | aaggaccctcagacaggttg | tcctttaaggcagacaaggg |

TD = TouchDown 10 cycles decrease of annealing temperature, then 25 stable cycles. Temperatures in Celsius degrees.

For some exons, it was possible to set up dHPLC conditions to detect variants. Primers different from those used for direct sequencing were specifically designed but they can also be used for direct sequencing. The PCR conditions and dHPLC conditions are indicated on table 5.

TABLE 5 dHPLC conditions to analyze exons of KIAA1840. Temperature in Celsius degrees.

| Exon | Size | T° PCR | T° DHPLC |
|---|---|---|---|
| 2 | 323 | 62°-1'-35x | 55.3° |
| 3 | 305 | 58°-1'-35x | 55.1° |
| 4 | 320 | 62°-1'-35x | 54.8°-52.8° |
| 5 | 330 | 60°-1'-35x | 54.9° |
| 6 | 450 | 58°-1'-35x | 54°-53° |
| 7 | 275 | 58°-1'-35x | 50.6°-52.6° |
| 9 | 342 | 62°-1'-35x | 54.1 |
| 11 | 293 | 57°-1'-35x | 54.6° |
| 12 | 210 | 62°-1'-35x | 52.5° |
| 13 | 289 | 62°-1'-35x | 51.5° |
| 14 | 246 | 62°-1'-35x | 55.8° |
| 16 | 309 | 62°-1'-35x | 55.2° |
| 17 | 239 | 62°-1'-35x | 53.9° |
| 18 | 324 | 58°-1'-35x | 53°-50° |
| 20 | 311 | 62°-1'-35x | 52.3° |
| 22 | 383 | 62°-1'-35x | 55.8° |
| 23 | 356 | 62°-1'-35x | 53.1° |
| 24 | 267 | 60°-1'-35x | 57.1° |
| 25 | 361 | 60°-1'-35x | 56.6° |
| 27 | 330 | 62°-1'-35x | 53.6° |
| 28 | 329 | 62°-1'-35x | 53.5° |
| 29 | 330 | 56°-1'-35x | 54.2°-56.2° |
| 32 | 323 | 60°-1'-35x | 58.8° |
| 33 | 349 | 62°-1'-35x | 57.6° |
| 35 | 312 | 62°-1'-35x | 54° |
| 36 | 376 | 62°-1'-35x | 52° |
| 37 | 313 | 62°-1'-35x | 57.6° |
| 38 | 315 | 62°-1'-35x | 56.9° |
| 39 | 380 | 62°-1'-35x | 53.2° |
| 40 | 390 | 62°-1'-35x | 54.4° |
| 40 | 321 | 58°-1'-35x | 54.2° |

TABLE 6 dHPLC primers to analyze exons of KIAA1840

| Exon | PRIMERS F (5' - 3')/R (5' - 3') | SEQ ID NO: |
|---|---|---|
| 2 | accaggtcaactaaactgttctct/tatgctgaaagaccacctgtaga | 107/108 |
| 3 | ccagttgtaaaattgtgacc/tcaatcaacacttctaccac | 6/8 |
| 4 | gttaggcatacttacaaaactggc/cgaggatatttttaacctcttatca | 11/12 |
| 5 | caggagcagtagtaacacaa/aaagggtacagcgtcagcat | 109/110 |
| 6 | ctgtgacaggtgttaagtta/atctaatacaagacagtctc | 14/16 |
| 7 | tagtactgaagtattgagta/ttaagtaatgttcttgggca | 18/20 |
| 9 | gcaggtaataagcctgcagaa/ccccccttcctagctgctatt | 111/112 |
| 11 | gttacataaatgtataatccctg/cattttaagactttatggattac | 24/26 |
| 12 | tgttcaaaatagttccattacaaaa/tttcttccaaggttttcttcca | 113/114 |
| 13 | tttgcaaaagtgcttgattt/tgcaggctcagttccacata | 115/116 |
| 14 | ggaatgatgcctttttctcc/tctcacacttgccttctgga | 117/118 |
| 16 | tgtgggcatgatttggtcta/acctgctcaaggacaaatgc | 30/32 |
| 17 | aatcatcgcctgagcaaaat/ccagtgactgatccaaagca | 119/120 |

TABLE 6-continued dHPLC primers to analyze exons of KIAA1840

| Exon | PRIMERS F (5' - 3')/R (5' - 3') | SEQ ID NO: |
|---|---|---|
| 18 | ccctcttaaggagaaaaacac/cagccttatcctctgctctt | 121/122 |
| 20 | tggaaaaggggagcagacta/tgcgaactattttcctttgg | 123/124 |
| 22 | gaggaggccacaaatcacat/gccttagacctcgtcacacc | 125/126 |
| 23 | tgctcaggttttgactttttctc/tttcactgatggcaagatgc | 127/128 |
| 24 | accacccccacctctaattc/ctacacaacagaaagaatgc | 129/130 |
| 25 | ccagctgaaactgaaagttgg/ctgggtacttacttcaggct | 131/132 |
| 27 | cactgtgccctgccttatta/tgtgcctgagtaaccgagtg | 133/134 |
| 28 | tcccagatttggaggttttg/tgcattttaatttcctaactaccc | 135/136 |
| 29 | gctgtagtggcattttattg/cctgggtgacagagcaagac | 137/138 |
| 32 | cctggcttctaaaagtggcc/aagcacaacatccaaatcctt | 36/38 |
| 33 | agctgcagagctccataagc/taggcatccagagcaggaac | 139/140 |
| 35 | ggcatctgaaagcaaccact/ccctccattttcccaagagt | 141/142 |
| 36 | caacaggaaagcacacatgc/gtgtggctgtgacctcactc | 42/44 |
| 37 | aacatggctgggatgtttct/ttcctggttggcctatgatg | 46/48 |
| 38 | ggggtgaataccgttgtgag/acctctgggttccatgagtg | 143/144 |
| 39 | aatgccaaacagacacctga/ctcaaagcagaggcaaggag | 50/52 |
| 40 | agactgctcctctgcactcc/ccgggattgttcaactttagc | 145/146 |
| 40 | cagtatcttaacctgtacat/ccgggattgttcaactttagc | 147/148 |

Overexpression studies: The KIAA1840 cDNA from clone pf01011 (Kazusa DNA research Institute, Japan) was excised from the pBluescript II SK(+) vector using XhoI/NotI restriction enzymes and cloned in fusion with EGFP in a SalI/Bsp120I digested pEGFP-C1 vector (Clontech). The construction was verified by direct sequencing after ligation, transformation and plasmid extraction using standard procedures.

COS-7 cells were maintained in DMEM (Invitrogen) supplemented with 10% fetal bovine serum, penicillin (100 UI/ml) and streptomycin (100 µg/ml). Cells were plated 24 h before transfection on cover slips coated with polyethylenimine and transfected with Lipofectamine-PLUS reagents according to the manufacturer's instructions (Invitrogen). For 6-well plates, 1-2 µg of plasmid DNA was used per well. Cells were analyzed by immunofluorescence 120 h post-transfection. The spatacsin-EGFP fusion protein was observed directly after fixation for 15 min with 4% formaldehyde. Immunocytochemistry was performed, using classical procedures with the following antibodies: rabbit anti-Cox2 (1/200, kind gift of A. Lombes, Paris) and rabbit anti-alpha-COP (1/1000ᵉ; Affinity Bioreagent). Cells were counterstained with DAPI (1 µg/ml, Sigma) and mounted with Fluoromount-G (Southern Biotech). Samples were observed with a Leica SP1 confocal microscope. Leica confocal software was used to acquire the images.

Northern-Blot analysis (Human): Total RNA was extracted from the human post-mortem brain cortex of an healthy individual (Brain Bank of INSERM U679) using the RNAeasy Mini kit (Qiagen). The corresponding cDNAs were synthesized using random hexamers in the presence of Thermoscript reverse transcriptase as recommended by the supplier (Invitrogen). A series of 7 probes of 1.2 Kb covering the entire KIAA1840 cDNA was amplified by PCR at an annealing temperature of 60° C. (primer sequences available on request). Human multiple tissue northern blots (Clontech) were hybridized at 68° C. for 1 hour with a mix of these probes $\alpha P^{32}$-labeled by random priming (Prime-it II Random Primer Labeling kit, Stratagene) and purified using ProbeQuant G-50 micro columns (Amersham Biosciences) in accordance to the manufacturer's recommendations to reach a specific activity of at least $1 \times 10^9$ cpm/µg. Membranes were then washed as recommended by Clontech then exposed to X-Ray film for autoradiography.

In situ hybridization (Rat): Young (P1, P6, P15 and P21, n=1 each) and adult (P68, 200 g, n=2) Sprague Dawley rats (Charles River) were killed by decapitation and their brains were rapidly extracted and frozen in isopentane at −50° C. Sections were prepared with a cryostat at −20° C., from medulla to striatum (+1.7 from bregma) 600 µm-spaced, thaw-mounted on glass slides and stored at −80° C. until usage. KIAA1840 mRNA expression was analyzed using 3 antisens oligonucleotides designed using Helios ETC oligo design software (Helios Biosciences, Paris, France) on the mRNA sequence (XM-242139) of Rattus norvegicus similar to hypothetical protein FLJ21439 (LOC311372). Each oligonucleotide or a mix of the 3 oligonucleotides were used for the hybridization step and gave identical results. A mix of three sens oligonucleotides was used as a negative control.

In situ hybridization was performed as described in Moutsimilli et al. (2005) Briefly, oligonucleotides were labeled with [35S]-dATP (Amersham Biosciences) using terminal transferase (Amersham Biosciences) to a specific activity of $5\times10^8$ dpm/µg. The day of the experiment, slides were fixed in 4% formaldehyde in PBS, washed with PBS, rinsed with water, dehydrated in 70% ethanol and air-dried. Sections were then covered with 140 µl of hybridization medium (Helios Biosciences, Paris, France) containing $3-5\times10^5$ dpm of the labeled oligonucleotide mix. Slides were incubated overnight at 42° C., washed and exposed to a BAS-SR Fujifilm Imaging Plate for 5-10 days. The plates were scanned with a Fujifilm BioImaging Analyzer BAS-5000 and analyzed with Multi Gauge Software (Fuji).

For double labeling experiments, brains were processed as for in situ hybridization. After the last wash step, sections were fixed in 4% paraformaldehyde in PBS and preincubated in PBS containing 6% goat serum and 0.1% triton. Sections were next incubated with mouse antibodies directed against Neu-N (Chemicon International, 1/250), in the same buffer, processed with biotinylated horse anti-mouse IgG antibodies and ABC reagents (Vector Laboratories, Burlingame, Calif.) and submitted to emulsion autoradiography. The labeling with the antisense probe in comparison with the Neu-N neuronal specific counterstaining was observed.

Bioinformatics: Functional domains were searched using bioinformatics tools available online at BABEL (http://babel.infobiogen.fr:1984/), Ressource Parisienne en Bioinformatique Structurale (http://bioserv.rpbs.jussieu.fr/RPBS) and PSORT (http://psort.nibb.ac.jp/). Psi-blast (www.ncbi.nlm.nih.gov) was used to look for homologous proteins or peptides. Alignment of homologous proteins was performed using CLUSTALW (http://www.ebi.ac.uk/clustalw/). Alteration of splicing sites was verified in the Alternative Splicing Database at http://rulai.cshtedu/new_alt_exon_db2/HTML/score.html.

HCA is a method that allows to represent a protein sequence on a bidimensional scaffold that increases the density of the amino acids, and consequently, evidences local compacity of hydrophobic residues. They form clusters according to a connectivity that is the one of an alpha helix. It has been shown that the centers of the clusters and the centers of the secondary structures statistically match, (Woodcocks et al. 1992) and on the other hand the shape of a cluster is related to the nature of the secondary structure (Callebaut et al. 1997). HCA is a very efficient tool for recovery of highly divergent internal duplication of domains and for the detection of globular domain limits.

Results:

We selected a series of 91 families of European or North-African origins, all without mutations in the SPG7 gene and with a typical AR-HSP-TCC phenotype. Six of these families were previously reported as linked to SPG11 using a subset of polymorphic markers from the interval (Casali et al, 2004; Stevanin et al, 2006; Lossos et al, 2006). The other families were new. All available family members of 16 most informative families were genotyped using 34 microsatellite markers for linkage to three successive loci on chromosome 15 which have been associated with thin corpus callosum; SPG11, SPG21 and the locus for agenesis of corpus callosum with polyneuropathy (ACCPN). Positive multipoint LOD scores ranging from 0.60 to 3.85 and corresponding to the maximal expected values in the pedigrees were obtained in the 16 most informative families (FIGS. 1 and 2). Mutations in the ACCPN or SPG21 loci were excluded by direct sequencing in all families that showed positive linkage to these regions (data not shown). A significant combined multipoint LOD score of 28.1 was reached in the 3.3 cM interval flanked by markers D15S778 and D15S659 in the linked kindreds (FIGS. 1 and 2). Haplotype reconstructions identified two critical recombination events that allowed to restrict the candidate interval to 6.6 cM between markers D15S1044 and D15S123. The 3.2 cM of the D15S778-D15S659 interval was considered to be the region most likely containing the responsible gene on the basis of homozygosity in all consanguineous patients of two significantly linked families; family FSP221 linked to SPG11 with a maximal LOD score of 3.85 and family FSP672 linked to the same locus with a 2.6 LOD score value (FIGS. 3 and 4). In addition, a genome wide screen performed in family FSP221 at a resolution of 10 cM on all chromosomes only identified three other possible locations with multipoint lod scores of 2.2 to 2.5 that were excluded using 18 additional microsatellite markers (data not shown), therefore highly supporting linkage to SPG11.

The narrowed interval contained 40 genes in accordance with the National Center for Biotechnology Information (NCBI) and the Ensembl databases. Two were excluded in previous studies (SEMA6D and MAP1A, Stevanin et al, 2006). We evaluated 16 additional genes from the interval as candidates for SPG11, prioritizing those with a known or putative function in mitochondrial metabolism, intra-cellular trafficking or cytoskeleton integrity (FIG. 5). All coding and non-coding exons as well as their splicing sites with at least 50 bp of intronic sequences on each side were sequenced on genomic DNA of 5 index patients from 5 linked families. No mutations were found in 15 genes but sequence variations were found in the KIAA1840 gene. We then screened one affected member from the 16 linked families as well as of the uninformative kindreds and checked all other members of the families, when available, for sequence variations. 43 different mutations were identified in 47 families, including the 16 linked ones, 31 at the homozygous state, (FIGS. 5 to 9). They were either nonsense mutations (n=13), deletions (n=17), insertions (n=7) or splice site mutations (n=6) in the coding sequence, and resulted in an abnormally truncated protein or predicted to alter the splicing of the messenger RNA in all cases. In two families (FSP670 and ITA28VAC, FIG. 8), we found a missense change (R945G or R815M) affecting a nucleotide of the 5'-splice site consensus and predicted to alter the splicing of the mRNA. This could be confirmed in family FSP670 by the analysis of mRNA from one patient (c.2833A>G, r.2834+1_2834+65ins, p.R945GfsX950). Four mutations affected the intronic part of the consensus sequence for the acceptor splicing site (see Table 2) that also likely affect the splicing of the mRNA. The mutations segregated completely in the families with the disease and were not found on at least 140 chromosomes from unrelated control individuals of European and North-African origin suggesting that these mutations were not polymorphisms. Only 4 mutations were found in more than one pedigree (FIGS. 6 and 7). A c.6100C>T substitution that replaces an arginine by a stop codon in exon 32 (R2034X), shortening the protein from 2443 to 2034 amino acids (SEQ ID NO:160), was identified, in the homozygous state, in 4 Algerian, 3 Tunisian and 2 Moroccan consanguineous kindreds (FIG. 6). A 5 bp deletion in exon 3 (c.529_533delATATT) leading to a frameshift and a stop codon at aa 178 (SEQ ID NO:150) was found at the homozygous state in all patients of 3 Portuguese families and at the heterozygous state in one Brazilian kindred (FIG. 7). Interestingly, alleles at close flanking markers were partially similar in families with identical mutations (when it could be tested) suggesting founder effects in North-Africa and Portugal for these mutations. The c.733_734del AT mutation was also found in 4 Tunisian pedigrees, sharing partial common haplotypes (data not shown) and one French kindred. Finally, the c.1951C>T variant was found at the heterozygous state in 2 Italian and one Kindred from Romania for which we are extending the pedigrees to check for haplotype conservation.

No mutations were found in 44 families, suggesting that the responsible mutations were either in non-coding regions of KIAA1840 or in another unidentified gene.

SPG11 mutations were thus found in the majority of the families with the typical AR-HSP-TCC studied here (47/91). Most families originated from the Mediterranean basin. Complete examination of 22 affected members (Stevanin et al, 2007), 12 men and 10 women, showed a mean age of 24.8±9.5 years ranging from 12 to 49. Onset of the disease always occurred before age 24 years (mean age 11.8±5.5 years; range 2-23) and consisted in either spastic gait (57%, 12/21) or cognitive impairment (19%, 4/21), sometimes diagnosed as mental retardation. After about 10 years of evolution, the full-blown clinical picture consisted in progressive and severe spastic paraplegia with distal wasting and cognitive problems. In several cases (n=6), cognitive dysfunction clearly worsened with disease progression. Cerebral imaging showed a thin corpus callosum, but also periventricular white matter changes and cortical atrophy, in the majority of the patients. Pseudo-bulbar dysarthria was frequent (54%, n=12) and dystonic voice was noted in one patient. Interestingly, although a few patients had normal electromyographic recordings, peripheral neuropathy was frequent (72%, 13 out of 18 patients) and was mostly associated with pure motor changes. Additional signs, such as optic atrophy, retinitis pigmentosa, mild cerebellar signs, cataract, and clinodactily were occasionally observed, a finding that expands the clinical spectrum of this entity.

The human KIAA1840 gene contains 40 exons spanning 101 Kbases of genomic DNA on chromosome 15q21.1. The full length transcript encodes a predicted protein of 2443 amino acids of unknown function called spatacsin for SPAsticity with Thin or Atrophied Corpus callosum Syndrome proteIN. The sequence of spatacsin is strongly conserved through evolution with orthologues in mammalians and other vertebrates: human KIAA1840 shares 85% identity with the homologous protein in dog, 76 and 73% with the mouse and rat homologues and 59% with the chicken homologue, all of similar sizes. Less similarity was found with homologous proteins of smaller sizes from fugu (44%), tetraodon (39%), and drosophila (22%).

Neither the gene nor the predicted protein it encodes in many species show any significant sequence similarity to known cDNA or protein sequences. We then looked for protein motifs and domains (FIG. 3). Four putative transmembrane domains were predicted by various algorithms (aa 163-194, 200-240, 1239-1267 and 1471-1493). A glycosyl hydrolase F1 signature was also detected (aa 482-490). This motif is based on a conserved glutamic acid residue which has been shown in the beta-glucosidase of various bacteria and plants and mammalian lactase-phlorizin hydrolase, an integral membrane glycoprotein that splits lactose in the small intestine. Interestingly, this protein is assigned to the aromatic compound dioxygenase superfamily because of a 22% identity with the consensus sequence between aa 2104-2381. A leucine zipper (aa 611 to 632), involved in dimerization of many gene-regulatory proteins (C/EBP, CREB, CRE-BP1, ATFs and Jun/AP1 family of transcription factors) and a Myb domain (aa 1766 to 1774), involved in the DNA-binding of drosophila and vertebrate myb and related proteins, were also identified. Interestingly, there is a 47% identity, over 44 aa, with thymosyl-like peptides, small peptides which play an important role in the organization of the cytoskeleton; these peptides, bind to and sequester actin monomers, thereby inhibiting actin polymerization (Low and Golstein 1985). Furthermore, a probable coiled-coil domain of 33 residues from 1556 to 1590 was also present and such domains are reported in structural or motor proteins such as spectrin, laminin, dynein or neurofilament proteins.

Figure 10:
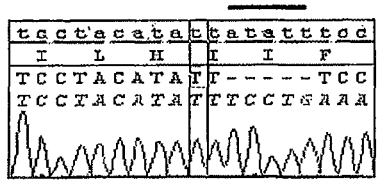
Figure 10:
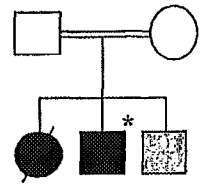
Figure 10:
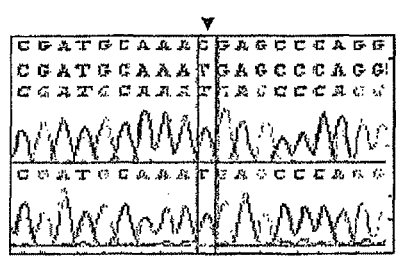
Figure 10:
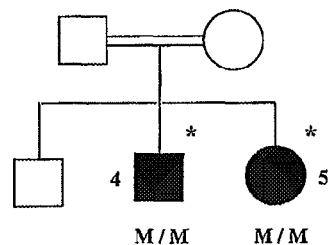
Figure 10:
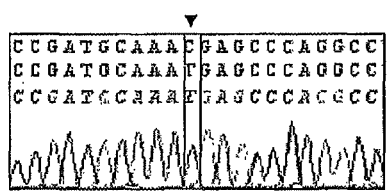
Figure 10:
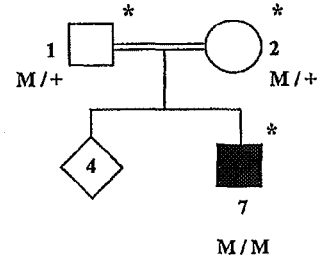
Figure 10:
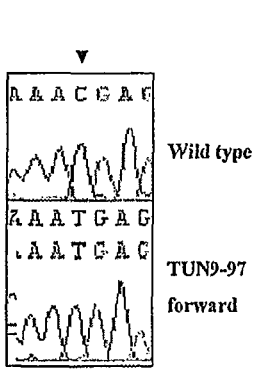
Figure 10:
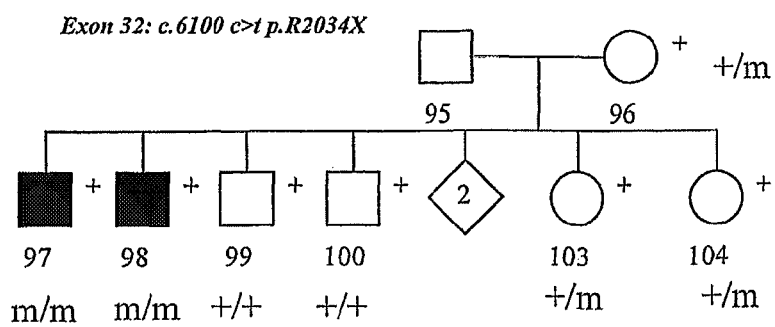

We then looked at the structure of the predicted protein. The level of hydrophobicity (34.2%) over the entire sequence was typical of a globular protein. Because of it's size, a succession of globular domains is likely and we tried to identify them by the identification of inter domain regions, corresponding to a low density of hydrophobic clusters with the DomHCA software (Prat-Albeau et al, 2006). Except a small linker located between positions 1410 and 1440, no domain separation was evidenced. From the HCA plots, one of the putative transmembrane regions was confirmed at amino acids 200 to 240 on spatacsin from 5 vertebrates, but it was lacking in the homologous sequences from tetraodon and drosophila, as these last two sequences presented a shortened N-terminal domain. A thorough analysis of putative duplication highlighted two structurally similar regions (aa 560-700 and 2250-2390) in all vertebrate homologues of the protein with 19% sequence identity in human sequences (FIG. 10). Amino acid proportion shows a non standard distribution in some cases: high amount of leucines (13.8% vs 9.6% in standard reference databases), a low level of methionines (1.9% instead of 2.38%) and glycines (3.9% vs 6.93% in Swiss Prot). The proportion of cysteins was over 2 fold higher (2.9%) compared to the mean in databases but did not gave rise to disulfide bridges, according to the predictions of the CysState software (Mucchielli-Girgi, 2002). Cluster shapes claim for a mainly helical behavior of this protein, which is confirmed by standard prediction tools.

The spatacsin protein, fused with GFP, had a diffuse cytosolic and nuclear distribution that sometimes excluded the nucleus of COS-7 cells. In rare cases (<5%), spatacsin formed small perinuclear dots or aggresome-like structures in cells with high expression levels after 4 days post-transfection that did not colocalized with the mitochondrial marker Cox2 or the Golgi marker alpha-COP.

Figure 11:
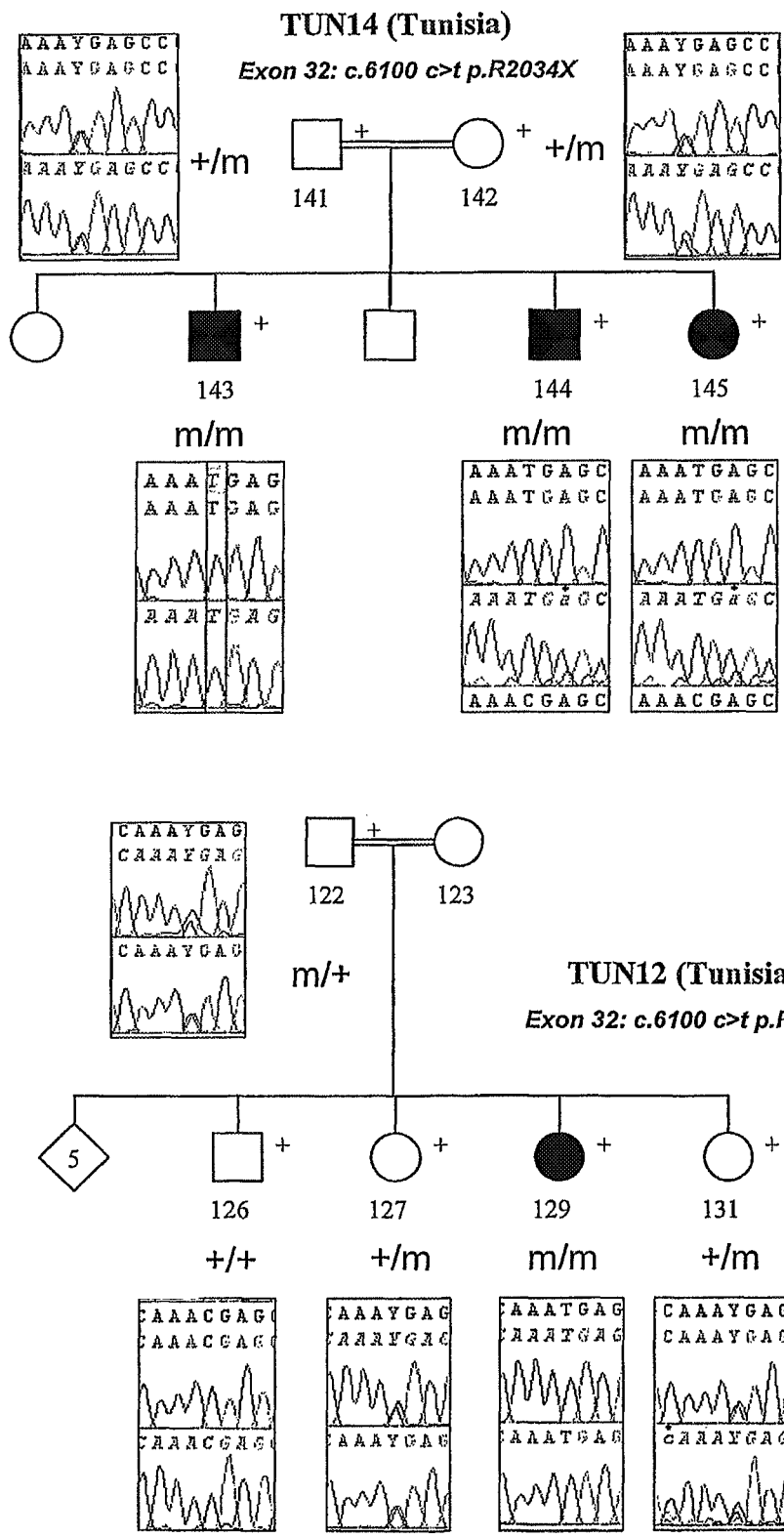
Figure 12:
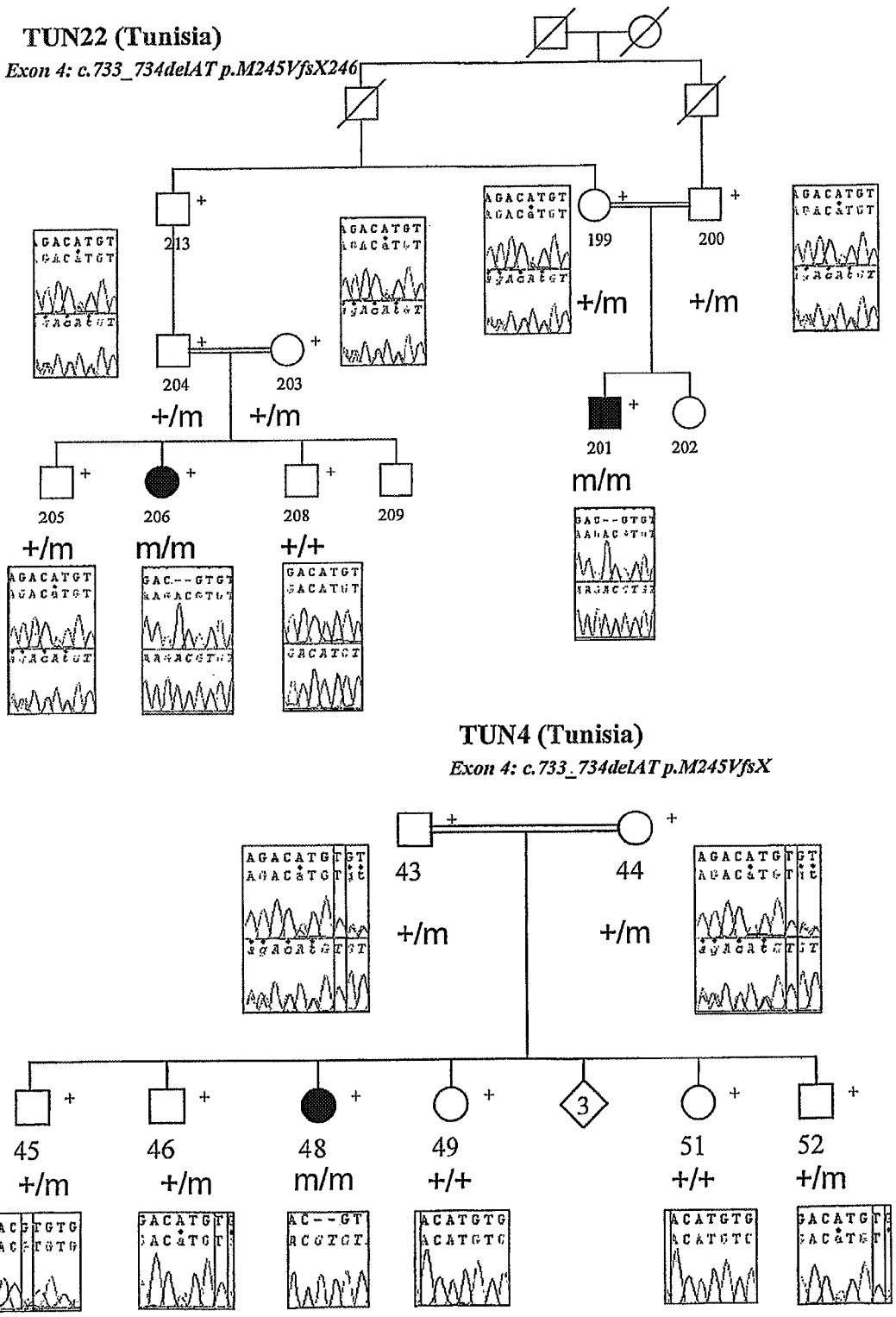
Figure 13:
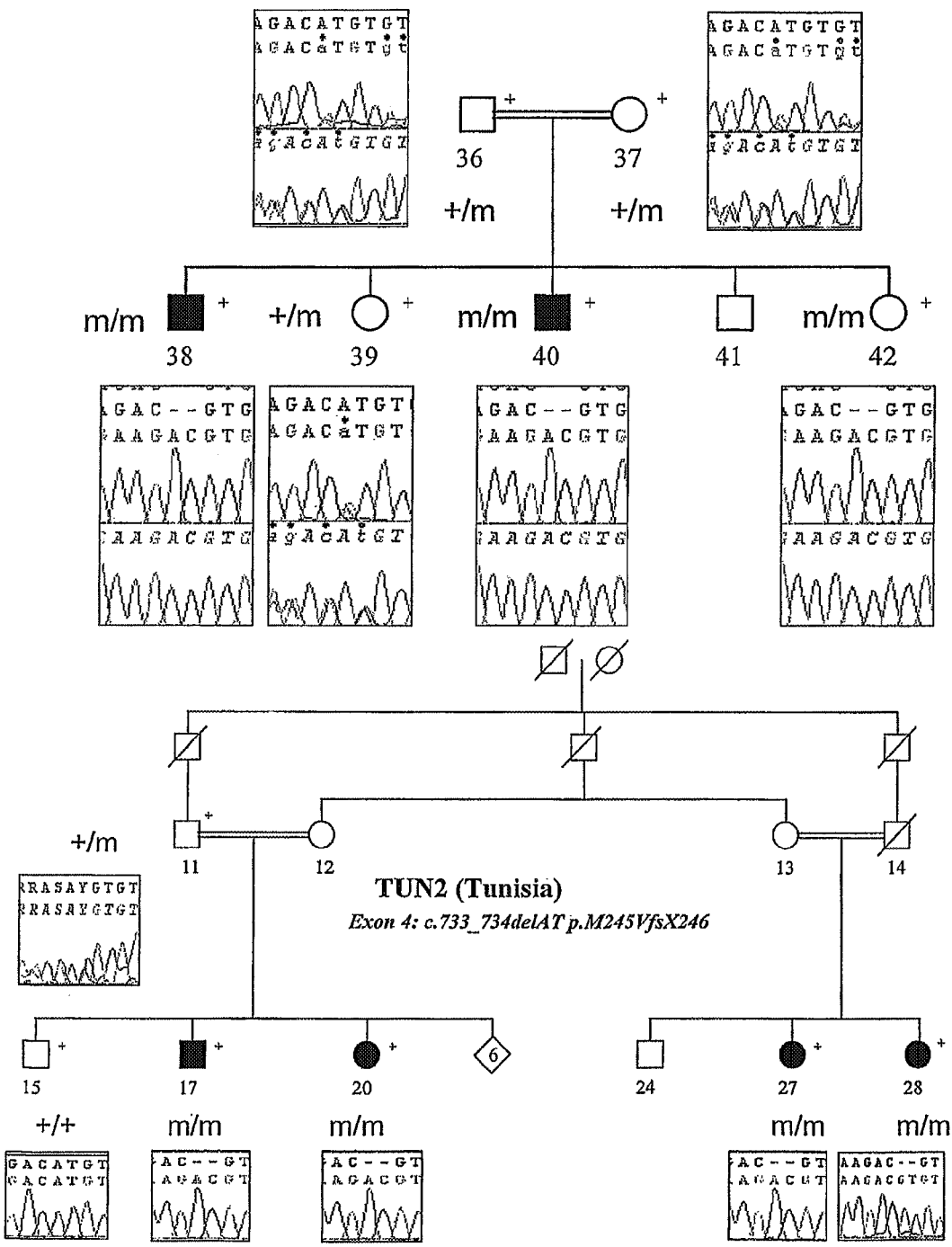
Figure 14:
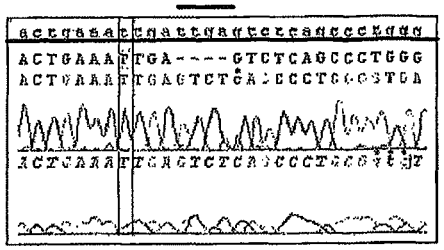
Figure 14:
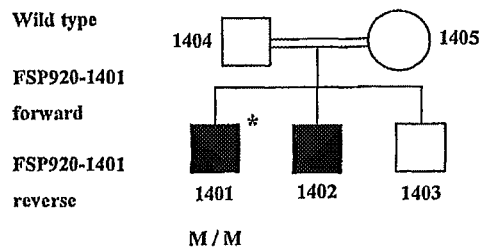
Figure 14:
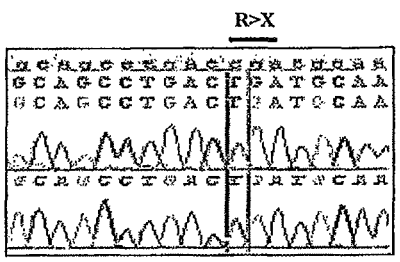
Figure 14:
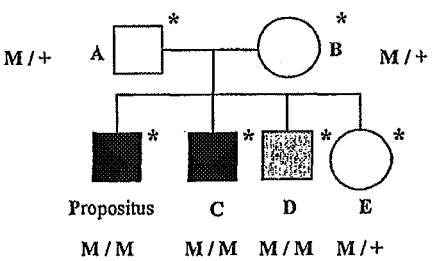
Figure 14:
Figure 14:
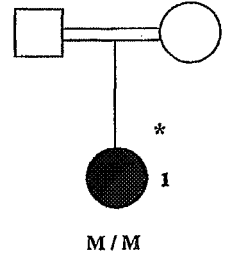
Figure 14:
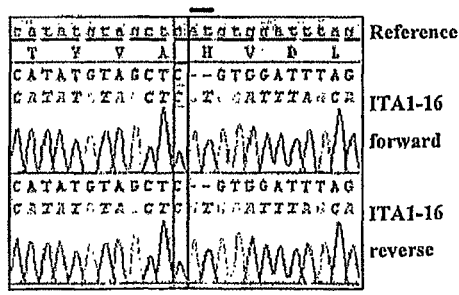
Figure 14:
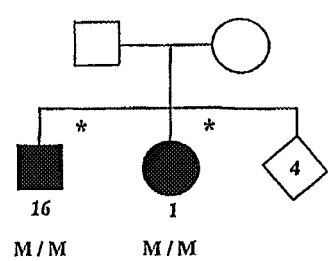
Figure 15:
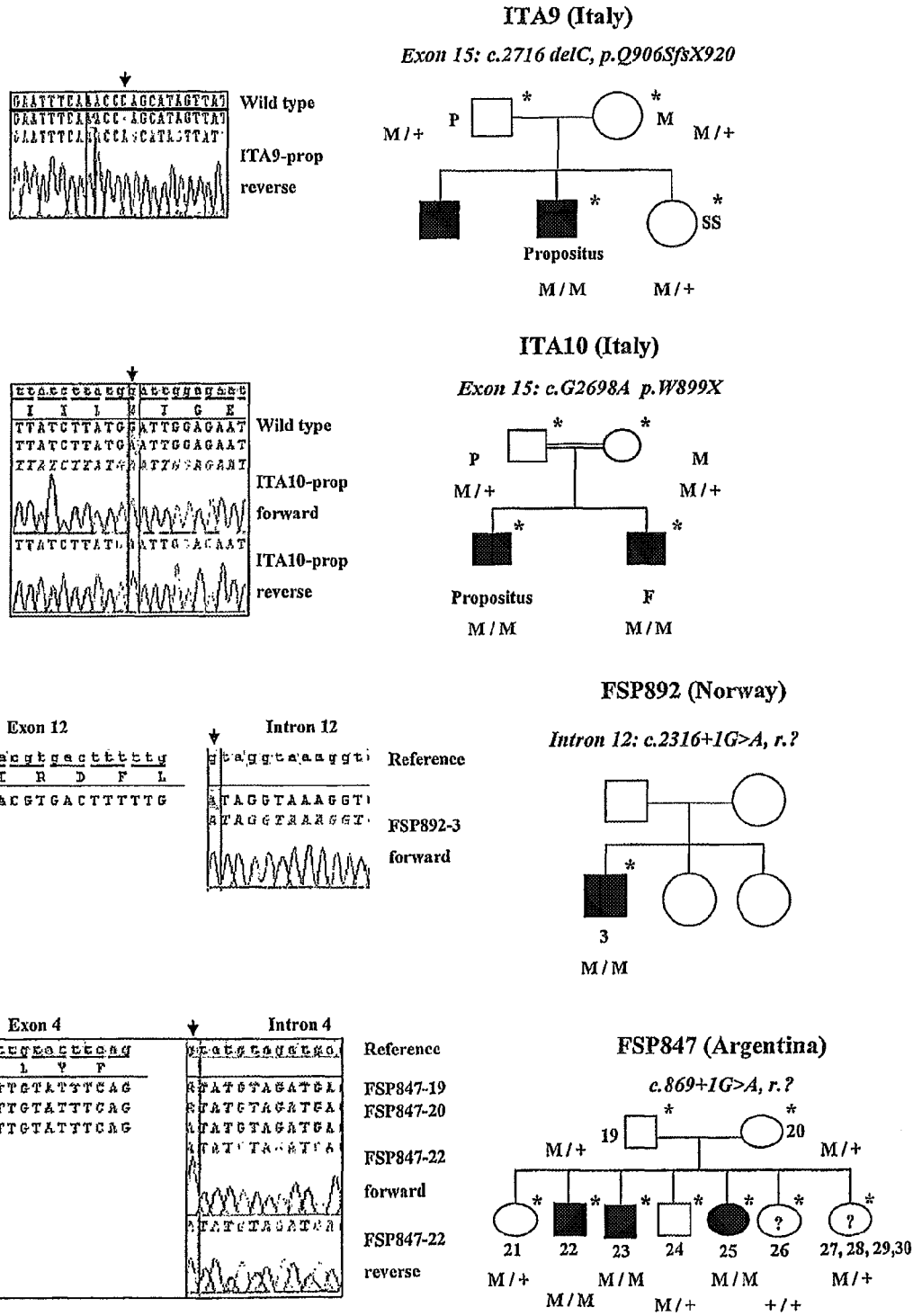
Figure 16:
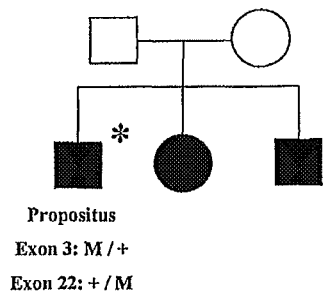
Figure 16:
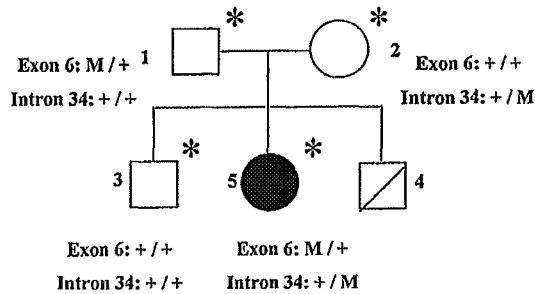
Figure 16:
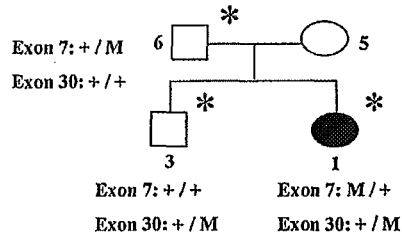
Figure 16:
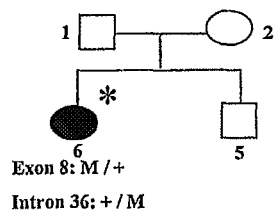
Figure 16:
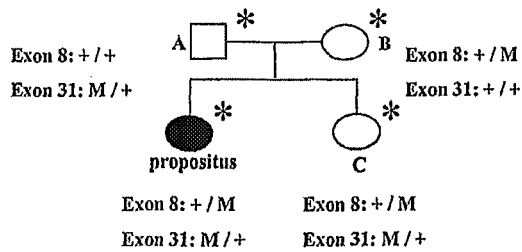
Figure 16:
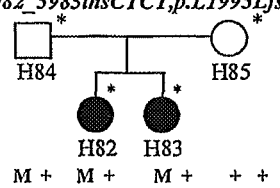
Figure 17:
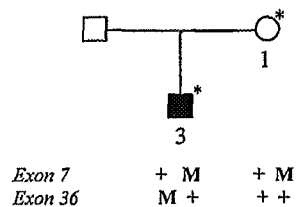
Figure 17:
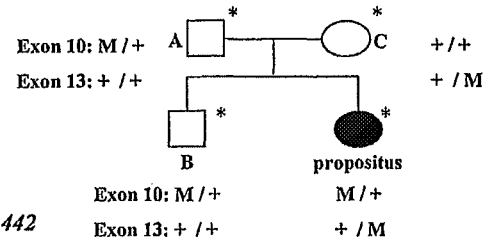
Figure 17:
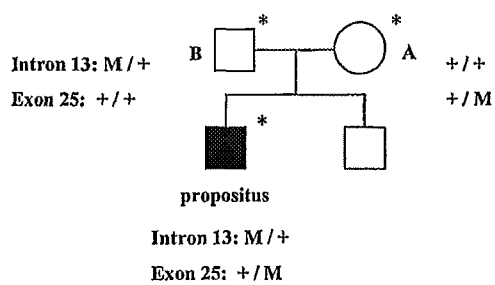
Figure 17:
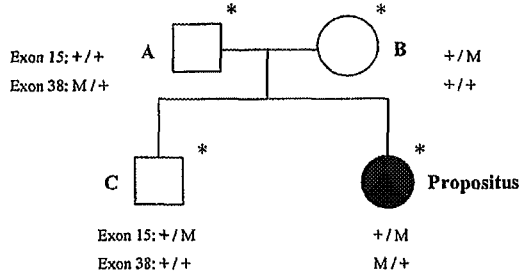
Figure 17:
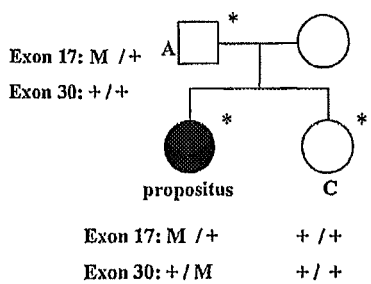
Figure 17:
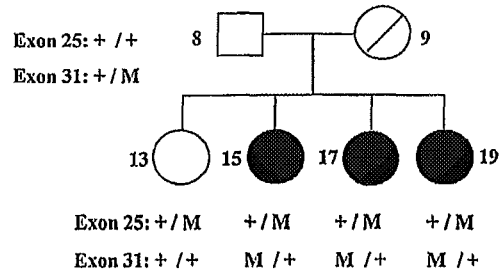

Previous expression profiling of the SPG11 gene showed that it is expressed ubiquitously at low levels in mouse tissues, including the brain (Nagase et al, 2001). Ubiquitous low level expression, even in structures apparently not related to the phenotype, has been shown for other genes responsible for neurodegenerative diseases (Paisan-Ruiz et al, 2004). We successfully amplified seven overlapping cDNA fragments from the KIAA1840 mRNA extracted from human cerebral cortex and used them to probe human adult multiple-tissue northern blots. At least three alternative transcripts were detected in all structures of adult brain. The full-length transcript (~8 Kb) was most highly expressed in the cerebellum, the 5.5-Kb transcript in the cerebral cortex (FIG. 11).

When the temporal and regional expression of the mouse KIAA1840 mRNA was investigated by in situ hybridization in rat brain, it was undetectable in newborn rats (P1). It was detected in the cerebellum, however, from P6 to P21. At adulthood (P68), expression was found throughout the brain. Expression was generally low, but stronger signals were observed in the pineal gland, the edges of the lateral ventricles, the granular layer of the cerebellum and the hippocampus. In contrast to human adult northern blots, only a weak expression was detected in the cerebral cortex. Understanding the function of spatacsin in these structures would help to explain the major features of the disease phenotype: e.g., expression in the hippocampus could be related to the cognitive impairment observed in the patients. In addition, whether the labeling of the edges of the lateral ventricles, where oligodendrocyte progenitors are located, is related to the white matter changes in patients remains to be investigated.

Our study identified the gene responsible for spastic paraplegia with thin corpus callosum linked to SPG11, KIAA1840. This is supported by four pieces of evidence; first, we have excluded 17 out of the 40 genes assigned to the SPG11 candidate interval; second, we have identified 43 different mutations segregating in 47 families, 16 of which linked previously to the SPG11 locus, and not found in at least 140 control chromosomes; third, all, these mutations were leading to a truncated protein and/or abnormally spliced mRNA, and fourth all mutated families presented with the typical AR-HSP-TCC phenotype or at least a compatible phenotype in 2 families in which cerebral imaging was not available. Mutations in KIAA1840 affected 47 of 91 AR-HSP-TCC families in this study making this genetic entity very frequent among AR-HSP-TCC (52%), 75% was estimated in a previous study (Stevanin et al, 2006), but also among recessive spastic paraplegias. At least another gene might however exist as previously shown (Lossos et al, 2006; Stevanin et al, 2006; Casali et al, 2004).

This gene has a widespread low level expression, including in the brain where it is more strongly expressed in the cerebellum, the cerebral cortex, the hippocampus, the pineal gland and the edges of the ventricles. Spastic paraplegias are supposed to results from a dying back mechanism of the exons and mitochondrial metabolism or axonal transport has been implicated in several genetic entities of HSP (Crosby et al, 2002). Indeed, three causative genes identified in AR-HSP have been implicated in defective intracellular trafficking: mutations in the mitochondrial metalloprotease protein paraplegin impair axonal transport in SPG7; spartin (SPG20) mutations affect endosomal trafficking and microtubule dynamics; maspardin (SPG21) mutations may interfere with endosomal/trans-Golgi vesicle transportation. Although, the function of spatacsin remains unknown, given it's basal expression in all tissues and it's high conservation in all species, this protein might have a crucial function which might explain the degeneration of the corticospinal tracts which might rely on the post-translational modifications or modeling/carriage of other proteins involved in axonal transport, mitochondrial metabolism as well as cerebral development. The presence of at least one transmembrane domain suggests that spatacsin may act as a receptor of a transporter.

All mutations identified so far in the KIAA1840 gene cause or are predicted to cause truncation of the protein, suggesting that pathogenicity results from loss of function. They are located in many exons, including exon 1 and exon 39 suggesting that the C-terminal domain of the protein has also an important function or effect on the structure of the protein. It is also conceivable that, given its position in the 5' splice site consensus sequence, the missense mutation R815M would also affect the transcription of the gene as demonstrated for mutation c.2833A>G, r.2834+1_2834+65ins, p.R945GfsX950. Similarly, the mutations found in the intronic part of the acceptor splicing sites in introns 4, 12, 13 and 34 (Table 2) are likely altering the splicing of the surrounding exons and therefore the synthesis and/or stability of the mRNA or protein. No tissues from patients were available yet, however, to validate this hypothesis.

The identification of the SPG11 gene will now improve the diagnostic procedure, as well as patient management, and permit more accurate genetic counseling. This is invaluable for patients and their families.

References

The following are all incorporated herein by reference:

Antonarakis et al. (1989), N. Engl. J. Med. 320:153-163 Diagnosis of genetic disorders at the DNA level Barbas C F, Bain J D, Hoekstra D M, Lerner R A. (1992), Semisynthetic combinatorial antibody libraries: a chemical solution to the diversity problem. PNAS USA, 89, 4457-4461

Callebaut, I. et al. Deciphering protein sequence information through hydrophobic cluster analysis (HCA): current status and perspectives. Cell Mol. Life Sci. 53, 621-645 (1997).

Casali, C. et al. Clinical and genetic studies in hereditary spastic paraplegia with thin corpus callosum. Neurology 62, 262-268 (2004).

Casari, G. et al. Spastic paraplegia and OXPHOS impairment caused by mutations in paraplegin, a nuclear-encoded mitochondrial metalloprotease. Cell 93, 973-983 (1998).

Chomocyznski et al., Anal. Biochem., 162:156, 1987

Colas et al., 1996

Cooper et al. (1991) Diagnosis of genetic disease using recombinant DNA, 3rd edition, Hum. Genet, 87:519-560

Den Dunnen J. T., Antonarakis S. E.: Hum Genet 109(1): 121-124, 2001.

Engert, J. C. et al. ARSACS, a spastic ataxia common in northeastern Quebec, is caused by mutations in a new gene encoding an 11.5-kb ORF. Nat. Genet 24, 120-125 (2000).

Fink, J. K. Advances in the hereditary spastic paraplegias. Exp. Neurol 184 Suppl 1, S106-S110 (2003).

Fink, J. K. Hereditary spastic paraplegia. Curr. Neurol. Neurosci. Rep. 6, 65-76 (2006).

Grompe M. The rapid detection of unknown mutations in nucleic acids (1993) Nat. Genet. 5(2):111-7

Gudbjartsson, D. F., Jonasson, K., Frigge, M. L., & Kong, A. Allegro, a new computer program for multipoint linkage analysis. Nature Genet. 25, 12-13 (2000).

Harding, A. E. Classification of the hereditary ataxias and paraplegias. Lancet 1, 1151-1155 (1983).

Harlow E. et al., Antibodies: A Laboratory Manual, Cold Spring Harbor Laboratory, New York, (1988).

Hazan, J. et al. Spastin, a new AAA protein, is altered in the most frequent form of autosomal dominant spastic paraplegia. Nature Genet. 23, 296-303 (1999).

Kohler and Milstein (1975) Continuous cultures of fused cells secreting antibody of predefined specificity. Nature; 256, 495-7.

Kuklin et al. Detection of single-nucleotide polymorphisms with the WAVE DNA fragment analysis system Genet. Test (1997-98), 1(3):201-6

Lossos, A. et al. Hereditary spastic paraplegia with thin corpus callosum: reduction of the SPG11 interval and evidence for further heterogeneity. Arch Neurol 63(5):756-60 (2006).

Martinez, M. F. et al. Genetic localization of a new locus for recessive familial spastic paraparesis to 15q13-15. Neurology 53, 50-56 (1999).

Moutsimilli, L. et al. Selective cortical VGLUTI increase as a marker for antidepressant activity. Neuropharmacology 49, 890-900 (2005).

Nickerson et al., 1990

Olmez et al. Further Clinical and Genetic Characterization of SPG11: Hereditary Spastic Paraplegia with Thin Corpus Callosum. Neuropediatrics. 2006; 37:59-66.

Patel, H. et al. SPG20 is mutated in Troyer syndrome, an hereditary spastic paraplegia. Nature Genet. 31, 347-348 (2002).

Saiki et al., Science 1988, 239:487

Sambrook, Fritsch & Maniatis, Molecular Cloning: A Laboratory Manual, Second Edition (1989) Cold Spring Harbor Laboratory Press, Cold Spring Harbor, N.Y.

Shibasaki, Y. et al. Linkage of autosomal recessive hereditary spastic paraplegia with mental impairment and thin corpus callosum to chromosome 15A13-15. Ann Neurol 48, 108-112 (2000).

Simpson, M. A. et al. Maspardin is mutated in mast syndrome, a complicated form of hereditary spastic paraplegia associated with dementia. Am. J. Hum. Genet. 73, 1147-1156 (2003).

Stevanin, G. et al. Spastic paraplegia with thin corpus callosum: description of 20 new families, refinement of the SPG11 locus, candidate gene analysis and evidence of genetic heterogeneity. Neurogenetics, 7, 149-156 (2006).

Stevanin, G. et al., Mutations in SPG11, encoding spatacsin, are a major cause of spastic paraplegia with thin corpus callosum Nat Genet Mar; 39(3):366-72. Epub 2007 Feb. 18. (2007)

Tallaksen, C. M., Durr, A., & Brice, A. Recent advances in hereditary spastic paraplegia. Curr. Opin. Neurol. 14, 457-463 (2001).

Waterhouse P, Griffiths A D, Johnson K S, Winter G. (1993) Combinatorial infection and in vivo recombination: a strategy for making large phage antibody repertoires. Nucleic Acids Research, 21, 2265-2266.

Winner, B. et al. Clinical progression and genetic analysis in hereditary spastic paraplegia with thin corpus callosum in spastic gait gene 11 (SPG11). Arch. Neurol. 61, 117-121 (2004).

Winner, B. et al. Thin corpus callosum and amyotrophy in spastic paraplegia-Case report and review of literature. Clin. Neurol. Neurosurg. (2005).

Woodcock, S., Mornon, J. P., & Henrissat, B. Detection of secondary structure elements in proteins by hydrophobic cluster analysis. Protein Eng 5, 629-635 (1992).

Zhao, X. et al. Mutations in a newly identified GTPase gene cause autosomal dominant hereditary spastic paraplegia. Nature Genet. 29, 326-331 (2001).

Reid, E. Pure hereditary spastic paraplegia. J. Med. Genet. 34, 499-503 (1997).

---

What is claimed is:

1. An ex vivo method of diagnosing or predicting an hereditary spastic paraplegias (HSP) in a subject, which method comprises
   assaying a sample containing a KIAA1840 nucleic acid from said subject to determine the presence of a mutated KIAA1840 nucleic acid as compared to a control population, wherein said mutated KIAA1840 nucleic acid sequence is at least 90% identical to SEQ ID NO: 1 and results in a truncated form of the KIAA1840 protein,
   detecting the mutation in the sample, thereby indicating the subject has, or is likely to develop, HSP, and
   identifying said subject as having or as likely to develop HSP when said mutation is detected.

2. The method according to claim 1, wherein said KIAA1840 mutation is selected from the group consisting of:
   the substitutions: c.6100C>T, c.2198T>G, c.118C>T, c.1235C>G, c.2833A>G, c.1951C>T, c.869+1G>A, c.1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T, c.5974C>T,
   the deletions: c.529-533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA c.733_734delAT, and
   the insertions: c.7029_7030insT, c.2850_2851insT, c.3741_3742insA, c.5982_5983insCTCT, c.5986_5987insT, c.3075_3076insA c.2842_2843insG.

3. The method according to claim 1, wherein the truncated KIAA1840 protein is selected from the group consisting of SEQ ID NO:149 to SEQ ID NO:164 and SEQ ID NO:166 to SEQ ID NO:188.

4. The method according to claim 1, wherein said sample containing KIAA 1840 nucleic acid is a RNA sample or a DNA sample.

5. The method according to claim 1, wherein said sample containing KIAA 1840 nucleic acid is obtained from a cell selected from the group consisting of blood cells, buccal cells, epithelial cells, fibroblasts, and any cells present in a tissue obtained by biopsy or post-mortem examination.

6. The method according to claim 1, wherein said method further comprises a step of subjecting the sample containing KIAA 1840 nucleic acid to coupled reverse transcription and amplification using oligonucleotide primers that are specific for a mutated site or that enable amplification of a region containing the mutant site.

7. The method according to claim 6, wherein said mutated site is detected in the amplified sequence by hybridization with a suitable probe or by direct sequencing.

8. The method according to claim 1, wherein said mutation is identified by a process selected from the group consisting of direct sequencing, restriction fragment length polymorphism analysis, hybridization with allele-specific oligonucleotides, allele-specific PCR, PCR using mutagenic primers, ligase-PCR, HOT cleavage, denaturing gradient gel electrophoresis, temperature denaturing gradient gel electrophoresis, single stranded conformational polymorphism and denaturing high performance liquid chromatography.

9. A method for detecting the presence of a mutation in the KIAA1840 nucleic acid in an individual, which method comprises
   a) assaying a sample containing a KIAA1840 nucleic acid from said individual to detect the presence of a mutated KIAA1840 nucleic acid as compared to a control population, wherein said mutated KIAA1840 nucleic acid sequence is at least 90% identical to SEQ ID NO: 1 and results in a truncated form of the KIAA1840 protein; and
   b) detecting the mutation in the sample, thereby indicating the individual has a mutation in the KIAA1840 nucleic acid.

10. The method according to claim 9, wherein said KIAA1840 mutation is selected from the group consisting of:
    the substitutions: c.6100C>T, c.2198T>G, c.118C>T, c.1235C>G, c.2833A>G, c.1951C>T, c.869+1G>A, c.1679 C>G, c.2316+1G>A, c.2444G>T, c.2444+1 G>C, c.2697G>A, c.5470C>T, c.5870C>G, c.6091 C>T, c.6477+4 A>G, c.6856C>T, c.1282A>T, c.5974C>T,
    the deletions: c.529-533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA c.733_734delAT, and
    the insertions: c.7029_7030insT, c.2850_2851insT, c.3741_3742insA, c.5982_5983insCTCT, c.5986_5987insT, c.3075_3076insA c.2842_2843insG.

11. The method according to claim 9, wherein the truncated KIAA1840 protein is selected from the group consisting of SEQ ID NO:149 to SEQ ID NO:164 and SEQ ID NO:166 to SEQ ID NO:188.

12. The method according to claim 9, wherein said sample containing KIAA 1840 nucleic acid is a RNA sample or a DNA sample.

13. The method according to claim 9, wherein said sample containing KIAA 1840 nucleic acid is obtained from a cell selected from the group consisting of blood cells, buccal cells, epithelial cells, fibroblasts, and any cells present in a tissue obtained by biopsy or post-mortem examination.

14. The method according to claim 9, wherein said method further comprises a step of subjecting the sample containing KIAA 1840 nucleic acid to coupled reverse transcription and amplification using oligonucleotide primers that are specific for a mutated site or that enable amplification of a region containing the mutant site.

15. The method according to claim 14, wherein said mutated site is detected in the amplified sequence by hybridization with a suitable probe or by direct sequencing.

16. The method according to claim 9, wherein said mutation is identified by a process selected from the group consisting of direct sequencing, restriction fragment length polymorphism analysis, hybridization with allele-specific oligonucleotides, allele-specific PCR, PCR using mutagenic primers, ligase-PCR, HOT cleavage, denaturing gradient gel electrophoresis, temperature denaturing gradient gel electrophoresis, single stranded conformational polymorphism and denaturing high performance liquid chromatography.

* * * * *

SEQUENCE LISTING

```
<160> NUMBER OF SEQ ID NOS: 188

<210> SEQ ID NO 1
<211> LENGTH: 7751
<212> TYPE: DNA
<213> ORGANISM: homo sapiens

<400> SEQUENCE: 1
atggctgcag aggaaggggt cgcgagtgct gcttccgccg gcggtagctg gggcaccgcg      60
gccatggggc gggttctacc gatgctgttg gtgccagtcc ccgccgaggc gatggggcag     120
ctcggctccc gggcgcagct gcgcacacag ccggaggctc tggggagcct gacggctgcg     180
ggcagcctcc aagtgctttc tttgacgcct ggcagccggg gcggggtcg ctgctgcctg      240 gagggcccct tctggcactt tctatgggag gattctcgta acagcagcac accaactgaa     300
aagcccaaac tgctcgctct tggtgaaaat tatgaactgc ttatctatga atttaatttg     360
aaagatggaa gatgtgatgc aaccattttg tatagctgta gtagggaggc attgcaaaag     420
ctcattgacg atcaagatat cagtatttcc ttattgtctt tgagaatcct gtcatttcac     480
aataacacat cattactgtt catcaacaaa tgtgtcatcc tacatattat atttcctgaa     540
agagatgctg caattagagt actcaactgt ttcacacttc ccttgcctgc acaggcagtg     600
gacatgatta ttgacacgca gctctgcaga ggaattcttt ttgttttgag tagtttaggc     660
tggatctaca tttttgatgt tgtggatggt acatatgtag ctcatgtgga tttagcactt     720
cacaaagaag acatgtgtaa tgagcagcaa caggagccag ccaagatttc ttcatttact     780
tcactgaaag tttctcaaga cctcgatgtt gcagtgattg tcagctcctc caactccgca     840
gttgctctta acttaaattt gtatttcagg caacacccag gacacctact gtgtgaaaga     900
atactagaag atcttcctat tcaaggacct aagggcgtag atgaagatga tcctgttaac     960
tctgcctaca acatgaaact ggccaagttt tccttccaaa ttgataggtc ttggaaagcc    1020
cagctatcat cattgaatga aacaataaag aactccaaac tggaggtttc ctgttgtgct    1080
ccatggttcc aggatatttt gcatttggag tcacctgaat ctggtaacca cagtacaagt    1140
gtgcagagct gggccttcat tccacaggac ataatgcatg gcaatataa tgttctacag    1200 aaagatcatg ccaagaccag tgatccagga agatcatgga aaataatgca catcagtgaa    1260
caagaggaac ccatagagct taaatgtgtg tctgtgacag gattcactgc actgtttact    1320
```

```
tgggaagtgg aaaggatggg ctataccatt accctctggg atttggagac ccagggcatg    1380
cagtgttttt cccttggcac aaagtgtatt cctgtagaca gtagtggaga ccagcagctg    1440
tgctttgttt tgacagagaa tggactctct ctgattttgt ttggtttgac tcaagaagag    1500
tttttaaaca gactcatgat ccatggaagt gccagcactg tggacactct tgtcatctc     1560 aatggctggg aaggtgctc aattcccata catgcactag aggccgggat agaaaatcgt     1620
cagctggaca cagtaaattt cttttttgaag agcaaggaaa atctttttaa tccatcctca   1680
aaatcttctg tatctgatca gtttgatcac ttgtcatccc atttatattt aagaaatgtg    1740
gaagagctga taccagcatt ggatttactt tgctcggcaa ttagagaaag ttattctgaa    1800
ccccaaagca aacactttc agaacaattg cttaatctta cactgtcttt ccttaacaac     1860
caaataaagg agcttttcat tcacactgaa gaactagatg aacatctgca aaaaggagtg    1920
aacattttga ctagctacat taatgaactt cgaaccttca tgataaagtt tccttggaag    1980
ctaacagatg ctatagatga atatgatgta catgaaaatg tccccaaagt aaaggagagc    2040
aatatatgga agaaactcag ctttgaggaa gttattgcca gcgccatttt aaacaacaaa    2100
ataccagagg cacagacttt cttcaggatt gatagtcatt ctgctcaaaa acttgaggag    2160
cttattggca taggcctaaa tttggtcttt gacaatttaa aaaagaacaa tataaaggaa    2220
gcctctgaac ttttgaagaa tatggggttt gatgtaaaag gccaattgct caagatctgc    2280
ttctatacaa ctaataaaaa tatacgtgac ttttggttg aattttaaa agaaaaaaat     2340 tattttctg aaaaagagaa aagaactata gacttcgtgc atcaagttga gaagctttat    2400
ttgggacatt ccaagaaaa tatgcaaatc cagtcatttc ccaggtactg gataaaggaa    2460
caagattttt tcaagcacaa gtctgttttg gactcattcc tgaaatatga ttgtaaagat    2520
gaatttaaca acaggacca tagaattgtg ttaaattggg ctctgtggtg ggatcaacta    2580
acacaagaat ccatccttct ccccaggata agtccagaag aatacaaatc atattcccct    2640
gaagccctct ggagatacct cacagctcgc catgattggt taaacattat cttatggatt    2700
ggagaatttc aaacccagca tagttatgct tcacttcagc agaacaaatg ccccttctg    2760 actgttgatg ttattaacca gaatacttcc tgtaacaact acatgaggaa tgaaatttta    2820
gataagctgc caggaatgg ggttttttg gcatctgaac tggaagactt tgaatgcttc    2880
ctcctaagac tgagccgtat tggaggtgta atacaggata ccctccctgt tcaaaactac    2940
aagaccaaag aaggttggga tttccattct caattcattc tctattgttt ggagcacagt    3000
ctgcagcatc ttctttatgt ctaccttgac tgttacaaac ttagtcctga aaattgtccc    3060
tttttggaaa aaaagagtt acatgaagca cacccttggt ttgaatttt agttcagtgt    3120 cgacaagttg ccagtaactt aacagatccc aaactgatct tccaggctag ccttgcaaat    3180
gctcagattt tgattcccac caatcaggcc agtgtaagca gtatgctatt ggaaggacat    3240
accctcctgg cccttgctac tacaatgtat tctcctgggg gtgtcagtca ggttgttcag    3300
aatgaagaaa atgaaaactg tttgaagaaa gtggatcccc agctattgaa gatggcatta    3360
actccttacc ccaagctaaa aactgctctc ttcccacagt gcactcctcc tagtgtcctg    3420
ccatctgata ttacaatcta ccaccttatt cagtcattat caccctttga tcctagcaga    3480
ttgtttggct ggcagtctgc taacacacta gctataggag atgcatggag tcatctccca    3540
catttctcta gccctgacct ggttaataaa tatgctatag tggaacgtct gaattttgct    3600
tattatttac ataatgggcg gccatcattt gcatttggta ctttttctggt ccaggaatta    3660 atcaagagca agactcccaa gcagctgatc cagcaagtag gcaatgaagc ctatgttata    3720
```

```
gggctctcct ccttccacat accttcaata ggagctgcat gtgtttgttt cttagaattg   3780
cttggccttg acagcctcaa gctcagagtt gatatgaaag tggccaatat aattttgagc   3840
tacaagtgca gaaatgaaga tgctcagtac agctttatca gagagtctgt agccgaaaaa   3900
ctatctaaac tagctgatgg tgaaaagaca accacagaag aattgcttgt tctcttagaa   3960
gaaggtacat ggaacagcat tcagcaacag gaaataaaga ggttatccag tgaatctagc   4020
agccaatggg cattagtggt gcagttctgc aggctacaca atatgaaact aagcatatct   4080
taccttagag aatgtgccaa agcaaatgat tggctgcagt tcattattca cagccaactc   4140
cacaactacc acccagcaga ggtgaaatcc cttatccagt acttcagccc agtcattcaa   4200
gaccacttaa ggctggcttt tgagaacttg ccctcagtgc ccacctccaa aatggacagc   4260
gatcaagtct gcaataagtg cccccaggaa cttcaaggaa gcaaacaaga gatgaccgat   4320
ttatttgaaa ttctgctcca atgctcagag gagccagact cctggcactg gcttctggtt   4380
gaagcagtga acaacaggc ccctatcctc agtgttctgg cctcatgtct ccagggtgcc   4440
agtgccattt cttgtctctg tgtttggatc atcacttctg tggaggacaa tgttgcaact   4500
gaagcaatgg gacacattca ggactcaaca gaggaccata cctggaacct tgaggatctt   4560
tcagtcatct ggagaacatt attaacaaga caaagagca aaactctcat cagaggtttc   4620
cagcttttct ttaaggattc cccgttacta ctggtgatgg agatgtatga actgtgtatg   4680
ttcttcagga attataaaga agctgaagct aaacttctgg agtttcagaa gagccttgaa   4740
acgcttaaca cagcagccac aaaggtccac cctgtcatcc ctgccatgtg gctggaggat   4800
caggtgtgtt tccttttgaa gcttatgcta cagcagtgta agacccagta tgagctgggg   4860
aagcttttac agctctttgt tgaaagagag catctcttct ctgatggtcc agatgtgaaa   4920
aagctttgca tcctttgcca gattttgaag gatacatcca tagccattaa tcatacaatt   4980
attaccagct acagcattga gaatcttcag catgaatgta gatctatttt ggaaagactg   5040
cagacagatg gacaattcgc tttggccagg agggtagcag aattagctga gttacctgtg   5100
gacaacttgg ttattaaaga gataacacag gaaatgcaga ccctaaaaca cattgaacag   5160
tggtcactaa aacaagcaag aattgacttc tggaaaaaat gccatgagaa tttttaagaaa   5220
aattcaattt caagcaaagc agcttcttcc ttttcctcaa cccaggccca tgtggcatgt   5280
gagcacccaa ctggatggag cagcatggag gagcgccatc tgctgctcac cttggcaggg   5340
cactggcttg cccaggagga cgtggtgccc ttggataagc tggaggagct ggagaagcag   5400
atctggctgt gccgcatcac ccagcacact cttggaagaa atcaggagga aacagagccc   5460
agattttctc gacagatctc aactagtggt gaactttcct ttgatagttt agccagtgag   5520
ttttccttct ccaagttggc tgctctgaac acatcaaaat acttagaact taacagcctt   5580
ccatccaaag agacatgcga gaatagattg gattggaaag agcaggagtc actaaacttt   5640
ttgattgggc gcctactgga tgatggctgt gtgcatgaag caagtagagt atgccggtat   5700
tttcattttt ataatccaga tgtcgccttg gtattgcact gcagagcact ggcctcaggg   5760
gaagctagta tggaggatct gcacccagag atccatgctc tcctacaaag tgctgagctg   5820
cttgaggaag aagcacccga cattccccta aggagagtcc acagcacttc aagtctggat   5880
agtcagaagt ttgtgacagt gccctccagt aatgaagtgg taactaacct ggaagtgctg   5940
acaagcaaat gcctccatgg gaagaactac tgtcgacagg tcctctgtct gtatgatctt   6000
gccaaggagt tgggctgttc ctacacagat gttgctgctc aggatggtga agccatgctc   6060
cggaaaatct tggcctctca gcagcctgac cgatgcaaac gagcccaggc cttcatcagc   6120
```

```
acacagggcc ttaagccaga tactgtggct gaactcgtgg cagaagaggt gacacgggag    6180
ctgcttactt catcacaggg aacaggacat aagcagatgt tcaacccaac agaggaaagc    6240
cagacatttc ttcagctgac cactctgtgt caagaccgca cattggtagg catgaagttg    6300
ttggataaga tttcctccgt tccccatggg gaactgtctt gcaccacaga gctcctgatc    6360
ctggcccatc attgcttcac cctgacgtgc cacatggagg gcatcatccg agtcctacag    6420
gccgcccaca tgctcacaga taaccacctg gcccccagtg aggagtatgg gctggtggta    6480 cggctccctca ctggcattgg aaggtacaac gagatgacat acatatttga tttgctgcat    6540
aaaaagcact actttgaagt gctaatgagg aagaagttgg atccgagtgg taccctgaaa    6600
acagccctgc tggactacat caaacgctgc cgtcctggag acagtgaaaa gcacaatatg    6660
attgccctgt gcttcagcat gtgccgggag attggcgaga ccacgaggc agctgcccgc    6720 atccaactga aattgattga gtctcagccc tgggaggaca gcctcaagga tgggcaccag    6780
ctgaaacaac tgctgctgaa ggccctgact ctgatgttgg atgcagcaga gagttatgcc    6840
aaggactcct gtgtgcgaca ggcccagcac tgtcagcggc tcaccaagtt gataactctg    6900
cagattcact ttctgaacac tggccagaac acaatgctca tcaacttggg ccgccacaag    6960
ctgatggact gtattctggc cctacctcgg ttctaccagg cttctattgt ggctgaggcc    7020
tacgattttg ttccagattg ggctgaaatt ttataccagc aagtgattct taaggagac    7080 tttaattact tggaagaatt taagcagcaa aggttattaa agtccagtat atttgaagag    7140
atttccaaaa aatataaaca acatcagcct actgacatgg tcatggaaaa cctgaagaaa    7200
ttactcacat attgtgaaga tgtttacctg tattacaagt tggcatacga acacaagttt    7260
tatgaaattg taaatgtgct tctgaaggac cctcagacag gttgctgtct aaaggacatg    7320
ctagcaggtt agatgatttc ataggtgtct gttttcttgt actgttagca gattctgaca    7380
gatgtgatga agaagaat gcattggaga tctttgctaa agttgaacaa tcccggtact    7440
gtaccatatc agtcctttgt gggtagtagg tagcaagtaa gaaactttc aggaggaaat    7500 tcctatttaa aatagattga ttttagatga ttgttcatcc acaccatttt atatagatac    7560
tagtattaag atcaaaagct tcctcttcct caggacagct tctactttag atgatccaat    7620
aatgattaaa gaatacctgt acctgcagat tccagtttca aagaaattta attattattt    7680
acacagttaa ggaacaggtg atacattttc atttgttaga aactgatctt tctgtaataa    7740
aatagatttt c                                                         7751
```

<210> SEQ ID NO 2
<211> LENGTH: 2443
<212> TYPE: PRT
<213> ORGANISM: homo sapiens

<400> SEQUENCE: 2

```
Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Gly Arg Cys Cys Leu
65                  70                  75                  80
```

```
Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Phe Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510
```

```
Thr Val Asp Thr Leu Cys His Leu Asn Gly Trp Gly Arg Cys Ser Ile
        515                 520                 525
Pro Ile His Ala Leu Glu Ala Gly Ile Glu Asn Arg Gln Leu Asp Thr
        530                 535                 540
Val Asn Phe Phe Leu Lys Ser Lys Glu Asn Leu Phe Asn Pro Ser Ser
545                 550                 555                 560
Lys Ser Ser Val Ser Asp Gln Phe Asp His Leu Ser Ser His Leu Tyr
                565                 570                 575
Leu Arg Asn Val Glu Glu Leu Ile Pro Ala Leu Asp Leu Leu Cys Ser
                580                 585                 590
Ala Ile Arg Glu Ser Tyr Ser Glu Pro Gln Ser Lys His Phe Ser Glu
        595                 600                 605
Gln Leu Leu Asn Leu Thr Leu Ser Phe Leu Asn Asn Gln Ile Lys Glu
        610                 615                 620
Leu Phe Ile His Thr Glu Glu Leu Asp Glu His Leu Gln Lys Gly Val
625                 630                 635                 640
Asn Ile Leu Thr Ser Tyr Ile Asn Glu Leu Arg Thr Phe Met Ile Lys
                645                 650                 655
Phe Pro Trp Lys Leu Thr Asp Ala Ile Asp Glu Tyr Asp Val His Glu
                660                 665                 670
Asn Val Pro Lys Val Lys Glu Ser Asn Ile Trp Lys Lys Leu Ser Phe
        675                 680                 685
Glu Glu Val Ile Ala Ser Ala Ile Leu Asn Asn Lys Ile Pro Glu Ala
        690                 695                 700
Gln Thr Phe Phe Arg Ile Asp Ser His Ser Ala Gln Lys Leu Glu Glu
705                 710                 715                 720
Leu Ile Gly Ile Gly Leu Asn Leu Val Phe Asp Asn Leu Lys Lys Asn
                725                 730                 735
Asn Ile Lys Glu Ala Ser Glu Leu Leu Lys Asn Met Gly Phe Asp Val
                740                 745                 750
Lys Gly Gln Leu Leu Lys Ile Cys Phe Tyr Thr Thr Asn Lys Asn Ile
        755                 760                 765
Arg Asp Phe Leu Val Glu Ile Leu Lys Glu Lys Asn Tyr Phe Ser Glu
        770                 775                 780
Lys Glu Lys Arg Thr Ile Asp Phe Val His Gln Val Glu Lys Leu Tyr
785                 790                 795                 800
Leu Gly His Phe Gln Glu Asn Met Gln Ile Gln Ser Phe Pro Arg Tyr
                805                 810                 815
Trp Ile Lys Glu Gln Asp Phe Phe Lys His Lys Ser Val Leu Asp Ser
                820                 825                 830
Phe Leu Lys Tyr Asp Cys Lys Asp Glu Phe Asn Lys Gln Asp His Arg
        835                 840                 845
Ile Val Leu Asn Trp Ala Leu Trp Trp Asp Gln Leu Thr Gln Glu Ser
        850                 855                 860
Ile Leu Leu Pro Arg Ile Ser Pro Glu Glu Tyr Lys Ser Tyr Ser Pro
865                 870                 875                 880
Glu Ala Leu Trp Arg Tyr Leu Thr Ala Arg His Asp Trp Leu Asn Ile
                885                 890                 895
Ile Leu Trp Ile Gly Glu Phe Gln Thr His Ser Tyr Ala Ser Leu
                900                 905                 910
Gln Gln Asn Lys Trp Pro Leu Leu Thr Val Asp Val Ile Asn Gln Asn
        915                 920                 925
Thr Ser Cys Asn Asn Tyr Met Arg Asn Glu Ile Leu Asp Lys Leu Ala
```

-continued

```
              930             935             940
Arg Asn Gly Val Phe Leu Ala Ser Glu Leu Glu Asp Phe Glu Cys Phe
945                     950             955                 960

Leu Leu Arg Leu Ser Arg Ile Gly Gly Val Ile Gln Asp Thr Leu Pro
                965             970                 975

Val Gln Asn Tyr Lys Thr Lys Glu Gly Trp Asp Phe His Ser Gln Phe
                    980             985                 990

Ile Leu Tyr Cys Leu Glu His Ser Leu Gln His Leu Leu Tyr Val Tyr
                995             1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320

Trp Asn Ser Ile Gln Gln Gln Glu Ile Lys Arg Leu Ser Ser Glu
    1325                1330                1335
```

-continued

Ser Ser Ser Gln Trp Ala Leu Val Val Gln Phe Cys Arg Leu His
1340            1345                1350

Asn Met Lys Leu Ser Ile Ser Tyr Leu Arg Glu Cys Ala Lys Ala
1355            1360                1365

Asn Asp Trp Leu Gln Phe Ile Ile His Ser Gln Leu His Asn Tyr
1370            1375                1380

His Pro Ala Glu Val Lys Ser Leu Ile Gln Tyr Phe Ser Pro Val
1385            1390                1395

Ile Gln Asp His Leu Arg Leu Ala Phe Glu Asn Leu Pro Ser Val
1400            1405                1410

Pro Thr Ser Lys Met Asp Ser Asp Gln Val Cys Asn Lys Cys Pro
1415            1420                1425

Gln Glu Leu Gln Gly Ser Lys Gln Glu Met Thr Asp Leu Phe Glu
1430            1435                1440

Ile Leu Leu Gln Cys Ser Glu Glu Pro Asp Ser Trp His Trp Leu
1445            1450                1455

Leu Val Glu Ala Val Lys Gln Gln Ala Pro Ile Leu Ser Val Leu
1460            1465                1470

Ala Ser Cys Leu Gln Gly Ala Ser Ala Ile Ser Cys Leu Cys Val
1475            1480                1485

Trp Ile Ile Thr Ser Val Glu Asp Asn Val Ala Thr Glu Ala Met
1490            1495                1500

Gly His Ile Gln Asp Ser Thr Glu Asp His Thr Trp Asn Leu Glu
1505            1510                1515

Asp Leu Ser Val Ile Trp Arg Thr Leu Leu Thr Arg Gln Lys Ser
1520            1525                1530

Lys Thr Leu Ile Arg Gly Phe Gln Leu Phe Phe Lys Asp Ser Pro
1535            1540                1545

Leu Leu Leu Val Met Glu Met Tyr Glu Leu Cys Met Phe Phe Arg
1550            1555                1560

Asn Tyr Lys Glu Ala Glu Ala Lys Leu Leu Glu Phe Gln Lys Ser
1565            1570                1575

Leu Glu Thr Leu Asn Thr Ala Ala Thr Lys Val His Pro Val Ile
1580            1585                1590

Pro Ala Met Trp Leu Glu Asp Gln Val Cys Phe Leu Leu Lys Leu
1595            1600                1605

Met Leu Gln Gln Cys Lys Thr Gln Tyr Glu Leu Gly Lys Leu Leu
1610            1615                1620

Gln Leu Phe Val Glu Arg Glu His Leu Phe Ser Asp Gly Pro Asp
1625            1630                1635

Val Lys Lys Leu Cys Ile Leu Cys Gln Ile Leu Lys Asp Thr Ser
1640            1645                1650

Ile Ala Ile Asn His Thr Ile Ile Thr Ser Tyr Ser Ile Glu Asn
1655            1660                1665

Leu Gln His Glu Cys Arg Ser Ile Leu Glu Arg Leu Gln Thr Asp
1670            1675                1680

Gly Gln Phe Ala Leu Ala Arg Arg Val Ala Glu Leu Ala Glu Leu
1685            1690                1695

Pro Val Asp Asn Leu Val Ile Lys Glu Ile Thr Gln Glu Met Gln
1700            1705                1710

Thr Leu Lys His Ile Glu Gln Trp Ser Leu Lys Gln Ala Arg Ile
1715            1720                1725

Asp Phe Trp Lys Lys Cys His Glu Asn Phe Lys Lys Asn Ser Ile
1730            1735                1740

```
Ser Ser Lys Ala Ala Ser Ser Phe Phe Ser Thr Gln Ala His Val
    1745            1750                1755
Ala Cys Glu His Pro Thr Gly Trp Ser Ser Met Glu Glu Arg His
    1760            1765                1770
Leu Leu Leu Thr Leu Ala Gly His Trp Leu Ala Gln Glu Asp Val
    1775            1780                1785
Val Pro Leu Asp Lys Leu Glu Glu Leu Glu Lys Gln Ile Trp Leu
    1790            1795                1800
Cys Arg Ile Thr Gln His Thr Leu Gly Arg Asn Gln Glu Glu Thr
    1805            1810                1815
Glu Pro Arg Phe Ser Arg Gln Ile Ser Thr Ser Gly Glu Leu Ser
    1820            1825                1830
Phe Asp Ser Leu Ala Ser Glu Phe Ser Phe Ser Lys Leu Ala Ala
    1835            1840                1845
Leu Asn Thr Ser Lys Tyr Leu Glu Leu Asn Ser Leu Pro Ser Lys
    1850            1855                1860
Glu Thr Cys Glu Asn Arg Leu Asp Trp Lys Glu Gln Glu Ser Leu
    1865            1870                1875
Asn Phe Leu Ile Gly Arg Leu Leu Asp Asp Gly Cys Val His Glu
    1880            1885                1890
Ala Ser Arg Val Cys Arg Tyr Phe His Phe Tyr Asn Pro Asp Val
    1895            1900                1905
Ala Leu Val Leu His Cys Arg Ala Leu Ala Ser Gly Glu Ala Ser
    1910            1915                1920
Met Glu Asp Leu His Pro Glu Ile His Ala Leu Leu Gln Ser Ala
    1925            1930                1935
Glu Leu Leu Glu Glu Glu Ala Pro Asp Ile Pro Leu Arg Arg Val
    1940            1945                1950
His Ser Thr Ser Ser Leu Asp Ser Gln Lys Phe Val Thr Val Pro
    1955            1960                1965
Ser Ser Asn Glu Val Val Thr Asn Leu Glu Val Leu Thr Ser Lys
    1970            1975                1980
Cys Leu His Gly Lys Asn Tyr Cys Arg Gln Val Leu Cys Leu Tyr
    1985            1990                1995
Asp Leu Ala Lys Glu Leu Gly Cys Ser Tyr Thr Asp Val Ala Ala
    2000            2005                2010
Gln Asp Gly Glu Ala Met Leu Arg Lys Ile Leu Ala Ser Gln Gln
    2015            2020                2025
Pro Asp Arg Cys Lys Arg Ala Gln Ala Phe Ile Ser Thr Gln Gly
    2030            2035                2040
Leu Lys Pro Asp Thr Val Ala Glu Leu Val Ala Glu Glu Val Thr
    2045            2050                2055
Arg Glu Leu Leu Thr Ser Ser Gln Gly Thr Gly His Lys Gln Met
    2060            2065                2070
Phe Asn Pro Thr Glu Glu Ser Gln Thr Phe Leu Gln Leu Thr Thr
    2075            2080                2085
Leu Cys Gln Asp Arg Thr Leu Val Gly Met Lys Leu Leu Asp Lys
    2090            2095                2100
Ile Ser Ser Val Pro His Gly Glu Leu Ser Cys Thr Thr Glu Leu
    2105            2110                2115
Leu Ile Leu Ala His His Cys Phe Thr Leu Thr Cys His Met Glu
    2120            2125                2130
Gly Ile Ile Arg Val Leu Gln Ala Ala His Met Leu Thr Asp Asn
```

```
                    2135                2140                2145

His Leu Ala Pro Ser Glu Glu Tyr Gly Leu Val Val Arg Leu Leu
    2150                2155                2160

Thr Gly Ile Gly Arg Tyr Asn Glu Met Thr Tyr Ile Phe Asp Leu
    2165                2170                2175

Leu His Lys Lys His Tyr Phe Glu Val Leu Met Arg Lys Lys Leu
    2180                2185                2190

Asp Pro Ser Gly Thr Leu Lys Thr Ala Leu Leu Asp Tyr Ile Lys
    2195                2200                2205

Arg Cys Arg Pro Gly Asp Ser Glu Lys His Asn Met Ile Ala Leu
    2210                2215                2220

Cys Phe Ser Met Cys Arg Glu Ile Gly Glu Asn His Glu Ala Ala
    2225                2230                2235

Ala Arg Ile Gln Leu Lys Leu Ile Glu Ser Gln Pro Trp Glu Asp
    2240                2245                2250

Ser Leu Lys Asp Gly His Gln Leu Lys Gln Leu Leu Lys Ala
    2255                2260                2265

Leu Thr Leu Met Leu Asp Ala Ala Glu Ser Tyr Ala Lys Asp Ser
    2270                2275                2280

Cys Val Arg Gln Ala Gln His Cys Gln Arg Leu Thr Lys Leu Ile
    2285                2290                2295

Thr Leu Gln Ile His Phe Leu Asn Thr Gly Gln Asn Thr Met Leu
    2300                2305                2310

Ile Asn Leu Gly Arg His Lys Leu Met Asp Cys Ile Leu Ala Leu
    2315                2320                2325

Pro Arg Phe Tyr Gln Ala Ser Ile Val Ala Glu Ala Tyr Asp Phe
    2330                2335                2340

Val Pro Asp Trp Ala Glu Ile Leu Tyr Gln Gln Val Ile Leu Lys
    2345                2350                2355

Gly Asp Phe Asn Tyr Leu Glu Glu Phe Lys Gln Gln Arg Leu Leu
    2360                2365                2370

Lys Ser Ser Ile Phe Glu Glu Ile Ser Lys Lys Tyr Lys Gln His
    2375                2380                2385

Gln Pro Thr Asp Met Val Met Glu Asn Leu Lys Lys Leu Leu Thr
    2390                2395                2400

Tyr Cys Glu Asp Val Tyr Leu Tyr Tyr Lys Leu Ala Tyr Glu His
    2405                2410                2415

Lys Phe Tyr Glu Ile Val Asn Val Leu Leu Lys Asp Pro Gln Thr
    2420                2425                2430

Gly Cys Cys Leu Lys Asp Met Leu Ala Gly
    2435                2440

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
ccacaggaaa cgaatggaat                                              20

<210> SEQ ID NO 4
<211> LENGTH: 20
<212> TYPE: DNA
<213> ORGANISM: Artificial
<220> FEATURE:
```

```
<223> OTHER INFORMATION: primer

<400> SEQUENCE: 4
ggttctgtga ggaaaccacg                                              20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
cagggacatt gtaggccatc                                              20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ccagttgtaa aattgtgacc                                              20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
tcccagctcc caaaactaaa                                              20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
tcaatcaaca cttctaccac                                              20

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
caggttcttt cttgtggcat ca                                           22

<210> SEQ ID NO 10
<211> LENGTH: 25
<212> TYPE: DNA
<213> ORGANISM: Artificial
<220> FEATURE:
<223> OTHER INFORMATION: primer

<400> SEQUENCE: 10
cgaggatatt tttaacctct tatca                                        25

<210> SEQ ID NO 11
```

-continued

```
<211> LENGTH: 24
<212> TYPE: DNA
<213> ORGANISM: Artificial
<220> FEATURE:
<223> OTHER INFORMATION: primer

<400> SEQUENCE: 11
gttaggcata cttacaaaac tggc                                        24

<210> SEQ ID NO 12
<211> LENGTH: 25
<212> TYPE: DNA
<213> ORGANISM: Artificial
<220> FEATURE:
<223> OTHER INFORMATION: primer

<400> SEQUENCE: 12
cgaggatatt tttaacctct tatca                                       25

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
gaacatcttt gccctggttt                                             20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
ctgtgacagg tgttaagtta                                             20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
caggcactga ggcagaagta                                             20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
atctaataca agacagtctc                                             20

<210> SEQ ID NO 17
<211> LENGTH: 26
<212> TYPE: DNA
<213> ORGANISM: Artificial
<220> FEATURE:
<223> OTHER INFORMATION: primer

<400> SEQUENCE: 17
```

```
aaaaatcaat tcctaaatca taatcc                                  26

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
tagtactgaa gtattgagta                                         20

<210> SEQ ID NO 19
<211> LENGTH: 24
<212> TYPE: DNA
<213> ORGANISM: Artificial
<220> FEATURE:
<223> OTHER INFORMATION: primer

<400> SEQUENCE: 19
tcttttaaag ccaaaaaggg taaa                                    24

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
ttaagtaatg ttcttgggca                                         20

<210> SEQ ID NO 21
<211> LENGTH: 21
<212> TYPE: DNA
<213> ORGANISM: Artificial
<220> FEATURE:
<223> OTHER INFORMATION: primer

<400> SEQUENCE: 21
cccaggacta atcatgaagg a                                       21

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
atccccaaac cgataaaacc                                         20

<210> SEQ ID NO 23
<211> LENGTH: 21
<212> TYPE: DNA
<213> ORGANISM: Artificial
<220> FEATURE:
<223> OTHER INFORMATION: primer

<400> SEQUENCE: 23
cggtgtgtct tccactagct c                                       21

<210> SEQ ID NO 24
<211> LENGTH: 23
<212> TYPE: DNA
<213> ORGANISM: Artificial
<220> FEATURE:
```

```
<223> OTHER INFORMATION: primer

<400> SEQUENCE: 24
gttacataaa tgtataatcc ctg                                           23

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
acccagccat tctcagtgtt                                               20

<210> SEQ ID NO 26
<211> LENGTH: 23
<212> TYPE: DNA
<213> ORGANISM: Artificial
<220> FEATURE:
<223> OTHER INFORMATION: primer

<400> SEQUENCE: 26
cattttaaga ctttatggat tac                                           23

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
cacagcgaga tcctgtctca                                               20

<210> SEQ ID NO 28
<211> LENGTH: 21
<212> TYPE: DNA
<213> ORGANISM: Artificial
<220> FEATURE:
<223> OTHER INFORMATION: primer

<400> SEQUENCE: 28
cctcactgta agatgatgcc c                                             21

<210> SEQ ID NO 29
<211> LENGTH: 25
<212> TYPE: DNA
<213> ORGANISM: Artificial
<220> FEATURE:
<223> OTHER INFORMATION: primer

<400> SEQUENCE: 29
cctttaaata ctacagtggt gcaga                                         25

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
tgtgggcatg atttggtcta                                               20

<210> SEQ ID NO 31
```

```
<211> LENGTH: 22
<212> TYPE: DNA
<213> ORGANISM: Artificial
<220> FEATURE:
<223> OTHER INFORMATION: primer

<400> SEQUENCE: 31
ccaactgttg agatggagaa aa                                              22

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
acctgctcaa ggacaaatgc                                                 20

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
tttgaagtat cccagggtgg                                                 20

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
ccaccattcc ccaaagataa                                                 20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
ttacctggat ttggctttgg                                                 20

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
cctggcttct aaaagtggcc                                                 20

<210> SEQ ID NO 37
<211> LENGTH: 22
<212> TYPE: DNA
<213> ORGANISM: Artificial
<220> FEATURE:
<223> OTHER INFORMATION: primer

<400> SEQUENCE: 37
```

-continued tgcaatccag aaacttgaga ga　　　　　　　　　　　　　　　　　　22

<210> SEQ ID NO 38
<211> LENGTH: 21
<212> TYPE: DNA
<213> ORGANISM: Artificial
<220> FEATURE:
<223> OTHER INFORMATION: primer

<400> SEQUENCE: 38
aagcacaaca tccaaatcct t　　　　　　　　　　　　　　　　　　21

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
atgttggcag gaactccatc　　　　　　　　　　　　　　　　　　　20

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
ctcctttgga gcaacctctg　　　　　　　　　　　　　　　　　　　20

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
ttccaacagg aaagcacaca　　　　　　　　　　　　　　　　　　　20

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
caacaggaaa gcacacatgc　　　　　　　　　　　　　　　　　　　20

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
cagctacttg ggaggctgag　　　　　　　　　　　　　　　　　　　20

<210> SEQ ID NO 44
<211> LENGTH: 20
<212> TYPE: DNA
<213> ORGANISM: Artificial
<220> FEATURE:

<223> OTHER INFORMATION: primer

<400> SEQUENCE: 44
gtgtggctgt gacctcactc                                               20

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
gcattagaag gggcactgaa                                               20

<210> SEQ ID NO 46
<211> LENGTH: 20
<212> TYPE: DNA
<213> ORGANISM: Artificial
<220> FEATURE:
<223> OTHER INFORMATION: primer

<400> SEQUENCE: 46
aacatggctg ggatgtttct                                               20

<210> SEQ ID NO 47
<211> LENGTH: 20
<212> TYPE: DNA
<213> ORGANISM: Artificial
<220> FEATURE:
<223> OTHER INFORMATION: primer

<400> SEQUENCE: 47
ctcacaacgg tattcacccc                                               20

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
ttcctggttg gcctatgatg                                               20

<210> SEQ ID NO 49
<211> LENGTH: 23
<212> TYPE: DNA
<213> ORGANISM: Artificial
<220> FEATURE:
<223> OTHER INFORMATION: primer

<400> SEQUENCE: 49
aagggtttaa gataatttgg gga                                           23

<210> SEQ ID NO 50
<211> LENGTH: 20
<212> TYPE: DNA
<213> ORGANISM: Artificial
<220> FEATURE:
<223> OTHER INFORMATION: primer

<400> SEQUENCE: 50
aatgccaaac acacacctga                                               20

<210> SEQ ID NO 51

```
<211> LENGTH: 22
<212> TYPE: DNA
<213> ORGANISM: Artificial
<220> FEATURE:
<223> OTHER INFORMATION: primer

<400> SEQUENCE: 51
ggattcttga tactgctttg cc                                          22

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
ctcaaagcag aggcaaggag                                             20

<210> SEQ ID NO 53
<211> LENGTH: 20
<212> TYPE: DNA
<213> ORGANISM: Artificial
<220> FEATURE:
<223> OTHER INFORMATION: primer

<400> SEQUENCE: 53
ctgagcccca cattttttgtt                                            20

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
caagtgctca atagccccat                                             20

<210> SEQ ID NO 55
<211> LENGTH: 25
<212> TYPE: DNA
<213> ORGANISM: Artificial
<220> FEATURE:
<223> OTHER INFORMATION: primer

<400> SEQUENCE: 55
gctaactgcc cttaatagag taaaa                                       25

<210> SEQ ID NO 56
<211> LENGTH: 20
<212> TYPE: DNA
<213> ORGANISM: Artificial
<220> FEATURE:
<223> OTHER INFORMATION: primer

<400> SEQUENCE: 56
aaagggtaca gcgtcagcat                                             20

<210> SEQ ID NO 57
<211> LENGTH: 20
<212> TYPE: DNA
<213> ORGANISM: Artificial
<220> FEATURE:
<223> OTHER INFORMATION: primer

<400> SEQUENCE: 57
```
cttgccccag attgcataat                                                    20

<210> SEQ ID NO 58
<211> LENGTH: 23
<212> TYPE: DNA
<213> ORGANISM: Artificial
<220> FEATURE:
<223> OTHER INFORMATION: primer

<400> SEQUENCE: 58
tccaaaaagt acgtaaaatc cca                                                23

<210> SEQ ID NO 59
<211> LENGTH: 22
<212> TYPE: DNA
<213> ORGANISM: Artificial
<220> FEATURE:
<223> OTHER INFORMATION: primer

<400> SEQUENCE: 59
cagcaaaagg gtaatagcag tg                                                 22

<210> SEQ ID NO 60
<211> LENGTH: 20
<212> TYPE: DNA
<213> ORGANISM: Artificial
<220> FEATURE:
<223> OTHER INFORMATION: primer

<400> SEQUENCE: 60
cccaaatgta gtaaatggcg                                                    20

<210> SEQ ID NO 61
<211> LENGTH: 23
<212> TYPE: DNA
<213> ORGANISM: Artificial
<220> FEATURE:
<223> OTHER INFORMATION: primer

<400> SEQUENCE: 61
tttgaaagag cagaaagcta tgg                                                23

<210> SEQ ID NO 62
<211> LENGTH: 21
<212> TYPE: DNA
<213> ORGANISM: Artificial
<220> FEATURE:
<223> OTHER INFORMATION: primer

<400> SEQUENCE: 62
tgaaggggtt gtcacacttt t                                                  21

<210> SEQ ID NO 63
<211> LENGTH: 22
<212> TYPE: DNA
<213> ORGANISM: Artificial
<220> FEATURE:
<223> OTHER INFORMATION: primer

<400> SEQUENCE: 63
ttgtggcaaa agaaaatttg tg                                                 22

<210> SEQ ID NO 64
<211> LENGTH: 20
<212> TYPE: DNA
<213> ORGANISM: Artificial
<220> FEATURE:

```
<223> OTHER INFORMATION: primer

<400> SEQUENCE: 64
gagaatgcag gctcagttcc                                              20

<210> SEQ ID NO 65
<211> LENGTH: 20
<212> TYPE: DNA
<213> ORGANISM: Artificial
<220> FEATURE:
<223> OTHER INFORMATION: primer

<400> SEQUENCE: 65
atgtggaact gagcctgcat                                              20

<210> SEQ ID NO 66
<211> LENGTH: 23
<212> TYPE: DNA
<213> ORGANISM: Artificial
<220> FEATURE:
<223> OTHER INFORMATION: primer

<400> SEQUENCE: 66
cgacttgcat tttaaagaac ctg                                          23

<210> SEQ ID NO 67
<211> LENGTH: 25
<212> TYPE: DNA
<213> ORGANISM: Artificial
<220> FEATURE:
<223> OTHER INFORMATION: primer

<400> SEQUENCE: 67
ttgtttccag atcatgaaga atatg                                        25

<210> SEQ ID NO 68
<211> LENGTH: 20
<212> TYPE: DNA
<213> ORGANISM: Artificial
<220> FEATURE:
<223> OTHER INFORMATION: primer

<400> SEQUENCE: 68
tcagatagct gaccacagcc                                              20

<210> SEQ ID NO 69
<211> LENGTH: 24
<212> TYPE: DNA
<213> ORGANISM: Artificial
<220> FEATURE:
<223> OTHER INFORMATION: primer

<400> SEQUENCE: 69
tccctcttaa ggagaaaaac actg                                         24

<210> SEQ ID NO 70
<211> LENGTH: 20
<212> TYPE: DNA
<213> ORGANISM: Artificial
<220> FEATURE:
<223> OTHER INFORMATION: primer

<400> SEQUENCE: 70
accgggccga gatataaaat                                              20

<210> SEQ ID NO 71
```

```
<211> LENGTH: 25
<212> TYPE: DNA
<213> ORGANISM: Artificial
<220> FEATURE:
<223> OTHER INFORMATION: primer

<400> SEQUENCE: 71
gctagtttgt cttagaacca gaaca                                           25

<210> SEQ ID NO 72
<211> LENGTH: 23
<212> TYPE: DNA
<213> ORGANISM: Artificial
<220> FEATURE:
<223> OTHER INFORMATION: primer

<400> SEQUENCE: 72 ttttggttg tctcactatc aca                                              23

<210> SEQ ID NO 73
<211> LENGTH: 24
<212> TYPE: DNA
<213> ORGANISM: Artificial
<220> FEATURE:
<223> OTHER INFORMATION: primer

<400> SEQUENCE: 73
aaggaacata gccagttctg tttt                                            24

<210> SEQ ID NO 74
<211> LENGTH: 21
<212> TYPE: DNA
<213> ORGANISM: Artificial
<220> FEATURE:
<223> OTHER INFORMATION: primer

<400> SEQUENCE: 74
tgcgaactat ttttcctttg g                                               21

<210> SEQ ID NO 75
<211> LENGTH: 23
<212> TYPE: DNA
<213> ORGANISM: Artificial
<220> FEATURE:
<223> OTHER INFORMATION: primer

<400> SEQUENCE: 75
tgcaacttct caggtacaca tct                                             23

<210> SEQ ID NO 76
<211> LENGTH: 20
<212> TYPE: DNA
<213> ORGANISM: Artificial
<220> FEATURE:
<223> OTHER INFORMATION: primer

<400> SEQUENCE: 76
aggctagagt gcagtggcat                                                 20

<210> SEQ ID NO 77
<211> LENGTH: 20
<212> TYPE: DNA
<213> ORGANISM: Artificial
<220> FEATURE:
<223> OTHER INFORMATION: primer

<400> SEQUENCE: 77
```

```
agtcagctta agggaagcgg                                             20
```

<210> SEQ ID NO 78
<211> LENGTH: 22
<212> TYPE: DNA
<213> ORGANISM: Artificial
<220> FEATURE:
<223> OTHER INFORMATION: primer

<400> SEQUENCE: 78

```
gaagataacc attttctccc ca                                          22
```

<210> SEQ ID NO 79
<211> LENGTH: 20
<212> TYPE: DNA
<213> ORGANISM: Artificial
<220> FEATURE:
<223> OTHER INFORMATION: primer

<400> SEQUENCE: 79

```
ttgtgagtgt ttggggagaa                                             20
```

<210> SEQ ID NO 80
<211> LENGTH: 21
<212> TYPE: DNA
<213> ORGANISM: Artificial
<220> FEATURE:
<223> OTHER INFORMATION: primer

<400> SEQUENCE: 80

```
ggggatttag tgaaaacacc a                                           21
```

<210> SEQ ID NO 81
<211> LENGTH: 24
<212> TYPE: DNA
<213> ORGANISM: Artificial
<220> FEATURE:
<223> OTHER INFORMATION: primer

<400> SEQUENCE: 81

```
tttgttggag aatacactgt gctt                                        24
```

<210> SEQ ID NO 82
<211> LENGTH: 25
<212> TYPE: DNA
<213> ORGANISM: Artificial
<220> FEATURE:
<223> OTHER INFORMATION: primer

<400> SEQUENCE: 82

```
catgtctaca caacagaaag aatgc                                       25
```

<210> SEQ ID NO 83
<211> LENGTH: 21
<212> TYPE: DNA
<213> ORGANISM: Artificial
<220> FEATURE:
<223> OTHER INFORMATION: primer

<400> SEQUENCE: 83

```
aaaaggcacc atacagcttt g                                           21
```

<210> SEQ ID NO 84
<211> LENGTH: 20
<212> TYPE: DNA
<213> ORGANISM: Artificial
<220> FEATURE:

<223> OTHER INFORMATION: primer

<400> SEQUENCE: 84
ggaaacacat gctggaacct                                              20

<210> SEQ ID NO 85
<211> LENGTH: 22
<212> TYPE: DNA
<213> ORGANISM: Artificial
<220> FEATURE:
<223> OTHER INFORMATION: primer

<400> SEQUENCE: 85
cttctgtctg cttcttggtc tt                                           22

<210> SEQ ID NO 86
<211> LENGTH: 22
<212> TYPE: DNA
<213> ORGANISM: Artificial
<220> FEATURE:
<223> OTHER INFORMATION: primer

<400> SEQUENCE: 86
tatcatcatt atctgttgtt gg                                           22

<210> SEQ ID NO 87
<211> LENGTH: 20
<212> TYPE: DNA
<213> ORGANISM: Artificial
<220> FEATURE:
<223> OTHER INFORMATION: primer

<400> SEQUENCE: 87
ttaggtgatc ccactggctc                                              20

<210> SEQ ID NO 88
<211> LENGTH: 20
<212> TYPE: DNA
<213> ORGANISM: Artificial
<220> FEATURE:
<223> OTHER INFORMATION: primer

<400> SEQUENCE: 88
cccaggagtt caaggctgta                                              20

<210> SEQ ID NO 89
<211> LENGTH: 20
<212> TYPE: DNA
<213> ORGANISM: Artificial
<220> FEATURE:
<223> OTHER INFORMATION: primer

<400> SEQUENCE: 89
ctgaggaggg cttgttttg                                               20

<210> SEQ ID NO 90
<211> LENGTH: 25
<212> TYPE: DNA
<213> ORGANISM: Artificial
<220> FEATURE:
<223> OTHER INFORMATION: primer

<400> SEQUENCE: 90
tctgtaactt gtttactccc agttg                                        25

<210> SEQ ID NO 91

<211> LENGTH: 20
<212> TYPE: DNA
<213> ORGANISM: Artificial
<220> FEATURE:
<223> OTHER INFORMATION: primer

<400> SEQUENCE: 91
gatcacacca ctgcattcca                                                    20

<210> SEQ ID NO 92
<211> LENGTH: 20
<212> TYPE: DNA
<213> ORGANISM: Artificial
<220> FEATURE:
<223> OTHER INFORMATION: primer

<400> SEQUENCE: 92
ggcacctgta gtcccagcta                                                    20

<210> SEQ ID NO 93
<211> LENGTH: 20
<212> TYPE: DNA
<213> ORGANISM: Artificial
<220> FEATURE:
<223> OTHER INFORMATION: primer

<400> SEQUENCE: 93
tgaggtggga ggatctcttg                                                    20

<210> SEQ ID NO 94
<211> LENGTH: 20
<212> TYPE: DNA
<213> ORGANISM: Artificial
<220> FEATURE:
<223> OTHER INFORMATION: primer

<400> SEQUENCE: 94
gatgtgttca gagcagccaa                                                    20

<210> SEQ ID NO 95
<211> LENGTH: 20
<212> TYPE: DNA
<213> ORGANISM: Artificial
<220> FEATURE:
<223> OTHER INFORMATION: primer

<400> SEQUENCE: 95
taagctggag gagctggaga                                                    20

<210> SEQ ID NO 96
<211> LENGTH: 20
<212> TYPE: DNA
<213> ORGANISM: Artificial
<220> FEATURE:
<223> OTHER INFORMATION: primer

<400> SEQUENCE: 96
ttgttgtccc cttaacttgg                                                    20

<210> SEQ ID NO 97
<211> LENGTH: 20
<212> TYPE: DNA
<213> ORGANISM: Artificial
<220> FEATURE:
<223> OTHER INFORMATION: primer

<400> SEQUENCE: 97

```
caataggcca agggtttcaa                                          20

<210> SEQ ID NO 98
<211> LENGTH: 20
<212> TYPE: DNA
<213> ORGANISM: Artificial
<220> FEATURE:
<223> OTHER INFORMATION: primer

<400> SEQUENCE: 98
tataactcct gctggagggc                                          20

<210> SEQ ID NO 99
<211> LENGTH: 20
<212> TYPE: DNA
<213> ORGANISM: Artificial
<220> FEATURE:
<223> OTHER INFORMATION: primer

<400> SEQUENCE: 99
ggtagcctgg aaattagccc                                          20

<210> SEQ ID NO 100
<211> LENGTH: 20
<212> TYPE: DNA
<213> ORGANISM: Artificial
<220> FEATURE:
<223> OTHER INFORMATION: primer

<400> SEQUENCE: 100
tgaaccagaa tctgaagcca                                          20

<210> SEQ ID NO 101
<211> LENGTH: 20
<212> TYPE: DNA
<213> ORGANISM: Artificial
<220> FEATURE:
<223> OTHER INFORMATION: primer

<400> SEQUENCE: 101
ttttgtcctt gggctctttc                                          20

<210> SEQ ID NO 102
<211> LENGTH: 20
<212> TYPE: DNA
<213> ORGANISM: Artificial
<220> FEATURE:
<223> OTHER INFORMATION: primer

<400> SEQUENCE: 102
cctggttctg tcactagccc                                          20

<210> SEQ ID NO 103
<211> LENGTH: 20
<212> TYPE: DNA
<213> ORGANISM: Artificial
<220> FEATURE:
<223> OTHER INFORMATION: primer

<400> SEQUENCE: 103
aattagccag ggtggtgaca                                          20

<210> SEQ ID NO 104
<211> LENGTH: 20
<212> TYPE: DNA
<213> ORGANISM: Artificial
<220> FEATURE:
```

<223> OTHER INFORMATION: primer

<400> SEQUENCE: 104
cccacaaagg actgatatgg                                          20

<210> SEQ ID NO 105
<211> LENGTH: 20
<212> TYPE: DNA
<213> ORGANISM: Artificial
<220> FEATURE:
<223> OTHER INFORMATION: primer

<400> SEQUENCE: 105
aaggaccctc agacaggttg                                          20

<210> SEQ ID NO 106
<211> LENGTH: 20
<212> TYPE: DNA
<213> ORGANISM: Artificial
<220> FEATURE:
<223> OTHER INFORMATION: primer

<400> SEQUENCE: 106
tcctttaagg cagacaaggg                                          20

<210> SEQ ID NO 107
<211> LENGTH: 24
<212> TYPE: DNA
<213> ORGANISM: Artificial
<220> FEATURE:
<223> OTHER INFORMATION: primer

<400> SEQUENCE: 107
accaggtcaa ctaaactgtt ctct                                     24

<210> SEQ ID NO 108
<211> LENGTH: 23
<212> TYPE: DNA
<213> ORGANISM: Artificial
<220> FEATURE:
<223> OTHER INFORMATION: primer

<400> SEQUENCE: 108
tatgctgaaa gaccacctgt aga                                      23

<210> SEQ ID NO 109
<211> LENGTH: 20
<212> TYPE: DNA
<213> ORGANISM: Artificial
<220> FEATURE:
<223> OTHER INFORMATION: primer

<400> SEQUENCE: 109
caggagcagt agtaacacaa                                          20

<210> SEQ ID NO 110
<211> LENGTH: 20
<212> TYPE: DNA
<213> ORGANISM: Artificial
<220> FEATURE:
<223> OTHER INFORMATION: primer

<400> SEQUENCE: 110
aaagggtaca gcgtcagcat                                          20

<210> SEQ ID NO 111

```
<211> LENGTH: 21
<212> TYPE: DNA
<213> ORGANISM: Artificial
<220> FEATURE:
<223> OTHER INFORMATION: primer

<400> SEQUENCE: 111
gcaggtaata agcctgcaga a                                              21

<210> SEQ ID NO 112
<211> LENGTH: 20
<212> TYPE: DNA
<213> ORGANISM: Artificial
<220> FEATURE:
<223> OTHER INFORMATION: primer

<400> SEQUENCE: 112
ccccCttcct agctgctatt                                                20

<210> SEQ ID NO 113
<211> LENGTH: 25
<212> TYPE: DNA
<213> ORGANISM: Artificial
<220> FEATURE:
<223> OTHER INFORMATION: primer

<400> SEQUENCE: 113
tgttcaaaat agttccatta caaaa                                          25

<210> SEQ ID NO 114
<211> LENGTH: 22
<212> TYPE: DNA
<213> ORGANISM: Artificial
<220> FEATURE:
<223> OTHER INFORMATION: primer

<400> SEQUENCE: 114
tttcttccaa ggttttcttc ca                                             22

<210> SEQ ID NO 115
<211> LENGTH: 21
<212> TYPE: DNA
<213> ORGANISM: Artificial
<220> FEATURE:
<223> OTHER INFORMATION: primer

<400> SEQUENCE: 115
tttgcaaaag tgcttgattt t                                              21

<210> SEQ ID NO 116
<211> LENGTH: 20
<212> TYPE: DNA
<213> ORGANISM: Artificial
<220> FEATURE:
<223> OTHER INFORMATION: primer

<400> SEQUENCE: 116
tgcaggctca gttccacata                                                20

<210> SEQ ID NO 117
<211> LENGTH: 20
<212> TYPE: DNA
<213> ORGANISM: Artificial
<220> FEATURE:
<223> OTHER INFORMATION: primer

<400> SEQUENCE: 117
```
ggaatgatgc cttttctcc                                            20

<210> SEQ ID NO 118
<211> LENGTH: 20
<212> TYPE: DNA
<213> ORGANISM: Artificial
<220> FEATURE:
<223> OTHER INFORMATION: primer

<400> SEQUENCE: 118
tctcacactt gccttctgga                                           20

<210> SEQ ID NO 119
<211> LENGTH: 20
<212> TYPE: DNA
<213> ORGANISM: Artificial
<220> FEATURE:
<223> OTHER INFORMATION: primer

<400> SEQUENCE: 119
aatcatcgcc tgagcaaaat                                           20

<210> SEQ ID NO 120
<211> LENGTH: 20
<212> TYPE: DNA
<213> ORGANISM: Artificial
<220> FEATURE:
<223> OTHER INFORMATION: primer

<400> SEQUENCE: 120
ccagtgactg atccaaagca                                           20

<210> SEQ ID NO 121
<211> LENGTH: 21
<212> TYPE: DNA
<213> ORGANISM: Artificial
<220> FEATURE:
<223> OTHER INFORMATION: primer

<400> SEQUENCE: 121
ccctcttaag gagaaaaaca c                                         21

<210> SEQ ID NO 122
<211> LENGTH: 20
<212> TYPE: DNA
<213> ORGANISM: Artificial
<220> FEATURE:
<223> OTHER INFORMATION: primer

<400> SEQUENCE: 122
cagccttatc ctctgctctt                                           20

<210> SEQ ID NO 123
<211> LENGTH: 20
<212> TYPE: DNA
<213> ORGANISM: Artificial
<220> FEATURE:
<223> OTHER INFORMATION: primer

<400> SEQUENCE: 123
tggaaaaggg gagcagacta                                           20

<210> SEQ ID NO 124
<211> LENGTH: 21
<212> TYPE: DNA
<213> ORGANISM: Artificial
<220> FEATURE:

<223> OTHER INFORMATION: primer

<400> SEQUENCE: 124
tgcgaactat ttttcctttg g                                              21

<210> SEQ ID NO 125
<211> LENGTH: 20
<212> TYPE: DNA
<213> ORGANISM: Artificial
<220> FEATURE:
<223> OTHER INFORMATION: primer

<400> SEQUENCE: 125
gaggaggcca caaatcacat                                                20

<210> SEQ ID NO 126
<211> LENGTH: 20
<212> TYPE: DNA
<213> ORGANISM: Artificial
<220> FEATURE:
<223> OTHER INFORMATION: primer

<400> SEQUENCE: 126
gccttagacc tcgtcacacc                                                20

<210> SEQ ID NO 127
<211> LENGTH: 23
<212> TYPE: DNA
<213> ORGANISM: Artificial
<220> FEATURE:
<223> OTHER INFORMATION: primer

<400> SEQUENCE: 127
tgctcaggtt ttgactttttt ctc                                           23

<210> SEQ ID NO 128
<211> LENGTH: 20
<212> TYPE: DNA
<213> ORGANISM: Artificial
<220> FEATURE:
<223> OTHER INFORMATION: primer

<400> SEQUENCE: 128
tttcactgat ggcaagatgc                                                20

<210> SEQ ID NO 129
<211> LENGTH: 20
<212> TYPE: DNA
<213> ORGANISM: Artificial
<220> FEATURE:
<223> OTHER INFORMATION: primer

<400> SEQUENCE: 129 accacccccca cctctaattc                                               20

<210> SEQ ID NO 130
<211> LENGTH: 20
<212> TYPE: DNA
<213> ORGANISM: Artificial
<220> FEATURE:
<223> OTHER INFORMATION: primer

<400> SEQUENCE: 130
ctacacaaca gaaagaatgc                                                20

<210> SEQ ID NO 131

```
<211> LENGTH: 21
<212> TYPE: DNA
<213> ORGANISM: Artificial
<220> FEATURE:
<223> OTHER INFORMATION: primer

<400> SEQUENCE: 131
ccagctgaaa ctgaaagttg g                                               21

<210> SEQ ID NO 132
<211> LENGTH: 20
<212> TYPE: DNA
<213> ORGANISM: Artificial
<220> FEATURE:
<223> OTHER INFORMATION: primer

<400> SEQUENCE: 132
ctgggtactt acttcaggct                                                 20

<210> SEQ ID NO 133
<211> LENGTH: 20
<212> TYPE: DNA
<213> ORGANISM: Artificial
<220> FEATURE:
<223> OTHER INFORMATION: primer

<400> SEQUENCE: 133
cactgtgccc tgccttatta                                                 20

<210> SEQ ID NO 134
<211> LENGTH: 20
<212> TYPE: DNA
<213> ORGANISM: Artificial
<220> FEATURE:
<223> OTHER INFORMATION: primer

<400> SEQUENCE: 134
tgtgcctgag taaccgagtg                                                 20

<210> SEQ ID NO 135
<211> LENGTH: 20
<212> TYPE: DNA
<213> ORGANISM: Artificial
<220> FEATURE:
<223> OTHER INFORMATION: primer

<400> SEQUENCE: 135
tcccagattt ggaggttttg                                                 20

<210> SEQ ID NO 136
<211> LENGTH: 24
<212> TYPE: DNA
<213> ORGANISM: Artificial
<220> FEATURE:
<223> OTHER INFORMATION: primer

<400> SEQUENCE: 136
tgcattttaa tttcctaact accc                                            24

<210> SEQ ID NO 137
<211> LENGTH: 20
<212> TYPE: DNA
<213> ORGANISM: Artificial
<220> FEATURE:
<223> OTHER INFORMATION: primer

<400> SEQUENCE: 137
```
gctgtagtgg cattttattg                                               20

<210> SEQ ID NO 138
<211> LENGTH: 20
<212> TYPE: DNA
<213> ORGANISM: Artificial
<220> FEATURE:
<223> OTHER INFORMATION: primer

<400> SEQUENCE: 138
cctgggtgac agagcaagac                                               20

<210> SEQ ID NO 139
<211> LENGTH: 20
<212> TYPE: DNA
<213> ORGANISM: Artificial
<220> FEATURE:
<223> OTHER INFORMATION: primer

<400> SEQUENCE: 139
agctgcagag ctccataagc                                               20

<210> SEQ ID NO 140
<211> LENGTH: 20
<212> TYPE: DNA
<213> ORGANISM: Artificial
<220> FEATURE:
<223> OTHER INFORMATION: primer

<400> SEQUENCE: 140
taggcatcca gagcaggaac                                               20

<210> SEQ ID NO 141
<211> LENGTH: 20
<212> TYPE: DNA
<213> ORGANISM: Artificial
<220> FEATURE:
<223> OTHER INFORMATION: primer

<400> SEQUENCE: 141
ggcatctgaa agcaaccact                                               20

<210> SEQ ID NO 142
<211> LENGTH: 20
<212> TYPE: DNA
<213> ORGANISM: Artificial
<220> FEATURE:
<223> OTHER INFORMATION: primer

<400> SEQUENCE: 142
ccctccattt tcccaagagt                                               20

<210> SEQ ID NO 143
<211> LENGTH: 20
<212> TYPE: DNA
<213> ORGANISM: Artificial
<220> FEATURE:
<223> OTHER INFORMATION: primer

<400> SEQUENCE: 143
ggggtgaata ccgttgtgag                                               20

<210> SEQ ID NO 144
<211> LENGTH: 20
<212> TYPE: DNA
<213> ORGANISM: Artificial
<220> FEATURE:

<223> OTHER INFORMATION: primer

<400> SEQUENCE: 144
acctctgggt tccatgagtg                                                    20

<210> SEQ ID NO 145
<211> LENGTH: 20
<212> TYPE: DNA
<213> ORGANISM: Artificial
<220> FEATURE:
<223> OTHER INFORMATION: primer

<400> SEQUENCE: 145
agactgctcc tctgcactcc                                                    20

<210> SEQ ID NO 146
<211> LENGTH: 21
<212> TYPE: DNA
<213> ORGANISM: Artificial
<220> FEATURE:
<223> OTHER INFORMATION: primer

<400> SEQUENCE: 146
ccgggattgt tcaactttag c                                                  21

<210> SEQ ID NO 147
<211> LENGTH: 20
<212> TYPE: DNA
<213> ORGANISM: Artificial
<220> FEATURE:
<223> OTHER INFORMATION: primer

<400> SEQUENCE: 147
cagtatctta acctgtacat                                                    20

<210> SEQ ID NO 148
<211> LENGTH: 21
<212> TYPE: DNA
<213> ORGANISM: Artificial
<220> FEATURE:
<223> OTHER INFORMATION: primer

<400> SEQUENCE: 148
ccgggattgt tcaactttag c                                                  21

<210> SEQ ID NO 149
<211> LENGTH: 40
<212> TYPE: PRT
<213> ORGANISM: Homo sapiens
<220> FEATURE:
<221> NAME/KEY: misc_feature
<222> LOCATION: (40)..(40)
<223> OTHER INFORMATION: Xaa can be any naturally occurring amino acid

<400> SEQUENCE: 149

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Xaa
        35                  40

<210> SEQ ID NO 150
<211> LENGTH: 178
<212> TYPE: PRT
<213> ORGANISM: Homo sapiens

```
<220> FEATURE:
<221> NAME/KEY: misc_feature
<222> LOCATION: (178)..(178)
<223> OTHER INFORMATION: Xaa can be any naturally occurring amino acid

<400> SEQUENCE: 150

Met Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ser Xaa

<210> SEQ ID NO 151
<211> LENGTH: 246
<212> TYPE: PRT
<213> ORGANISM: Homo sapiens
<220> FEATURE:
<221> NAME/KEY: misc_feature
<222> LOCATION: (246)..(246)
<223> OTHER INFORMATION: Xaa can be any naturally occurring amino acid

<400> SEQUENCE: 151

Met Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
130                 135                 140
```

-continued

```
Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Val Xaa
                245

<210> SEQ ID NO 152
<211> LENGTH: 415
<212> TYPE: PRT
<213> ORGANISM: Homo sapiens
<220> FEATURE:
<221> NAME/KEY: misc_feature
<222> LOCATION: (415)..(415)
<223> OTHER INFORMATION: Xaa can be any naturally occurring amino acid

<400> SEQUENCE: 152

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
```

-continued

```
                    245                 250                 255
Ser Ser Phe Thr Ser Leu Lys Val Ser Gln Asp Leu Asp Val Ala Val
                260                 265                 270
Ile Val Ser Ser Asn Ser Ala Val Ala Leu Asn Leu Asn Leu Tyr
                275                 280                 285
Phe Arg Gln His Pro Gly His Leu Leu Cys Glu Arg Ile Leu Glu Asp
            290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
                340                 345                 350
Lys Leu Glu Val Ser Cys Cys Ala Pro Trp Phe Gln Asp Ile Leu His
            355                 360                 365
Leu Glu Ser Pro Glu Ser Gly Asn His Ser Thr Ser Val Gln Ser Trp
370                 375                 380
Ala Phe Ile Pro Gln Asp Ile Met His Gly Gln Tyr Asn Val Leu Gln
385                 390                 395                 400
Lys Ile Met Pro Arg Pro Val Ile Gln Glu Asp His Gly Lys Xaa
                405                 410                 415
```

<210> SEQ ID NO 153
<211> LENGTH: 412
<212> TYPE: PRT
<213> ORGANISM: Homo sapiens
<220> FEATURE:
<221> NAME/KEY: misc_feature
<222> LOCATION: (412)..(412)
<223> OTHER INFORMATION: Xaa can be any naturally occurring amino acid

<400> SEQUENCE: 153

```
Met Ala Ala Glu Glu Gly Val Ser Ala Ala Ser Ala Gly Gly Ser
1               5                   10                  15
Trp Gly Thr Ala Ala Met Gly Arg Val Leu Pro Met Leu Leu Val Pro
                20                  25                  30
Val Pro Ala Glu Ala Met Gly Gln Leu Gly Ser Arg Ala Gln Leu Arg
            35                  40                  45
Thr Gln Pro Glu Ala Leu Gly Ser Leu Thr Ala Ala Gly Ser Leu Gln
        50                  55                  60
Val Leu Ser Leu Thr Pro Gly Ser Arg Gly Gly Arg Cys Cys Leu
65                  70                  75                  80
Glu Gly Pro Phe Trp His Phe Leu Trp Glu Asp Ser Arg Asn Ser Ser
                85                  90                  95
Thr Pro Thr Glu Lys Pro Lys Leu Leu Ala Leu Gly Glu Asn Tyr Glu
                100                 105                 110
Leu Leu Ile Tyr Glu Phe Asn Leu Lys Asp Gly Arg Cys Asp Ala Thr
            115                 120                 125
Ile Leu Tyr Ser Cys Ser Arg Glu Ala Leu Gln Lys Leu Ile Asp Asp
        130                 135                 140
Gln Asp Ile Ser Ile Ser Leu Leu Ser Leu Arg Ile Leu Ser Phe His
145                 150                 155                 160
Asn Asn Thr Ser Leu Leu Phe Ile Asn Lys Cys Val Ile Leu His Ile
                165                 170                 175
Ile Phe Pro Glu Arg Asp Ala Ala Ile Arg Val Leu Asn Cys Phe Thr
                180                 185                 190
```

-continued

```
Leu Pro Leu Pro Ala Gln Ala Val Asp Met Ile Ile Asp Thr Gln Leu
            195                 200                 205
Cys Arg Gly Ile Leu Phe Val Leu Ser Ser Leu Gly Trp Ile Tyr Ile
        210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Gln Glu Pro Ala Lys Ile
                245                 250                 255
Ser Ser Phe Thr Ser Leu Lys Val Ser Gln Asp Leu Asp Val Ala Val
            260                 265                 270
Ile Val Ser Ser Asn Ser Ala Val Ala Leu Asn Leu Asn Leu Tyr
        275                 280                 285
Phe Arg Gln His Pro Gly His Leu Leu Cys Glu Arg Ile Leu Glu Asp
290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
        355                 360                 365
Leu Glu Ser Pro Glu Ser Gly Asn His Ser Thr Ser Val Gln Ser Trp
370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Xaa
                405                 410

<210> SEQ ID NO 154
<211> LENGTH: 556
<212> TYPE: PRT
<213> ORGANISM: Homo sapiens
<220> FEATURE:
<221> NAME/KEY: misc_feature
<222> LOCATION: (556)..(556)
<223> OTHER INFORMATION: Xaa can be any naturally occurring amino acid

<400> SEQUENCE: 154

Met Ala Ala Glu Glu Gly Val Ala Ser Ala Ala Ser Ala Gly Gly Ser
1               5                   10                  15
Trp Gly Thr Ala Ala Met Gly Arg Val Leu Pro Met Leu Leu Val Pro
            20                  25                  30
Val Pro Ala Glu Ala Met Gly Gln Leu Gly Ser Arg Ala Gln Leu Arg
        35                  40                  45
Thr Gln Pro Glu Ala Leu Gly Ser Leu Thr Ala Ala Gly Ser Leu Gln
    50                  55                  60
Val Leu Ser Leu Thr Pro Gly Ser Arg Gly Gly Arg Cys Cys Leu
65                  70                  75                  80
Glu Gly Pro Phe Trp His Phe Leu Trp Glu Asp Ser Arg Asn Ser Ser
                85                  90                  95
Thr Pro Thr Glu Lys Pro Lys Leu Leu Ala Leu Gly Glu Asn Tyr Glu
            100                 105                 110
Leu Leu Ile Tyr Glu Phe Asn Leu Lys Asp Gly Arg Cys Asp Ala Thr
        115                 120                 125
Ile Leu Tyr Ser Cys Ser Arg Glu Ala Leu Gln Lys Leu Ile Asp Asp
    130                 135                 140
```

```
Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
            165                 170                 175

Ile Phe Pro Glu Arg Asp Ala Ala Ile Arg Val Leu Asn Cys Phe Thr
        180                 185                 190

Leu Pro Leu Pro Ala Gln Ala Val Asp Met Ile Ile Asp Thr Gln Leu
    195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
        290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
        370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
        450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Ser Ser Gln Trp Leu Gly Lys Val Leu Asn Ser
        515                 520                 525

His Thr Cys Thr Arg Gly Arg Asp Arg Lys Ser Ala Gly His Ser
    530                 535                 540

Lys Phe Leu Phe Glu Glu Gln Gly Lys Ser Phe Xaa
545                 550                 555
```

<210> SEQ ID NO 155
<211> LENGTH: 651
<212> TYPE: PRT
<213> ORGANISM: Homo sapiens
<220> FEATURE:
<221> NAME/KEY: misc_feature
<222> LOCATION: (651)..(651)
<223> OTHER INFORMATION: Xaa can be any naturally occurring amino acid

<400> SEQUENCE: 155

```
Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
                35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
        210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
        290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
            355                 360                 365
```

```
Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Xaa
                645                 650

<210> SEQ ID NO 156
<211> LENGTH: 733
<212> TYPE: PRT
<213> ORGANISM: Homo sapiens
<220> FEATURE:
<221> NAME/KEY: misc_feature
<222> LOCATION: (733)..(733)
<223> OTHER INFORMATION: Xaa can be any naturally occurring amino acid

<400> SEQUENCE: 156

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Gly Arg Cys Cys Leu
65                  70                  75                  80
```

-continued

```
Glu Gly Pro Phe Trp His Phe Leu Trp Glu Asp Ser Arg Asn Ser Ser
                85                  90                  95
Thr Pro Thr Glu Lys Pro Lys Leu Leu Ala Leu Gly Glu Asn Tyr Glu
            100                 105                 110
Leu Leu Ile Tyr Glu Phe Asn Leu Lys Asp Gly Arg Cys Asp Ala Thr
        115                 120                 125
Ile Leu Tyr Ser Cys Ser Arg Glu Ala Leu Gln Lys Leu Ile Asp Asp
    130                 135                 140
Gln Asp Ile Ser Ile Ser Leu Leu Ser Leu Arg Ile Leu Ser Phe His
145                 150                 155                 160
Asn Asn Thr Ser Leu Leu Phe Ile Asn Lys Cys Val Ile Leu His Ile
                165                 170                 175
Ile Phe Pro Glu Arg Asp Ala Ala Ile Arg Val Leu Asn Cys Phe Thr
            180                 185                 190
Leu Pro Leu Pro Ala Gln Ala Val Asp Met Ile Ile Asp Thr Gln Leu
        195                 200                 205
Cys Arg Gly Ile Leu Phe Val Leu Ser Ser Leu Gly Trp Ile Tyr Ile
    210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Gln Glu Pro Ala Lys Ile
                245                 250                 255
Ser Ser Phe Thr Ser Leu Lys Val Ser Gln Asp Leu Asp Val Ala Val
            260                 265                 270
Ile Val Ser Ser Ser Asn Ser Ala Val Ala Leu Asn Leu Asn Leu Tyr
        275                 280                 285
Phe Arg Gln His Pro Gly His Leu Leu Cys Glu Arg Ile Leu Glu Asp
    290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
        355                 360                 365
Leu Glu Ser Pro Glu Ser Gly Asn His Ser Thr Ser Val Gln Ser Trp
    370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
                405                 410                 415
His Ile Ser Glu Gln Glu Glu Pro Ile Glu Leu Lys Cys Val Ser Val
            420                 425                 430
Thr Gly Phe Thr Ala Leu Phe Thr Trp Glu Val Glu Arg Met Gly Tyr
        435                 440                 445
Thr Ile Thr Leu Trp Asp Leu Glu Thr Gln Gly Met Gln Cys Ser Ser
    450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
                485                 490                 495
Thr Gln Glu Glu Phe Leu Asn Arg Leu Met Ile His Gly Ser Ala Ser
```

```
                      500                 505                 510
Thr Val Asp Thr Leu Cys His Leu Asn Gly Trp Gly Arg Cys Ser Ile
                515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Xaa
                725                 730

<210> SEQ ID NO 157
<211> LENGTH: 953
<212> TYPE: PRT
<213> ORGANISM: Homo sapiens
<220> FEATURE:
<221> NAME/KEY: misc_feature
<222> LOCATION: (953)..(953)
<223> OTHER INFORMATION: Xaa can be any naturally occurring amino acid

<400> SEQUENCE: 157

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
            50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125
```

-continued

```
Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
545                 550                 555                 560
```

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
            725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
            805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
            850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
            885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
            930                 935                 940

Arg Asn Gly Gly Phe Phe Gly Ile Xaa
945                 950

<210> SEQ ID NO 158
<211> LENGTH: 953
<212> TYPE: PRT

```
<213> ORGANISM: Homo sapiens
<220> FEATURE:
<221> NAME/KEY: misc_feature
<222> LOCATION: (953)..(953)
<223> OTHER INFORMATION: Xaa can be any naturally occurring amino acid

<400> SEQUENCE: 158
```

| | | | | | | | | | | | | | | | |
|---|---|---|---|---|---|---|---|---|---|---|---|---|---|---|---|
| Met | Ala | Ala | Glu | Glu | Gly | Val | Ala | Ser | Ala | Ser | Ala | Gly | Gly | Ser | |
| 1 | | | | 5 | | | | | 10 | | | | | 15 | |
| Trp | Gly | Thr | Ala | Ala | Met | Gly | Arg | Val | Leu | Pro | Met | Leu | Leu | Val | Pro |
| | | | 20 | | | | | 25 | | | | | 30 | | |
| Val | Pro | Ala | Glu | Ala | Met | Gly | Gln | Leu | Gly | Ser | Arg | Ala | Gln | Leu | Arg |
| | | 35 | | | | | 40 | | | | | 45 | | | |
| Thr | Gln | Pro | Glu | Ala | Leu | Gly | Ser | Leu | Thr | Ala | Ala | Gly | Ser | Leu | Gln |
| | 50 | | | | | 55 | | | | | 60 | | | | |
| Val | Leu | Ser | Leu | Thr | Pro | Gly | Ser | Arg | Gly | Gly | Arg | Cys | Cys | Leu | |
| 65 | | | | | 70 | | | | | 75 | | | | | 80 |
| Glu | Gly | Pro | Phe | Trp | His | Phe | Leu | Trp | Glu | Asp | Ser | Arg | Asn | Ser | Ser |
| | | | | 85 | | | | | 90 | | | | | 95 | |
| Thr | Pro | Thr | Glu | Lys | Pro | Lys | Leu | Leu | Ala | Leu | Gly | Glu | Asn | Tyr | Glu |
| | | | 100 | | | | | 105 | | | | | 110 | | |
| Leu | Leu | Ile | Tyr | Glu | Phe | Asn | Leu | Lys | Asp | Gly | Arg | Cys | Asp | Ala | Thr |
| | | | 115 | | | | | 120 | | | | | 125 | | |
| Ile | Leu | Tyr | Ser | Cys | Ser | Arg | Glu | Ala | Leu | Gln | Lys | Leu | Ile | Asp | Asp |
| | 130 | | | | | 135 | | | | | 140 | | | | |
| Gln | Asp | Ile | Ser | Ile | Ser | Leu | Leu | Ser | Leu | Arg | Ile | Leu | Ser | Phe | His |
| 145 | | | | | 150 | | | | | 155 | | | | | 160 |
| Asn | Asn | Thr | Ser | Leu | Leu | Phe | Ile | Asn | Lys | Cys | Val | Ile | Leu | His | Ile |
| | | | | 165 | | | | | 170 | | | | | 175 | |
| Ile | Phe | Pro | Glu | Arg | Asp | Ala | Ala | Ile | Arg | Val | Leu | Asn | Cys | Phe | Thr |
| | | | 180 | | | | | 185 | | | | | 190 | | |
| Leu | Pro | Leu | Pro | Ala | Gln | Ala | Val | Asp | Met | Ile | Ile | Asp | Thr | Gln | Leu |
| | | 195 | | | | | 200 | | | | | 205 | | | |
| Cys | Arg | Gly | Ile | Leu | Phe | Val | Leu | Ser | Ser | Leu | Gly | Trp | Ile | Tyr | Ile |
| | 210 | | | | | 215 | | | | | 220 | | | | |
| Phe | Asp | Val | Val | Asp | Gly | Thr | Tyr | Val | Ala | His | Val | Asp | Leu | Ala | Leu |
| 225 | | | | | 230 | | | | | 235 | | | | | 240 |
| His | Lys | Glu | Asp | Met | Cys | Asn | Glu | Gln | Gln | Gln | Glu | Pro | Ala | Lys | Ile |
| | | | | 245 | | | | | 250 | | | | | 255 | |
| Ser | Ser | Phe | Thr | Ser | Leu | Lys | Val | Ser | Gln | Asp | Leu | Asp | Val | Ala | Val |
| | | | 260 | | | | | 265 | | | | | 270 | | |
| Ile | Val | Ser | Ser | Asn | Ser | Ala | Val | Ala | Leu | Asn | Leu | Asn | Leu | Tyr | |
| | | 275 | | | | | 280 | | | | | 285 | | | |
| Phe | Arg | Gln | His | Pro | Gly | His | Leu | Leu | Cys | Glu | Arg | Ile | Leu | Glu | Asp |
| | 290 | | | | | 295 | | | | | 300 | | | | |
| Leu | Pro | Ile | Gln | Gly | Pro | Lys | Gly | Val | Asp | Glu | Asp | Pro | Val | Asn | |
| 305 | | | | | 310 | | | | | 315 | | | | | 320 |
| Ser | Ala | Tyr | Asn | Met | Lys | Leu | Ala | Lys | Phe | Ser | Phe | Gln | Ile | Asp | Arg |
| | | | | 325 | | | | | 330 | | | | | 335 | |
| Ser | Trp | Lys | Ala | Gln | Leu | Ser | Ser | Leu | Asn | Glu | Thr | Ile | Lys | Asn | Ser |
| | | | 340 | | | | | 345 | | | | | 350 | | |
| Lys | Leu | Glu | Val | Ser | Cys | Cys | Ala | Pro | Trp | Phe | Gln | Asp | Ile | Leu | His |
| | | | 355 | | | | | 360 | | | | | 365 | | |
| Leu | Glu | Ser | Pro | Glu | Ser | Gly | Asn | His | Ser | Thr | Ser | Val | Gln | Ser | Trp |
| | 370 | | | | | 375 | | | | | 380 | | | | |

```
Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
        420                 425                 430

Thr Gly Phe Thr Ala Leu Phe Thr Trp Glu Val Glu Arg Met Gly Tyr
    435                 440                 445

Thr Ile Thr Leu Trp Asp Leu Glu Thr Gln Gly Met Gln Cys Ser Ser
        450                 455                 460

Leu Gly Thr Lys Cys Ile Pro Val Asp Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815
```

```
Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
            850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
                900                 905                 910

Gln Gln Asn Lys Trp Pro Leu Leu Thr Val Asp Val Ile Asn Gln Asn
                915                 920                 925

Thr Ser Cys Asn Asn Tyr Met Arg Asn Glu Ile Leu Asp Lys Leu Ala
            930                 935                 940

Arg Asn Gly Val Phe Phe Gly Ile Xaa
945                 950

<210> SEQ ID NO 159
<211> LENGTH: 1992
<212> TYPE: PRT
<213> ORGANISM: Homo sapiens
<220> FEATURE:
<221> NAME/KEY: misc_feature
<222> LOCATION: (1992)..(1992)
<223> OTHER INFORMATION: Xaa can be any naturally occurring amino acid

<400> SEQUENCE: 159

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
```

```
               210                 215                 220
Phe Asp Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Asn Ser Ala Val Ala Leu Asn Leu Asn Leu Tyr
                275                 280                 285

Phe Arg Gln His Pro Gly His Leu Leu Cys Glu Arg Ile Leu Glu Asp
                290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Pro Ile Glu Leu Lys Cys Val Ser Val
                420                 425                 430

Thr Gly Phe Thr Ala Leu Phe Thr Trp Glu Val Glu Arg Met Gly Tyr
                435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
                515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
                595                 600                 605

Gln Leu Leu Asn Leu Thr Leu Ser Phe Leu Asn Asn Gln Ile Lys Glu
                610                 615                 620

Leu Phe Ile His Thr Glu Glu Leu Asp Glu His Leu Gln Lys Gly Val
625                 630                 635                 640
```

-continued

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
        690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
            725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
            995                 1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

```
Gln Ala Ser Val Ser Ser Met Leu Leu Glu Gly His Thr Leu Leu
    1070            1075                1080

Ala Leu Ala Thr Thr Met Tyr Ser Pro Gly Val Ser Gln Val
    1085            1090                1095

Val Gln Asn Glu Glu Asn Asn Cys Leu Lys Lys Val Asp Pro
    1100            1105                1110

Gln Leu Leu Lys Met Ala Leu Thr Pro Tyr Pro Lys Leu Lys Thr
    1115            1120                1125

Ala Leu Phe Pro Gln Cys Thr Pro Pro Ser Val Leu Pro Ser Asp
    1130            1135                1140

Ile Thr Ile Tyr His Leu Ile Gln Ser Leu Ser Pro Phe Asp Pro
    1145            1150                1155

Ser Arg Leu Phe Gly Trp Gln Ser Ala Asn Thr Leu Ala Ile Gly
    1160            1165                1170

Asp Ala Trp Ser His Leu Pro His Phe Ser Ser Pro Asp Leu Val
    1175            1180                1185

Asn Lys Tyr Ala Ile Val Glu Arg Leu Asn Phe Ala Tyr Tyr Leu
    1190            1195                1200

His Asn Gly Arg Pro Ser Phe Ala Phe Gly Thr Phe Leu Val Gln
    1205            1210                1215

Glu Leu Ile Lys Ser Lys Thr Pro Lys Gln Leu Ile Gln Gln Val
    1220            1225                1230

Gly Asn Glu Ala Tyr Val Ile Gly Leu Ser Ser Phe His Ile Pro
    1235            1240                1245

Ser Ile Gly Ala Ala Cys Val Cys Phe Leu Glu Leu Leu Gly Leu
    1250            1255                1260

Asp Ser Leu Lys Leu Arg Val Asp Met Lys Val Ala Asn Ile Ile
    1265            1270                1275

Leu Ser Tyr Lys Cys Arg Asn Glu Asp Ala Gln Tyr Ser Phe Ile
    1280            1285                1290

Arg Glu Ser Val Ala Glu Lys Leu Ser Lys Leu Ala Asp Gly Glu
    1295            1300                1305

Lys Thr Thr Thr Glu Glu Leu Leu Val Leu Leu Glu Glu Gly Thr
    1310            1315                1320

Trp Asn Ser Ile Gln Gln Gln Glu Ile Lys Arg Leu Ser Ser Glu
    1325            1330                1335

Ser Ser Ser Gln Trp Ala Leu Val Val Gln Phe Cys Arg Leu His
    1340            1345                1350

Asn Met Lys Leu Ser Ile Ser Tyr Leu Arg Glu Cys Ala Lys Ala
    1355            1360                1365

Asn Asp Trp Leu Gln Phe Ile Ile His Ser Gln Leu His Asn Tyr
    1370            1375                1380

His Pro Ala Glu Val Lys Ser Leu Ile Gln Tyr Phe Ser Pro Val
    1385            1390                1395

Ile Gln Asp His Leu Arg Leu Ala Phe Glu Asn Leu Pro Ser Val
    1400            1405                1410

Pro Thr Ser Lys Met Asp Ser Asp Gln Val Cys Asn Lys Cys Pro
    1415            1420                1425

Gln Glu Leu Gln Gly Ser Lys Gln Glu Met Thr Asp Leu Phe Glu
    1430            1435                1440

Ile Leu Leu Gln Cys Ser Glu Glu Pro Asp Ser Trp His Trp Leu
    1445            1450                1455

Leu Val Glu Ala Val Lys Gln Gln Ala Pro Ile Leu Ser Val Leu
```

```
            1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860
```

```
Glu Thr Cys Glu Asn Arg Leu Asp Trp Lys Glu Gln Glu Ser Leu
    1865            1870                1875

Asn Phe Leu Ile Gly Arg Leu Leu Asp Asp Gly Cys Val His Glu
    1880            1885                1890

Ala Ser Arg Val Cys Arg Tyr Phe His Phe Tyr Asn Pro Asp Val
    1895            1900                1905

Ala Leu Val Leu His Cys Arg Ala Leu Ala Ser Gly Glu Ala Ser
    1910            1915                1920

Met Glu Asp Leu His Pro Glu Ile His Ala Leu Leu Gln Ser Ala
    1925            1930                1935

Glu Leu Leu Glu Glu Glu Ala Pro Asp Ile Pro Leu Arg Arg Val
    1940            1945                1950

His Ser Thr Ser Ser Leu Asp Ser Gln Lys Phe Val Thr Val Pro
    1955            1960                1965

Ser Ser Asn Glu Val Val Thr Asn Leu Glu Val Leu Thr Ser Lys
    1970            1975                1980

Cys Leu His Gly Lys Asn Tyr Cys Xaa
    1985            1990

<210> SEQ ID NO 160
<211> LENGTH: 2034
<212> TYPE: PRT
<213> ORGANISM: Homo sapiens
<220> FEATURE:
<221> NAME/KEY: misc_feature
<222> LOCATION: (2034)..(2034)
<223> OTHER INFORMATION: Xaa can be any naturally occurring amino acid

<400> SEQUENCE: 160

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220
```

```
Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
            245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
            290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
            325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
```

```
                        645                 650                 655
Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
                820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
            850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
                900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
            930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser  Leu Gln His Leu Leu  Tyr Val Tyr
            995                 1000                1005

Leu Asp Cys Tyr Lys Leu Ser  Pro Glu Asn Cys Pro  Phe Leu Glu
    1010                1015                1020

Lys Lys  Glu Leu His Glu Ala  His Pro Trp Phe Glu  Phe Leu Val
    1025                1030                1035

Gln Cys  Arg Gln Val Ala Ser  Asn Leu Thr Asp Pro  Lys Leu Ile
    1040                1045                1050

Phe Gln  Ala Ser Leu Ala Asn  Ala Gln Ile Leu Ile  Pro Thr Asn
    1055                1060                1065
```

-continued

```
Gln Ala Ser Val Ser Met Leu Leu Glu Gly His Thr Leu Leu
1070            1075            1080

Ala Leu Ala Thr Thr Met Tyr Ser Pro Gly Gly Val Ser Gln Val
1085            1090            1095

Val Gln Asn Glu Glu Asn Glu Asn Cys Leu Lys Lys Val Asp Pro
1100            1105            1110

Gln Leu Leu Lys Met Ala Leu Thr Pro Tyr Pro Lys Leu Lys Thr
1115            1120            1125

Ala Leu Phe Pro Gln Cys Thr Pro Pro Ser Val Leu Pro Ser Asp
1130            1135            1140

Ile Thr Ile Tyr His Leu Ile Gln Ser Leu Ser Pro Phe Asp Pro
1145            1150            1155

Ser Arg Leu Phe Gly Trp Gln Ser Ala Asn Thr Leu Ala Ile Gly
1160            1165            1170

Asp Ala Trp Ser His Leu Pro His Phe Ser Ser Pro Asp Leu Val
1175            1180            1185

Asn Lys Tyr Ala Ile Val Glu Arg Leu Asn Phe Ala Tyr Tyr Leu
1190            1195            1200

His Asn Gly Arg Pro Ser Phe Ala Phe Gly Thr Phe Leu Val Gln
1205            1210            1215

Glu Leu Ile Lys Ser Lys Thr Pro Lys Gln Leu Ile Gln Gln Val
1220            1225            1230

Gly Asn Glu Ala Tyr Val Ile Gly Leu Ser Ser Phe His Ile Pro
1235            1240            1245

Ser Ile Gly Ala Ala Cys Val Cys Phe Leu Glu Leu Leu Gly Leu
1250            1255            1260

Asp Ser Leu Lys Leu Arg Val Asp Met Lys Val Ala Asn Ile Ile
1265            1270            1275

Leu Ser Tyr Lys Cys Arg Asn Glu Asp Ala Gln Tyr Ser Phe Ile
1280            1285            1290

Arg Glu Ser Val Ala Glu Lys Leu Ser Lys Leu Ala Asp Gly Glu
1295            1300            1305

Lys Thr Thr Thr Glu Glu Leu Leu Val Leu Leu Glu Glu Gly Thr
1310            1315            1320

Trp Asn Ser Ile Gln Gln Gln Glu Ile Lys Arg Leu Ser Ser Glu
1325            1330            1335

Ser Ser Ser Gln Trp Ala Leu Val Val Gln Phe Cys Arg Leu His
1340            1345            1350

Asn Met Lys Leu Ser Ile Ser Tyr Leu Arg Glu Cys Ala Lys Ala
1355            1360            1365

Asn Asp Trp Leu Gln Phe Ile Ile His Ser Gln Leu His Asn Tyr
1370            1375            1380

His Pro Ala Glu Val Lys Ser Leu Ile Gly Tyr Phe Ser Pro Val
1385            1390            1395

Ile Gln Asp His Leu Arg Leu Ala Phe Glu Asn Leu Pro Ser Val
1400            1405            1410

Pro Thr Ser Lys Met Asp Ser Asp Gln Val Cys Asn Lys Cys Pro
1415            1420            1425

Gln Glu Leu Gln Gly Ser Lys Gln Glu Met Thr Asp Leu Phe Glu
1430            1435            1440

Ile Leu Leu Gln Cys Ser Glu Glu Pro Asp Ser Trp His Trp Leu
1445            1450            1455

Leu Val Glu Ala Val Lys Gln Gln Ala Pro Ile Leu Ser Val Leu
1460            1465            1470
```

```
Ala Ser Cys Leu Gln Gly Ala Ser Ala Ile Ser Cys Leu Cys Val
1475                1480                1485

Trp Ile Ile Thr Ser Val Glu Asp Asn Val Ala Thr Glu Ala Met
1490                1495                1500

Gly His Ile Gln Asp Ser Thr Glu Asp His Thr Trp Asn Leu Glu
1505                1510                1515

Asp Leu Ser Val Ile Trp Arg Thr Leu Leu Thr Arg Gln Lys Ser
1520                1525                1530

Lys Thr Leu Ile Arg Gly Phe Gln Leu Phe Phe Lys Asp Ser Pro
1535                1540                1545

Leu Leu Leu Val Met Glu Met Tyr Glu Leu Cys Met Phe Phe Arg
1550                1555                1560

Asn Tyr Lys Glu Ala Glu Ala Lys Leu Leu Glu Phe Gln Lys Ser
1565                1570                1575

Leu Glu Thr Leu Asn Thr Ala Ala Thr Lys Val His Pro Val Ile
1580                1585                1590

Pro Ala Met Trp Leu Glu Asp Gln Val Cys Phe Leu Leu Lys Leu
1595                1600                1605

Met Leu Gln Gln Cys Lys Thr Gln Tyr Glu Leu Gly Lys Leu Leu
1610                1615                1620

Gln Leu Phe Val Glu Arg Glu His Leu Phe Ser Asp Gly Pro Asp
1625                1630                1635

Val Lys Lys Leu Cys Ile Leu Cys Gln Ile Leu Lys Asp Thr Ser
1640                1645                1650

Ile Ala Ile Asn His Thr Ile Ile Thr Ser Tyr Ser Ile Glu Asn
1655                1660                1665

Leu Gln His Glu Cys Arg Ser Ile Leu Glu Arg Leu Gln Thr Asp
1670                1675                1680

Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
1700                1705                1710

Thr Leu Lys His Ile Glu Gln Trp Ser Leu Lys Gln Ala Arg Ile
1715                1720                1725

Asp Phe Trp Lys Lys Cys His Glu Asn Phe Lys Lys Asn Ser Ile
1730                1735                1740

Ser Ser Lys Ala Ala Ser Ser Phe Phe Ser Thr Gln Ala His Val
1745                1750                1755

Ala Cys Glu His Pro Thr Gly Trp Ser Ser Met Glu Glu Arg His
1760                1765                1770

Leu Leu Leu Thr Leu Ala Gly His Trp Leu Ala Gln Glu Asp Val
1775                1780                1785

Val Pro Leu Asp Lys Leu Glu Glu Leu Glu Lys Gln Ile Trp Leu
1790                1795                1800

Cys Arg Ile Thr Gln His Thr Leu Gly Arg Asn Gln Glu Glu Thr
1805                1810                1815

Glu Pro Arg Phe Ser Arg Gln Ile Ser Thr Ser Gly Glu Leu Ser
1820                1825                1830

Phe Asp Ser Leu Ala Ser Glu Phe Ser Phe Ser Lys Leu Ala Ala
1835                1840                1845

Leu Asn Thr Ser Lys Tyr Leu Glu Leu Asn Ser Leu Pro Ser Lys
1850                1855                1860

Glu Thr Cys Glu Asn Arg Leu Asp Trp Lys Glu Gln Glu Ser Leu
```

```
                    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Leu Tyr
    1985                1990                1995

Asp Leu Ala Lys Glu Leu Gly Cys Ser Tyr Thr Asp Val Ala Ala
    2000                2005                2010

Gln Asp Gly Glu Ala Met Leu Arg Lys Ile Leu Ala Ser Gln Gln
    2015                2020                2025

Pro Asp Arg Cys Lys Xaa
    2030

<210> SEQ ID NO 161
<211> LENGTH: 2172
<212> TYPE: PRT
<213> ORGANISM: Homo sapiens
<220> FEATURE:
<221> NAME/KEY: misc_feature
<222> LOCATION: (2172)..(2172)
<223> OTHER INFORMATION: Xaa can be any naturally occurring amino acid

<400> SEQUENCE: 161

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Asn Tyr Glu
                100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175
```

-continued

```
Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
        210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Pro Ala Lys Ile
                245                 250                 255

Ser Ser Phe Thr Ser Leu Lys Val Ser Gln Asp Leu Val Ala Val
            260                 265                 270

Ile Val Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605
```

-continued

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
              645                 650                 655

Phe Pro Trp Lys Leu Thr Asp Ala Ile Asp Glu Tyr Asp Val His Glu
              660                 665                 670

Asn Val Pro Lys Val Lys Glu Ser Asn Ile Trp Lys Lys Leu Ser Phe
              675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
              725                 730                 735

Asn Ile Lys Glu Ala Ser Glu Leu Leu Lys Asn Met Gly Phe Asp Val
              740                 745                 750

Lys Gly Gln Leu Leu Lys Ile Cys Phe Tyr Thr Thr Asn Lys Asn Ile
              755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
              805                 810                 815

Trp Ile Lys Glu Gln Asp Phe Phe Lys His Lys Ser Val Leu Asp Ser
              820                 825                 830

Phe Leu Lys Tyr Asp Cys Lys Asp Glu Phe Asn Lys Gln Asp His Arg
              835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
              885                 890                 895

Ile Leu Trp Ile Gly Glu Phe Gln Thr Gln His Ser Tyr Ala Ser Leu
              900                 905                 910

Gln Gln Asn Lys Trp Pro Leu Leu Thr Val Asp Val Ile Asn Gln Asn
              915                 920                 925

Thr Ser Cys Asn Asn Tyr Met Arg Asn Glu Ile Leu Asp Lys Leu Ala
              930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
              965                 970                 975

Val Gln Asn Tyr Lys Thr Lys Glu Gly Trp Asp Phe His Ser Gln Phe
              980                 985                 990

Ile Leu Tyr Cys Leu Glu His Ser Leu Gln His Leu Leu Tyr Val Tyr
              995                1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val

-continued

```
            1025                1030                1035
Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320

Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
    1340                1345                1350

Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425
```

```
Gln Glu Leu Gln Gly Ser Lys Gln Glu Met Thr Asp Leu Phe Glu
1430                1435                1440

Ile Leu Leu Gln Cys Ser Glu Glu Pro Asp Ser Trp His Trp Leu
1445                1450                1455

Leu Val Glu Ala Val Lys Gln Gln Ala Pro Ile Leu Ser Val Leu
1460                1465                1470

Ala Ser Cys Leu Gln Gly Ala Ser Ala Ile Ser Cys Leu Cys Val
1475                1480                1485

Trp Ile Ile Thr Ser Val Glu Asp Asn Val Ala Thr Glu Ala Met
1490                1495                1500

Gly His Ile Gln Asp Ser Thr Glu Asp His Thr Trp Asn Leu Glu
1505                1510                1515

Asp Leu Ser Val Ile Trp Arg Thr Leu Leu Thr Arg Gln Lys Ser
1520                1525                1530

Lys Thr Leu Ile Arg Gly Phe Gln Leu Phe Phe Lys Asp Ser Pro
1535                1540                1545

Leu Leu Leu Val Met Glu Met Tyr Glu Leu Cys Met Phe Phe Arg
1550                1555                1560

Asn Tyr Lys Glu Ala Glu Ala Lys Leu Leu Glu Phe Gln Lys Ser
1565                1570                1575

Leu Glu Thr Leu Asn Thr Ala Ala Thr Lys Val His Pro Val Ile
1580                1585                1590

Pro Ala Met Trp Leu Glu Asp Gln Val Cys Phe Leu Leu Lys Leu
1595                1600                1605

Met Leu Gln Gln Cys Lys Thr Gln Tyr Glu Leu Gly Lys Leu Leu
1610                1615                1620

Gln Leu Phe Val Glu Arg Glu His Leu Phe Ser Asp Gly Pro Asp
1625                1630                1635

Val Lys Lys Leu Cys Ile Leu Cys Gln Ile Leu Lys Asp Thr Ser
1640                1645                1650

Ile Ala Ile Asn His Thr Ile Ile Thr Ser Tyr Ser Ile Glu Asn
1655                1660                1665

Leu Gln His Glu Cys Arg Ser Ile Leu Glu Arg Leu Gln Thr Asp
1670                1675                1680

Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
1700                1705                1710

Thr Leu Lys His Ile Glu Gln Trp Ser Leu Lys Gln Ala Arg Ile
1715                1720                1725

Asp Phe Trp Lys Lys Cys His Glu Asn Phe Lys Lys Asn Ser Ile
1730                1735                1740

Ser Ser Lys Ala Ala Ser Ser Phe Phe Ser Thr Gln Ala His Val
1745                1750                1755

Ala Cys Glu His Pro Thr Gly Trp Ser Ser Met Glu Glu Arg His
1760                1765                1770

Leu Leu Leu Thr Leu Ala Gly His Trp Leu Ala Gln Glu Asp Val
1775                1780                1785

Val Pro Leu Asp Lys Leu Glu Leu Glu Lys Gln Ile Trp Leu
1790                1795                1800

Cys Arg Ile Thr Gln His Thr Leu Gly Arg Asn Gln Glu Glu Thr
1805                1810                1815

Glu Pro Arg Phe Ser Arg Gln Ile Ser Thr Ser Gly Glu Leu Ser
1820                1825                1830
```

```
Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Glu Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Leu Tyr
    1985                1990                1995

Asp Leu Ala Lys Glu Leu Gly Cys Ser Tyr Thr Asp Val Ala Ala
    2000                2005                2010

Gln Asp Gly Glu Ala Met Leu Arg Lys Ile Leu Ala Ser Gln Gln
    2015                2020                2025

Pro Asp Arg Cys Lys Arg Ala Gln Ala Phe Ile Ser Thr Gln Gly
    2030                2035                2040

Leu Lys Pro Asp Thr Val Ala Glu Leu Val Ala Glu Glu Val Thr
    2045                2050                2055

Arg Glu Leu Leu Thr Ser Ser Gln Gly Thr Gly His Lys Gln Met
    2060                2065                2070

Phe Asn Pro Thr Glu Glu Ser Gln Thr Phe Leu Gln Leu Thr Thr
    2075                2080                2085

Leu Cys Gln Asp Arg Thr Leu Val Gly Met Lys Leu Leu Asp Lys
    2090                2095                2100

Ile Ser Ser Val Pro His Gly Glu Leu Ser Cys Thr Thr Glu Leu
    2105                2110                2115

Leu Ile Leu Ala His His Cys Phe Thr Leu Thr Cys His Met Glu
    2120                2125                2130

Gly Ile Ile Arg Val Leu Gln Ala Ala His Met Leu Thr Asp Asn
    2135                2140                2145

His Leu Pro Pro Val Arg Ser Met Gly Trp Trp Tyr Gly Ser Ser
    2150                2155                2160

Leu Ala Leu Glu Gly Thr Thr Arg Xaa
    2165                2170

<210> SEQ ID NO 162
<211> LENGTH: 2260
<212> TYPE: PRT
<213> ORGANISM: Homo sapiens
<220> FEATURE:
<221> NAME/KEY: misc_feature
<222> LOCATION: (2260)..(2260)
<223> OTHER INFORMATION: Xaa can be any naturally occurring amino acid
```

<400> SEQUENCE: 162

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

```
His Ile Ser Glu Gln Glu Pro Ile Glu Leu Lys Cys Val Ser Val
                420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
        450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845
```

```
Ile Val Leu Asn Trp Ala Leu Trp Trp Asp Gln Leu Thr Gln Glu Ser
850             855             860

Ile Leu Leu Pro Arg Ile Ser Pro Glu Glu Tyr Lys Ser Tyr Ser Pro
865             870             875             880

Glu Ala Leu Trp Arg Tyr Leu Thr Ala Arg His Asp Trp Leu Asn Ile
                885             890             895

Ile Leu Trp Ile Gly Glu Phe Gln Thr Gln His Ser Tyr Ala Ser Leu
            900             905             910

Gln Gln Asn Lys Trp Pro Leu Leu Thr Val Asp Val Ile Asn Gln Asn
            915             920             925

Thr Ser Cys Asn Asn Tyr Met Arg Asn Glu Ile Leu Asp Lys Leu Ala
        930             935             940

Arg Asn Gly Val Phe Leu Ala Ser Glu Leu Glu Asp Phe Glu Cys Phe
945             950             955             960

Leu Leu Arg Leu Ser Arg Ile Gly Gly Val Ile Gln Asp Thr Leu Pro
                965             970             975

Val Gln Asn Tyr Lys Thr Lys Glu Gly Trp Asp Phe His Ser Gln Phe
            980             985             990

Ile Leu Tyr Cys Leu Glu His Ser Leu Gln His Leu Leu Tyr Val Tyr
            995             1000            1005

Leu Asp Cys Tyr Lys Leu Ser Pro Glu Asn Cys Pro Phe Leu Glu
    1010            1015            1020

Lys Lys Glu Leu His Glu Ala His Pro Trp Phe Glu Phe Leu Val
    1025            1030            1035

Gln Cys Arg Gln Val Ala Ser Asn Leu Thr Asp Pro Lys Leu Ile
    1040            1045            1050

Phe Gln Ala Ser Leu Ala Asn Ala Gln Ile Leu Ile Pro Thr Asn
    1055            1060            1065

Gln Ala Ser Val Ser Ser Met Leu Leu Glu Gly His Thr Leu Leu
    1070            1075            1080

Ala Leu Ala Thr Thr Met Tyr Ser Pro Gly Gly Val Ser Gln Val
    1085            1090            1095

Val Gln Asn Glu Glu Asn Glu Asn Cys Leu Lys Lys Val Asp Pro
    1100            1105            1110

Gln Leu Leu Lys Met Ala Leu Thr Pro Tyr Pro Lys Leu Lys Thr
    1115            1120            1125

Ala Leu Phe Pro Gln Cys Thr Pro Pro Ser Val Leu Pro Ser Asp
    1130            1135            1140

Ile Thr Ile Tyr His Leu Ile Gln Ser Leu Ser Pro Phe Asp Pro
    1145            1150            1155

Ser Arg Leu Phe Gly Trp Gln Ser Ala Asn Thr Leu Ala Ile Gly
    1160            1165            1170

Asp Ala Trp Ser His Leu Pro His Phe Ser Ser Pro Asp Leu Val
    1175            1180            1185

Asn Lys Tyr Ala Ile Val Glu Arg Leu Asn Phe Ala Tyr Tyr Leu
    1190            1195            1200

His Asn Gly Arg Pro Ser Phe Ala Phe Gly Thr Phe Leu Val Gln
    1205            1210            1215

Glu Leu Ile Lys Ser Lys Thr Pro Lys Gln Leu Ile Gln Gln Val
    1220            1225            1230

Gly Asn Glu Ala Tyr Val Ile Gly Leu Ser Ser Phe His Ile Pro
    1235            1240            1245

Ser Ile Gly Ala Ala Cys Val Cys Phe Leu Glu Leu Leu Gly Leu
```

```
                    1250                    1255                    1260
Asp Ser Leu Lys Leu Arg Val Asp Met Lys Val Ala Asn Ile Ile
        1265                    1270                    1275
Leu Ser Tyr Lys Cys Arg Asn Glu Asp Ala Gln Tyr Ser Phe Ile
        1280                    1285                    1290
Arg Glu Ser Val Ala Glu Lys Leu Ser Lys Leu Ala Asp Gly Glu
        1295                    1300                    1305
Lys Thr Thr Thr Glu Glu Leu Leu Val Leu Leu Glu Glu Gly Thr
        1310                    1315                    1320
Trp Asn Ser Ile Gln Gln Gln Glu Ile Lys Arg Leu Ser Ser Glu
        1325                    1330                    1335
Ser Ser Ser Gln Trp Ala Leu Val Val Gln Phe Cys Arg Leu His
        1340                    1345                    1350
Asn Met Lys Leu Ser Ile Ser Tyr Leu Arg Glu Cys Ala Lys Ala
        1355                    1360                    1365
Asn Asp Trp Leu Gln Phe Ile Ile His Ser Gln Leu His Asn Tyr
        1370                    1375                    1380
His Pro Ala Glu Val Lys Ser Leu Ile Gln Tyr Phe Ser Pro Val
        1385                    1390                    1395
Ile Gln Asp His Leu Arg Leu Ala Phe Glu Asn Leu Pro Ser Val
        1400                    1405                    1410
Pro Thr Ser Lys Met Asp Ser Asp Gln Val Cys Asn Lys Cys Pro
        1415                    1420                    1425
Gln Glu Leu Gln Gly Ser Lys Gln Glu Met Thr Asp Leu Phe Glu
        1430                    1435                    1440
Ile Leu Leu Gln Cys Ser Glu Glu Pro Asp Ser Trp His Trp Leu
        1445                    1450                    1455
Leu Val Glu Ala Val Lys Gln Gln Ala Pro Ile Leu Ser Val Leu
        1460                    1465                    1470
Ala Ser Cys Leu Gln Gly Ala Ser Ala Ile Ser Cys Leu Cys Val
        1475                    1480                    1485
Trp Ile Ile Thr Ser Val Glu Asp Asn Val Ala Thr Glu Ala Met
        1490                    1495                    1500
Gly His Ile Gln Asp Ser Thr Glu Asp His Thr Trp Asn Leu Glu
        1505                    1510                    1515
Asp Leu Ser Val Ile Trp Arg Thr Leu Leu Thr Arg Gln Lys Ser
        1520                    1525                    1530
Lys Thr Leu Ile Arg Gly Phe Gln Leu Phe Phe Lys Asp Ser Pro
        1535                    1540                    1545
Leu Leu Leu Val Met Glu Met Tyr Glu Leu Cys Met Phe Phe Arg
        1550                    1555                    1560
Asn Tyr Lys Glu Ala Glu Ala Lys Leu Leu Glu Phe Gln Lys Ser
        1565                    1570                    1575
Leu Glu Thr Leu Asn Thr Ala Ala Thr Lys Val His Pro Val Ile
        1580                    1585                    1590
Pro Ala Met Trp Leu Glu Asp Gln Val Cys Phe Leu Leu Lys Leu
        1595                    1600                    1605
Met Leu Gln Gln Cys Lys Thr Gln Tyr Glu Leu Gly Lys Leu Leu
        1610                    1615                    1620
Gln Leu Phe Val Glu Arg Glu His Leu Phe Ser Asp Gly Pro Asp
        1625                    1630                    1635
Val Lys Lys Leu Cys Ile Leu Cys Gln Ile Leu Lys Asp Thr Ser
        1640                    1645                    1650
```

```
Ile Ala Ile Asn His Thr Ile Ile Thr Ser Tyr Ser Ile Glu Asn
1655                1660                1665

Leu Gln His Glu Cys Arg Ser Ile Leu Glu Arg Leu Gln Thr Asp
1670                1675                1680

Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
1700                1705                1710

Thr Leu Lys His Ile Glu Gln Trp Ser Leu Lys Gln Ala Arg Ile
1715                1720                1725

Asp Phe Trp Lys Lys Cys His Glu Asn Phe Lys Lys Asn Ser Ile
1730                1735                1740

Ser Ser Lys Ala Ala Ser Ser Phe Phe Ser Thr Gln Ala His Val
1745                1750                1755

Ala Cys Glu His Pro Thr Gly Trp Ser Ser Met Glu Glu Arg His
1760                1765                1770

Leu Leu Leu Thr Leu Ala Gly His Trp Leu Ala Gln Glu Asp Val
1775                1780                1785

Val Pro Leu Asp Lys Leu Glu Glu Leu Glu Lys Gln Ile Trp Leu
1790                1795                1800

Cys Arg Ile Thr Gln His Thr Leu Gly Arg Asn Gln Glu Glu Thr
1805                1810                1815

Glu Pro Arg Phe Ser Arg Gln Ile Ser Thr Ser Gly Glu Leu Ser
1820                1825                1830

Phe Asp Ser Leu Ala Ser Glu Phe Ser Phe Ser Lys Leu Ala Ala
1835                1840                1845

Leu Asn Thr Ser Lys Tyr Leu Glu Leu Asn Ser Leu Pro Ser Lys
1850                1855                1860

Glu Thr Cys Glu Asn Arg Leu Asp Trp Lys Glu Gln Glu Ser Leu
1865                1870                1875

Asn Phe Leu Ile Gly Arg Leu Leu Asp Asp Gly Cys Val His Glu
1880                1885                1890

Ala Ser Arg Val Cys Arg Tyr Phe His Phe Tyr Asn Pro Asp Val
1895                1900                1905

Ala Leu Val Leu His Cys Arg Ala Leu Ala Ser Gly Glu Ala Ser
1910                1915                1920

Met Glu Asp Leu His Pro Glu Ile His Ala Leu Leu Gln Ser Ala
1925                1930                1935

Glu Leu Leu Glu Glu Glu Ala Pro Asp Ile Pro Leu Arg Arg Val
1940                1945                1950

His Ser Thr Ser Ser Leu Asp Ser Gln Lys Phe Val Thr Val Pro
1955                1960                1965

Ser Ser Asn Glu Val Val Thr Asn Leu Glu Val Leu Thr Ser Lys
1970                1975                1980

Cys Leu His Gly Lys Asn Tyr Cys Arg Gln Val Leu Cys Leu Tyr
1985                1990                1995

Asp Leu Ala Lys Glu Leu Gly Cys Ser Tyr Thr Asp Val Ala Ala
2000                2005                2010

Gln Asp Gly Glu Ala Met Leu Arg Lys Ile Leu Ala Ser Gln Gln
2015                2020                2025

Pro Asp Arg Cys Lys Arg Ala Gln Ala Phe Ile Ser Thr Gln Gly
2030                2035                2040

Leu Lys Pro Asp Thr Val Ala Glu Leu Val Ala Glu Glu Val Thr
2045                2050                2055
```

```
Arg Glu  Leu Leu Thr Ser  Ser Gln Gly Thr Gly  His Lys Gln Met
    2060         2065              2070

Phe Asn  Pro Thr Glu Glu  Ser Gln Thr Phe Leu  Gln Leu Thr Thr
    2075         2080              2085

Leu Cys  Gln Asp Arg Thr  Leu Val Gly Met Lys  Leu Leu Asp Lys
    2090         2095              2100

Ile Ser  Ser Val Pro His  Gly Glu Leu Ser Cys  Thr Thr Glu Leu
    2105         2110              2115

Leu Ile  Leu Ala His His  Cys Phe Thr Leu Thr  Cys His Met Glu
    2120         2125              2130

Gly Ile  Ile Arg Val Leu  Gln Ala Ala His Met  Leu Thr Asp Asn
    2135         2140              2145

His Leu  Ala Pro Ser Glu  Glu Tyr Gly Leu Val  Val Arg Leu Leu
    2150         2155              2160

Thr Gly  Ile Gly Arg Tyr  Asn Glu Met Thr Tyr  Ile Phe Asp Leu
    2165         2170              2175

Leu His  Lys Lys His Tyr  Phe Glu Val Leu Met  Arg Lys Lys Leu
    2180         2185              2190

Asp Pro  Ser Gly Thr Leu  Lys Thr Ala Leu Leu  Asp Tyr Ile Lys
    2195         2200              2205

Arg Cys  Arg Pro Gly Asp  Ser Glu Lys His Asn  Met Ile Ala Leu
    2210         2215              2220

Cys Phe  Ser Met Cys Arg  Glu Ile Gly Glu Asn  His Glu Ala Ala
    2225         2230              2235

Ala Arg  Ile Gln Leu Lys  Leu Ser Leu Ser Pro  Gly Arg Thr Ala
    2240         2245              2250

Ser Arg  Met Gly Thr Ser  Xaa
    2255         2260

<210> SEQ ID NO 163
<211> LENGTH: 2338
<212> TYPE: PRT
<213> ORGANISM: Homo sapiens
<220> FEATURE:
<221> NAME/KEY: misc_feature
<222> LOCATION: (2338)..(2338)
<223> OTHER INFORMATION: Xaa can be any naturally occurring amino acid

<400> SEQUENCE: 163

Met Ala  Ala Glu Glu Gly  Val Ala Ser Ala Ala  Ser Ala Gly Gly Ser
1             5                   10                  15

Trp Gly  Thr Ala Ala Met  Gly Arg Val Leu Pro  Met Leu Leu Val Pro
             20                  25                  30

Val Pro  Ala Glu Ala Met  Gly Gln Leu Gly Ser  Arg Ala Gln Leu Arg
         35                  40                  45

Thr Gln  Pro Glu Ala Leu  Gly Ser Leu Thr Ala  Ala Gly Ser Leu Gln
    50                   55                  60

Val Leu  Ser Leu Thr Pro  Gly Ser Arg Gly Gly  Gly Arg Cys Cys Leu
65                   70                  75                  80

Glu Gly  Pro Phe Trp His  Phe Leu Trp Glu Asp  Ser Arg Asn Ser Ser
                 85                  90                  95

Thr Pro  Thr Glu Lys Pro  Lys Leu Leu Ala Leu  Gly Glu Asn Tyr Glu
             100                 105                 110

Leu Leu  Ile Tyr Glu Phe  Asn Leu Lys Asp Gly  Arg Cys Asp Ala Thr
         115                 120                 125

Ile Leu  Tyr Ser Cys Ser  Arg Glu Ala Leu Gln  Lys Leu Ile Asp Asp
```

-continued

```
            130                 135                 140
Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                    180                 185                 190

Leu Pro Leu Pro Ala Gln Ala Val Asp Met Ile Ile Asp Thr Gln Leu
                195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Asn Ser Ala Val Ala Leu Asn Leu Asn Leu Tyr
                275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Pro Ile Glu Leu Lys Cys Val Ser Val
                420                 425                 430

Thr Gly Phe Thr Ala Leu Phe Thr Trp Glu Val Glu Arg Met Gly Tyr
                435                 440                 445

Thr Ile Thr Leu Trp Asp Leu Glu Thr Gln Gly Met Gln Cys Ser Ser
                450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
                515                 520                 525

Pro Ile His Ala Leu Glu Ala Gly Ile Glu Asn Arg Gln Leu Asp Thr
                530                 535                 540

Val Asn Phe Phe Leu Lys Ser Lys Glu Asn Leu Phe Asn Pro Ser Ser
545                 550                 555                 560
```

-continued

```
Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
    850                 855                 860

Ile Leu Leu Pro Arg Ile Ser Pro Glu Gly Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990
```

-continued

```
Ile Leu Tyr Cys Leu Glu His Ser Leu Gln His Leu Leu Tyr Val Tyr
        995                 1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320

Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
    1340                1345                1350

Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
```

```
                1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425

Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785
```

```
Val Pro Leu Asp Lys Leu Glu Glu Leu Glu Lys Gln Ile Trp Leu
1790            1795                1800

Cys Arg Ile Thr Gln His Thr Leu Gly Arg Asn Gln Glu Glu Thr
1805            1810                1815

Glu Pro Arg Phe Ser Arg Gln Ile Ser Thr Ser Gly Glu Leu Ser
1820            1825                1830

Phe Asp Ser Leu Ala Ser Glu Phe Ser Phe Ser Lys Leu Ala Ala
1835            1840                1845

Leu Asn Thr Ser Lys Tyr Leu Glu Leu Asn Ser Leu Pro Ser Lys
1850            1855                1860

Glu Thr Cys Glu Asn Arg Leu Asp Trp Lys Glu Gln Glu Ser Leu
1865            1870                1875

Asn Phe Leu Ile Gly Arg Leu Leu Asp Asp Gly Cys Val His Glu
1880            1885                1890

Ala Ser Arg Val Cys Arg Tyr Phe His Phe Tyr Asn Pro Asp Val
1895            1900                1905

Ala Leu Val Leu His Cys Arg Ala Leu Ala Ser Gly Glu Ala Ser
1910            1915                1920

Met Glu Asp Leu His Pro Glu Ile His Ala Leu Leu Gln Ser Ala
1925            1930                1935

Glu Leu Leu Glu Glu Glu Ala Pro Asp Ile Pro Leu Arg Arg Val
1940            1945                1950

His Ser Thr Ser Ser Leu Asp Ser Gln Lys Phe Val Thr Val Pro
1955            1960                1965

Ser Ser Asn Glu Val Val Thr Asn Leu Glu Val Leu Thr Ser Lys
1970            1975                1980

Cys Leu His Gly Lys Asn Tyr Cys Arg Gln Val Leu Cys Leu Tyr
1985            1990                1995

Asp Leu Ala Lys Glu Leu Gly Cys Ser Tyr Thr Asp Val Ala Ala
2000            2005                2010

Gln Asp Gly Glu Ala Met Leu Arg Lys Ile Leu Ala Ser Gln Gln
2015            2020                2025

Pro Asp Arg Cys Lys Arg Ala Gln Ala Phe Ile Ser Thr Gln Gly
2030            2035                2040

Leu Lys Pro Asp Thr Val Ala Glu Leu Val Ala Glu Glu Val Thr
2045            2050                2055

Arg Glu Leu Leu Thr Ser Ser Gln Gly Thr Gly His Lys Gln Met
2060            2065                2070

Phe Asn Pro Thr Glu Glu Ser Gln Thr Phe Leu Gln Leu Thr Thr
2075            2080                2085

Leu Cys Gln Asp Arg Thr Leu Val Gly Met Lys Leu Leu Asp Lys
2090            2095                2100

Ile Ser Ser Val Pro His Gly Glu Leu Ser Cys Thr Thr Glu Leu
2105            2110                2115

Leu Ile Leu Ala His His Cys Phe Thr Leu Thr Cys His Met Glu
2120            2125                2130

Gly Ile Ile Arg Val Leu Gln Ala Ala His Met Leu Thr Asp Asn
2135            2140                2145

His Leu Ala Pro Ser Glu Glu Tyr Gly Leu Val Val Arg Leu Leu
2150            2155                2160

Thr Gly Ile Gly Arg Tyr Asn Glu Met Thr Tyr Ile Phe Asp Leu
2165            2170                2175

Leu His Lys Lys His Tyr Phe Glu Val Leu Met Arg Lys Lys Leu
2180            2185                2190
```

-continued

```
Asp Pro Ser Gly Thr Leu Lys Thr Ala Leu Leu Asp Tyr Ile Lys
    2195                2200                2205

Arg Cys Arg Pro Gly Asp Ser Glu Lys His Asn Met Ile Ala Leu
    2210                2215                2220

Cys Phe Ser Met Cys Arg Glu Ile Gly Glu Asn His Glu Ala Ala
    2225                2230                2235

Ala Arg Ile Gln Leu Lys Leu Ile Glu Ser Gln Pro Trp Glu Asp
    2240                2245                2250

Ser Leu Lys Asp Gly His Gln Leu Lys Gln Leu Leu Lys Ala
    2255                2260                2265

Leu Thr Leu Met Leu Asp Ala Ala Glu Leu Cys Gln Gly Leu Leu
    2270                2275                2280

Cys Ala Thr Gly Pro Ala Leu Ser Ala Ala His Gln Val Asp Asn
    2285                2290                2295

Ser Ala Asp Ser Leu Ser Glu His Trp Pro Glu His Asn Ala His
    2300                2305                2310

Gln Leu Gly Pro Pro Gln Ala Asp Gly Leu Tyr Ser Gly Pro Thr
    2315                2320                2325

Ser Val Leu Pro Gly Phe Tyr Cys Gly Xaa
    2330                2335
```

<210> SEQ ID NO 164
<211> LENGTH: 2349
<212> TYPE: PRT
<213> ORGANISM: Homo sapiens
<220> FEATURE:
<221> NAME/KEY: misc_feature
<222> LOCATION: (2349)..(2349)
<223> OTHER INFORMATION: Xaa can be any naturally occurring amino acid

<400> SEQUENCE: 164

```
Met Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
                35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
```

-continued

```
            195                 200                 205
Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
        245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
            325                 330                 335

Ser Trp Lys Ala Gln Leu Ser Ser Leu Asn Glu Thr Ile Lys Asn Ser
        340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
        420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
        500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
        580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
        610                 615                 620
```

```
Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
        690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
        850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
        930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
            995                 1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050
```

```
Phe Gln Ala Ser Leu Ala Asn Ala Gln Ile Leu Ile Pro Thr Asn
    1055                1060                1065
Gln Ala Ser Val Ser Ser Met Leu Leu Glu Gly His Thr Leu Leu
    1070                1075                1080
Ala Leu Ala Thr Thr Met Tyr Ser Pro Gly Gly Val Ser Gln Val
    1085                1090                1095
Val Gln Asn Glu Glu Asn Glu Asn Cys Leu Lys Lys Val Asp Pro
    1100                1105                1110
Gln Leu Leu Lys Met Ala Leu Thr Pro Tyr Pro Lys Leu Lys Thr
    1115                1120                1125
Ala Leu Phe Pro Gln Cys Thr Pro Pro Ser Val Leu Pro Ser Asp
    1130                1135                1140
Ile Thr Ile Tyr His Leu Ile Gln Ser Leu Ser Pro Phe Asp Pro
    1145                1150                1155
Ser Arg Leu Phe Gly Trp Gln Ser Ala Asn Thr Leu Ala Ile Gly
    1160                1165                1170
Asp Ala Trp Ser His Leu Pro His Phe Ser Ser Pro Asp Leu Val
    1175                1180                1185
Asn Lys Tyr Ala Ile Val Glu Arg Leu Asn Phe Ala Tyr Tyr Leu
    1190                1195                1200
His Asn Gly Arg Pro Ser Phe Ala Phe Gly Thr Phe Leu Val Gln
    1205                1210                1215
Glu Leu Ile Lys Ser Lys Thr Pro Lys Gln Leu Ile Gln Gln Val
    1220                1225                1230
Gly Asn Glu Ala Tyr Val Ile Gly Leu Ser Ser Phe His Ile Pro
    1235                1240                1245
Ser Ile Gly Ala Ala Cys Val Cys Phe Leu Glu Leu Leu Gly Leu
    1250                1255                1260
Asp Ser Leu Lys Leu Arg Val Asp Met Lys Val Ala Asn Ile Ile
    1265                1270                1275
Leu Ser Tyr Lys Cys Arg Asn Glu Asp Ala Gln Tyr Ser Phe Ile
    1280                1285                1290
Arg Glu Ser Val Ala Glu Lys Leu Ser Lys Leu Ala Asp Gly Glu
    1295                1300                1305
Lys Thr Thr Thr Glu Glu Leu Leu Val Leu Leu Glu Glu Gly Thr
    1310                1315                1320
Trp Asn Ser Ile Gln Gln Gln Glu Ile Lys Arg Leu Ser Ser Glu
    1325                1330                1335
Ser Ser Ser Gln Trp Ala Leu Val Val Gln Phe Cys Arg Leu His
    1340                1345                1350
Asn Met Lys Leu Ser Ile Ser Tyr Leu Arg Glu Cys Ala Lys Ala
    1355                1360                1365
Asn Asp Trp Leu Gln Phe Ile Ile His Ser Gln Leu His Asn Tyr
    1370                1375                1380
His Pro Ala Glu Val Lys Ser Leu Ile Gln Tyr Phe Ser Pro Val
    1385                1390                1395
Ile Gln Asp His Leu Arg Leu Ala Phe Glu Asn Leu Pro Ser Val
    1400                1405                1410
Pro Thr Ser Lys Met Asp Ser Asp Gln Val Cys Asn Lys Cys Pro
    1415                1420                1425
Gln Glu Leu Gln Gly Ser Lys Gln Glu Met Thr Asp Leu Phe Glu
    1430                1435                1440
Ile Leu Leu Gln Cys Ser Glu Glu Pro Asp Ser Trp His Trp Leu
```

-continued

```
              1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845
```

-continued

```
Leu Asn Thr Ser Lys Tyr Leu Glu Leu Asn Ser Leu Pro Ser Lys
    1850            1855            1860

Glu Thr Cys Glu Asn Arg Leu Asp Trp Lys Glu Gln Glu Ser Leu
    1865            1870            1875

Asn Phe Leu Ile Gly Arg Leu Leu Asp Asp Gly Cys Val His Glu
    1880            1885            1890

Ala Ser Arg Val Cys Arg Tyr Phe His Phe Tyr Asn Pro Asp Val
    1895            1900            1905

Ala Leu Val Leu His Cys Arg Ala Leu Ala Ser Gly Glu Ala Ser
    1910            1915            1920

Met Glu Asp Leu His Pro Glu Ile His Ala Leu Leu Gln Ser Ala
    1925            1930            1935

Glu Leu Leu Glu Glu Glu Ala Pro Asp Ile Pro Leu Arg Arg Val
    1940            1945            1950

His Ser Thr Ser Ser Leu Asp Ser Gln Lys Phe Val Thr Val Pro
    1955            1960            1965

Ser Ser Asn Glu Val Val Thr Asn Leu Glu Val Leu Thr Ser Lys
    1970            1975            1980

Cys Leu His Gly Lys Asn Tyr Cys Arg Gln Val Leu Cys Leu Tyr
    1985            1990            1995

Asp Leu Ala Lys Glu Leu Gly Cys Ser Tyr Thr Asp Val Ala Ala
    2000            2005            2010

Gln Asp Gly Glu Ala Met Leu Arg Lys Ile Leu Ala Ser Gln Gln
    2015            2020            2025

Pro Asp Arg Cys Lys Arg Ala Gln Ala Phe Ile Ser Thr Gln Gly
    2030            2035            2040

Leu Lys Pro Asp Thr Val Ala Glu Leu Val Ala Glu Glu Val Thr
    2045            2050            2055

Arg Glu Leu Leu Thr Ser Ser Gln Gly Thr Gly His Lys Gln Met
    2060            2065            2070

Phe Asn Pro Thr Glu Glu Ser Gln Thr Phe Leu Gln Leu Thr Thr
    2075            2080            2085

Leu Cys Gln Asp Arg Thr Leu Val Gly Met Lys Leu Leu Asp Lys
    2090            2095            2100

Ile Ser Ser Val Pro His Gly Glu Leu Ser Cys Thr Thr Glu Leu
    2105            2110            2115

Leu Ile Leu Ala His His Cys Phe Thr Leu Thr Cys His Met Glu
    2120            2125            2130

Gly Ile Ile Arg Val Leu Gln Ala Ala His Met Leu Thr Asp Asn
    2135            2140            2145

His Leu Ala Pro Ser Glu Glu Tyr Gly Leu Val Val Arg Leu Leu
    2150            2155            2160

Thr Gly Ile Gly Arg Tyr Asn Glu Met Thr Tyr Ile Phe Asp Leu
    2165            2170            2175

Leu His Lys Lys His Tyr Phe Glu Val Leu Met Arg Lys Lys Leu
    2180            2185            2190

Asp Pro Ser Gly Thr Leu Lys Thr Ala Leu Leu Asp Tyr Ile Lys
    2195            2200            2205

Arg Cys Arg Pro Gly Asp Ser Glu Lys His Asn Met Ile Ala Leu
    2210            2215            2220

Cys Phe Ser Met Cys Arg Glu Ile Gly Glu Asn His Glu Ala Ala
    2225            2230            2235

Ala Arg Ile Gln Leu Lys Leu Ile Glu Ser Gln Pro Trp Glu Asp
    2240            2245            2250
```

```
Ser Leu Lys Asp Gly His Gln Leu Lys Gln Leu Leu Lys Ala
    2255            2260                2265

Leu Thr Leu Met Leu Asp Ala Ala Glu Ser Tyr Ala Lys Asp Ser
    2270            2275                2280

Cys Val Arg Gln Ala Gln His Cys Gln Arg Leu Thr Lys Leu Ile
    2285            2290                2295

Thr Leu Gln Ile His Phe Leu Asn Thr Gly Gln Asn Thr Met Leu
    2300            2305                2310

Ile Asn Leu Gly Arg His Lys Leu Met Asp Cys Ile Leu Ala Leu
    2315            2320                2325

Pro Arg Phe Tyr Gln Ala Ser Ile Val Ala Glu Ala Tyr Asp Phe
    2330            2335                2340

Cys Ser Arg Leu Gly Xaa
    2345

<210> SEQ ID NO 165
<211> LENGTH: 2443
<212> TYPE: PRT
<213> ORGANISM: homo sapiens

<400> SEQUENCE: 165

Met Ala Ala Glu Glu Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
                35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                    85                  90                  95

Thr Pro Thr Glu Lys Pro Lys Leu Leu Ala Leu Gly Asn Tyr Glu
                100                 105                 110

Leu Leu Ile Tyr Glu Phe Asn Leu Lys Asp Gly Arg Cys Asp Ala Thr
                115                 120                 125

Ile Leu Tyr Ser Cys Ser Arg Glu Ala Leu Gln Lys Leu Ile Asp Asp
                130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                    165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
                195                 200                 205

Cys Arg Gly Ile Leu Phe Val Leu Ser Ser Leu Gly Trp Ile Tyr Ile
                210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                    245                 250                 255

Ser Ser Phe Thr Ser Leu Lys Val Ser Gln Asp Leu Asp Val Ala Val
                    260                 265                 270
```

```
Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
        290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
        370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
        450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
        530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Pro Gln Ser Lys His Phe Ser Glu
            595                 600                 605

Gln Leu Leu Asn Leu Thr Leu Ser Phe Leu Asn Gln Ile Lys Glu
        610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
```

```
            690             695             700
Gln Thr Phe Phe Arg Ile Asp Ser His Ser Ala Gln Lys Leu Glu Glu
705             710             715             720

Leu Ile Gly Ile Gly Leu Asn Leu Val Phe Asp Asn Leu Lys Lys Asn
            725             730             735

Asn Ile Lys Glu Ala Ser Glu Leu Leu Lys Asn Met Gly Phe Asp Val
            740             745             750

Lys Gly Gln Leu Leu Lys Ile Cys Phe Tyr Thr Thr Asn Lys Asn Ile
            755             760             765

Arg Asp Phe Leu Val Glu Ile Leu Lys Glu Lys Asn Tyr Phe Ser Glu
770             775             780

Lys Glu Lys Arg Thr Ile Asp Phe Val His Gln Val Glu Lys Leu Tyr
785             790             795             800

Leu Gly His Phe Gln Glu Asn Met Gln Ile Gln Ser Phe Pro Arg Tyr
                805             810             815

Trp Ile Lys Glu Gln Asp Phe Phe Lys His Lys Ser Val Leu Asp Ser
            820             825             830

Phe Leu Lys Tyr Asp Cys Lys Asp Glu Phe Asn Lys Gln Asp His Arg
            835             840             845

Ile Val Leu Asn Trp Ala Leu Trp Trp Asp Gln Leu Thr Gln Glu Ser
850             855             860

Ile Leu Leu Pro Arg Ile Ser Pro Glu Glu Tyr Lys Ser Tyr Ser Pro
865             870             875             880

Glu Ala Leu Trp Arg Tyr Leu Thr Ala Arg His Asp Trp Leu Asn Ile
                885             890             895

Ile Leu Trp Ile Gly Glu Phe Gln Thr Gln His Ser Tyr Ala Ser Leu
            900             905             910

Gln Gln Asn Lys Trp Pro Leu Leu Thr Val Asp Val Ile Asn Gln Asn
            915             920             925

Thr Ser Cys Asn Asn Tyr Met Arg Asn Glu Ile Leu Asp Lys Leu Ala
            930             935             940

Gly Asn Gly Val Phe Leu Ala Ser Glu Leu Glu Asp Phe Glu Cys Phe
945             950             955             960

Leu Leu Arg Leu Ser Arg Ile Gly Gly Val Ile Gln Asp Thr Leu Pro
            965             970             975

Val Gln Asn Tyr Lys Thr Lys Glu Gly Trp Asp Phe His Ser Gln Phe
            980             985             990

Ile Leu Tyr Cys Leu Glu His Ser  Leu Gln His Leu Leu  Tyr Val Tyr
            995             1000            1005

Leu Asp Cys Tyr Lys Leu Ser  Pro Glu Asn Cys Pro  Phe Leu Glu
     1010            1015            1020

Lys Lys  Glu Leu His Glu Ala  His Pro Trp Phe Glu  Phe Leu Val
     1025            1030            1035

Gln Cys  Arg Gln Val Ala Ser  Asn Leu Thr Asp Pro  Lys Leu Ile
     1040            1045            1050

Phe Gln  Ala Ser Leu Ala Asn  Ala Gln Ile Leu Ile  Pro Thr Asn
     1055            1060            1065

Gln Ala  Ser Val Ser Ser Met  Leu Leu Glu Gly His  Thr Leu Leu
     1070            1075            1080

Ala Leu  Ala Thr Thr Met Tyr  Ser Pro Gly Gly Val  Ser Gln Val
     1085            1090            1095

Val Gln  Asn Glu Glu Asn Glu  Asn Cys Leu Lys Lys  Val Asp Pro
     1100            1105            1110
```

-continued

```
Gln Leu Leu Lys Met Ala Leu Thr Pro Tyr Pro Lys Leu Lys Thr
1115                1120                1125

Ala Leu Phe Pro Gln Cys Thr Pro Pro Ser Val Leu Pro Ser Asp
1130                1135                1140

Ile Thr Ile Tyr His Leu Ile Gln Ser Leu Ser Pro Phe Asp Pro
1145                1150                1155

Ser Arg Leu Phe Gly Trp Gln Ser Ala Asn Thr Leu Ala Ile Gly
1160                1165                1170

Asp Ala Trp Ser His Leu Pro His Phe Ser Ser Pro Asp Leu Val
1175                1180                1185

Asn Lys Tyr Ala Ile Val Glu Arg Leu Asn Phe Ala Tyr Tyr Leu
1190                1195                1200

His Asn Gly Arg Pro Ser Phe Ala Phe Gly Thr Phe Leu Val Gln
1205                1210                1215

Glu Leu Ile Lys Ser Lys Thr Pro Lys Gln Leu Ile Gln Gln Val
1220                1225                1230

Gly Asn Glu Ala Tyr Val Ile Gly Leu Ser Ser Phe His Ile Pro
1235                1240                1245

Ser Ile Gly Ala Ala Cys Val Cys Phe Leu Glu Leu Leu Gly Leu
1250                1255                1260

Asp Ser Leu Lys Leu Arg Val Asp Met Lys Val Ala Asn Ile Ile
1265                1270                1275

Leu Ser Tyr Lys Cys Arg Asn Glu Asp Ala Gln Tyr Ser Phe Ile
1280                1285                1290

Arg Glu Ser Val Ala Glu Lys Leu Ser Lys Leu Ala Asp Gly Glu
1295                1300                1305

Lys Thr Thr Thr Glu Glu Leu Leu Val Leu Leu Glu Glu Gly Thr
1310                1315                1320

Trp Asn Ser Ile Gln Gln Gln Glu Ile Lys Arg Leu Ser Ser Glu
1325                1330                1335

Ser Ser Ser Gln Trp Ala Leu Val Val Gln Phe Cys Arg Leu His
1340                1345                1350

Asn Met Lys Leu Ser Ile Ser Tyr Leu Arg Glu Cys Ala Lys Ala
1355                1360                1365

Asn Asp Trp Leu Gln Phe Ile Ile His Ser Gln Leu His Asn Tyr
1370                1375                1380

His Pro Ala Glu Val Lys Ser Leu Ile Gln Tyr Phe Ser Pro Val
1385                1390                1395

Ile Gln Asp His Leu Arg Leu Ala Phe Glu Asn Leu Pro Ser Val
1400                1405                1410

Pro Thr Ser Lys Met Asp Ser Asp Gln Val Cys Asn Lys Cys Pro
1415                1420                1425

Gln Glu Leu Gln Gly Ser Lys Gln Glu Met Thr Asp Leu Phe Glu
1430                1435                1440

Ile Leu Leu Gln Cys Ser Glu Glu Pro Asp Ser Trp His Trp Leu
1445                1450                1455

Leu Val Glu Ala Val Lys Gln Gln Ala Pro Ile Leu Ser Val Leu
1460                1465                1470

Ala Ser Cys Leu Gln Gly Ala Ser Ala Ile Ser Cys Leu Cys Val
1475                1480                1485

Trp Ile Ile Thr Ser Val Glu Asp Asn Val Ala Thr Glu Ala Met
1490                1495                1500

Gly His Ile Gln Asp Ser Thr Glu Asp His Thr Trp Asn Leu Glu
1505                1510                1515
```

```
Asp Leu Ser Val Ile Trp Arg Thr Leu Leu Thr Arg Gln Lys Ser
    1520            1525                1530

Lys Thr Leu Ile Arg Gly Phe Gln Leu Phe Lys Asp Ser Pro
    1535            1540                1545

Leu Leu Leu Val Met Glu Met Tyr Glu Leu Cys Met Phe Phe Arg
    1550            1555                1560

Asn Tyr Lys Glu Ala Glu Ala Lys Leu Leu Glu Phe Gln Lys Ser
    1565            1570                1575

Leu Glu Thr Leu Asn Thr Ala Ala Thr Lys Val His Pro Val Ile
    1580            1585                1590

Pro Ala Met Trp Leu Glu Asp Gln Val Cys Phe Leu Leu Lys Leu
    1595            1600                1605

Met Leu Gln Gln Cys Lys Thr Gln Tyr Glu Leu Gly Lys Leu Leu
    1610            1615                1620

Gln Leu Phe Val Glu Arg Glu His Leu Phe Ser Asp Gly Pro Asp
    1625            1630                1635

Val Lys Lys Leu Cys Ile Leu Cys Gln Ile Leu Lys Asp Thr Ser
    1640            1645                1650

Ile Ala Ile Asn His Thr Ile Ile Thr Ser Tyr Ser Ile Glu Asn
    1655            1660                1665

Leu Gln His Glu Cys Arg Ser Ile Leu Glu Arg Leu Gln Thr Asp
    1670            1675                1680

Gly Gln Phe Ala Leu Ala Arg Arg Val Ala Glu Leu Ala Glu Leu
    1685            1690                1695

Pro Val Asp Asn Leu Val Ile Lys Glu Ile Thr Gln Glu Met Gln
    1700            1705                1710

Thr Leu Lys His Ile Glu Gln Trp Ser Leu Lys Gln Ala Arg Ile
    1715            1720                1725

Asp Phe Trp Lys Lys Cys His Glu Asn Phe Lys Lys Asn Ser Ile
    1730            1735                1740

Ser Ser Lys Ala Ala Ser Ser Phe Phe Ser Thr Gln Ala His Val
    1745            1750                1755

Ala Cys Glu His Pro Thr Gly Trp Ser Ser Met Glu Glu Arg His
    1760            1765                1770

Leu Leu Leu Thr Leu Ala Gly His Trp Leu Ala Gln Glu Asp Val
    1775            1780                1785

Val Pro Leu Asp Lys Leu Glu Glu Leu Glu Lys Gln Ile Trp Leu
    1790            1795                1800

Cys Arg Ile Thr Gln His Thr Leu Gly Arg Asn Gln Glu Glu Thr
    1805            1810                1815

Glu Pro Arg Phe Ser Arg Gln Ile Ser Thr Ser Gly Glu Leu Ser
    1820            1825                1830

Phe Asp Ser Leu Ala Ser Glu Phe Ser Phe Ser Lys Leu Ala Ala
    1835            1840                1845

Leu Asn Thr Ser Lys Tyr Leu Glu Leu Asn Ser Leu Pro Ser Lys
    1850            1855                1860

Glu Thr Cys Glu Asn Arg Leu Asp Trp Lys Glu Gln Glu Ser Leu
    1865            1870                1875

Asn Phe Leu Ile Gly Arg Leu Leu Asp Asp Gly Cys Val His Glu
    1880            1885                1890

Ala Ser Arg Val Cys Arg Tyr Phe His Phe Tyr Asn Pro Asp Val
    1895            1900                1905

Ala Leu Val Leu His Cys Arg Ala Leu Ala Ser Gly Glu Ala Ser
```

-continued

```
            1910                1915                1920
Met Glu Asp Leu His Pro Glu Ile His Ala Leu Leu Gln Ser Ala
    1925                1930                1935
Glu Leu Leu Glu Glu Glu Ala Pro Asp Ile Pro Leu Arg Arg Val
    1940                1945                1950
His Ser Thr Ser Ser Leu Asp Ser Gln Lys Phe Val Thr Val Pro
    1955                1960                1965
Ser Ser Asn Glu Val Val Thr Asn Leu Glu Val Leu Thr Ser Lys
    1970                1975                1980
Cys Leu His Gly Lys Asn Tyr Cys Arg Gln Val Leu Cys Leu Tyr
    1985                1990                1995
Asp Leu Ala Lys Glu Leu Gly Cys Ser Tyr Thr Asp Val Ala Ala
    2000                2005                2010
Gln Asp Gly Glu Ala Met Leu Arg Lys Ile Leu Ala Ser Gln Gln
    2015                2020                2025
Pro Asp Arg Cys Lys Arg Ala Gln Ala Phe Ile Ser Thr Gln Gly
    2030                2035                2040
Leu Lys Pro Asp Thr Val Ala Glu Leu Val Ala Glu Glu Val Thr
    2045                2050                2055
Arg Glu Leu Leu Thr Ser Ser Gln Gly Thr Gly His Lys Gln Met
    2060                2065                2070
Phe Asn Pro Thr Glu Glu Ser Gln Thr Phe Leu Gln Leu Thr Thr
    2075                2080                2085
Leu Cys Gln Asp Arg Thr Leu Val Gly Met Lys Leu Leu Asp Lys
    2090                2095                2100
Ile Ser Ser Val Pro His Gly Glu Leu Ser Cys Thr Thr Glu Leu
    2105                2110                2115
Leu Ile Leu Ala His His Cys Phe Thr Leu Thr Cys His Met Glu
    2120                2125                2130
Gly Ile Ile Arg Val Leu Gln Ala Ala His Met Leu Thr Asp Asn
    2135                2140                2145
His Leu Ala Pro Ser Glu Glu Tyr Gly Leu Val Val Arg Leu Leu
    2150                2155                2160
Thr Gly Ile Gly Arg Tyr Asn Glu Met Thr Tyr Ile Phe Asp Leu
    2165                2170                2175
Leu His Lys Lys His Tyr Phe Glu Val Leu Met Arg Lys Lys Leu
    2180                2185                2190
Asp Pro Ser Gly Thr Leu Lys Thr Ala Leu Leu Asp Tyr Ile Lys
    2195                2200                2205
Arg Cys Arg Pro Gly Asp Ser Glu Lys His Asn Met Ile Ala Leu
    2210                2215                2220
Cys Phe Ser Met Cys Arg Glu Ile Gly Glu Asn His Glu Ala Ala
    2225                2230                2235
Ala Arg Ile Gln Leu Lys Leu Ile Glu Ser Gln Pro Trp Glu Asp
    2240                2245                2250
Ser Leu Lys Asp Gly His Gln Leu Lys Gln Leu Leu Lys Ala
    2255                2260                2265
Leu Thr Leu Met Leu Asp Ala Ala Glu Ser Tyr Ala Lys Asp Ser
    2270                2275                2280
Cys Val Arg Gln Ala Gln His Cys Gln Arg Leu Thr Lys Leu Ile
    2285                2290                2295
Thr Leu Gln Ile His Phe Leu Asn Thr Gly Gln Asn Thr Met Leu
    2300                2305                2310
```

-continued

```
Ile Asn Leu Gly Arg His Lys Leu Met Asp Cys Ile Leu Ala Leu
2315                2320                2325

Pro Arg Phe Tyr Gln Ala Ser Ile Val Ala Glu Ala Tyr Asp Phe
2330                2335                2340

Val Pro Asp Trp Ala Glu Ile Leu Tyr Gln Gln Val Ile Leu Lys
2345                2350                2355

Gly Asp Phe Asn Tyr Leu Glu Glu Phe Lys Gln Gln Arg Leu Leu
2360                2365                2370

Lys Ser Ser Ile Phe Glu Glu Ile Ser Lys Lys Tyr Lys Gln His
2375                2380                2385

Gln Pro Thr Asp Met Val Met Glu Asn Leu Lys Lys Leu Leu Thr
2390                2395                2400

Tyr Cys Glu Asp Val Tyr Leu Tyr Tyr Lys Leu Ala Tyr Glu His
2405                2410                2415

Lys Phe Tyr Glu Ile Val Asn Val Leu Leu Lys Asp Pro Gln Thr
2420                2425                2430

Gly Cys Cys Leu Lys Asp Met Leu Ala Gly
2435                2440

<210> SEQ ID NO 166
<211> LENGTH: 245
<212> TYPE: PRT
<213> ORGANISM: homo sapiens

<400> SEQUENCE: 166

Met Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala Arg Gly Phe Ser Thr Ser
225                 230                 235                 240
```

-continued

Gln Arg Arg His Val
            245

<210> SEQ ID NO 167
<211> LENGTH: 427
<212> TYPE: PRT
<213> ORGANISM: Homo sapiens

<400> SEQUENCE: 167

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

```
Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu
                420                 425

<210> SEQ ID NO 168
<211> LENGTH: 555
<212> TYPE: PRT
<213> ORGANISM: Homo sapiens

<400> SEQUENCE: 168

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Val Asp Glu Asp Pro Val Asn
305                 310                 315                 320
```

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Asp Phe Val Trp Phe Asp
                485                 490                 495

Ser Arg Arg Val Phe Lys Gln Thr His Asp Pro Trp Lys Cys Gln His
            500                 505                 510

Cys Gly His Ser Leu Ser Ser Gln Trp Leu Gly Lys Val Leu Asn Ser
        515                 520                 525

His Thr Cys Thr Arg Gly Arg Asp Arg Lys Ser Ser Ala Gly His Ser
    530                 535                 540

Lys Phe Leu Phe Glu Glu Gln Gly Lys Ser Phe
545                 550                 555

<210> SEQ ID NO 169
<211> LENGTH: 576
<212> TYPE: PRT
<213> ORGANISM: Homo sapiens

<400> SEQUENCE: 169

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

-continued

```
Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Leu Ile His Pro Gln
545                 550                 555                 560

Asn Leu Leu Tyr Leu Ile Ser Leu Ile Thr Cys His Pro Ile Tyr Ile
                565                 570                 575
```

<210> SEQ ID NO 170
<211> LENGTH: 559
<212> TYPE: PRT
<213> ORGANISM: Homo sapiens

<400> SEQUENCE: 170

```
Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
                35                  40                  45

Thr Gln Pro Glu Ala Leu Gly Ser Leu Thr Ala Ala Gly Ser Leu Gln
            50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                    85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
370                 375                 380
```

```
Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
        420                 425                 430

Thr Gly Phe Thr Ala Leu Phe Thr Trp Glu Val Glu Arg Met Gly Tyr
    435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser
545                 550                 555

<210> SEQ ID NO 171
<211> LENGTH: 576
<212> TYPE: PRT
<213> ORGANISM: Homo sapiens

<400> SEQUENCE: 171

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205
```

```
Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
545                 550                 555                 560

Lys Ser Ser Val Leu Ile Ser Leu Ile Thr Cys His Pro Ile Tyr Ile
                565                 570                 575

<210> SEQ ID NO 172
<211> LENGTH: 2443
<212> TYPE: PRT
<213> ORGANISM: Homo sapiens

<400> SEQUENCE: 172

Met Ala Ala Glu Glu Gly Val Ala Ser Ala Ser Ala Gly Gly Ser
1               5                   10                  15
```

```
Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                    85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
                115                 120                 125

Ile Leu Tyr Ser Cys Ser Arg Glu Ala Leu Gln Lys Leu Ile Asp Asp
            130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
                195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
            290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
```

```
                435                 440                 445
Thr Ile Thr Leu Trp Asp Leu Glu Thr Gln Gly Met Gln Cys Ser Ser
450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
                    485                 490                 495
Thr Gln Glu Glu Phe Leu Asn Arg Leu Met Ile His Gly Ser Ala Ser
                500                 505                 510
Thr Val Asp Thr Leu Cys His Leu Asn Gly Trp Gly Arg Cys Ser Ile
                515                 520                 525
Pro Ile His Ala Leu Glu Ala Gly Ile Glu Asn Arg Gln Leu Asp Thr
530                 535                 540
Val Asn Phe Phe Leu Lys Ser Lys Glu Asn Leu Phe Asn Pro Ser Ser
545                 550                 555                 560
Lys Ser Ser Val Ser Asp Gln Phe Asp His Leu Ser Ser His Leu Tyr
                565                 570                 575
Leu Arg Asn Val Glu Glu Leu Ile Pro Ala Leu Asp Leu Leu Cys Ser
                580                 585                 590
Ala Ile Arg Glu Ser Tyr Ser Glu Pro Gln Ser Lys His Phe Ser Glu
                595                 600                 605
Gln Leu Leu Asn Leu Thr Leu Ser Phe Leu Asn Asn Gln Ile Lys Glu
610                 615                 620
Leu Phe Ile His Thr Glu Glu Leu Asp Glu His Leu Gln Lys Gly Val
625                 630                 635                 640
Asn Ile Leu Thr Ser Tyr Ile Asn Glu Leu Arg Thr Phe Met Ile Lys
                645                 650                 655
Phe Pro Trp Lys Leu Thr Asp Ala Ile Asp Glu Tyr Asp Val His Glu
                660                 665                 670
Asn Val Pro Lys Val Lys Glu Ser Asn Ile Trp Lys Lys Leu Ser Phe
                675                 680                 685
Glu Glu Val Ile Ala Ser Ala Ile Leu Asn Asn Lys Ile Pro Glu Ala
690                 695                 700
Gln Thr Phe Phe Arg Ile Asp Ser His Ser Ala Gln Lys Leu Glu Glu
705                 710                 715                 720
Leu Ile Gly Ile Gly Leu Asn Leu Val Phe Asp Asn Leu Lys Lys Asn
                725                 730                 735
Asn Ile Lys Glu Ala Ser Glu Leu Leu Lys Asn Met Gly Phe Asp Val
                740                 745                 750
Lys Gly Gln Leu Leu Lys Ile Cys Phe Tyr Thr Thr Asn Lys Asn Ile
                755                 760                 765
Arg Asp Phe Leu Val Glu Ile Leu Lys Glu Lys Asn Tyr Phe Ser Glu
770                 775                 780
Lys Glu Lys Arg Thr Ile Asp Phe Val His Gln Val Lys Leu Tyr
785                 790                 795                 800
Leu Gly His Phe Gln Glu Asn Met Gln Ile Gln Ser Phe Pro Met Tyr
                805                 810                 815
Trp Ile Lys Glu Gln Asp Phe Phe Lys His Lys Ser Val Leu Asp Ser
                820                 825                 830
Phe Leu Lys Tyr Asp Cys Lys Asp Glu Phe Asn Lys Gln Asp His Arg
                835                 840                 845
Ile Val Leu Asn Trp Ala Leu Trp Trp Asp Gln Leu Thr Gln Glu Ser
850                 855                 860
```

-continued

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
        995                 1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

```
Leu Ser Tyr Lys Cys Arg Asn Glu Asp Ala Gln Tyr Ser Phe Ile
    1280              1285                1290

Arg Glu Ser Val Ala Glu Lys Leu Ser Lys Leu Ala Asp Gly Glu
    1295              1300                1305

Lys Thr Thr Thr Glu Glu Leu Leu Val Leu Leu Glu Glu Gly Thr
    1310              1315                1320

Trp Asn Ser Ile Gln Gln Glu Ile Lys Arg Leu Ser Ser Glu
    1325              1330                1335

Ser Ser Ser Gln Trp Ala Leu Val Val Gln Phe Cys Arg Leu His
    1340              1345                1350

Asn Met Lys Leu Ser Ile Ser Tyr Leu Arg Glu Cys Ala Lys Ala
    1355              1360                1365

Asn Asp Trp Leu Gln Phe Ile Ile His Ser Gln Leu His Asn Tyr
    1370              1375                1380

His Pro Ala Glu Val Lys Ser Leu Ile Gln Tyr Phe Ser Pro Val
    1385              1390                1395

Ile Gln Asp His Leu Arg Leu Ala Phe Glu Asn Leu Pro Ser Val
    1400              1405                1410

Pro Thr Ser Lys Met Asp Ser Asp Gln Val Cys Asn Lys Cys Pro
    1415              1420                1425

Gln Glu Leu Gln Gly Ser Lys Gln Glu Met Thr Asp Leu Phe Glu
    1430              1435                1440

Ile Leu Leu Gln Cys Ser Glu Glu Pro Asp Ser Trp His Trp Leu
    1445              1450                1455

Leu Val Glu Ala Val Lys Gln Gln Ala Pro Ile Leu Ser Val Leu
    1460              1465                1470

Ala Ser Cys Leu Gln Gly Ala Ser Ala Ile Ser Cys Leu Cys Val
    1475              1480                1485

Trp Ile Ile Thr Ser Val Glu Asp Asn Val Ala Thr Glu Ala Met
    1490              1495                1500

Gly His Ile Gln Asp Ser Thr Glu Asp His Thr Trp Asn Leu Glu
    1505              1510                1515

Asp Leu Ser Val Ile Trp Arg Thr Leu Leu Thr Arg Gln Lys Ser
    1520              1525                1530

Lys Thr Leu Ile Arg Gly Phe Gln Leu Phe Phe Lys Asp Ser Pro
    1535              1540                1545

Leu Leu Leu Val Met Glu Met Tyr Glu Leu Cys Met Phe Phe Arg
    1550              1555                1560

Asn Tyr Lys Glu Ala Glu Ala Lys Leu Leu Glu Phe Gln Lys Ser
    1565              1570                1575

Leu Glu Thr Leu Asn Thr Ala Ala Thr Lys Val His Pro Val Ile
    1580              1585                1590

Pro Ala Met Trp Leu Glu Asp Gln Val Cys Phe Leu Leu Lys Leu
    1595              1600                1605

Met Leu Gln Gln Cys Lys Thr Gln Tyr Glu Leu Gly Lys Leu Leu
    1610              1615                1620

Gln Leu Phe Val Glu Arg Glu His Leu Phe Ser Asp Gly Pro Asp
    1625              1630                1635

Val Lys Lys Leu Cys Ile Leu Cys Gln Ile Leu Lys Asp Thr Ser
    1640              1645                1650

Ile Ala Ile Asn His Thr Ile Ile Thr Ser Tyr Ser Ile Glu Asn
    1655              1660                1665

Leu Gln His Glu Cys Arg Ser Ile Leu Glu Arg Leu Gln Thr Asp
```

-continued

```
              1670                1675                1680

Gly Gln Phe Ala Leu Ala Arg Arg Val Ala Glu Leu Ala Glu Leu
          1685                1690                1695

Pro Val Asp Asn Leu Val Ile Lys Glu Ile Thr Gln Glu Met Gln
          1700                1705                1710

Thr Leu Lys His Ile Glu Gln Trp Ser Leu Lys Gln Ala Arg Ile
          1715                1720                1725

Asp Phe Trp Lys Lys Cys His Glu Asn Phe Lys Lys Asn Ser Ile
          1730                1735                1740

Ser Ser Lys Ala Ala Ser Ser Phe Phe Ser Thr Gln Ala His Val
          1745                1750                1755

Ala Cys Glu His Pro Thr Gly Trp Ser Ser Met Glu Glu Arg His
          1760                1765                1770

Leu Leu Leu Thr Leu Ala Gly His Trp Leu Ala Gln Glu Asp Val
          1775                1780                1785

Val Pro Leu Asp Lys Leu Glu Glu Leu Glu Lys Gln Ile Trp Leu
          1790                1795                1800

Cys Arg Ile Thr Gln His Thr Leu Gly Arg Asn Gln Glu Glu Thr
          1805                1810                1815

Glu Pro Arg Phe Ser Arg Gln Ile Ser Thr Ser Gly Glu Leu Ser
          1820                1825                1830

Phe Asp Ser Leu Ala Ser Glu Phe Ser Phe Ser Lys Leu Ala Ala
          1835                1840                1845

Leu Asn Thr Ser Lys Tyr Leu Glu Leu Asn Ser Leu Pro Ser Lys
          1850                1855                1860

Glu Thr Cys Glu Asn Arg Leu Asp Trp Lys Gln Glu Ser Leu
          1865                1870                1875

Asn Phe Leu Ile Gly Arg Leu Leu Asp Asp Gly Cys Val His Glu
          1880                1885                1890

Ala Ser Arg Val Cys Arg Tyr Phe His Phe Tyr Asn Pro Asp Val
          1895                1900                1905

Ala Leu Val Leu His Cys Arg Ala Leu Ala Ser Gly Glu Ala Ser
          1910                1915                1920

Met Glu Asp Leu His Pro Glu Ile His Ala Leu Leu Gln Ser Ala
          1925                1930                1935

Glu Leu Leu Glu Glu Glu Ala Pro Asp Ile Pro Leu Arg Arg Val
          1940                1945                1950

His Ser Thr Ser Ser Leu Asp Ser Gln Lys Phe Val Thr Val Pro
          1955                1960                1965

Ser Ser Asn Glu Val Val Thr Asn Leu Glu Val Leu Thr Ser Lys
          1970                1975                1980

Cys Leu His Gly Lys Asn Tyr Cys Arg Gln Val Leu Cys Leu Tyr
          1985                1990                1995

Asp Leu Ala Lys Glu Leu Gly Cys Ser Tyr Thr Asp Val Ala Ala
          2000                2005                2010

Gln Asp Gly Glu Ala Met Leu Arg Lys Ile Leu Ala Ser Gln Gln
          2015                2020                2025

Pro Asp Arg Cys Lys Arg Ala Gln Ala Phe Ile Ser Thr Gln Gly
          2030                2035                2040

Leu Lys Pro Asp Thr Val Ala Glu Leu Val Ala Glu Val Thr
          2045                2050                2055

Arg Glu Leu Leu Thr Ser Ser Gln Gly Thr Gly His Lys Gln Met
          2060                2065                2070
```

Phe Asn Pro Thr Glu Glu Ser Gln Thr Phe Leu Gln Leu Thr Thr
2075                2080                2085

Leu Cys Gln Asp Arg Thr Leu Val Gly Met Lys Leu Leu Asp Lys
2090                2095                2100

Ile Ser Ser Val Pro His Gly Glu Leu Ser Cys Thr Thr Glu Leu
2105                2110                2115

Leu Ile Leu Ala His His Cys Phe Thr Leu Thr Cys His Met Glu
2120                2125                2130

Gly Ile Ile Arg Val Leu Gln Ala Ala His Met Leu Thr Asp Asn
2135                2140                2145

His Leu Ala Pro Ser Glu Glu Tyr Gly Leu Val Val Arg Leu Leu
2150                2155                2160

Thr Gly Ile Gly Arg Tyr Asn Glu Met Thr Tyr Ile Phe Asp Leu
2165                2170                2175

Leu His Lys Lys His Tyr Phe Glu Val Leu Met Arg Lys Lys Leu
2180                2185                2190

Asp Pro Ser Gly Thr Leu Lys Thr Ala Leu Leu Asp Tyr Ile Lys
2195                2200                2205

Arg Cys Arg Pro Gly Asp Ser Glu Lys His Asn Met Ile Ala Leu
2210                2215                2220

Cys Phe Ser Met Cys Arg Glu Ile Gly Glu Asn His Glu Ala Ala
2225                2230                2235

Ala Arg Ile Gln Leu Lys Leu Ile Glu Ser Gln Pro Trp Glu Asp
2240                2245                2250

Ser Leu Lys Asp Gly His Gln Leu Lys Gln Leu Leu Lys Ala
2255                2260                2265

Leu Thr Leu Met Leu Asp Ala Ala Glu Ser Tyr Ala Lys Asp Ser
2270                2275                2280

Cys Val Arg Gln Ala Gln His Cys Gln Arg Leu Thr Lys Leu Ile
2285                2290                2295

Thr Leu Gln Ile His Phe Leu Asn Thr Gly Gln Asn Thr Met Leu
2300                2305                2310

Ile Asn Leu Gly Arg His Lys Leu Met Asp Cys Ile Leu Ala Leu
2315                2320                2325

Pro Arg Phe Tyr Gln Ala Ser Ile Val Ala Glu Ala Tyr Asp Phe
2330                2335                2340

Val Pro Asp Trp Ala Glu Ile Leu Tyr Gln Gln Val Ile Leu Lys
2345                2350                2355

Gly Asp Phe Asn Tyr Leu Glu Glu Phe Lys Gln Gln Arg Leu Leu
2360                2365                2370

Lys Ser Ser Ile Phe Glu Glu Ile Ser Lys Lys Tyr Lys Gln His
2375                2380                2385

Gln Pro Thr Asp Met Val Met Glu Asn Leu Lys Lys Leu Leu Thr
2390                2395                2400

Tyr Cys Glu Asp Val Tyr Leu Tyr Tyr Lys Leu Ala Tyr Glu His
2405                2410                2415

Lys Phe Tyr Glu Ile Val Asn Val Leu Leu Lys Asp Pro Gln Thr
2420                2425                2430

Gly Cys Cys Leu Lys Asp Met Leu Ala Gly
2435                2440

<210> SEQ ID NO 173
<211> LENGTH: 898
<212> TYPE: PRT
<213> ORGANISM: Homo sapiens

<400> SEQUENCE: 173

```
Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
                35                  40                  45

Thr Gln Pro Glu Ala Leu Gly Ser Leu Thr Ala Ala Gly Ser Leu Gln
            50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415
```

```
His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
            725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
            805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
```

```
                835                 840                 845
Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
            885                 890                 895

Ile Leu

<210> SEQ ID NO 174
<211> LENGTH: 919
<212> TYPE: PRT
<213> ORGANISM: Homo sapiens

<400> SEQUENCE: 174

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320
```

```
Ser Ala Tyr Asn Met Lys Leu Ala Lys Phe Ser Phe Gln Ile Asp Arg
            325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
```

```
                    740                 745                 750
Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
        770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
    850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Ser Ile Val Met Leu His Phe
            900                 905                 910

Ser Arg Thr Asn Gly Pro Phe
        915

<210> SEQ ID NO 175
<211> LENGTH: 1028
<212> TYPE: PRT
<213> ORGANISM: Homo sapiens

<400> SEQUENCE: 175

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
```

-continued

```
                195                 200                 205
Cys Arg Gly Ile Leu Phe Val Leu Ser Ser Leu Gly Trp Ile Tyr Ile
210                     215                 220

Phe Asp Val Val Asp Gly Thr Tyr Val Ala His Val Asp Leu Ala Leu
225                     230                 235                 240

His Lys Glu Asp Met Cys Asn Glu Gln Gln Glu Pro Ala Lys Ile
                    245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
                275                 280                 285

Phe Arg Gln His Pro Gly His Leu Leu Cys Glu Arg Ile Leu Glu Asp
290                     295                 300

Leu Pro Ile Gln Gly Pro Lys Gly Val Asp Glu Asp Pro Val Asn
305                     310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
370                     375                 380

Ala Phe Ile Pro Gln Asp Ile Met His Gly Gln Tyr Asn Val Leu Gln
385                     390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
                435                 440                 445

Thr Ile Thr Leu Trp Asp Leu Glu Thr Gln Gly Met Gln Cys Ser Ser
450                     455                 460

Leu Gly Thr Lys Cys Ile Pro Val Asp Ser Ser Gly Asp Gln Gln Leu
465                     470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
                515                 520                 525

Pro Ile His Ala Leu Glu Ala Gly Ile Glu Asn Arg Gln Leu Asp Thr
530                     535                 540

Val Asn Phe Phe Leu Lys Ser Lys Glu Asn Leu Phe Asn Pro Ser Ser
545                     550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
                595                 600                 605

Gln Leu Leu Asn Leu Thr Leu Ser Phe Leu Asn Asn Gln Ile Lys Glu
610                     615                 620
```

```
Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
        660                 665                 670

Asn Val Pro Lys Val Lys Glu Ser Asn Ile Trp Lys Lys Leu Ser Phe
    675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
    850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser  Leu Gln His Leu Leu  Tyr Val Tyr
        995                 1000                1005

Leu Asp Cys Tyr Lys Leu Ser  Pro Glu Asn Cys Pro  Phe Leu Glu
    1010                1015                1020

Lys Lys  Arg Val Thr
    1025
```

<210> SEQ ID NO 176

<211> LENGTH: 1263
<212> TYPE: PRT
<213> ORGANISM: Homo sapiens

<400> SEQUENCE: 176

```
Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400
```

```
Lys Asp His Ala Lys Thr Ser Asp Pro Gly Arg Ser Trp Lys Ile Met
            405                 410                 415

His Ile Ser Glu Gln Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
```

-continued

```
                820                 825                 830
Phe Leu Lys Tyr Asp Cys Lys Asp Glu Phe Asn Lys Gln Asp His Arg
            835                 840                 845
Ile Val Leu Asn Trp Ala Leu Trp Trp Asp Gln Leu Thr Gln Glu Ser
850                 855                 860
Ile Leu Leu Pro Arg Ile Ser Pro Glu Tyr Lys Ser Tyr Ser Pro
865                 870                 875                 880
Glu Ala Leu Trp Arg Tyr Leu Thr Ala Arg His Asp Trp Leu Asn Ile
            885                 890                 895
Ile Leu Trp Ile Gly Glu Phe Gln Thr Gln His Ser Tyr Ala Ser Leu
            900                 905                 910
Gln Gln Asn Lys Trp Pro Leu Leu Thr Val Asp Val Ile Asn Gln Asn
            915                 920                 925
Thr Ser Cys Asn Asn Tyr Met Arg Asn Glu Ile Leu Asp Lys Leu Ala
            930                 935                 940
Arg Asn Gly Val Phe Leu Ala Ser Glu Leu Glu Asp Phe Glu Cys Phe
945                 950                 955                 960
Leu Leu Arg Leu Ser Arg Ile Gly Gly Val Ile Gln Asp Thr Leu Pro
            965                 970                 975
Val Gln Asn Tyr Lys Thr Lys Glu Gly Trp Asp Phe His Ser Gln Phe
            980                 985                 990
Ile Leu Tyr Cys Leu Glu His Ser  Leu Gln His Leu Leu  Tyr Val Tyr
            995                 1000                1005
Leu Asp  Cys Tyr Lys Leu Ser  Pro Glu Asn Cys Pro  Phe Leu Glu
    1010                1015                1020
Lys Lys  Glu Leu His Glu Ala  His Pro Trp Phe Glu  Phe Leu Val
    1025                1030                1035
Gln Cys  Arg Gln Val Ala Ser  Asn Leu Thr Asp Pro  Lys Leu Ile
    1040                1045                1050
Phe Gln  Ala Ser Leu Ala Asn  Ala Gln Ile Leu Ile  Pro Thr Asn
    1055                1060                1065
Gln Ala  Ser Val Ser Ser Met  Leu Leu Glu Gly His  Thr Leu Leu
    1070                1075                1080
Ala Leu  Ala Thr Thr Met Tyr  Ser Pro Gly Gly Val  Ser Gln Val
    1085                1090                1095
Val Gln  Asn Glu Glu Asn Glu  Asn Cys Leu Lys Lys  Val Asp Pro
    1100                1105                1110
Gln Leu  Leu Lys Met Ala Leu  Thr Pro Tyr Pro Lys  Leu Lys Thr
    1115                1120                1125
Ala Leu  Phe Pro Gln Cys Thr  Pro Pro Ser Val Leu  Pro Ser Asp
    1130                1135                1140
Ile Thr  Ile Tyr His Leu Ile  Gln Ser Leu Ser Pro  Phe Asp Pro
    1145                1150                1155
Ser Arg  Leu Phe Gly Trp Gln  Ser Ala Asn Thr Leu  Ala Ile Gly
    1160                1165                1170
Asp Ala  Trp Ser His Leu Pro  His Phe Ser Pro  Asp Leu Val
    1175                1180                1185
Asn Lys  Tyr Ala Ile Val Glu  Arg Leu Asn Phe Ala  Tyr Tyr Leu
    1190                1195                1200
His Asn  Gly Arg Pro Ser Phe  Ala Phe Gly Thr Phe  Leu Val Gln
    1205                1210                1215
Glu Leu  Ile Lys Ser Lys Thr  Pro Lys Gln Leu Ile  Gln Gln Val
    1220                1225                1230
```

```
Gly Asn Glu Ala Tyr Val Ile Gly Leu Ser Ser Phe His Ile Thr
    1235                1240                1245

Phe Asn Arg Ser Cys Met Cys Leu Phe Leu Arg Ile Ala Trp Pro
    1250                1255                1260

<210> SEQ ID NO 177
<211> LENGTH: 1441
<212> TYPE: PRT
<213> ORGANISM: Homo sapiens

<400> SEQUENCE: 177

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
                35                  40                  45

Thr Gln Pro Glu Ala Leu Gly Ser Leu Thr Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                    85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
                115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
                195                 200                 205

Cys Arg Gly Ile Leu Phe Val Leu Ser Ser Leu Gly Trp Ile Tyr Ile
                210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
                275                 280                 285

Phe Arg Gln His Pro Gly His Leu Leu Cys Glu Arg Ile Leu Glu Asp
                290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Gln Ile Asp Arg
                325                 330                 335

Ser Trp Lys Ala Gln Leu Ser Ser Leu Asn Glu Thr Ile Lys Asn Ser
                340                 345                 350
```

-continued

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
        450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
            805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
            885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
            930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
            965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
            995                 1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Ser Pro Asp Leu Val
    1175                1180                1185

Asn Lys Tyr Ala Ile Val Glu Arg Leu Asn Phe Ala Tyr Tyr Leu

```
              1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320

Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
    1340                1345                1350

Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425

Gln Glu Leu Gln Gly Ser Lys Arg Asp Asp Arg Phe Ile
    1430                1435                1440

<210> SEQ ID NO 178
<211> LENGTH: 1823
<212> TYPE: PRT
<213> ORGANISM: Homo sapiens

<400> SEQUENCE: 178

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
```

```
                115                 120                 125
Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540
```

```
Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
            725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
            805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
            885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
            965                 970                 975
```

```
Val Gln Asn Tyr Lys Thr Lys Glu Gly Trp Asp Phe His Ser Gln Phe
            980             985                 990

Ile Leu Tyr Cys Leu Glu His Ser Leu Gln His Leu Leu Tyr Val Tyr
            995            1000                 1005

Leu Asp Cys Tyr Lys Leu Ser Pro Glu Asn Cys Pro Phe Leu Glu
        1010                1015                1020

Lys Lys Glu Leu His Glu Ala His Pro Trp Phe Glu Phe Leu Val
        1025                1030                1035

Gln Cys Arg Gln Val Ala Ser Asn Leu Thr Asp Pro Lys Leu Ile
        1040                1045                1050

Phe Gln Ala Ser Leu Ala Asn Ala Gln Ile Leu Ile Pro Thr Asn
        1055                1060                1065

Gln Ala Ser Val Ser Ser Met Leu Leu Glu Gly His Thr Leu Leu
        1070                1075                1080

Ala Leu Ala Thr Thr Met Tyr Ser Pro Gly Gly Val Ser Gln Val
        1085                1090                1095

Val Gln Asn Glu Glu Asn Glu Asn Cys Leu Lys Lys Val Asp Pro
        1100                1105                1110

Gln Leu Leu Lys Met Ala Leu Thr Pro Tyr Pro Lys Leu Lys Thr
        1115                1120                1125

Ala Leu Phe Pro Gln Cys Thr Pro Pro Ser Val Leu Pro Ser Asp
        1130                1135                1140

Ile Thr Ile Tyr His Leu Ile Gln Ser Leu Ser Pro Phe Asp Pro
        1145                1150                1155

Ser Arg Leu Phe Gly Trp Gln Ser Ala Asn Thr Leu Ala Ile Gly
        1160                1165                1170

Asp Ala Trp Ser His Leu Pro His Phe Ser Pro Asp Leu Val
        1175                1180                1185

Asn Lys Tyr Ala Ile Val Glu Arg Leu Asn Phe Ala Tyr Tyr Leu
        1190                1195                1200

His Asn Gly Arg Pro Ser Phe Ala Phe Gly Thr Phe Leu Val Gln
        1205                1210                1215

Glu Leu Ile Lys Ser Lys Thr Pro Lys Gln Leu Ile Gln Gln Val
        1220                1225                1230

Gly Asn Glu Ala Tyr Val Ile Gly Leu Ser Ser Phe His Ile Pro
        1235                1240                1245

Ser Ile Gly Ala Ala Cys Val Cys Phe Leu Glu Leu Leu Gly Leu
        1250                1255                1260

Asp Ser Leu Lys Leu Arg Val Asp Met Lys Val Ala Asn Ile Ile
        1265                1270                1275

Leu Ser Tyr Lys Cys Arg Asn Glu Asp Ala Gln Tyr Ser Phe Ile
        1280                1285                1290

Arg Glu Ser Val Ala Glu Lys Leu Ser Lys Leu Ala Asp Gly Glu
        1295                1300                1305

Lys Thr Thr Thr Glu Glu Leu Leu Val Leu Leu Glu Glu Gly Thr
        1310                1315                1320

Trp Asn Ser Ile Gln Gln Gln Glu Ile Lys Arg Leu Ser Ser Glu
        1325                1330                1335

Ser Ser Ser Gln Trp Ala Leu Val Val Gln Phe Cys Arg Leu His
        1340                1345                1350

Asn Met Lys Leu Ser Ile Ser Tyr Leu Arg Glu Cys Ala Lys Ala
        1355                1360                1365

Asn Asp Trp Leu Gln Phe Ile Ile His Ser Gln Leu His Asn Tyr
```

```
              1370              1375              1380
His Pro Ala Glu Val Lys Ser Leu Ile Gln Tyr Phe Ser Pro Val
    1385                1390                1395
Ile Gln Asp His Leu Arg Leu Ala Phe Glu Asn Leu Pro Ser Val
    1400                1405                1410
Pro Thr Ser Lys Met Asp Ser Asp Gln Val Cys Asn Lys Cys Pro
    1415                1420                1425
Gln Glu Leu Gln Gly Ser Lys Gln Glu Met Thr Asp Leu Phe Glu
    1430                1435                1440
Ile Leu Leu Gln Cys Ser Glu Glu Pro Asp Ser Trp His Trp Leu
    1445                1450                1455
Leu Val Glu Ala Val Lys Gln Gln Ala Pro Ile Leu Ser Val Leu
    1460                1465                1470
Ala Ser Cys Leu Gln Gly Ala Ser Ala Ile Ser Cys Leu Cys Val
    1475                1480                1485
Trp Ile Ile Thr Ser Val Glu Asp Asn Val Ala Thr Glu Ala Met
    1490                1495                1500
Gly His Ile Gln Asp Ser Thr Glu Asp His Thr Trp Asn Leu Glu
    1505                1510                1515
Asp Leu Ser Val Ile Trp Arg Thr Leu Leu Thr Arg Gln Lys Ser
    1520                1525                1530
Lys Thr Leu Ile Arg Gly Phe Gln Leu Phe Phe Lys Asp Ser Pro
    1535                1540                1545
Leu Leu Leu Val Met Glu Met Tyr Glu Leu Cys Met Phe Phe Arg
    1550                1555                1560
Asn Tyr Lys Glu Ala Glu Ala Lys Leu Leu Glu Phe Gln Lys Ser
    1565                1570                1575
Leu Glu Thr Leu Asn Thr Ala Ala Thr Lys Val His Pro Val Ile
    1580                1585                1590
Pro Ala Met Trp Leu Glu Asp Gln Val Cys Phe Leu Leu Lys Leu
    1595                1600                1605
Met Leu Gln Gln Cys Lys Thr Gln Tyr Glu Leu Gly Lys Leu Leu
    1610                1615                1620
Gln Leu Phe Val Glu Arg Glu His Leu Phe Ser Asp Gly Pro Asp
    1625                1630                1635
Val Lys Lys Leu Cys Ile Leu Cys Gln Ile Leu Lys Asp Thr Ser
    1640                1645                1650
Ile Ala Ile Asn His Thr Ile Ile Thr Ser Tyr Ser Ile Glu Asn
    1655                1660                1665
Leu Gln His Glu Cys Arg Ser Ile Leu Glu Arg Leu Gln Thr Asp
    1670                1675                1680
Gly Gln Phe Ala Leu Ala Arg Arg Val Ala Glu Leu Ala Glu Leu
    1685                1690                1695
Pro Val Asp Asn Leu Val Ile Lys Glu Ile Thr Gln Glu Met Gln
    1700                1705                1710
Thr Leu Lys His Ile Glu Gln Trp Ser Leu Lys Gln Ala Arg Ile
    1715                1720                1725
Asp Phe Trp Lys Lys Cys His Glu Asn Phe Lys Lys Asn Ser Ile
    1730                1735                1740
Ser Ser Lys Ala Ala Ser Phe Phe Ser Thr Gln Ala His Val
    1745                1750                1755
Ala Cys Glu His Pro Thr Gly Trp Ser Ser Met Glu Glu Arg His
    1760                1765                1770
```

```
Leu Leu Leu Thr Leu Ala Gly His Trp Leu Ala Gln Glu Asp Val
    1775                1780                1785

Val Pro Leu Asp Lys Leu Glu Glu Leu Lys Gln Ile Trp Leu
1790                1795                1800

Cys Arg Ile Thr Gln His Thr Leu Gly Arg Asn Gln Glu Glu Thr
1805                1810                1815

Glu Pro Arg Phe Ser
    1820

<210> SEQ ID NO 179
<211> LENGTH: 1856
<212> TYPE: PRT
<213> ORGANISM: Homo sapiens

<400> SEQUENCE: 179

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320
```

```
Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
        420                 425                 430

Thr Gly Phe Thr Ala Leu Phe Thr Trp Glu Val Glu Arg Met Gly Tyr
    435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
        500                 505                 510

Thr Val Asp Thr Leu Cys His Leu Asn Gly Trp Gly Arg Cys Ser Ile
    515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
        580                 585                 590

Ala Ile Arg Glu Ser Tyr Ser Glu Pro Gln Ser Lys His Phe Ser Glu
    595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
        660                 665                 670

Asn Val Pro Lys Val Lys Glu Ser Asn Ile Trp Lys Lys Leu Ser Phe
    675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
            725                 730                 735

Asn Ile Lys Glu Ala Ser Glu Leu Leu Lys Asn Met Gly Phe Asp Val
        740                 745                 750
```

Lys Gly Gln Leu Leu Lys Ile Cys Phe Tyr Thr Thr Asn Lys Asn Ile
    755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
                820                 825                 830

Phe Leu Lys Tyr Asp Cys Lys Asp Glu Phe Asn Lys Gln Asp His Arg
                835                 840                 845

Ile Val Leu Asn Trp Ala Leu Trp Trp Asp Gly Leu Thr Gln Glu Ser
    850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
                900                 905                 910

Gln Gln Asn Lys Trp Pro Leu Leu Thr Val Asp Val Ile Asn Gln Asn
                915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Gly Gly Trp Asp Phe His Ser Gln Phe
                980                 985                 990

Ile Leu Tyr Cys Leu Glu His Ser Leu Gln His Leu Leu Tyr Val Tyr
                995                1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly

-continued

```
            1160               1165               1170
Asp Ala Trp Ser His Leu Pro His Phe Ser Ser Pro Asp Leu Val
        1175               1180               1185
Asn Lys Tyr Ala Ile Val Glu Arg Leu Asn Phe Ala Tyr Tyr Leu
        1190               1195               1200
His Asn Gly Arg Pro Ser Phe Ala Phe Gly Thr Phe Leu Val Gln
        1205               1210               1215
Glu Leu Ile Lys Ser Lys Thr Pro Lys Gln Leu Ile Gln Gln Val
        1220               1225               1230
Gly Asn Glu Ala Tyr Val Ile Gly Leu Ser Ser Phe His Ile Pro
        1235               1240               1245
Ser Ile Gly Ala Ala Cys Val Cys Phe Leu Glu Leu Leu Gly Leu
        1250               1255               1260
Asp Ser Leu Lys Leu Arg Val Asp Met Lys Val Ala Asn Ile Ile
        1265               1270               1275
Leu Ser Tyr Lys Cys Arg Asn Glu Asp Ala Gln Tyr Ser Phe Ile
        1280               1285               1290
Arg Glu Ser Val Ala Glu Lys Leu Ser Lys Leu Ala Asp Gly Glu
        1295               1300               1305
Lys Thr Thr Thr Glu Glu Leu Leu Val Leu Leu Glu Glu Gly Thr
        1310               1315               1320
Trp Asn Ser Ile Gln Gln Glu Ile Lys Arg Leu Ser Ser Glu
        1325               1330               1335
Ser Ser Ser Gln Trp Ala Leu Val Val Gln Phe Cys Arg Leu His
        1340               1345               1350
Asn Met Lys Leu Ser Ile Ser Tyr Leu Arg Glu Cys Ala Lys Ala
        1355               1360               1365
Asn Asp Trp Leu Gln Phe Ile Ile His Ser Gln Leu His Asn Tyr
        1370               1375               1380
His Pro Ala Glu Val Lys Ser Leu Ile Gln Tyr Phe Ser Pro Val
        1385               1390               1395
Ile Gln Asp His Leu Arg Leu Ala Phe Glu Asn Leu Pro Ser Val
        1400               1405               1410
Pro Thr Ser Lys Met Asp Ser Asp Gln Val Cys Asn Lys Cys Pro
        1415               1420               1425
Gln Glu Leu Gln Gly Ser Lys Gln Glu Met Thr Asp Leu Phe Glu
        1430               1435               1440
Ile Leu Leu Gln Cys Ser Glu Glu Pro Asp Ser Trp His Trp Leu
        1445               1450               1455
Leu Val Glu Ala Val Lys Gln Gln Ala Pro Ile Leu Ser Val Leu
        1460               1465               1470
Ala Ser Cys Leu Gln Gly Ala Ser Ala Ile Ser Cys Leu Cys Val
        1475               1480               1485
Trp Ile Ile Thr Ser Val Glu Asp Asn Val Ala Thr Glu Ala Met
        1490               1495               1500
Gly His Ile Gln Asp Ser Thr Glu Asp His Thr Trp Asn Leu Glu
        1505               1510               1515
Asp Leu Ser Val Ile Trp Arg Thr Leu Leu Thr Arg Gln Lys Ser
        1520               1525               1530
Lys Thr Leu Ile Arg Gly Phe Gln Leu Phe Phe Lys Asp Ser Pro
        1535               1540               1545
Leu Leu Leu Val Met Glu Met Tyr Glu Leu Cys Met Phe Phe Arg
        1550               1555               1560
```

```
Asn Tyr Lys Glu Ala Glu Ala Lys Leu Leu Glu Phe Gln Lys Ser
    1565            1570                1575

Leu Glu Thr Leu Asn Thr Ala Ala Thr Lys Val His Pro Val Ile
    1580            1585                1590

Pro Ala Met Trp Leu Glu Asp Gln Val Cys Phe Leu Leu Lys Leu
    1595            1600                1605

Met Leu Gln Gln Cys Lys Thr Gln Tyr Glu Leu Gly Lys Leu Leu
    1610            1615                1620

Gln Leu Phe Val Glu Arg Glu His Leu Phe Ser Asp Gly Pro Asp
    1625            1630                1635

Val Lys Lys Leu Cys Ile Leu Cys Gln Ile Leu Lys Asp Thr Ser
    1640            1645                1650

Ile Ala Ile Asn His Thr Ile Ile Thr Ser Tyr Ser Ile Glu Asn
    1655            1660                1665

Leu Gln His Glu Cys Arg Ser Ile Leu Glu Arg Leu Gln Thr Asp
    1670            1675                1680

Gly Gln Phe Ala Leu Ala Arg Arg Val Ala Glu Leu Ala Glu Leu
    1685            1690                1695

Pro Val Asp Asn Leu Val Ile Lys Glu Ile Thr Gln Glu Met Gln
    1700            1705                1710

Thr Leu Lys His Ile Glu Gln Trp Ser Leu Lys Gln Ala Arg Ile
    1715            1720                1725

Asp Phe Trp Lys Lys Cys His Glu Asn Phe Lys Lys Asn Ser Ile
    1730            1735                1740

Ser Ser Lys Ala Ala Ser Ser Phe Phe Ser Thr Gln Ala His Val
    1745            1750                1755

Ala Cys Glu His Pro Thr Gly Trp Ser Ser Met Glu Glu Arg His
    1760            1765                1770

Leu Leu Leu Thr Leu Ala Gly His Trp Leu Ala Gln Glu Asp Val
    1775            1780                1785

Val Pro Leu Asp Lys Leu Glu Glu Leu Glu Lys Gln Ile Trp Leu
    1790            1795                1800

Cys Arg Ile Thr Gln His Thr Leu Gly Arg Asn Gln Glu Glu Thr
    1805            1810                1815

Glu Pro Arg Phe Ser Arg Gln Ile Ser Thr Ser Gly Glu Leu Ser
    1820            1825                1830

Phe Asp Ser Leu Ala Ser Glu Phe Ser Phe Ser Val Gly Cys Ser
    1835            1840                1845

Glu His Ile Lys Ile Leu Arg Thr
    1850            1855

<210> SEQ ID NO 180
<211> LENGTH: 1949
<212> TYPE: PRT
<213> ORGANISM: Homo sapiens

<400> SEQUENCE: 180

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60
```

```
Val Leu Ser Leu Thr Pro Gly Ser Arg Gly Gly Arg Cys Cys Leu
 65                  70                  75                  80

Glu Gly Pro Phe Trp His Phe Leu Trp Glu Asp Ser Arg Asn Ser Ser
                 85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495
```

```
Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
                820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
            850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
                900                 905                 910

Gln Gln Asn Lys Trp Pro Leu Leu Thr Val Asp Val Ile Asn Gln Asn
```

-continued

```
                915                 920                 925
Thr Ser Cys Asn Asn Tyr Met Arg Asn Glu Ile Leu Asp Lys Leu Ala
    930                 935                 940
Arg Asn Gly Val Phe Leu Ala Ser Glu Leu Glu Asp Phe Glu Cys Phe
945                 950                 955                 960
Leu Leu Arg Leu Ser Arg Ile Gly Gly Val Ile Gln Asp Thr Leu Pro
                965                 970                 975
Val Gln Asn Tyr Lys Thr Lys Glu Gly Trp Asp Phe His Ser Gln Phe
            980                 985                 990
Ile Leu Tyr Cys Leu Glu His Ser Leu Gln His Leu Leu Tyr Val Tyr
                995                1000                1005
Leu Asp Cys Tyr Lys Leu Ser Pro Glu Asn Cys Pro Phe Leu Glu
    1010                1015                1020
Lys Lys Glu Leu His Glu Ala His Pro Trp Phe Glu Phe Leu Val
    1025                1030                1035
Gln Cys Arg Gln Val Ala Ser Asn Leu Thr Asp Pro Lys Leu Ile
    1040                1045                1050
Phe Gln Ala Ser Leu Ala Asn Ala Gln Ile Leu Ile Pro Thr Asn
    1055                1060                1065
Gln Ala Ser Val Ser Ser Met Leu Leu Glu Gly His Thr Leu Leu
    1070                1075                1080
Ala Leu Ala Thr Thr Met Tyr Ser Pro Gly Gly Val Ser Gln Val
    1085                1090                1095
Val Gln Asn Glu Glu Asn Glu Asn Cys Leu Lys Lys Val Asp Pro
    1100                1105                1110
Gln Leu Leu Lys Met Ala Leu Thr Pro Tyr Pro Lys Leu Lys Thr
    1115                1120                1125
Ala Leu Phe Pro Gln Cys Thr Pro Pro Ser Val Leu Pro Ser Asp
    1130                1135                1140
Ile Thr Ile Tyr His Leu Ile Gln Ser Leu Ser Pro Phe Asp Pro
    1145                1150                1155
Ser Arg Leu Phe Gly Trp Gln Ser Ala Asn Thr Leu Ala Ile Gly
    1160                1165                1170
Asp Ala Trp Ser His Leu Pro His Phe Ser Ser Pro Asp Leu Val
    1175                1180                1185
Asn Lys Tyr Ala Ile Val Glu Arg Leu Asn Phe Ala Tyr Tyr Leu
    1190                1195                1200
His Asn Gly Arg Pro Ser Phe Ala Phe Gly Thr Phe Leu Val Gln
    1205                1210                1215
Glu Leu Ile Lys Ser Lys Thr Pro Lys Gln Leu Ile Gln Gln Val
    1220                1225                1230
Gly Asn Glu Ala Tyr Val Ile Gly Leu Ser Ser Phe His Ile Pro
    1235                1240                1245
Ser Ile Gly Ala Ala Cys Val Cys Phe Leu Glu Leu Leu Gly Leu
    1250                1255                1260
Asp Ser Leu Lys Leu Arg Val Asp Met Lys Val Ala Asn Ile Ile
    1265                1270                1275
Leu Ser Tyr Lys Cys Arg Asn Glu Asp Ala Gln Tyr Ser Phe Ile
    1280                1285                1290
Arg Glu Ser Val Ala Glu Lys Leu Ser Lys Leu Ala Asp Gly Glu
    1295                1300                1305
Lys Thr Thr Thr Glu Glu Leu Leu Val Leu Leu Glu Glu Gly Thr
    1310                1315                1320
```

-continued

Trp Asn Ser Ile Gln Gln Gln Glu Ile Lys Arg Leu Ser Ser Glu
1325                 1330                1335

Ser Ser Ser Gln Trp Ala Leu Val Val Gln Phe Cys Arg Leu His
1340                1345                1350

Asn Met Lys Leu Ser Ile Ser Tyr Leu Arg Glu Cys Ala Lys Ala
1355                1360                1365

Asn Asp Trp Leu Gln Phe Ile Ile His Ser Gln Leu His Asn Tyr
1370                1375                1380

His Pro Ala Glu Val Lys Ser Leu Ile Gln Tyr Phe Ser Pro Val
1385                1390                1395

Ile Gln Asp His Leu Arg Leu Ala Phe Glu Asn Leu Pro Ser Val
1400                1405                1410

Pro Thr Ser Lys Met Asp Ser Asp Gln Val Cys Asn Lys Cys Pro
1415                1420                1425

Gln Glu Leu Gln Gly Ser Lys Gln Glu Met Thr Asp Leu Phe Glu
1430                1435                1440

Ile Leu Leu Gln Cys Ser Glu Glu Pro Asp Ser Trp His Trp Leu
1445                1450                1455

Leu Val Glu Ala Val Lys Gln Gln Ala Pro Ile Leu Ser Val Leu
1460                1465                1470

Ala Ser Cys Leu Gln Gly Ala Ser Ala Ile Ser Cys Leu Cys Val
1475                1480                1485

Trp Ile Ile Thr Ser Val Glu Asp Asn Val Ala Thr Glu Ala Met
1490                1495                1500

Gly His Ile Gln Asp Ser Thr Glu Asp His Thr Trp Asn Leu Glu
1505                1510                1515

Asp Leu Ser Val Ile Trp Arg Thr Leu Leu Thr Arg Gln Lys Ser
1520                1525                1530

Lys Thr Leu Ile Arg Gly Phe Gln Leu Phe Phe Lys Asp Ser Pro
1535                1540                1545

Leu Leu Leu Val Met Glu Met Tyr Glu Leu Cys Met Phe Phe Arg
1550                1555                1560

Asn Tyr Lys Glu Ala Glu Ala Lys Leu Leu Glu Phe Gln Lys Ser
1565                1570                1575

Leu Glu Thr Leu Asn Thr Ala Ala Thr Lys Val His Pro Val Ile
1580                1585                1590

Pro Ala Met Trp Leu Glu Asp Gln Val Cys Phe Leu Leu Lys Leu
1595                1600                1605

Met Leu Gln Gln Cys Lys Thr Gln Tyr Glu Leu Gly Lys Leu Leu
1610                1615                1620

Gln Leu Phe Val Glu Arg Glu His Leu Phe Ser Asp Gly Pro Asp
1625                1630                1635

Val Lys Lys Leu Cys Ile Leu Cys Gln Ile Leu Lys Asp Thr Ser
1640                1645                1650

Ile Ala Ile Asn His Thr Ile Ile Thr Ser Tyr Ser Ile Glu Asn
1655                1660                1665

Leu Gln His Glu Cys Arg Ser Ile Leu Glu Arg Leu Gln Thr Asp
1670                1675                1680

Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
1700                1705                1710

Thr Leu Lys His Ile Glu Gln Trp Ser Leu Lys Gln Ala Arg Ile
1715                1720                1725

```
Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Glu Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Arg
    1910                1915                1920

Trp Arg Ile Cys Thr Gln Arg Ser Met Leu Ser Tyr Lys Val Leu
    1925                1930                1935

Ser Cys Leu Arg Lys Lys His Pro Thr Phe Pro
    1940                1945

<210> SEQ ID NO 181
<211> LENGTH: 1956
<212> TYPE: PRT
<213> ORGANISM: Homo sapiens

<400> SEQUENCE: 181

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140
```

```
Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
```

-continued

```
                565                 570                 575
Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Asp Gln Leu Thr Gln Glu Ser
            850                 855                 860

Ile Leu Leu Pro Arg Ile Ser Pro Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990
```

-continued

```
Ile Leu Tyr Cys Leu Glu His Ser  Leu Gln His Leu Leu  Tyr Val Tyr
    995                 1000                  1005

Leu Asp Cys Tyr Lys Leu Ser Pro  Glu Asn Cys Pro  Phe Leu Glu
    1010                1015                 1020

Lys Lys Glu Leu His Glu Ala His  Pro Trp Phe Glu  Phe Leu Val
    1025                1030                 1035

Gln Cys Arg Gln Val Ala Ser Asn  Leu Thr Asp Pro  Lys Leu Ile
    1040                1045                 1050

Phe Gln Ala Ser Leu Ala Asn Ala  Gln Ile Leu Ile  Pro Thr Asn
    1055                1060                 1065

Gln Ala Ser Val Ser Ser Met Leu  Leu Glu Gly His  Thr Leu Leu
    1070                1075                 1080

Ala Leu Ala Thr Thr Met Tyr Ser  Pro Gly Gly Val  Ser Gln Val
    1085                1090                 1095

Val Gln Asn Glu Glu Asn Glu Asn  Cys Leu Lys Lys  Val Asp Pro
    1100                1105                 1110

Gln Leu Leu Lys Met Ala Leu Thr  Pro Tyr Pro Lys  Leu Lys Thr
    1115                1120                 1125

Ala Leu Phe Pro Gln Cys Thr Pro  Pro Ser Val Leu  Pro Ser Asp
    1130                1135                 1140

Ile Thr Ile Tyr His Leu Ile Gln  Ser Leu Ser Pro  Phe Asp Pro
    1145                1150                 1155

Ser Arg Leu Phe Gly Trp Gln Ser  Ala Asn Thr Leu  Ala Ile Gly
    1160                1165                 1170

Asp Ala Trp Ser His Leu Pro His  Phe Ser Pro Asp  Leu Val
    1175                1180                 1185

Asn Lys Tyr Ala Ile Val Glu Arg  Leu Asn Phe Ala  Tyr Tyr Leu
    1190                1195                 1200

His Asn Gly Arg Pro Ser Phe Ala  Phe Gly Thr Phe  Leu Val Gln
    1205                1210                 1215

Glu Leu Ile Lys Ser Lys Thr Pro  Lys Gln Leu Ile  Gln Gln Val
    1220                1225                 1230

Gly Asn Glu Ala Tyr Val Ile Gly  Leu Ser Ser Phe  His Ile Pro
    1235                1240                 1245

Ser Ile Gly Ala Ala Cys Val Cys  Phe Leu Glu Leu  Leu Gly Leu
    1250                1255                 1260

Asp Ser Leu Lys Leu Arg Val Asp  Met Lys Val Ala  Asn Ile Ile
    1265                1270                 1275

Leu Ser Tyr Lys Cys Arg Asn Glu  Asp Ala Gln Tyr  Ser Phe Ile
    1280                1285                 1290

Arg Glu Ser Val Ala Glu Lys Leu  Ser Lys Leu Ala  Asp Gly Glu
    1295                1300                 1305

Lys Thr Thr Thr Glu Glu Leu Leu  Val Leu Leu Glu  Glu Gly Thr
    1310                1315                 1320

Trp Asn Ser Ile Gln Gln Gln Glu  Ile Lys Arg Leu  Ser Ser Glu
    1325                1330                 1335

Ser Ser Ser Gln Trp Ala Leu Val  Val Gln Phe Cys  Arg Leu His
    1340                1345                 1350

Asn Met Lys Leu Ser Ile Ser Tyr  Leu Arg Glu Cys  Ala Lys Ala
    1355                1360                 1365

Asn Asp Trp Leu Gln Phe Ile Ile  His Ser Gln Leu  His Asn Tyr
    1370                1375                 1380

His Pro Ala Glu Val Lys Ser Leu  Ile Gln Tyr Phe  Ser Pro Val
    1385                1390                 1395
```

```
Ile Gln Asp His Leu Arg Leu Ala Phe Glu Asn Leu Pro Ser Val
    1400            1405                1410

Pro Thr Ser Lys Met Asp Ser Asp Gln Val Cys Asn Lys Cys Pro
    1415            1420                1425

Gln Glu Leu Gln Gly Ser Lys Gln Glu Met Thr Asp Leu Phe Glu
    1430            1435                1440

Ile Leu Leu Gln Cys Ser Glu Glu Pro Asp Ser Trp His Trp Leu
    1445            1450                1455

Leu Val Glu Ala Val Lys Gln Gln Ala Pro Ile Leu Ser Val Leu
    1460            1465                1470

Ala Ser Cys Leu Gln Gly Ala Ser Ala Ile Ser Cys Leu Cys Val
    1475            1480                1485

Trp Ile Ile Thr Ser Val Glu Asp Asn Val Ala Thr Glu Ala Met
    1490            1495                1500

Gly His Ile Gln Asp Ser Thr Glu Asp His Thr Trp Asn Leu Glu
    1505            1510                1515

Asp Leu Ser Val Ile Trp Arg Thr Leu Leu Thr Arg Gln Lys Ser
    1520            1525                1530

Lys Thr Leu Ile Arg Gly Phe Gln Leu Phe Phe Lys Asp Ser Pro
    1535            1540                1545

Leu Leu Leu Val Met Glu Met Tyr Glu Leu Cys Met Phe Phe Arg
    1550            1555                1560

Asn Tyr Lys Glu Ala Glu Ala Lys Leu Leu Glu Phe Gln Lys Ser
    1565            1570                1575

Leu Glu Thr Leu Asn Thr Ala Ala Thr Lys Val His Pro Val Ile
    1580            1585                1590

Pro Ala Met Trp Leu Glu Asp Gln Val Cys Phe Leu Leu Lys Leu
    1595            1600                1605

Met Leu Gln Gln Cys Lys Thr Gln Tyr Glu Leu Gly Lys Leu Leu
    1610            1615                1620

Gln Leu Phe Val Glu Arg Glu His Leu Phe Ser Asp Gly Pro Asp
    1625            1630                1635

Val Lys Lys Leu Cys Ile Leu Cys Gln Ile Leu Lys Asp Thr Ser
    1640            1645                1650

Ile Ala Ile Asn His Thr Ile Ile Thr Ser Tyr Ser Ile Glu Asn
    1655            1660                1665

Leu Gln His Glu Cys Arg Ser Ile Leu Glu Arg Leu Gln Thr Asp
    1670            1675                1680

Gly Gln Phe Ala Leu Ala Arg Arg Val Ala Glu Leu Ala Glu Leu
    1685            1690                1695

Pro Val Asp Asn Leu Val Ile Lys Glu Ile Thr Gln Glu Met Gln
    1700            1705                1710

Thr Leu Lys His Ile Glu Gln Trp Ser Leu Lys Gln Ala Arg Ile
    1715            1720                1725

Asp Phe Trp Lys Lys Cys His Glu Asn Phe Lys Lys Asn Ser Ile
    1730            1735                1740

Ser Ser Lys Ala Ala Ser Ser Phe Phe Ser Thr Gln Ala His Val
    1745            1750                1755

Ala Cys Glu His Pro Thr Gly Trp Ser Ser Met Glu Glu Arg His
    1760            1765                1770

Leu Leu Leu Thr Leu Ala Gly His Trp Leu Ala Gln Glu Asp Val
    1775            1780                1785

Val Pro Leu Asp Lys Leu Glu Glu Leu Glu Lys Gln Ile Trp Leu
```

-continued

```
                    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr
    1955

<210> SEQ ID NO 182
<211> LENGTH: 1999
<212> TYPE: PRT
<213> ORGANISM: Homo sapiens

<400> SEQUENCE: 182

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Val Pro
                20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
```

-continued

```
            195                 200                 205
Cys Arg Gly Ile Leu Phe Val Leu Ser Ser Leu Gly Trp Ile Tyr Ile
210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Glu Pro Ala Lys Ile
            245                 250                 255
Ser Ser Phe Thr Ser Leu Lys Val Ser Gln Asp Leu Asp Val Ala Val
            260                 265                 270
Ile Val Ser Ser Asn Ser Ala Val Ala Leu Asn Leu Asn Leu Tyr
            275                 280                 285
Phe Arg Gln His Pro Gly His Leu Leu Cys Glu Arg Ile Leu Glu Asp
290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
            325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
            355                 360                 365
Leu Glu Ser Pro Glu Ser Gly Asn His Ser Thr Ser Val Gln Ser Trp
370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
            405                 410                 415
His Ile Ser Glu Gln Glu Glu Pro Ile Glu Leu Lys Cys Val Ser Val
            420                 425                 430
Thr Gly Phe Thr Ala Leu Phe Thr Trp Glu Val Glu Arg Met Gly Tyr
            435                 440                 445
Thr Ile Thr Leu Trp Asp Leu Glu Thr Gln Gly Met Gln Cys Ser Ser
450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
            485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
            515                 520                 525
Pro Ile His Ala Leu Glu Ala Gly Ile Glu Asn Arg Gln Leu Asp Thr
530                 535                 540
Val Asn Phe Phe Leu Lys Ser Lys Glu Asn Leu Phe Asn Pro Ser Ser
545                 550                 555                 560
Lys Ser Ser Val Ser Asp Gln Phe Asp His Leu Ser Ser His Leu Tyr
            565                 570                 575
Leu Arg Asn Val Glu Glu Leu Ile Pro Ala Leu Asp Leu Leu Cys Ser
            580                 585                 590
Ala Ile Arg Glu Ser Tyr Ser Glu Pro Gln Ser Lys His Phe Ser Glu
            595                 600                 605
Gln Leu Leu Asn Leu Thr Leu Ser Phe Leu Asn Asn Gln Ile Lys Glu
610                 615                 620
```

```
Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser  Leu Gln His Leu Leu  Tyr Val Tyr
            995                 1000                1005

Leu Asp Cys Tyr Lys Leu Ser  Pro Glu Asn Cys Pro  Phe Leu Glu
    1010                1015                1020

Lys Lys  Glu Leu His Glu Ala  His Pro Trp Phe Glu  Phe Leu Val
    1025                1030                1035

Gln Cys  Arg Gln Val Ala Ser  Asn Leu Thr Asp Pro  Lys Leu Ile
    1040                1045                1050
```

-continued

```
Phe Gln Ala Ser Leu Ala Asn Ala Gln Ile Leu Ile Pro Thr Asn
    1055                1060                1065
Gln Ala Ser Val Ser Ser Met Leu Leu Glu Gly His Thr Leu Leu
    1070                1075                1080
Ala Leu Ala Thr Thr Met Tyr Ser Pro Gly Gly Val Ser Gln Val
    1085                1090                1095
Val Gln Asn Glu Glu Asn Glu Asn Cys Leu Lys Lys Val Asp Pro
    1100                1105                1110
Gln Leu Leu Lys Met Ala Leu Thr Pro Tyr Pro Lys Leu Lys Thr
    1115                1120                1125
Ala Leu Phe Pro Gln Cys Thr Pro Pro Ser Val Leu Pro Ser Asp
    1130                1135                1140
Ile Thr Ile Tyr His Leu Ile Gln Ser Leu Ser Pro Phe Asp Pro
    1145                1150                1155
Ser Arg Leu Phe Gly Trp Gln Ser Ala Asn Thr Leu Ala Ile Gly
    1160                1165                1170
Asp Ala Trp Ser His Leu Pro His Phe Ser Ser Pro Asp Leu Val
    1175                1180                1185
Asn Lys Tyr Ala Ile Val Glu Arg Leu Asn Phe Ala Tyr Tyr Leu
    1190                1195                1200
His Asn Gly Arg Pro Ser Phe Ala Phe Gly Thr Phe Leu Val Gln
    1205                1210                1215
Glu Leu Ile Lys Ser Lys Thr Pro Lys Gln Leu Ile Gln Gln Val
    1220                1225                1230
Gly Asn Glu Ala Tyr Val Ile Gly Leu Ser Ser Phe His Ile Pro
    1235                1240                1245
Ser Ile Gly Ala Ala Cys Val Cys Phe Leu Glu Leu Leu Gly Leu
    1250                1255                1260
Asp Ser Leu Lys Leu Arg Val Asp Met Lys Val Ala Asn Ile Ile
    1265                1270                1275
Leu Ser Tyr Lys Cys Arg Asn Glu Asp Ala Gln Tyr Ser Phe Ile
    1280                1285                1290
Arg Glu Ser Val Ala Glu Lys Leu Ser Lys Leu Ala Asp Gly Glu
    1295                1300                1305
Lys Thr Thr Thr Glu Glu Leu Leu Val Leu Leu Glu Glu Gly Thr
    1310                1315                1320
Trp Asn Ser Ile Gln Gln Gln Glu Ile Lys Arg Leu Ser Ser Glu
    1325                1330                1335
Ser Ser Ser Gln Trp Ala Leu Val Val Gln Phe Cys Arg Leu His
    1340                1345                1350
Asn Met Lys Leu Ser Ile Ser Tyr Leu Arg Glu Cys Ala Lys Ala
    1355                1360                1365
Asn Asp Trp Leu Gln Phe Ile Ile His Ser Gln Leu His Asn Tyr
    1370                1375                1380
His Pro Ala Glu Val Lys Ser Leu Ile Gln Tyr Phe Ser Pro Val
    1385                1390                1395
Ile Gln Asp His Leu Arg Leu Ala Phe Glu Asn Leu Pro Ser Val
    1400                1405                1410
Pro Thr Ser Lys Met Asp Ser Asp Gln Val Cys Asn Lys Cys Pro
    1415                1420                1425
Gln Glu Leu Gln Gly Ser Lys Gln Glu Met Thr Asp Leu Phe Glu
    1430                1435                1440
Ile Leu Leu Gln Cys Ser Glu Glu Pro Asp Ser Trp His Trp Leu
```

```
              1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845
```

-continued

```
Leu Asn Thr Ser Lys Tyr Leu Glu Leu Asn Ser Leu Pro Ser Lys
    1850             1855             1860

Glu Thr Cys Glu Asn Arg Leu Asp Trp Lys Glu Gln Glu Ser Leu
    1865             1870             1875

Asn Phe Leu Ile Gly Arg Leu Leu Asp Asp Gly Cys Val His Glu
    1880             1885             1890

Ala Ser Arg Val Cys Arg Tyr Phe His Phe Tyr Asn Pro Asp Val
    1895             1900             1905

Ala Leu Val Leu His Cys Arg Ala Leu Ala Ser Gly Glu Ala Ser
    1910             1915             1920

Met Glu Asp Leu His Pro Glu Ile His Ala Leu Leu Gln Ser Ala
    1925             1930             1935

Glu Leu Leu Glu Glu Glu Ala Pro Asp Ile Pro Leu Arg Arg Val
    1940             1945             1950

His Ser Thr Ser Ser Leu Asp Ser Gln Lys Phe Val Thr Val Pro
    1955             1960             1965

Ser Ser Asn Glu Val Val Thr Asn Leu Glu Val Leu Thr Ser Lys
    1970             1975             1980

Cys Leu His Gly Lys Asn Tyr Cys Arg Gln Val Leu Ser Leu Ser
    1985             1990             1995

Val

<210> SEQ ID NO 183
<211> LENGTH: 1998
<212> TYPE: PRT
<213> ORGANISM: Homo sapiens

<400> SEQUENCE: 183

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
```

-continued

```
            210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Glu Pro Ala Lys Ile
            245                 250                 255
Ser Ser Phe Thr Ser Leu Lys Val Ser Gln Asp Leu Asp Val Ala Val
            260                 265                 270
Ile Val Ser Ser Asn Ser Ala Val Ala Leu Asn Leu Asn Leu Tyr
            275                 280                 285
Phe Arg Gln His Pro Gly His Leu Leu Cys Glu Arg Ile Leu Glu Asp
290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
            325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
            355                 360                 365
Leu Glu Ser Pro Glu Ser Gly Asn His Ser Thr Ser Val Gln Ser Trp
370                 375                 380
Ala Phe Ile Pro Gln Asp Ile Met His Gly Tyr Asn Val Leu Gln
385                 390                 395                 400
Lys Asp His Ala Lys Thr Ser Asp Pro Gly Arg Ser Trp Lys Ile Met
            405                 410                 415
His Ile Ser Glu Gln Glu Glu Pro Ile Glu Leu Lys Cys Val Ser Val
            420                 425                 430
Thr Gly Phe Thr Ala Leu Phe Thr Trp Glu Val Glu Arg Met Gly Tyr
            435                 440                 445
Thr Ile Thr Leu Trp Asp Leu Glu Thr Gln Gly Met Gln Cys Ser Ser
            450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
            485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
            515                 520                 525
Pro Ile His Ala Leu Glu Ala Gly Ile Glu Asn Arg Gln Leu Asp Thr
530                 535                 540
Val Asn Phe Phe Leu Lys Ser Lys Glu Asn Leu Phe Asn Pro Ser Ser
545                 550                 555                 560
Lys Ser Ser Val Ser Asp Gln Phe Asp His Leu Ser Ser His Leu Tyr
            565                 570                 575
Leu Arg Asn Val Glu Glu Leu Ile Pro Ala Leu Asp Leu Leu Cys Ser
            580                 585                 590
Ala Ile Arg Glu Ser Tyr Ser Glu Pro Gln Ser Lys His Phe Ser Glu
            595                 600                 605
Gln Leu Leu Asn Leu Thr Leu Ser Phe Leu Asn Asn Gln Ile Lys Glu
            610                 615                 620
Leu Phe Ile His Thr Glu Glu Leu Asp Glu His Leu Gln Lys Gly Val
625                 630                 635                 640
```

-continued

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
            725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
            805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
            885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Asp Phe Glu Cys Phe
945                 950                 955                 960

Leu Leu Arg Leu Ser Arg Ile Gly Gly Val Ile Gln Asp Thr Leu Pro
            965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
            995                1000                1005

Leu Asp Cys Tyr Lys Leu Ser Pro Glu Asn Cys Pro Phe Leu Glu
            1010                1015                1020

Lys Lys Glu Leu His Glu Ala His Pro Trp Phe Glu Phe Leu Val
            1025                1030                1035

Gln Cys Arg Gln Val Ala Ser Asn Leu Thr Asp Pro Lys Leu Ile
            1040                1045                1050

Phe Gln Ala Ser Leu Ala Asn Ala Gln Ile Leu Ile Pro Thr Asn
            1055                1060                1065

-continued

```
Gln Ala Ser Val Ser Ser Met Leu Leu Glu Gly His Thr Leu Leu
    1070            1075                1080
Ala Leu Ala Thr Thr Met Tyr Ser Pro Gly Val Ser Gln Val
    1085            1090                1095
Val Gln Asn Glu Glu Asn Asn Cys Leu Lys Lys Val Asp Pro
    1100            1105                1110
Gln Leu Leu Lys Met Ala Leu Thr Pro Tyr Pro Lys Leu Lys Thr
    1115            1120                1125
Ala Leu Phe Pro Gln Cys Thr Pro Pro Ser Val Leu Pro Ser Asp
    1130            1135                1140
Ile Thr Ile Tyr His Leu Ile Gln Ser Leu Ser Pro Phe Asp Pro
    1145            1150                1155
Ser Arg Leu Phe Gly Trp Gln Ser Ala Asn Thr Leu Ala Ile Gly
    1160            1165                1170
Asp Ala Trp Ser His Leu Pro His Phe Ser Ser Pro Asp Leu Val
    1175            1180                1185
Asn Lys Tyr Ala Ile Val Glu Arg Leu Asn Phe Ala Tyr Tyr Leu
    1190            1195                1200
His Asn Gly Arg Pro Ser Phe Ala Phe Gly Thr Phe Leu Val Gln
    1205            1210                1215
Glu Leu Ile Lys Ser Lys Thr Pro Lys Gln Leu Ile Gln Gln Val
    1220            1225                1230
Gly Asn Glu Ala Tyr Val Ile Gly Leu Ser Ser Phe His Ile Pro
    1235            1240                1245
Ser Ile Gly Ala Ala Cys Val Cys Phe Leu Glu Leu Leu Gly Leu
    1250            1255                1260
Asp Ser Leu Lys Leu Arg Val Asp Met Lys Val Ala Asn Ile Ile
    1265            1270                1275
Leu Ser Tyr Lys Cys Arg Asn Glu Asp Ala Gln Tyr Ser Phe Ile
    1280            1285                1290
Arg Glu Ser Val Ala Glu Lys Leu Ser Lys Leu Ala Asp Gly Glu
    1295            1300                1305
Lys Thr Thr Thr Glu Glu Leu Leu Val Leu Leu Glu Glu Gly Thr
    1310            1315                1320
Trp Asn Ser Ile Gln Gln Gln Glu Ile Lys Arg Leu Ser Ser Glu
    1325            1330                1335
Ser Ser Ser Gln Trp Ala Leu Val Val Gln Phe Cys Arg Leu His
    1340            1345                1350
Asn Met Lys Leu Ser Ile Ser Tyr Leu Arg Glu Cys Ala Lys Ala
    1355            1360                1365
Asn Asp Trp Leu Gln Phe Ile Ile His Ser Gln Leu His Asn Tyr
    1370            1375                1380
His Pro Ala Glu Val Lys Ser Leu Ile Gln Tyr Phe Ser Pro Val
    1385            1390                1395
Ile Gln Asp His Leu Arg Leu Ala Phe Glu Asn Leu Pro Ser Val
    1400            1405                1410
Pro Thr Ser Lys Met Asp Ser Asp Gln Val Cys Asn Lys Cys Pro
    1415            1420                1425
Gln Glu Leu Gln Gly Ser Lys Gln Glu Met Thr Asp Leu Phe Glu
    1430            1435                1440
Ile Leu Leu Gln Cys Ser Glu Glu Pro Asp Ser Trp His Trp Leu
    1445            1450                1455
Leu Val Glu Ala Val Lys Gln Gln Ala Pro Ile Leu Ser Val Leu
```

```
              1460              1465              1470
Ala Ser Cys Leu Gln Gly Ala Ser Ala Ile Ser Cys Leu Cys Val
    1475                1480                1485
Trp Ile Ile Thr Ser Val Glu Asp Asn Val Ala Thr Glu Ala Met
    1490                1495                1500
Gly His Ile Gln Asp Ser Thr Glu Asp His Thr Trp Asn Leu Glu
    1505                1510                1515
Asp Leu Ser Val Ile Trp Arg Thr Leu Leu Thr Arg Gln Lys Ser
    1520                1525                1530
Lys Thr Leu Ile Arg Gly Phe Gln Leu Phe Phe Lys Asp Ser Pro
    1535                1540                1545
Leu Leu Leu Val Met Glu Met Tyr Glu Leu Cys Met Phe Phe Arg
    1550                1555                1560
Asn Tyr Lys Glu Ala Glu Ala Lys Leu Leu Glu Phe Gln Lys Ser
    1565                1570                1575
Leu Glu Thr Leu Asn Thr Ala Ala Thr Lys Val His Pro Val Ile
    1580                1585                1590
Pro Ala Met Trp Leu Glu Asp Gln Val Cys Phe Leu Leu Lys Leu
    1595                1600                1605
Met Leu Gln Gln Cys Lys Thr Gln Tyr Glu Leu Gly Lys Leu Leu
    1610                1615                1620
Gln Leu Phe Val Glu Arg Glu His Leu Phe Ser Asp Gly Pro Asp
    1625                1630                1635
Val Lys Lys Leu Cys Ile Leu Cys Gln Ile Leu Lys Asp Thr Ser
    1640                1645                1650
Ile Ala Ile Asn His Thr Ile Ile Thr Ser Tyr Ser Ile Glu Asn
    1655                1660                1665
Leu Gln His Glu Cys Arg Ser Ile Leu Glu Arg Leu Gln Thr Asp
    1670                1675                1680
Gly Gln Phe Ala Leu Ala Arg Arg Val Ala Glu Leu Ala Glu Leu
    1685                1690                1695
Pro Val Asp Asn Leu Val Ile Lys Glu Ile Thr Gln Glu Met Gln
    1700                1705                1710
Thr Leu Lys His Ile Glu Gln Trp Ser Leu Lys Gln Ala Arg Ile
    1715                1720                1725
Asp Phe Trp Lys Lys Cys His Glu Asn Phe Lys Lys Asn Ser Ile
    1730                1735                1740
Ser Ser Lys Ala Ala Ser Phe Phe Ser Thr Gln Ala His Val
    1745                1750                1755
Ala Cys Glu His Pro Thr Gly Trp Ser Ser Met Glu Glu Arg His
    1760                1765                1770
Leu Leu Leu Thr Leu Ala Gly His Trp Leu Ala Gln Glu Asp Val
    1775                1780                1785
Val Pro Leu Asp Lys Leu Glu Glu Leu Glu Lys Gln Ile Trp Leu
    1790                1795                1800
Cys Arg Ile Thr Gln His Thr Leu Gly Arg Asn Gln Glu Glu Thr
    1805                1810                1815
Glu Pro Arg Phe Ser Arg Gln Ile Ser Thr Ser Gly Glu Leu Ser
    1820                1825                1830
Phe Asp Ser Leu Ala Ser Glu Phe Ser Phe Ser Lys Leu Ala Ala
    1835                1840                1845
Leu Asn Thr Ser Lys Tyr Leu Glu Leu Asn Ser Leu Pro Ser Lys
    1850                1855                1860
```

-continued

```
Glu  Thr  Cys  Glu  Asn  Arg  Leu  Asp  Trp  Lys  Glu  Gln  Glu  Ser  Leu
     1865                1870                1875

Asn  Phe  Leu  Ile  Gly  Arg  Leu  Leu  Asp  Asp  Gly  Cys  Val  His  Glu
     1880                1885                1890

Ala  Ser  Arg  Val  Cys  Arg  Tyr  Phe  His  Phe  Tyr  Asn  Pro  Asp  Val
     1895                1900                1905

Ala  Leu  Val  Leu  His  Cys  Arg  Ala  Leu  Ala  Ser  Gly  Glu  Ala  Ser
     1910                1915                1920

Met  Glu  Asp  Leu  His  Pro  Glu  Ile  His  Ala  Leu  Leu  Gln  Ser  Ala
     1925                1930                1935

Glu  Leu  Leu  Glu  Glu  Glu  Ala  Pro  Asp  Ile  Pro  Leu  Arg  Arg  Val
     1940                1945                1950

His  Ser  Thr  Ser  Ser  Leu  Asp  Ser  Gln  Lys  Phe  Val  Thr  Val  Pro
     1955                1960                1965

Ser  Ser  Asn  Glu  Val  Val  Thr  Asn  Leu  Glu  Val  Leu  Thr  Ser  Lys
     1970                1975                1980

Cys  Leu  His  Gly  Lys  Asn  Tyr  Cys  Arg  Gln  Val  Leu  Leu  Ser  Val
     1985                1990                1995
```

<210> SEQ ID NO 184
<211> LENGTH: 2055
<212> TYPE: PRT
<213> ORGANISM: Homo sapiens

<400> SEQUENCE: 184

```
Met  Ala  Ala  Glu  Glu  Gly  Val  Ala  Ser  Ala  Ser  Ala  Gly  Gly  Ser
1                   5                   10                  15

Trp  Gly  Thr  Ala  Ala  Met  Gly  Arg  Val  Leu  Pro  Met  Leu  Val  Pro
                    20                  25                  30

Val  Pro  Ala  Glu  Ala  Met  Gly  Gln  Leu  Gly  Ser  Arg  Ala  Gln  Leu  Arg
                    35                  40                  45

Thr  Gln  Pro  Glu  Ala  Leu  Gly  Ser  Leu  Thr  Ala  Ala  Gly  Ser  Leu  Gln
     50                  55                  60

Val  Leu  Ser  Leu  Thr  Pro  Gly  Ser  Arg  Gly  Gly  Gly  Arg  Cys  Cys  Leu
65                   70                  75                  80

Glu  Gly  Pro  Phe  Trp  His  Phe  Leu  Trp  Glu  Asp  Ser  Arg  Asn  Ser  Ser
                    85                  90                  95

Thr  Pro  Thr  Glu  Lys  Pro  Lys  Leu  Leu  Ala  Leu  Gly  Glu  Asn  Tyr  Glu
                    100                 105                 110

Leu  Leu  Ile  Tyr  Glu  Phe  Asn  Leu  Lys  Asp  Gly  Arg  Cys  Asp  Ala  Thr
                    115                 120                 125

Ile  Leu  Tyr  Ser  Cys  Ser  Arg  Glu  Ala  Leu  Gln  Lys  Leu  Ile  Asp  Asp
     130                 135                 140

Gln  Asp  Ile  Ser  Ile  Ser  Leu  Leu  Ser  Leu  Arg  Ile  Leu  Ser  Phe  His
145                  150                 155                 160

Asn  Asn  Thr  Ser  Leu  Leu  Phe  Ile  Asn  Lys  Cys  Val  Ile  Leu  His  Ile
                    165                 170                 175

Ile  Phe  Pro  Glu  Arg  Asp  Ala  Ala  Ile  Arg  Val  Leu  Asn  Cys  Phe  Thr
                    180                 185                 190

Leu  Pro  Leu  Pro  Ala  Gln  Ala  Val  Asp  Met  Ile  Ile  Asp  Thr  Gln  Leu
                    195                 200                 205

Cys  Arg  Gly  Ile  Leu  Phe  Val  Leu  Ser  Ser  Leu  Gly  Trp  Ile  Tyr  Ile
     210                 215                 220

Phe  Asp  Val  Val  Asp  Gly  Thr  Tyr  Val  Ala  His  Val  Asp  Leu  Ala  Leu
225                  230                 235                 240
```

```
His Lys Glu Asp Met Cys Asn Glu Gln Gln Gln Glu Pro Ala Lys Ile
            245                 250                 255

Ser Ser Phe Thr Ser Leu Lys Val Ser Gln Asp Leu Asp Val Ala Val
        260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
        290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
            325                 330                 335

Ser Trp Lys Ala Gln Leu Ser Ser Leu Asn Glu Thr Ile Lys Asn Ser
        340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
        420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
        450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
        500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
        530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
        660                 665                 670
```

```
Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser  Leu Gln His Leu Leu  Tyr Val Tyr
        995                 1000                1005

Leu Asp  Cys Tyr Lys Leu Ser  Pro Glu Asn Cys Pro  Phe Leu Glu
    1010                1015                1020

Lys Lys  Glu Leu His Glu Ala  His Pro Trp Phe Glu  Phe Leu Val
    1025                1030                1035

Gln Cys  Arg Gln Val Ala Ser  Asn Leu Thr Asp Pro  Lys Leu Ile
    1040                1045                1050

Phe Gln  Ala Ser Leu Ala Asn  Ala Gln Ile Leu Ile  Pro Thr Asn
    1055                1060                1065

Gln Ala  Ser Val Ser Ser Met  Leu Leu Glu Gly His  Thr Leu Leu
    1070                1075                1080

Ala Leu  Ala Thr Thr Met Tyr  Ser Pro Gly Gly Val  Ser Gln Val
```

-continued

```
                1085                1090                1095
    Val Gln Asn Glu Glu Asn Glu Asn Cys Leu Lys Lys Val Asp Pro
    1100                1105                1110
    Gln Leu Leu Lys Met Ala Leu Thr Pro Tyr Pro Lys Leu Lys Thr
    1115                1120                1125
    Ala Leu Phe Pro Gln Cys Thr Pro Pro Ser Val Leu Pro Ser Asp
    1130                1135                1140
    Ile Thr Ile Tyr His Leu Ile Gln Ser Leu Ser Pro Phe Asp Pro
    1145                1150                1155
    Ser Arg Leu Phe Gly Trp Gln Ser Ala Asn Thr Leu Ala Ile Gly
    1160                1165                1170
    Asp Ala Trp Ser His Leu Pro His Phe Ser Ser Pro Asp Leu Val
    1175                1180                1185
    Asn Lys Tyr Ala Ile Val Glu Arg Leu Asn Phe Ala Tyr Tyr Leu
    1190                1195                1200
    His Asn Gly Arg Pro Ser Phe Ala Phe Gly Thr Phe Leu Val Gln
    1205                1210                1215
    Glu Leu Ile Lys Ser Lys Thr Pro Lys Gln Leu Ile Gln Gln Val
    1220                1225                1230
    Gly Asn Glu Ala Tyr Val Ile Gly Leu Ser Ser Phe His Ile Pro
    1235                1240                1245
    Ser Ile Gly Ala Ala Cys Val Cys Phe Leu Glu Leu Leu Gly Leu
    1250                1255                1260
    Asp Ser Leu Lys Leu Arg Val Asp Met Lys Val Ala Asn Ile Ile
    1265                1270                1275
    Leu Ser Tyr Lys Cys Arg Asn Glu Asp Ala Gln Tyr Ser Phe Ile
    1280                1285                1290
    Arg Glu Ser Val Ala Glu Lys Leu Ser Lys Leu Ala Asp Gly Glu
    1295                1300                1305
    Lys Thr Thr Thr Glu Glu Leu Leu Val Leu Leu Glu Glu Gly Thr
    1310                1315                1320
    Trp Asn Ser Ile Gln Gln Gln Glu Ile Lys Arg Leu Ser Ser Glu
    1325                1330                1335
    Ser Ser Ser Gln Trp Ala Leu Val Val Gln Phe Cys Arg Leu His
    1340                1345                1350
    Asn Met Lys Leu Ser Ile Ser Tyr Leu Arg Glu Cys Ala Lys Ala
    1355                1360                1365
    Asn Asp Trp Leu Gln Phe Ile Ile His Ser Gln Leu His Asn Tyr
    1370                1375                1380
    His Pro Ala Glu Val Lys Ser Leu Ile Gln Tyr Phe Ser Pro Val
    1385                1390                1395
    Ile Gln Asp His Leu Arg Leu Ala Phe Glu Asn Leu Pro Ser Val
    1400                1405                1410
    Pro Thr Ser Lys Met Asp Ser Asp Gln Val Cys Asn Lys Cys Pro
    1415                1420                1425
    Gln Glu Leu Gln Gly Ser Lys Gln Glu Met Thr Asp Leu Phe Glu
    1430                1435                1440
    Ile Leu Leu Gln Cys Ser Glu Glu Pro Asp Ser Trp His Trp Leu
    1445                1450                1455
    Leu Val Glu Ala Val Lys Gln Gln Ala Pro Ile Leu Ser Val Leu
    1460                1465                1470
    Ala Ser Cys Leu Gln Gly Ala Ser Ala Ile Ser Cys Leu Cys Val
    1475                1480                1485
```

-continued

```
Trp Ile Ile Thr Ser Val Glu Asp Asn Val Ala Thr Glu Ala Met
1490                1495                1500

Gly His Ile Gln Asp Ser Thr Glu Asp His Thr Trp Asn Leu Glu
1505                1510                1515

Asp Leu Ser Val Ile Trp Arg Thr Leu Leu Thr Arg Gln Lys Ser
1520                1525                1530

Lys Thr Leu Ile Arg Gly Phe Gln Leu Phe Phe Lys Asp Ser Pro
1535                1540                1545

Leu Leu Leu Val Met Glu Met Tyr Glu Leu Cys Met Phe Phe Arg
1550                1555                1560

Asn Tyr Lys Glu Ala Glu Ala Lys Leu Leu Glu Phe Gln Lys Ser
1565                1570                1575

Leu Glu Thr Leu Asn Thr Ala Ala Thr Lys Val His Pro Val Ile
1580                1585                1590

Pro Ala Met Trp Leu Glu Asp Gln Val Cys Phe Leu Leu Lys Leu
1595                1600                1605

Met Leu Gln Gln Cys Lys Thr Gln Tyr Glu Leu Gly Lys Leu Leu
1610                1615                1620

Gln Leu Phe Val Glu Arg Glu His Leu Phe Ser Asp Gly Pro Asp
1625                1630                1635

Val Lys Lys Leu Cys Ile Leu Cys Gln Ile Leu Lys Asp Thr Ser
1640                1645                1650

Ile Ala Ile Asn His Thr Ile Ile Thr Ser Tyr Ser Ile Glu Asn
1655                1660                1665

Leu Gln His Glu Cys Arg Ser Ile Leu Glu Arg Leu Gln Thr Asp
1670                1675                1680

Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
1700                1705                1710

Thr Leu Lys His Ile Glu Gln Trp Ser Leu Lys Gln Ala Arg Ile
1715                1720                1725

Asp Phe Trp Lys Lys Cys His Glu Asn Phe Lys Lys Asn Ser Ile
1730                1735                1740

Ser Ser Lys Ala Ala Ser Ser Phe Phe Ser Thr Gln Ala His Val
1745                1750                1755

Ala Cys Glu His Pro Thr Gly Trp Ser Ser Met Glu Glu Arg His
1760                1765                1770

Leu Leu Leu Thr Leu Ala Gly His Trp Leu Ala Gln Glu Asp Val
1775                1780                1785

Val Pro Leu Asp Lys Leu Glu Glu Leu Glu Lys Gln Ile Trp Leu
1790                1795                1800

Cys Arg Ile Thr Gln His Thr Leu Gly Arg Asn Gln Glu Glu Thr
1805                1810                1815

Glu Pro Arg Phe Ser Arg Gln Ile Ser Thr Ser Gly Gly Leu Ser
1820                1825                1830

Phe Asp Ser Leu Ala Ser Glu Phe Ser Phe Ser Lys Leu Ala Ala
1835                1840                1845

Leu Asn Thr Ser Lys Tyr Leu Glu Leu Asn Ser Leu Pro Ser Lys
1850                1855                1860

Glu Thr Cys Glu Asn Arg Leu Asp Trp Lys Glu Gln Glu Ser Leu
1865                1870                1875

Asn Phe Leu Ile Gly Arg Leu Leu Asp Asp Gly Cys Val His Glu
1880                1885                1890
```

```
Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Met Ile
    1985                1990                1995

Leu Pro Arg Ser Trp Ala Val Pro Thr Gln Met Leu Leu Leu Arg
    2000                2005                2010

Met Val Lys Pro Cys Ser Gly Lys Ser Trp Pro Leu Ser Ser Leu
    2015                2020                2025

Thr Asp Ala Asn Glu Pro Arg Pro Ser Ser Ala His Arg Ala Leu
    2030                2035                2040

Ser Gln Ile Leu Trp Leu Asn Ser Trp Gln Lys Arg
    2045                2050                2055

<210> SEQ ID NO 185
<211> LENGTH: 2030
<212> TYPE: PRT
<213> ORGANISM: Homo sapiens

<400> SEQUENCE: 185

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205
```

```
Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
                435                 440                 445

Thr Ile Thr Leu Trp Asp Leu Glu Thr Gln Gly Met Gln Cys Ser Ser
                450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
                515                 520                 525

Pro Ile His Ala Leu Glu Ala Gly Ile Glu Asn Arg Gln Leu Asp Thr
                530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
                595                 600                 605

Gln Leu Leu Asn Leu Thr Leu Ser Phe Leu Asn Asn Gln Ile Lys Glu
                610                 615                 620

Leu Phe Ile His Thr Glu Glu Leu Asp Glu His Leu Gln Lys Gly Val
```

-continued

```
            625                 630                 635                 640
Asn Ile Leu Thr Ser Tyr Ile Asn Glu Leu Arg Thr Phe Met Ile Lys
                    645                 650                 655
Phe Pro Trp Lys Leu Thr Asp Ala Ile Asp Glu Tyr Asp Val His Glu
                660                 665                 670
Asn Val Pro Lys Val Lys Glu Ser Asn Ile Trp Lys Lys Leu Ser Phe
            675                 680                 685
Glu Glu Val Ile Ala Ser Ala Ile Leu Asn Asn Lys Ile Pro Glu Ala
        690                 695                 700
Gln Thr Phe Phe Arg Ile Asp Ser His Ser Ala Gln Lys Leu Glu Glu
705                 710                 715                 720
Leu Ile Gly Ile Gly Leu Asn Leu Val Phe Asp Asn Leu Lys Lys Asn
                725                 730                 735
Asn Ile Lys Glu Ala Ser Glu Leu Leu Lys Asn Met Gly Phe Asp Val
                740                 745                 750
Lys Gly Gln Leu Leu Lys Ile Cys Phe Tyr Thr Thr Asn Lys Asn Ile
            755                 760                 765
Arg Asp Phe Leu Val Glu Ile Leu Lys Glu Lys Asn Tyr Phe Ser Glu
        770                 775                 780
Lys Glu Lys Arg Thr Ile Asp Phe Val His Gln Val Glu Lys Leu Tyr
785                 790                 795                 800
Leu Gly His Phe Gln Glu Asn Met Gln Ile Gln Ser Phe Pro Arg Tyr
                805                 810                 815
Trp Ile Lys Glu Gln Asp Phe Phe Lys His Lys Ser Val Leu Asp Ser
                820                 825                 830
Phe Leu Lys Tyr Asp Cys Lys Asp Glu Phe Asn Lys Gln Asp His Arg
            835                 840                 845
Ile Val Leu Asn Trp Ala Leu Trp Trp Asp Gln Leu Thr Gln Glu Ser
        850                 855                 860
Ile Leu Leu Pro Arg Ile Ser Pro Glu Glu Tyr Lys Ser Tyr Ser Pro
865                 870                 875                 880
Glu Ala Leu Trp Arg Tyr Leu Thr Ala Arg His Asp Trp Leu Asn Ile
                885                 890                 895
Ile Leu Trp Ile Gly Glu Phe Gln Thr Gln His Ser Tyr Ala Ser Leu
                900                 905                 910
Gln Gln Asn Lys Trp Pro Leu Leu Thr Val Asp Val Ile Asn Gln Asn
            915                 920                 925
Thr Ser Cys Asn Asn Tyr Met Arg Asn Glu Ile Leu Asp Lys Leu Ala
        930                 935                 940
Arg Asn Gly Val Phe Leu Ala Ser Glu Leu Glu Asp Phe Glu Cys Phe
945                 950                 955                 960
Leu Leu Arg Leu Ser Arg Ile Gly Gly Val Ile Gln Asp Thr Leu Pro
                965                 970                 975
Val Gln Asn Tyr Lys Thr Lys Glu Gly Trp Asp Phe His Ser Gln Phe
                980                 985                 990
Ile Leu Tyr Cys Leu Glu His Ser Leu Gln His Leu Leu Tyr Val Tyr
            995                 1000                1005
Leu Asp Cys Tyr Lys Leu Ser Pro Glu Asn Cys Pro Phe Leu Glu
        1010                1015                1020
Lys Lys Glu Leu His Glu Ala His Pro Trp Phe Glu Phe Leu Val
        1025                1030                1035
Gln Cys Arg Gln Val Ala Ser Asn Leu Thr Asp Pro Lys Leu Ile
        1040                1045                1050
```

-continued

Phe Gln Ala Ser Leu Ala Asn Ala Gln Ile Leu Ile Pro Thr Asn
1055                1060                1065

Gln Ala Ser Val Ser Ser Met Leu Leu Glu Gly His Thr Leu Leu
1070                1075                1080

Ala Leu Ala Thr Thr Met Tyr Ser Pro Gly Gly Val Ser Gln Val
1085                1090                1095

Val Gln Asn Glu Glu Asn Glu Asn Cys Leu Lys Lys Val Asp Pro
1100                1105                1110

Gln Leu Leu Lys Met Ala Leu Thr Pro Tyr Pro Lys Leu Lys Thr
1115                1120                1125

Ala Leu Phe Pro Gln Cys Thr Pro Pro Ser Val Leu Pro Ser Asp
1130                1135                1140

Ile Thr Ile Tyr His Leu Ile Gln Ser Leu Ser Pro Phe Asp Pro
1145                1150                1155

Ser Arg Leu Phe Gly Trp Gln Ser Ala Asn Thr Leu Ala Ile Gly
1160                1165                1170

Asp Ala Trp Ser His Leu Pro His Phe Ser Ser Pro Asp Leu Val
1175                1180                1185

Asn Lys Tyr Ala Ile Val Glu Arg Leu Asn Phe Ala Tyr Tyr Leu
1190                1195                1200

His Asn Gly Arg Pro Ser Phe Ala Phe Gly Thr Phe Leu Val Gln
1205                1210                1215

Glu Leu Ile Lys Ser Lys Thr Pro Lys Gln Leu Ile Gln Gln Val
1220                1225                1230

Gly Asn Glu Ala Tyr Val Ile Gly Leu Ser Ser Phe His Ile Pro
1235                1240                1245

Ser Ile Gly Ala Ala Cys Val Cys Phe Leu Glu Leu Leu Gly Leu
1250                1255                1260

Asp Ser Leu Lys Leu Arg Val Asp Met Lys Val Ala Asn Ile Ile
1265                1270                1275

Leu Ser Tyr Lys Cys Arg Asn Glu Asp Ala Gln Tyr Ser Phe Ile
1280                1285                1290

Arg Glu Ser Val Ala Glu Lys Leu Ser Lys Leu Ala Asp Gly Glu
1295                1300                1305

Lys Thr Thr Thr Glu Glu Leu Leu Val Leu Leu Glu Glu Gly Thr
1310                1315                1320

Trp Asn Ser Ile Gln Gln Gln Glu Ile Lys Arg Leu Ser Ser Glu
1325                1330                1335

Ser Ser Ser Gln Trp Ala Leu Val Val Gln Phe Cys Arg Leu His
1340                1345                1350

Asn Met Lys Leu Ser Ile Ser Tyr Leu Arg Glu Cys Ala Lys Ala
1355                1360                1365

Asn Asp Trp Leu Gln Phe Ile Ile His Ser Gln Leu His Asn Tyr
1370                1375                1380

His Pro Ala Glu Val Lys Ser Leu Ile Gln Tyr Phe Ser Pro Val
1385                1390                1395

Ile Gln Asp His Leu Arg Leu Ala Phe Glu Asn Leu Pro Ser Val
1400                1405                1410

Pro Thr Ser Lys Met Asp Ser Asp Gln Val Cys Asn Lys Cys Pro
1415                1420                1425

Gln Glu Leu Gln Gly Ser Lys Gln Glu Met Thr Asp Leu Phe Glu
1430                1435                1440

Ile Leu Leu Gln Cys Ser Glu Glu Pro Asp Ser Trp His Trp Leu
1445                1450                1455

```
Leu Val Glu Ala Val Lys Gln Gln Ala Pro Ile Leu Ser Val Leu
    1460            1465                1470

Ala Ser Cys Leu Gln Gly Ala Ser Ala Ile Ser Cys Leu Cys Val
    1475            1480                1485

Trp Ile Ile Thr Ser Val Glu Asp Asn Val Ala Thr Glu Ala Met
    1490            1495                1500

Gly His Ile Gln Asp Ser Thr Glu Asp His Thr Trp Asn Leu Glu
    1505            1510                1515

Asp Leu Ser Val Ile Trp Arg Thr Leu Leu Thr Arg Gln Lys Ser
    1520            1525                1530

Lys Thr Leu Ile Arg Gly Phe Gln Leu Phe Phe Lys Asp Ser Pro
    1535            1540                1545

Leu Leu Leu Val Met Glu Met Tyr Glu Leu Cys Met Phe Phe Arg
    1550            1555                1560

Asn Tyr Lys Glu Ala Glu Ala Lys Leu Leu Glu Phe Gln Lys Ser
    1565            1570                1575

Leu Glu Thr Leu Asn Thr Ala Ala Thr Lys Val His Pro Val Ile
    1580            1585                1590

Pro Ala Met Trp Leu Glu Asp Gln Val Cys Phe Leu Leu Lys Leu
    1595            1600                1605

Met Leu Gln Gln Cys Lys Thr Gln Tyr Glu Leu Gly Lys Leu Leu
    1610            1615                1620

Gln Leu Phe Val Glu Arg Glu His Leu Phe Ser Asp Gly Pro Asp
    1625            1630                1635

Val Lys Lys Leu Cys Ile Leu Cys Gln Ile Leu Lys Asp Thr Ser
    1640            1645                1650

Ile Ala Ile Asn His Thr Ile Ile Thr Ser Tyr Ser Ile Glu Asn
    1655            1660                1665

Leu Gln His Glu Cys Arg Ser Ile Leu Glu Arg Leu Gln Thr Asp
    1670            1675                1680

Gly Gln Phe Ala Leu Ala Arg Arg Val Ala Glu Leu Ala Glu Leu
    1685            1690                1695

Pro Val Asp Asn Leu Val Ile Lys Glu Ile Thr Gln Glu Met Gln
    1700            1705                1710

Thr Leu Lys His Ile Glu Gln Trp Ser Leu Lys Gln Ala Arg Ile
    1715            1720                1725

Asp Phe Trp Lys Lys Cys His Glu Asn Phe Lys Lys Asn Ser Ile
    1730            1735                1740

Ser Ser Lys Ala Ala Ser Ser Phe Phe Ser Thr Gln Ala His Val
    1745            1750                1755

Ala Cys Glu His Pro Thr Gly Trp Ser Ser Met Glu Glu Arg His
    1760            1765                1770

Leu Leu Leu Thr Leu Ala Gly His Trp Leu Ala Gln Glu Asp Val
    1775            1780                1785

Val Pro Leu Asp Lys Leu Glu Glu Leu Glu Lys Gln Ile Trp Leu
    1790            1795                1800

Cys Arg Ile Thr Gln His Thr Leu Gly Arg Asn Gln Glu Glu Thr
    1805            1810                1815

Glu Pro Arg Phe Ser Arg Gln Ile Ser Thr Ser Gly Glu Leu Ser
    1820            1825                1830

Phe Asp Ser Leu Ala Ser Glu Phe Ser Phe Ser Lys Leu Ala Ala
    1835            1840                1845

Leu Asn Thr Ser Lys Tyr Leu Glu Leu Asn Ser Leu Pro Ser Lys
```

```
                  1850                1855                1860

Glu Thr Cys Glu Asn Arg Leu Asp Trp Lys Glu Gln Glu Ser Leu
        1865                1870                1875

Asn Phe Leu Ile Gly Arg Leu Leu Asp Asp Gly Cys Val His Glu
        1880                1885                1890

Ala Ser Arg Val Cys Arg Tyr Phe His Phe Tyr Asn Pro Asp Val
        1895                1900                1905

Ala Leu Val Leu His Cys Arg Ala Leu Ala Ser Gly Glu Ala Ser
        1910                1915                1920

Met Glu Asp Leu His Pro Glu Ile His Ala Leu Leu Gln Ser Ala
        1925                1930                1935

Glu Leu Leu Glu Glu Glu Ala Pro Asp Ile Pro Leu Arg Arg Val
        1940                1945                1950

His Ser Thr Ser Ser Leu Asp Ser Gln Lys Phe Val Thr Val Pro
        1955                1960                1965

Ser Ser Asn Glu Val Val Thr Asn Leu Glu Val Leu Thr Ser Lys
        1970                1975                1980

Cys Leu His Gly Lys Asn Tyr Cys Arg Gln Val Leu Cys Leu Tyr
        1985                1990                1995

Asp Leu Ala Lys Glu Leu Gly Cys Ser Tyr Thr Asp Val Ala Ala
        2000                2005                2010

Gln Asp Gly Glu Ala Met Leu Arg Lys Ile Leu Ala Ser Gln Gln
        2015                2020                2025

Pro Asp
    2030

<210> SEQ ID NO 186
<211> LENGTH: 2259
<212> TYPE: PRT
<213> ORGANISM: Homo sapiens

<400> SEQUENCE: 186

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
```

```
                    180                 185                 190
Leu Pro Leu Pro Ala Gln Ala Val Asp Met Ile Ile Asp Thr Gln Leu
            195                 200                 205
Cys Arg Gly Ile Leu Phe Val Leu Ser Ser Leu Gly Trp Ile Tyr Ile
        210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Gln Glu Pro Ala Lys Ile
                245                 250                 255
Ser Ser Phe Thr Ser Leu Lys Val Ser Gln Asp Leu Asp Val Ala Val
            260                 265                 270
Ile Val Ser Ser Ser Asn Ser Ala Val Ala Leu Asn Leu Asn Leu Tyr
        275                 280                 285
Phe Arg Gln His Pro Gly His Leu Leu Cys Glu Arg Ile Leu Glu Asp
290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
        355                 360                 365
Leu Glu Ser Pro Glu Ser Gly Asn His Ser Thr Ser Val Gln Ser Trp
        370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
                405                 410                 415
His Ile Ser Glu Gln Glu Glu Pro Ile Glu Leu Lys Cys Val Ser Val
            420                 425                 430
Thr Gly Phe Thr Ala Leu Phe Thr Trp Glu Val Glu Arg Met Gly Tyr
        435                 440                 445
Thr Ile Thr Leu Trp Asp Leu Glu Thr Gln Gly Met Gln Cys Ser Ser
        450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
                485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
        515                 520                 525
Pro Ile His Ala Leu Glu Ala Gly Ile Glu Asn Arg Gln Leu Asp Thr
        530                 535                 540
Val Asn Phe Phe Leu Lys Ser Lys Glu Asn Leu Phe Asn Pro Ser Ser
545                 550                 555                 560
Lys Ser Ser Val Ser Asp Gln Phe Asp His Leu Ser Ser His Leu Tyr
                565                 570                 575
Leu Arg Asn Val Glu Glu Leu Ile Pro Ala Leu Asp Leu Leu Cys Ser
            580                 585                 590
Ala Ile Arg Glu Ser Tyr Ser Glu Pro Gln Ser Lys His Phe Ser Glu
        595                 600                 605
```

```
Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Asp Gln Leu Thr Gln Glu Ser
    850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Gly Gly Trp Phe Ser Gln Phe
        980                 985                 990

Ile Leu Tyr Cys Leu Glu His Ser Leu Gln His Leu Leu Tyr Val Tyr
    995                 1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035
```

```
Gln Cys Arg Gln Val Ala Ser Asn Leu Thr Asp Pro Lys Leu Ile
    1040            1045                1050

Phe Gln Ala Ser Leu Ala Asn Ala Gln Ile Leu Ile Pro Thr Asn
    1055            1060                1065

Gln Ala Ser Val Ser Ser Met Leu Leu Glu Gly His Thr Leu Leu
    1070            1075                1080

Ala Leu Ala Thr Thr Met Tyr Ser Pro Gly Gly Val Ser Gln Val
    1085            1090                1095

Val Gln Asn Glu Glu Asn Glu Asn Cys Leu Lys Lys Val Asp Pro
    1100            1105                1110

Gln Leu Leu Lys Met Ala Leu Thr Pro Tyr Pro Lys Leu Lys Thr
    1115            1120                1125

Ala Leu Phe Pro Gln Cys Thr Pro Pro Ser Val Leu Pro Ser Asp
    1130            1135                1140

Ile Thr Ile Tyr His Leu Ile Gln Ser Leu Ser Pro Phe Asp Pro
    1145            1150                1155

Ser Arg Leu Phe Gly Trp Gln Ser Ala Asn Thr Leu Ala Ile Gly
    1160            1165                1170

Asp Ala Trp Ser His Leu Pro His Phe Ser Ser Pro Asp Leu Val
    1175            1180                1185

Asn Lys Tyr Ala Ile Val Glu Arg Leu Asn Phe Ala Tyr Tyr Leu
    1190            1195                1200

His Asn Gly Arg Pro Ser Phe Ala Phe Gly Thr Phe Leu Val Gln
    1205            1210                1215

Glu Leu Ile Lys Ser Lys Thr Pro Lys Gln Leu Ile Gln Gln Val
    1220            1225                1230

Gly Asn Glu Ala Tyr Val Ile Gly Leu Ser Ser Phe His Ile Pro
    1235            1240                1245

Ser Ile Gly Ala Ala Cys Val Cys Phe Leu Glu Leu Leu Gly Leu
    1250            1255                1260

Asp Ser Leu Lys Leu Arg Val Asp Met Lys Val Ala Asn Ile Ile
    1265            1270                1275

Leu Ser Tyr Lys Cys Arg Asn Glu Asp Ala Gln Tyr Ser Phe Ile
    1280            1285                1290

Arg Glu Ser Val Ala Glu Lys Leu Ser Lys Leu Ala Asp Gly Glu
    1295            1300                1305

Lys Thr Thr Thr Glu Glu Leu Leu Val Leu Leu Glu Glu Gly Thr
    1310            1315                1320

Trp Asn Ser Ile Gln Gln Gln Glu Ile Lys Arg Leu Ser Ser Glu
    1325            1330                1335

Ser Ser Ser Gln Trp Ala Leu Val Val Gln Phe Cys Arg Leu His
    1340            1345                1350

Asn Met Lys Leu Ser Ile Ser Tyr Leu Arg Glu Cys Ala Lys Ala
    1355            1360                1365

Asn Asp Trp Leu Gln Phe Ile Ile His Ser Gln Leu His Asn Tyr
    1370            1375                1380

His Pro Ala Glu Val Lys Ser Leu Ile Gln Tyr Phe Ser Pro Val
    1385            1390                1395

Ile Gln Asp His Leu Arg Leu Ala Phe Glu Asn Leu Pro Ser Val
    1400            1405                1410

Pro Thr Ser Lys Met Asp Ser Asp Gln Val Cys Asn Lys Cys Pro
    1415            1420                1425

Gln Glu Leu Gln Gly Ser Lys Gln Glu Met Thr Asp Leu Phe Glu
```

-continued

```
            1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830
```

```
Phe Asp Ser Leu Ala Ser Glu Phe Ser Phe Ser Lys Leu Ala Ala
1835                1840                1845

Leu Asn Thr Ser Lys Tyr Leu Glu Leu Asn Ser Leu Pro Ser Lys
1850                1855                1860

Glu Thr Cys Glu Asn Arg Leu Asp Trp Lys Glu Gln Glu Ser Leu
1865                1870                1875

Asn Phe Leu Ile Gly Arg Leu Leu Asp Asp Gly Cys Val His Glu
1880                1885                1890

Ala Ser Arg Val Cys Arg Tyr Phe His Phe Tyr Asn Pro Asp Val
1895                1900                1905

Ala Leu Val Leu His Cys Arg Ala Leu Ala Ser Gly Glu Ala Ser
1910                1915                1920

Met Glu Asp Leu His Pro Glu Ile His Ala Leu Leu Gln Ser Ala
1925                1930                1935

Glu Leu Leu Glu Glu Glu Ala Pro Asp Ile Pro Leu Arg Arg Val
1940                1945                1950

His Ser Thr Ser Ser Leu Asp Ser Gln Lys Phe Val Thr Val Pro
1955                1960                1965

Ser Ser Asn Glu Val Val Thr Asn Leu Glu Val Leu Thr Ser Lys
1970                1975                1980

Cys Leu His Gly Lys Asn Tyr Cys Arg Gln Val Leu Cys Leu Tyr
1985                1990                1995

Asp Leu Ala Lys Glu Leu Gly Cys Ser Tyr Thr Asp Val Ala Ala
2000                2005                2010

Gln Asp Gly Glu Ala Met Leu Arg Lys Ile Leu Ala Ser Gln Gln
2015                2020                2025

Pro Asp Arg Cys Lys Arg Ala Gln Ala Phe Ile Ser Thr Gln Gly
2030                2035                2040

Leu Lys Pro Asp Thr Val Ala Glu Leu Val Ala Glu Glu Val Thr
2045                2050                2055

Arg Glu Leu Leu Thr Ser Ser Gln Gly Thr Gly His Lys Gln Met
2060                2065                2070

Phe Asn Pro Thr Glu Glu Ser Gln Thr Phe Leu Gln Leu Thr Thr
2075                2080                2085

Leu Cys Gln Asp Arg Thr Leu Val Gly Met Lys Leu Leu Asp Lys
2090                2095                2100

Ile Ser Ser Val Pro His Gly Glu Leu Ser Cys Thr Thr Glu Leu
2105                2110                2115

Leu Ile Leu Ala His His Cys Phe Thr Leu Thr Cys His Met Glu
2120                2125                2130

Gly Ile Ile Arg Val Leu Gln Ala Ala His Met Leu Thr Asp Asn
2135                2140                2145

His Leu Ala Pro Ser Glu Glu Tyr Gly Leu Val Val Arg Leu Leu
2150                2155                2160

Thr Gly Ile Gly Arg Tyr Asn Glu Met Thr Tyr Ile Phe Asp Leu
2165                2170                2175

Leu His Lys Lys His Tyr Phe Glu Val Leu Met Arg Lys Lys Leu
2180                2185                2190

Asp Pro Ser Gly Thr Leu Lys Thr Ala Leu Leu Asp Tyr Ile Lys
2195                2200                2205

Arg Cys Arg Pro Gly Asp Ser Glu Lys His Asn Met Ile Ala Leu
2210                2215                2220

Cys Phe Ser Met Cys Arg Glu Ile Gly Glu Asn His Glu Ala Ala
2225                2230                2235
```

```
Ala Arg Ile Gln Leu Lys Leu Ile Leu Ser Pro Gly Arg Thr Ala
    2240                2245                2250

Ser Arg Met Gly Thr Ser
    2255

<210> SEQ ID NO 187
<211> LENGTH: 2285
<212> TYPE: PRT
<213> ORGANISM: Homo sapiens

<400> SEQUENCE: 187

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350
```

```
Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
        420                 425                 430

Thr Gly Phe Thr Ala Leu Phe Thr Trp Glu Val Glu Arg Met Gly Tyr
    435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
        500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
        580                 585                 590

Ala Ile Arg Glu Ser Tyr Ser Glu Pro Gln Ser Lys His Phe Ser Glu
    595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
        660                 665                 670

Asn Val Pro Lys Val Lys Glu Ser Asn Ile Trp Lys Lys Leu Ser Phe
    675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
            725                 730                 735

Asn Ile Lys Glu Ala Ser Glu Leu Leu Lys Asn Met Gly Phe Asp Val
        740                 745                 750

Lys Gly Gln Leu Leu Lys Ile Cys Phe Tyr Thr Thr Asn Lys Asn Ile
    755                 760                 765

Arg Asp Phe Leu Val Glu Ile Leu Lys Glu Lys Asn Tyr Phe Ser Glu
```

```
            770             775             780
Lys Glu Lys Arg Thr Ile Asp Phe Val His Gln Val Glu Lys Leu Tyr
785             790             795             800

Leu Gly His Phe Gln Glu Asn Met Gln Ile Gln Ser Phe Pro Arg Tyr
            805             810             815

Trp Ile Lys Glu Gln Asp Phe Phe Lys His Lys Ser Val Leu Asp Ser
            820             825             830

Phe Leu Lys Tyr Asp Cys Lys Asp Glu Phe Asn Lys Gln Asp His Arg
            835             840             845

Ile Val Leu Asn Trp Ala Leu Trp Trp Asp Gln Leu Thr Gln Glu Ser
850             855             860

Ile Leu Leu Pro Arg Ile Ser Pro Glu Glu Tyr Lys Ser Tyr Ser Pro
865             870             875             880

Glu Ala Leu Trp Arg Tyr Leu Thr Ala Arg His Asp Trp Leu Asn Ile
            885             890             895

Ile Leu Trp Ile Gly Glu Phe Gln Thr Gln His Ser Tyr Ala Ser Leu
            900             905             910

Gln Gln Asn Lys Trp Pro Leu Leu Thr Val Asp Val Ile Asn Gln Asn
            915             920             925

Thr Ser Cys Asn Asn Tyr Met Arg Asn Glu Ile Leu Asp Lys Leu Ala
930             935             940

Arg Asn Gly Val Phe Leu Ala Ser Glu Leu Glu Asp Phe Glu Cys Phe
945             950             955             960

Leu Leu Arg Leu Ser Arg Ile Gly Gly Val Ile Gln Asp Thr Leu Pro
            965             970             975

Val Gln Asn Tyr Lys Thr Lys Glu Gly Trp Asp Phe His Ser Gln Phe
            980             985             990

Ile Leu Tyr Cys Leu Glu His Ser Leu Gln His Leu Leu Tyr Val Tyr
            995             1000            1005

Leu Asp Cys Tyr Lys Leu Ser Pro Glu Asn Cys Pro Phe Leu Glu
            1010            1015            1020

Lys Lys Glu Leu His Glu Ala His Pro Trp Phe Glu Phe Leu Val
            1025            1030            1035

Gln Cys Arg Gln Val Ala Ser Asn Leu Thr Asp Pro Lys Leu Ile
            1040            1045            1050

Phe Gln Ala Ser Leu Ala Asn Ala Gln Ile Leu Ile Pro Thr Asn
            1055            1060            1065

Gln Ala Ser Val Ser Ser Met Leu Leu Glu Gly His Thr Leu Leu
            1070            1075            1080

Ala Leu Ala Thr Thr Met Tyr Ser Pro Gly Gly Val Ser Gln Val
            1085            1090            1095

Val Gln Asn Glu Glu Asn Glu Asn Cys Leu Lys Lys Val Asp Pro
            1100            1105            1110

Gln Leu Leu Lys Met Ala Leu Thr Pro Tyr Pro Lys Leu Lys Thr
            1115            1120            1125

Ala Leu Phe Pro Gln Cys Thr Pro Pro Ser Val Leu Pro Ser Asp
            1130            1135            1140

Ile Thr Ile Tyr His Leu Ile Gln Ser Leu Ser Pro Phe Asp Pro
            1145            1150            1155

Ser Arg Leu Phe Gly Trp Gln Ser Ala Asn Thr Leu Ala Ile Gly
            1160            1165            1170

Asp Ala Trp Ser His Leu Pro His Phe Ser Ser Pro Asp Leu Val
            1175            1180            1185
```

-continued

Asn Lys Tyr Ala Ile Val Glu Arg Leu Asn Phe Ala Tyr Tyr Leu
1190                1195                1200

His Asn Gly Arg Pro Ser Phe Ala Phe Gly Thr Phe Leu Val Gln
1205                1210                1215

Glu Leu Ile Lys Ser Lys Thr Pro Lys Gln Leu Ile Gln Gln Val
1220                1225                1230

Gly Asn Glu Ala Tyr Val Ile Gly Leu Ser Ser Phe His Ile Pro
1235                1240                1245

Ser Ile Gly Ala Ala Cys Val Cys Phe Leu Glu Leu Leu Gly Leu
1250                1255                1260

Asp Ser Leu Lys Leu Arg Val Asp Met Lys Val Ala Asn Ile Ile
1265                1270                1275

Leu Ser Tyr Lys Cys Arg Asn Glu Asp Ala Gln Tyr Ser Phe Ile
1280                1285                1290

Arg Glu Ser Val Ala Glu Lys Leu Ser Lys Leu Ala Asp Gly Glu
1295                1300                1305

Lys Thr Thr Thr Glu Glu Leu Leu Val Leu Leu Glu Glu Gly Thr
1310                1315                1320

Trp Asn Ser Ile Gln Gln Gln Glu Ile Lys Arg Leu Ser Ser Glu
1325                1330                1335

Ser Ser Ser Gln Trp Ala Leu Val Val Gln Phe Cys Arg Leu His
1340                1345                1350

Asn Met Lys Leu Ser Ile Ser Tyr Leu Arg Glu Cys Ala Lys Ala
1355                1360                1365

Asn Asp Trp Leu Gln Phe Ile Ile His Ser Gln Leu His Asn Tyr
1370                1375                1380

His Pro Ala Glu Val Lys Ser Leu Ile Gln Tyr Phe Ser Pro Val
1385                1390                1395

Ile Gln Asp His Leu Arg Leu Ala Phe Glu Asn Leu Pro Ser Val
1400                1405                1410

Pro Thr Ser Lys Met Asp Ser Asp Gln Val Cys Asn Lys Cys Pro
1415                1420                1425

Gln Glu Leu Gln Gly Ser Lys Gln Glu Met Thr Asp Leu Phe Glu
1430                1435                1440

Ile Leu Leu Gln Cys Ser Glu Glu Pro Asp Ser Trp His Trp Leu
1445                1450                1455

Leu Val Glu Ala Val Lys Gln Ala Pro Ile Leu Ser Val Leu
1460                1465                1470

Ala Ser Cys Leu Gln Gly Ala Ser Ala Ile Ser Cys Leu Cys Val
1475                1480                1485

Trp Ile Ile Thr Ser Val Glu Asp Asn Val Ala Thr Glu Ala Met
1490                1495                1500

Gly His Ile Gln Asp Ser Thr Glu Asp His Thr Trp Asn Leu Glu
1505                1510                1515

Asp Leu Ser Val Ile Trp Arg Thr Leu Leu Thr Arg Gln Lys Ser
1520                1525                1530

Lys Thr Leu Ile Arg Gly Phe Gln Leu Phe Phe Lys Asp Ser Pro
1535                1540                1545

Leu Leu Leu Val Met Glu Met Tyr Glu Leu Cys Met Phe Phe Arg
1550                1555                1560

Asn Tyr Lys Glu Ala Glu Ala Lys Leu Leu Glu Phe Gln Lys Ser
1565                1570                1575

Leu Glu Thr Leu Asn Thr Ala Ala Thr Lys Val His Pro Val Ile
1580                1585                1590

```
Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Leu Tyr
```

```
                      1985                1990                1995
Asp Leu Ala Lys Glu Leu Gly Cys Ser Tyr Thr Asp Val Ala Ala
    2000                2005                2010

Gln Asp Gly Glu Ala Met Leu Arg Lys Ile Leu Ala Ser Gln Gln
    2015                2020                2025

Pro Asp Arg Cys Lys Arg Ala Gln Ala Phe Ile Ser Thr Gln Gly
    2030                2035                2040

Leu Lys Pro Asp Thr Val Ala Glu Leu Val Ala Glu Glu Val Thr
    2045                2050                2055

Arg Glu Leu Leu Thr Ser Ser Gln Gly Thr Gly His Lys Gln Met
    2060                2065                2070

Phe Asn Pro Thr Glu Glu Ser Gln Thr Phe Leu Gln Leu Thr Thr
    2075                2080                2085

Leu Cys Gln Asp Arg Thr Leu Val Gly Met Lys Leu Leu Asp Lys
    2090                2095                2100

Ile Ser Ser Val Pro His Gly Glu Leu Ser Cys Thr Thr Glu Leu
    2105                2110                2115

Leu Ile Leu Ala His His Cys Phe Thr Leu Thr Cys His Met Glu
    2120                2125                2130

Gly Ile Ile Arg Val Leu Gln Ala Ala His Met Leu Thr Asp Asn
    2135                2140                2145

His Leu Ala Pro Ser Glu Glu Tyr Gly Leu Val Val Arg Leu Leu
    2150                2155                2160

Thr Gly Ile Gly Arg Tyr Asn Glu Met Thr Tyr Ile Phe Asp Leu
    2165                2170                2175

Leu His Lys Lys His Tyr Phe Glu Val Leu Met Arg Lys Lys Leu
    2180                2185                2190

Asp Pro Ser Gly Thr Leu Lys Thr Ala Leu Leu Asp Tyr Ile Lys
    2195                2200                2205

Arg Cys Arg Pro Gly Asp Ser Glu Lys His Asn Met Ile Ala Leu
    2210                2215                2220

Cys Phe Ser Met Cys Arg Glu Ile Gly Glu Asn His Glu Ala Ala
    2225                2230                2235

Ala Arg Ile Gln Leu Lys Leu Ile Glu Ser Gln Pro Trp Glu Asp
    2240                2245                2250

Ser Leu Lys Asp Gly His Gln Leu Lys Gln Leu Leu Lys Ala
    2255                2260                2265

Leu Thr Leu Met Leu Asp Ala Ala Glu Ser Tyr Ala Lys Asp Ser
    2270                2275                2280

Cys Val
    2285

<210> SEQ ID NO 188
<211> LENGTH: 949
<212> TYPE: PRT
<213> ORGANISM: Homo sapiens

<400> SEQUENCE: 188

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
```

-continued

```
            50                  55                  60
Val Leu Ser Leu Thr Pro Gly Ser Arg Gly Gly Arg Cys Cys Leu
 65                  70                  75                  80

Glu Gly Pro Phe Trp His Phe Leu Trp Glu Asp Ser Arg Asn Ser Ser
                     85                  90                  95

Thr Pro Thr Glu Lys Pro Lys Leu Leu Ala Leu Gly Glu Asn Tyr Glu
                    100                 105                 110

Leu Leu Ile Tyr Glu Phe Asn Leu Lys Asp Gly Arg Cys Asp Ala Thr
                115                 120                 125

Ile Leu Tyr Ser Cys Ser Arg Glu Ala Leu Gln Lys Leu Ile Asp Asp
                130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                    165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
                195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                    245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
                275                 280                 285

Phe Arg Gln His Pro Gly His Leu Leu Cys Glu Arg Ile Leu Glu Asp
                290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                    325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                    405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
                435                 440                 445

Thr Ile Thr Leu Trp Asp Leu Glu Thr Gln Gly Met Gln Cys Ser Ser
                450                 455                 460

Leu Gly Thr Lys Cys Ile Pro Val Asp Ser Ser Gly Asp Gln Gln Leu
465                 470                 475                 480
```

-continued

```
Cys Phe Val Leu Thr Glu Asn Gly Leu Ser Leu Ile Leu Phe Gly Leu
                485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
        515                 520                 525
Pro Ile His Ala Leu Glu Ala Gly Ile Glu Asn Arg Gln Leu Asp Thr
    530                 535                 540
Val Asn Phe Phe Leu Lys Ser Lys Glu Asn Leu Phe Asn Pro Ser Ser
545                 550                 555                 560
Lys Ser Ser Val Ser Asp Gln Phe Asp His Leu Ser Ser His Leu Tyr
                565                 570                 575
Leu Arg Asn Val Glu Glu Leu Ile Pro Ala Leu Asp Leu Leu Cys Ser
            580                 585                 590
Ala Ile Arg Glu Ser Tyr Ser Glu Pro Gln Ser Lys His Phe Ser Glu
        595                 600                 605
Gln Leu Leu Asn Leu Thr Leu Ser Phe Leu Asn Asn Gln Ile Lys Glu
    610                 615                 620
Leu Phe Ile His Thr Glu Glu Leu Asp Glu His Leu Gln Lys Gly Val
625                 630                 635                 640
Asn Ile Leu Thr Ser Tyr Ile Asn Glu Leu Arg Thr Phe Met Ile Lys
                645                 650                 655
Phe Pro Trp Lys Leu Thr Asp Ala Ile Asp Glu Tyr Asp Val His Glu
            660                 665                 670
Asn Val Pro Lys Val Lys Glu Ser Asn Ile Trp Lys Lys Leu Ser Phe
        675                 680                 685
Glu Glu Val Ile Ala Ser Ala Ile Leu Asn Asn Lys Ile Pro Glu Ala
    690                 695                 700
Gln Thr Phe Phe Arg Ile Asp Ser His Ser Ala Gln Lys Leu Glu Glu
705                 710                 715                 720
Leu Ile Gly Ile Gly Leu Asn Leu Val Phe Asp Asn Leu Lys Lys Asn
                725                 730                 735
Asn Ile Lys Glu Ala Ser Glu Leu Leu Lys Asn Met Gly Phe Asp Val
            740                 745                 750
Lys Gly Gln Leu Leu Lys Ile Cys Phe Tyr Thr Thr Asn Lys Asn Ile
        755                 760                 765
Arg Asp Phe Leu Val Glu Ile Leu Lys Glu Lys Asn Tyr Phe Ser Glu
    770                 775                 780
Lys Glu Lys Arg Thr Ile Asp Phe Val His Gln Val Lys Leu Tyr
785                 790                 795                 800
Leu Gly His Phe Gln Glu Asn Met Gln Ile Gln Ser Phe Pro Arg Tyr
                805                 810                 815
Trp Ile Lys Glu Gln Asp Phe Lys His Lys Ser Val Leu Asp Ser
            820                 825                 830
Phe Leu Lys Tyr Asp Cys Lys Asp Glu Phe Asn Lys Gln Asp His Arg
        835                 840                 845
Ile Val Leu Asn Trp Ala Leu Trp Trp Asp Gln Leu Thr Gln Glu Ser
    850                 855                 860
Ile Leu Leu Pro Arg Ile Ser Pro Glu Glu Tyr Lys Ser Tyr Ser Pro
865                 870                 875                 880
Glu Ala Leu Trp Arg Tyr Leu Thr Ala Arg His Asp Trp Leu Asn Ile
                885                 890                 895
Ile Leu Trp Ile Gly Glu Phe Gln Thr Gln His Ser Tyr Ala Ser Leu
            900                 905                 910
```

```
Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Gly Tyr Tyr Asn Cys
945
```